(12) United States Patent
Smith

(10) Patent No.: US 12,352,749 B2
(45) Date of Patent: Jul. 8, 2025

(54) HUMAN STREPTOCOCCUS PNEUMONIAE ANTIBODIES AND USES THEREFOR

(71) Applicant: Oklahoma Medical Research Foundation, Oklahoma City, OK (US)

(72) Inventor: Kenneth Smith, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 99 days.

(21) Appl. No.: 18/066,582

(22) Filed: Dec. 15, 2022

(65) Prior Publication Data

US 2023/0213512 A1 Jul. 6, 2023

Related U.S. Application Data

(60) Continuation of application No. 15/058,814, filed on Mar. 2, 2016, now Pat. No. 11,567,077, which is a division of application No. 13/740,934, filed on Jan. 14, 2013, now Pat. No. 9,279,815.

(60) Provisional application No. 61/593,654, filed on Feb. 1, 2012.

(51) Int. Cl.
| | |
|---|---|
| G01N 33/53 | (2006.01) |
| C07K 16/12 | (2006.01) |
| G01N 33/569 | (2006.01) |
| G01N 33/68 | (2006.01) |

(52) U.S. Cl.
CPC ............ G01N 33/56944 (2013.01); C07K 16/1275 (2013.01); G01N 33/6854 (2013.01); C07K 2317/21 (2013.01); C07K 2317/31 (2013.01); C07K 2317/33 (2013.01); C07K 2317/92 (2013.01); G01N 2333/3156 (2013.01); G01N 2469/10 (2013.01)

(58) Field of Classification Search
CPC .............................................. G01N 33/56944
See application file for complete search history.

(56) References Cited

U.S. PATENT DOCUMENTS

| | | |
|---|---|---|
| 2005/0014931 A1 | 1/2005 | Pirofski et al. |
| 2011/0053793 A1 | 3/2011 | Monsterio et al. |

FOREIGN PATENT DOCUMENTS

| | | |
|---|---|---|
| CN | 101163499 A | 4/2008 |
| CN | 101802198 A | 8/2010 |
| JP | 2010-276441 A | 12/2010 |
| WO | WO 02/079254 A1 | 10/2002 |

OTHER PUBLICATIONS

Antilla, et al. "Contribution of serotype-specific IgG concentration, IgG subclasses and relative antibody avidity to opsonophagocytic activity against Streptococcus pneumonia," vol. 118 No. 3, Clin Exp Immunol., pp. 402-407 (1999).
Baxendale et al., "Correlation of molecular characteristics, isotype, and in vitro functional activity of human antipneumococcal monoclonal antibodies," vol. 74 No. 2, Infect Immun., pp. 1025-1031 (2006).
Baxendale et al., "Immunogenetic analysis of the immune response to pneumococcal polysaccharide," vol. 30 No. 3, Eur J Immunol., pp. 1214-1223 (2000).
Chowdry et al., "Autoantibodies that bind glomeruli: cross-reactivity with bacterial antigen," vol. 52 No. 8, Arthritis Rheum., pp. 2403-2410 (2005).
Clutterbuck et al., "The kinetics and phenotype of the human B-cell response following immunization with a heptavalent pneumococcal-CRM conjugate vaccine," vol. 119 No. 3, Immunology, pp. 328-337 (2006).
Elkayam et al., "Pneumococcal vaccination of patients with systemic lupus erythematosus: effects on generation of autoantibodies," vol. 38 No. 7, Autoimmunity, pp. 493-496 (2005).
Nieminen et al., "Circulating antibody secreting cell response to parenteral pneumococcal vaccines as an indicator of a salivary IgA antibody response," vol. 16 No. 2-3, Vaccine, pp. 313-319 (1998).
Nieminen et al., "Pneumococcal conjugate vaccination in adults: circulating antibody secreting cell response and humoral antibody responses in saliva and in serum," vol. 16 No. 6, Vaccine, pp. 630-636 (1998).
PCT International Search Report and Written Opinion issued in International Application No. PCT/US13/21381, dated Jan. 14, 2013.
Smith et al., "Rapid generation of fully human monoclonal antibodies against influenza virus," vol. 4 No. 3, Nat. Protocol., pp. 372-384; especially abstract p. 18 para 1 (2009).
Wrammert et al., "Rapid cloning of high-affinity human monoclonal antibodies against influenza virus," vol. 453 No. 7195, Nature, pp. 667-671 (2008).
Zhou et al., "Recurrent variable region gene usage and somatic mutation in the human antibody response to the capsular polysaccharise of Streptococcus pneumonia type 23F," vol. 70 No. 8, pp. 4083-4091 (2002).
Zhou, et al., "Somatic Hypermutation and Diverse Immunoglobulin Gene Usage in the Human Antibody Response to the Capsular Polysaccharide of Streptococcus pneumonia Type 6B," vol. 72, Period 6, Infection and Immunity, pp. 3505-3535 (2004).
Lucas, "Combinatorial Library Cloning of Human Antibodies to Streptococcus pneumonia Capsular Polysaccharides: Variable Region Primary Structures and Evidence for Somatic Mutation of Fab Fragments Specific for Capsular Serotypes 6B, 14 and 23F," vol. 69, No. 2, Infection and Immunity, pp. 853-864 (2000).
Yu, "A rapid pneumococcal serotyping system based on monoclonal antibodies and PCR," vol. 57, Journal of Medical Microbiology, pp. 171-178 (2008).

(Continued)

Primary Examiner — Albert M Navarro
(74) Attorney, Agent, or Firm — Edwin S. Flores; Daniel J. Chalker; Chalker Flores, LLP

(57) ABSTRACT

The present invention is directed to particular monoclonal antibodies and fragments thereof that find use in the detection, prevention and treatment of Streptococcus pneumoniae infections. In particular, these antibodies may kill Streptococcus pneumoniae or limit the replication of Streptococcus pneumoniae. Also disclosed are improved methods for producing such monoclonal antibodies.

13 Claims, 7 Drawing Sheets

Specification includes a Sequence Listing.

(56) References Cited

OTHER PUBLICATIONS

Yu, "Development of a multiplexed and automated serotyping assay for *Streptococcus pneumonia*," vol. 18 Clinical and Vaccine Immunology, pp. 1-25 (2011).

Lin, "Validation of a Multiplex Pneumococcal Serotyping Assay with Clinical Samples," vol. 44, No. 2, Journal of Clinical Microbiology, pp. 383-388 (2006).

Meng, "Specificity of antibody response to 23-valent pneumococcal polysaccharide vaccine in patients with chronic pulmonary diseases," vol. 36, No. 17 Jiangsu Medical Journal, pp. 2002-2004 (2010).

Office Action issued in corresponding Chinese Application No. 201380017988.6, dated Jun. 30, 2015.

Office Action issued in corresponding Chinese Application No. 201380017988.6, dated Dec. 10, 2015.

Examination Report issued in corresponding Australian Application No. 2013215630, dated Sep. 4, 2015.

European Search Report issued in corresponding European Application No. 13744086.3, dated Sep. 25, 2015.

Extended European Search Report in corresponding European Application No. 13744086.3, dated Jan. 19, 2016.

Yu et al., "Development of an Automated and Multiplexed Serotyping Assay for *Streptococcus pneumonia*", Clinical and Vaccine Immunology, vol. 18, No. 11, pp. 1900-1907 (2011).

Examination Report issued in related Australian Patent Application No. 2016219587, dated Aug. 18, 2017.

Yu et al., "A Rapid Pneumococcal Serotyping System Based on Monoclonal Antibodies and PCR," *Journal of Medical Microbiology*, vol. 57, pp. 171-178 (2008).

Office Action issued in related Japanese Patent Application No. 2014-555559, dated Oct. 20, 2016.

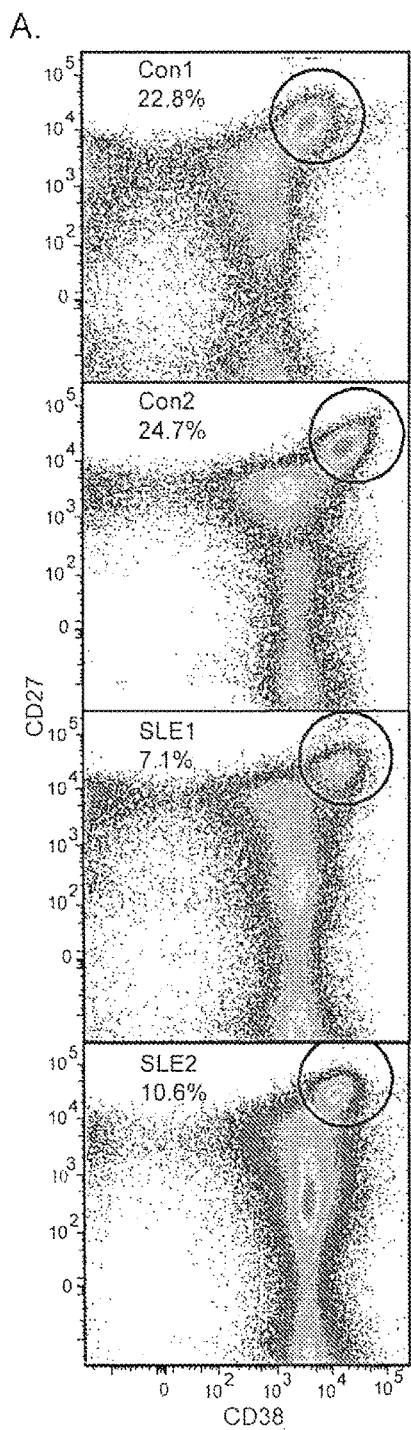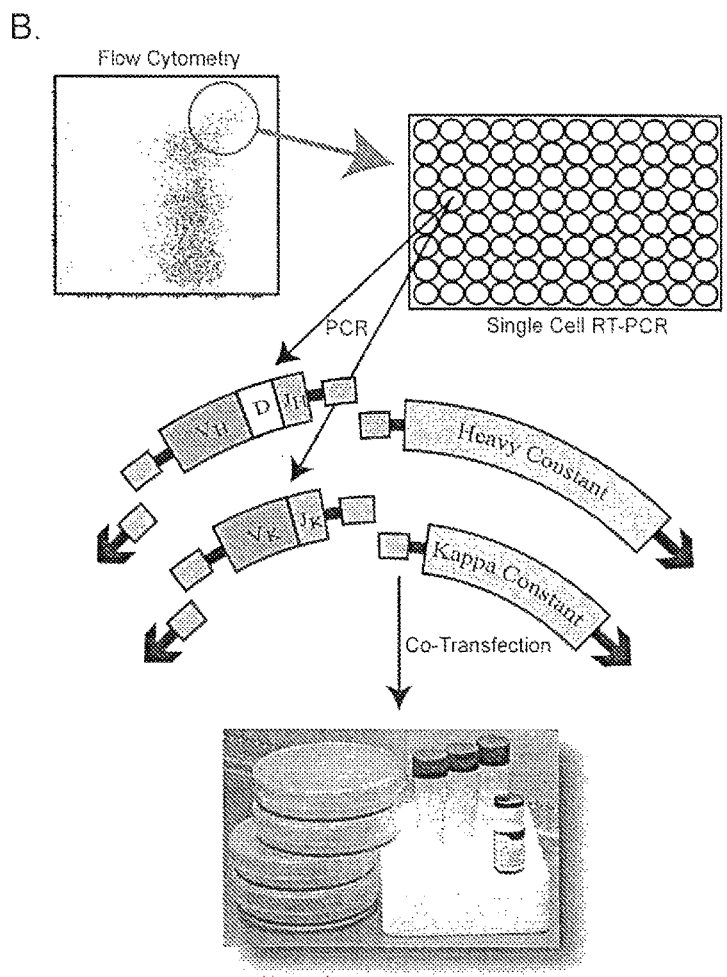
FIG. 1A-B

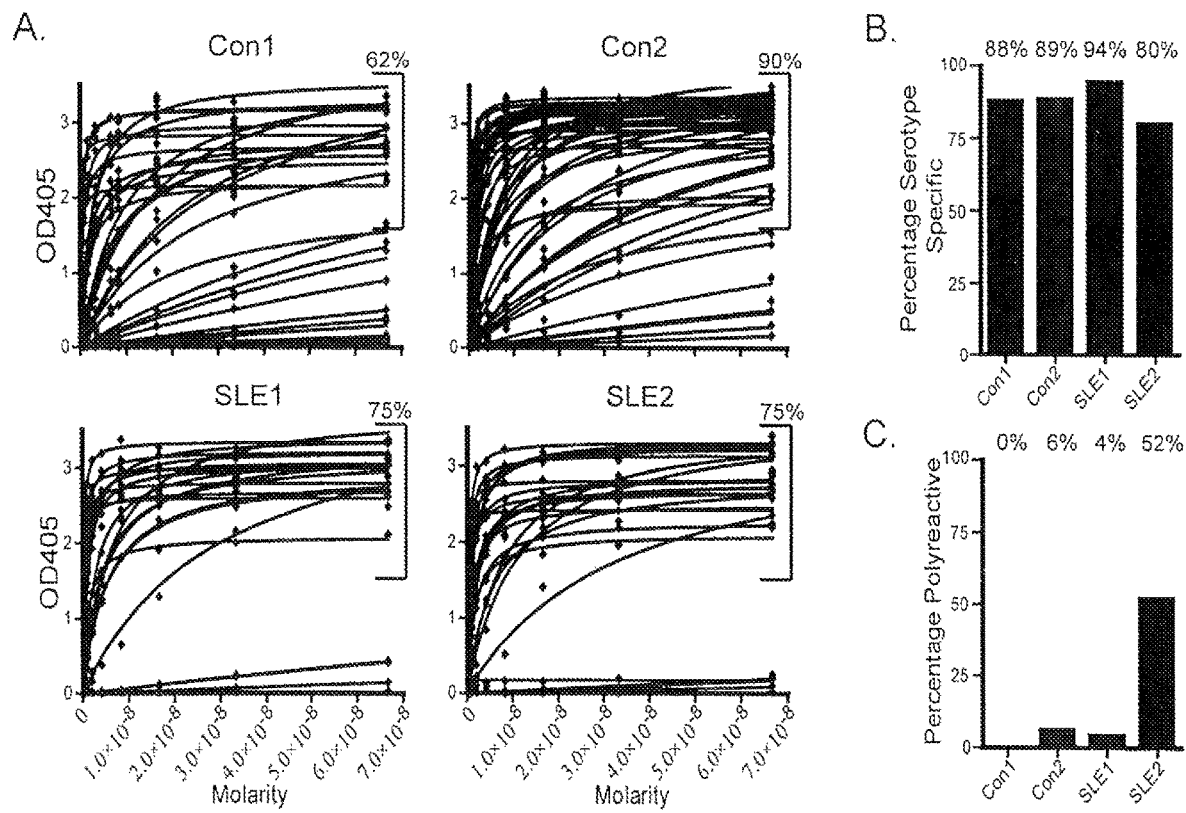
FIG. 2A-C

A.
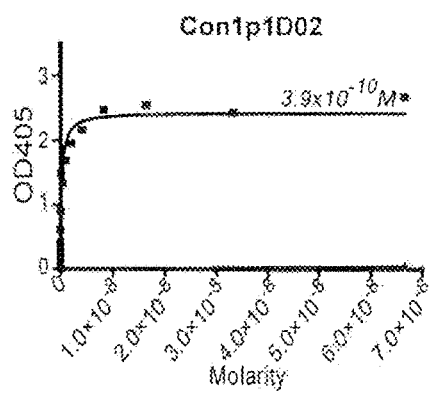 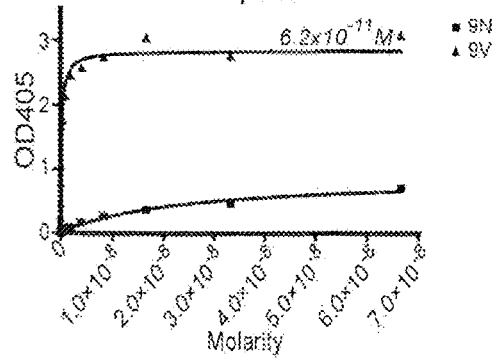
B.
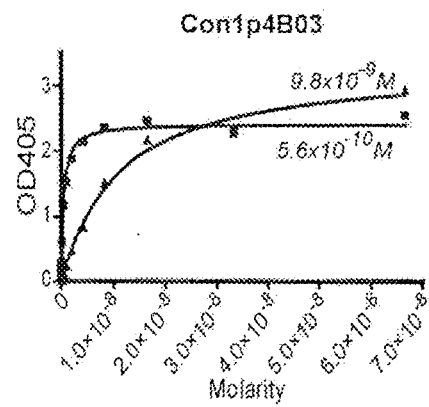 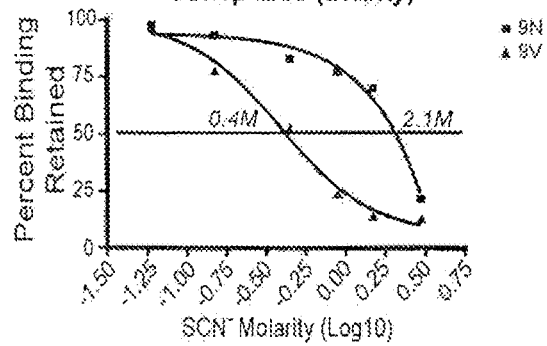
C.
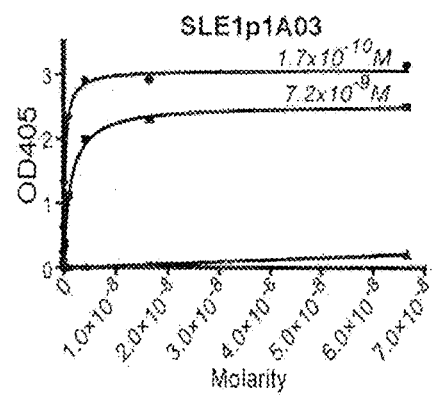 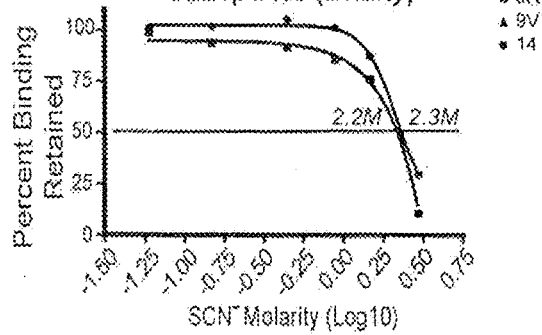
D.
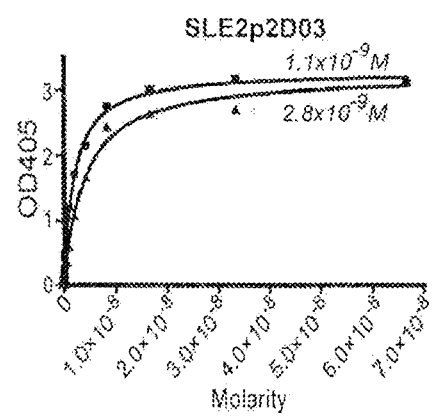 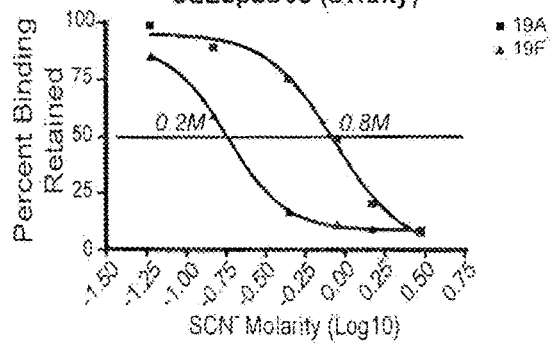
FIG. 3A-D A.
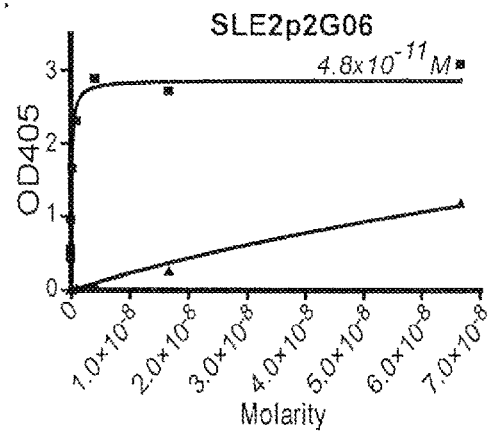 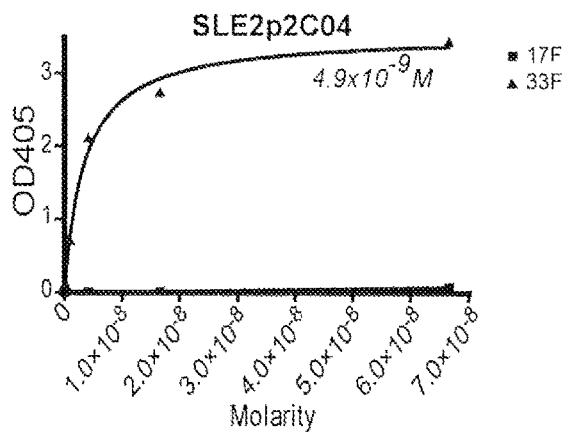
B.
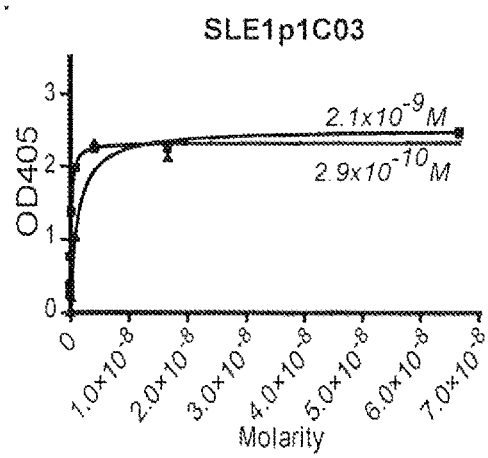 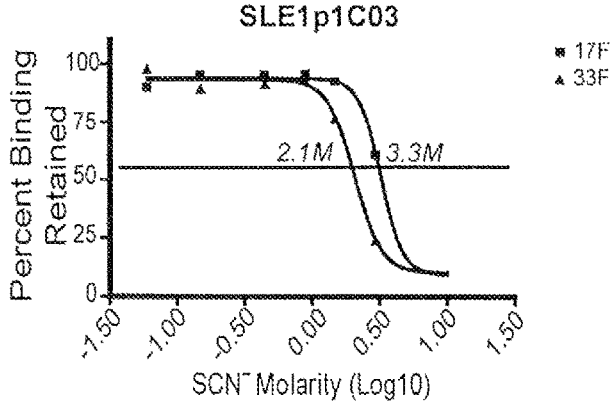
C.
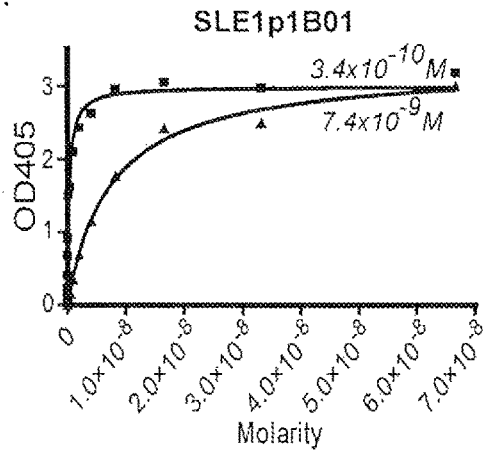 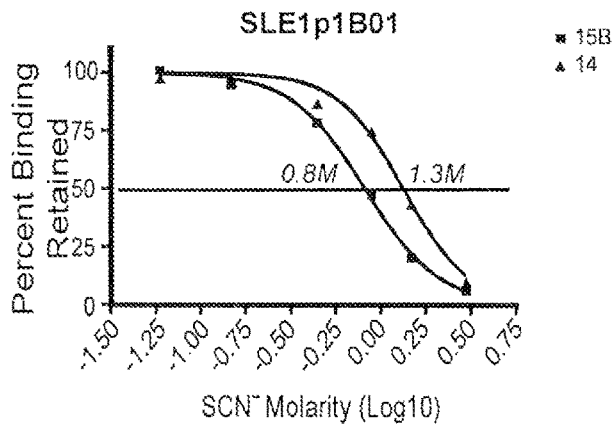
FIG. 4A-C

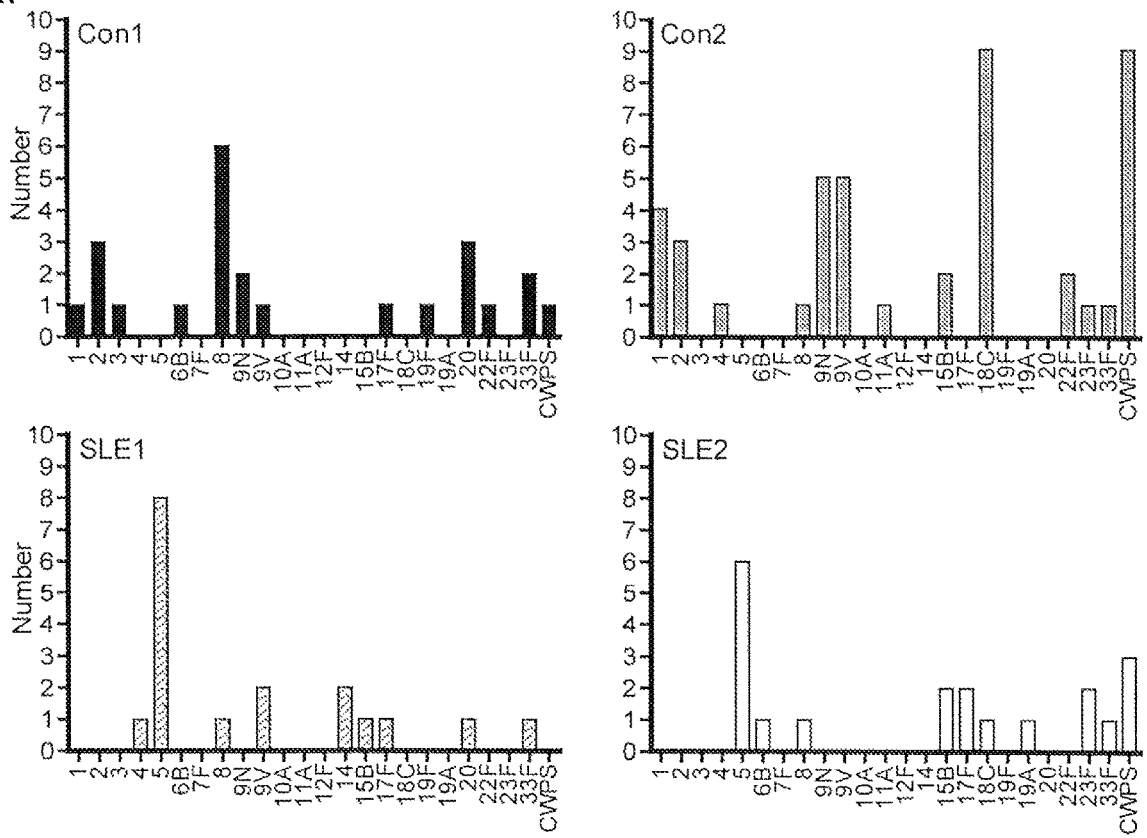
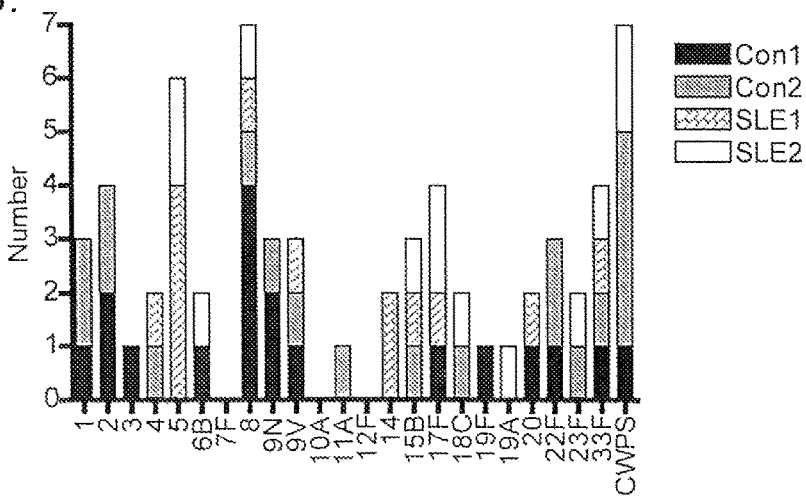
FIG. 6A-B

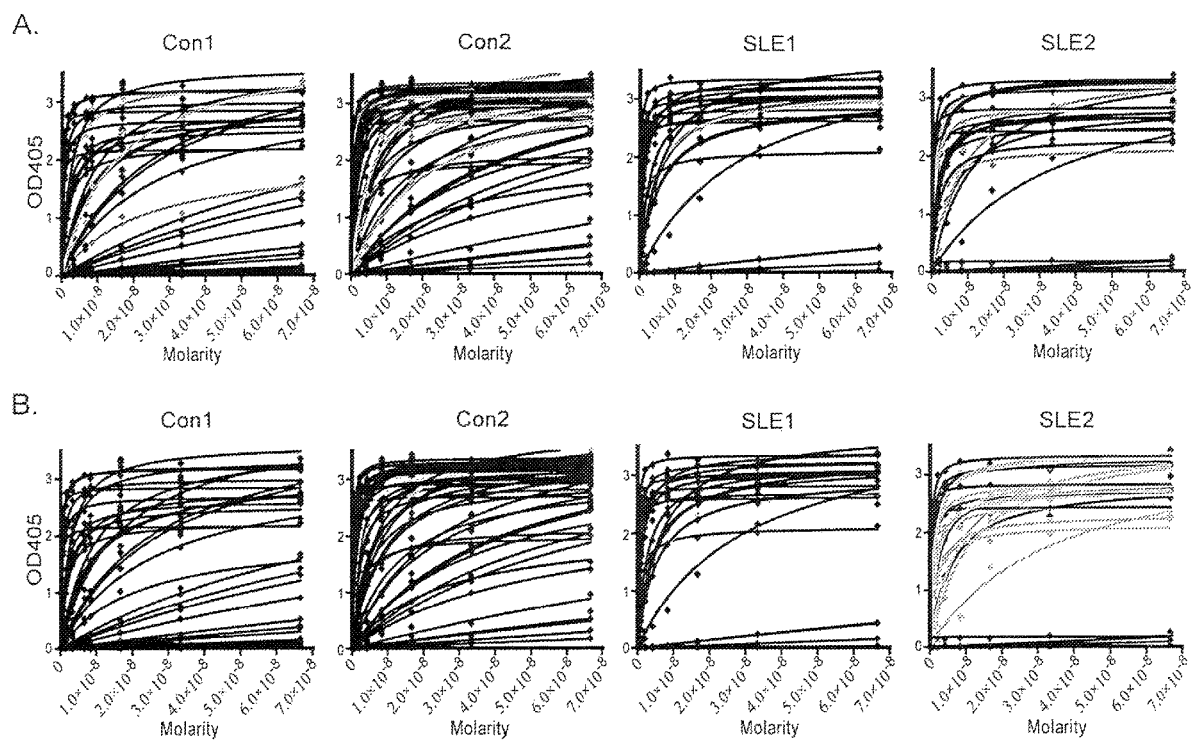
FIG. 7A-B

SEQUENCE LISTING

```
Sequence total quantity: 378
SEQ ID NO: 1            moltype = AA  length = 9
FEATURE                 Location/Qualifiers
source                  1..9
                        mol_type = protein
                        organism = Streptococcus pneumoniae
SEQUENCE: 1
AKGVTSFDY                                                                   9

SEQ ID NO: 2            moltype = AA  length = 10
FEATURE                 Location/Qualifiers
source                  1..10
                        mol_type = protein
                        organism = Streptococcus pneumoniae
SEQUENCE: 2
QQFGSSPPDT                                                                 10

SEQ ID NO: 3            moltype = AA  length = 12
```

```
                             -continued

FEATURE                 Location/Qualifiers
source                  1..12
                        mol_type = protein
                        organism = Streptococcus pneumoniae
SEQUENCE: 3
ARDPGIRNGM GV                                                              12

SEQ ID NO: 4            moltype = AA   length = 9
FEATURE                 Location/Qualifiers
source                  1..9
                        mol_type = protein
                        organism = Streptococcus pneumoniae
SEQUENCE: 4
MQVTHWPRT                                                                   9

SEQ ID NO: 5            moltype = AA   length = 14
FEATURE                 Location/Qualifiers
source                  1..14
                        mol_type = protein
                        organism = Streptococcus pneumoniae
SEQUENCE: 5
AKAHRGDWNN FFDY                                                            14

SEQ ID NO: 6            moltype = AA   length = 9
FEATURE                 Location/Qualifiers
source                  1..9
                        mol_type = protein
                        organism = Streptococcus pneumoniae
SEQUENCE: 6
QQSGDWPLT                                                                   9

SEQ ID NO: 7            moltype = AA   length = 9
FEATURE                 Location/Qualifiers
source                  1..9
                        mol_type = protein
                        organism = Streptococcus pneumoniae
SEQUENCE: 7
AREWSGFDF                                                                   9

SEQ ID NO: 8            moltype = AA   length = 9
FEATURE                 Location/Qualifiers
source                  1..9
                        mol_type = protein
                        organism = Streptococcus pneumoniae
SEQUENCE: 8
QQYGSLPRT                                                                   9

SEQ ID NO: 9            moltype = AA   length = 8
FEATURE                 Location/Qualifiers
source                  1..8
                        mol_type = protein
                        organism = Streptococcus pneumoniae
SEQUENCE: 9
ARGQWLAF                                                                    8

SEQ ID NO: 10           moltype = AA   length = 9
FEATURE                 Location/Qualifiers
source                  1..9
                        mol_type = protein
                        organism = Streptococcus pneumoniae
SEQUENCE: 10
MQGTHWPYT                                                                   9

SEQ ID NO: 11           moltype = AA   length = 9
FEATURE                 Location/Qualifiers
source                  1..9
                        mol_type = protein
                        organism = Streptococcus pneumoniae
SEQUENCE: 11
ARGRNNFRH                                                                   9

SEQ ID NO: 12           moltype = AA   length = 9
FEATURE                 Location/Qualifiers
source                  1..9
                        mol_type = protein
                        organism = Streptococcus pneumoniae
SEQUENCE: 12
QQFESFPRT                                                                   9
```

```
SEQ ID NO: 13        moltype = AA   length = 20
FEATURE              Location/Qualifiers
source               1..20
                     mol_type = protein
                     organism = Streptococcus pneumoniae
SEQUENCE: 13
ARELGVFHSG GDQWLGPLDC                                                   20

SEQ ID NO: 14        moltype = AA   length = 11
FEATURE              Location/Qualifiers
source               1..11
                     mol_type = protein
                     organism = Streptococcus pneumoniae
SEQUENCE: 14
HQYKNWPPMG T                                                            11

SEQ ID NO: 15        moltype = AA   length = 11
FEATURE              Location/Qualifiers
source               1..11
                     mol_type = protein
                     organism = Streptococcus pneumoniae
SEQUENCE: 15
RWTGGVSFGA Y                                                            11

SEQ ID NO: 16        moltype = AA   length = 8
FEATURE              Location/Qualifiers
source               1..8
                     mol_type = protein
                     organism = Streptococcus pneumoniae
SEQUENCE: 16
QQYDIYLT                                                                 8

SEQ ID NO: 17        moltype = AA   length = 10
FEATURE              Location/Qualifiers
source               1..10
                     mol_type = protein
                     organism = Streptococcus pneumoniae
SEQUENCE: 17
ARDYYHSVDY                                                              10

SEQ ID NO: 18        moltype = AA   length = 9
FEATURE              Location/Qualifiers
source               1..9
                     mol_type = protein
                     organism = Streptococcus pneumoniae
SEQUENCE: 18
MQGTHWPYT                                                                9

SEQ ID NO: 19        moltype = AA   length = 11
FEATURE              Location/Qualifiers
source               1..11
                     mol_type = protein
                     organism = Streptococcus pneumoniae
SEQUENCE: 19
ARGPDAHKTG Y                                                            11

SEQ ID NO: 20        moltype = AA   length = 9
FEATURE              Location/Qualifiers
source               1..9
                     mol_type = protein
                     organism = Streptococcus pneumoniae
SEQUENCE: 20
QQYAATPWT                                                                9

SEQ ID NO: 21        moltype = AA   length = 10
FEATURE              Location/Qualifiers
source               1..10
                     mol_type = protein
                     organism = Streptococcus pneumoniae
SEQUENCE: 21
ARDSYTSPDY                                                              10

SEQ ID NO: 22        moltype = AA   length = 9
FEATURE              Location/Qualifiers
source               1..9
                     mol_type = protein
                     organism = Streptococcus pneumoniae
SEQUENCE: 22
MQGSHWPLT                                                                9
```

```
SEQ ID NO: 23            moltype = AA   length = 11
FEATURE                  Location/Qualifiers
source                   1..11
                         mol_type = protein
                         organism = Streptococcus pneumoniae
SEQUENCE: 23
TTDNGVKAFD I                                                              11

SEQ ID NO: 24            moltype = AA   length = 9
FEATURE                  Location/Qualifiers
source                   1..9
                         mol_type = protein
                         organism = Streptococcus pneumoniae
SEQUENCE: 24
HQYYTTPFA                                                                  9

SEQ ID NO: 25            moltype = AA   length = 11
FEATURE                  Location/Qualifiers
source                   1..11
                         mol_type = protein
                         organism = Streptococcus pneumoniae
SEQUENCE: 25
TRGGSGATIN Y                                                              11

SEQ ID NO: 26            moltype = AA   length = 9
FEATURE                  Location/Qualifiers
source                   1..9
                         mol_type = protein
                         organism = Streptococcus pneumoniae
SEQUENCE: 26
QQSHSSPLT                                                                  9

SEQ ID NO: 27            moltype = AA   length = 16
FEATURE                  Location/Qualifiers
source                   1..16
                         mol_type = protein
                         organism = Streptococcus pneumoniae
SEQUENCE: 27
ARDRAGIDGY NYYFDY                                                         16

SEQ ID NO: 28            moltype = AA   length = 8
FEATURE                  Location/Qualifiers
source                   1..8
                         mol_type = protein
                         organism = Streptococcus pneumoniae
SEQUENCE: 28
QQYYSFYT                                                                   8

SEQ ID NO: 29            moltype = AA   length = 13
FEATURE                  Location/Qualifiers
source                   1..13
                         mol_type = protein
                         organism = Streptococcus pneumoniae
SEQUENCE: 29
AREVAAEGKA FDY                                                            13

SEQ ID NO: 30            moltype = AA   length = 9
FEATURE                  Location/Qualifiers
source                   1..9
                         mol_type = protein
                         organism = Streptococcus pneumoniae
SEQUENCE: 30
QQYTPPLT                                                                   9

SEQ ID NO: 31            moltype = AA   length = 9
FEATURE                  Location/Qualifiers
source                   1..9
                         mol_type = protein
                         organism = Streptococcus pneumoniae
SEQUENCE: 31
ARGQSYPGI                                                                  9

SEQ ID NO: 32            moltype = AA   length = 9
FEATURE                  Location/Qualifiers
source                   1..9
                         mol_type = protein
                         organism = Streptococcus pneumoniae
```

```
SEQUENCE: 32
QQYNNWPRT                                                                       9

SEQ ID NO: 33           moltype = AA  length = 15
FEATURE                 Location/Qualifiers
source                  1..15
                        mol_type = protein
                        organism = Streptococcus pneumoniae
SEQUENCE: 33
AGRAYSSGYY YLIDY                                                               15

SEQ ID NO: 34           moltype = AA  length = 9
FEATURE                 Location/Qualifiers
source                  1..9
                        mol_type = protein
                        organism = Streptococcus pneumoniae
SEQUENCE: 34
QHYHNWPPT                                                                       9

SEQ ID NO: 35           moltype = AA  length = 15
FEATURE                 Location/Qualifiers
source                  1..15
                        mol_type = protein
                        organism = Streptococcus pneumoniae
SEQUENCE: 35
AKGCSNGGNC FLIDY                                                               15

SEQ ID NO: 36           moltype = AA  length = 9
FEATURE                 Location/Qualifiers
source                  1..9
                        mol_type = protein
                        organism = Streptococcus pneumoniae
SEQUENCE: 36
QQYYNAPLT                                                                       9

SEQ ID NO: 37           moltype = AA  length = 16
FEATURE                 Location/Qualifiers
source                  1..16
                        mol_type = protein
                        organism = Streptococcus pneumoniae
SEQUENCE: 37
AKGGYYESGT MRAFDI                                                              16

SEQ ID NO: 38           moltype = AA  length = 9
FEATURE                 Location/Qualifiers
source                  1..9
                        mol_type = protein
                        organism = Streptococcus pneumoniae
SEQUENCE: 38
QQRSNWPAT                                                                       9

SEQ ID NO: 39           moltype = AA  length = 9
FEATURE                 Location/Qualifiers
source                  1..9
                        mol_type = protein
                        organism = Streptococcus pneumoniae
SEQUENCE: 39
ARGESNFRY                                                                       9

SEQ ID NO: 40           moltype = AA  length = 9
FEATURE                 Location/Qualifiers
source                  1..9
                        mol_type = protein
                        organism = Streptococcus pneumoniae
SEQUENCE: 40
QQFVSFPRT                                                                       9

SEQ ID NO: 41           moltype = AA  length = 12
FEATURE                 Location/Qualifiers
source                  1..12
                        mol_type = protein
                        organism = Streptococcus pneumoniae
SEQUENCE: 41
ARDSTSPARF GY                                                                  12

SEQ ID NO: 42           moltype = AA  length = 11
FEATURE                 Location/Qualifiers
```

```
source                    1..11
                          mol_type = protein
                          organism = Streptococcus pneumoniae
SEQUENCE: 42
QHYGTSPPRY T                                                              11

SEQ ID NO: 43             moltype = AA  length = 12
FEATURE                   Location/Qualifiers
source                    1..12
                          mol_type = protein
                          organism = Streptococcus pneumoniae
SEQUENCE: 43
ATGGMTSSWY GY                                                             12

SEQ ID NO: 44             moltype = AA  length = 9
FEATURE                   Location/Qualifiers
source                    1..9
                          mol_type = protein
                          organism = Streptococcus pneumoniae
SEQUENCE: 44
QQYYSTPYT                                                                 9

SEQ ID NO: 45             moltype = AA  length = 18
FEATURE                   Location/Qualifiers
source                    1..18
                          mol_type = protein
                          organism = Streptococcus pneumoniae
SEQUENCE: 45
SMGPPYCTGG SCYSACDF                                                       18

SEQ ID NO: 46             moltype = AA  length = 10
FEATURE                   Location/Qualifiers
source                    1..10
                          mol_type = protein
                          organism = Streptococcus pneumoniae
SEQUENCE: 46
QRYGNSPPYT                                                                10

SEQ ID NO: 47             moltype = AA  length = 15
FEATURE                   Location/Qualifiers
source                    1..15
                          mol_type = protein
                          organism = Streptococcus pneumoniae
SEQUENCE: 47
TTDIGKGWYT HYPDL                                                          15

SEQ ID NO: 48             moltype = AA  length = 9
FEATURE                   Location/Qualifiers
source                    1..9
                          mol_type = protein
                          organism = Streptococcus pneumoniae
SEQUENCE: 48
LQYRSAPFT                                                                 9

SEQ ID NO: 49             moltype = AA  length = 14
FEATURE                   Location/Qualifiers
source                    1..14
                          mol_type = protein
                          organism = Streptococcus pneumoniae
SEQUENCE: 49
VKEYSWGYYR TADY                                                           14

SEQ ID NO: 50             moltype = AA  length = 9
FEATURE                   Location/Qualifiers
source                    1..9
                          mol_type = protein
                          organism = Streptococcus pneumoniae
SEQUENCE: 50
QQYSTYPWT                                                                 9

SEQ ID NO: 51             moltype = AA  length = 10
FEATURE                   Location/Qualifiers
source                    1..10
                          mol_type = protein
                          organism = Streptococcus pneumoniae
SEQUENCE: 51
ARSPGGYFDY                                                                10

SEQ ID NO: 52             moltype = AA  length = 9
```

-continued

```
FEATURE                 Location/Qualifiers
source                  1..9
                        mol_type = protein
                        organism = Streptococcus pneumoniae
SEQUENCE: 52
QQYSTWLWT                                                                        9

SEQ ID NO: 53           moltype = AA  length = 7
FEATURE                 Location/Qualifiers
source                  1..7
                        mol_type = protein
                        organism = Streptococcus pneumoniae
SEQUENCE: 53
TTDDLKN                                                                          7

SEQ ID NO: 54           moltype = AA  length = 9
FEATURE                 Location/Qualifiers
source                  1..9
                        mol_type = protein
                        organism = Streptococcus pneumoniae
SEQUENCE: 54
QQRYRIPYS                                                                        9

SEQ ID NO: 55           moltype = AA  length = 22
FEATURE                 Location/Qualifiers
source                  1..22
                        mol_type = protein
                        organism = Streptococcus pneumoniae
SEQUENCE: 55
ARGRDCYGGN CVIYFHYYGL DV                                                        22

SEQ ID NO: 56           moltype = AA  length = 9
FEATURE                 Location/Qualifiers
source                  1..9
                        mol_type = protein
                        organism = Streptococcus pneumoniae
SEQUENCE: 56
MRALQTPYT                                                                        9

SEQ ID NO: 57           moltype = AA  length = 14
FEATURE                 Location/Qualifiers
source                  1..14
                        mol_type = protein
                        organism = Streptococcus pneumoniae
SEQUENCE: 57
VKESATGWYR TADY                                                                 14

SEQ ID NO: 58           moltype = AA  length = 9
FEATURE                 Location/Qualifiers
source                  1..9
                        mol_type = protein
                        organism = Streptococcus pneumoniae
SEQUENCE: 58
HQYNKYPWT                                                                        9

SEQ ID NO: 59           moltype = AA  length = 16
FEATURE                 Location/Qualifiers
source                  1..16
                        mol_type = protein
                        organism = Streptococcus pneumoniae
SEQUENCE: 59
ARDIPTTFGI GEAFDI                                                               16

SEQ ID NO: 60           moltype = AA  length = 8
FEATURE                 Location/Qualifiers
source                  1..8
                        mol_type = protein
                        organism = Streptococcus pneumoniae
SEQUENCE: 60
QQYYSWGT                                                                         8

SEQ ID NO: 61           moltype = AA  length = 9
FEATURE                 Location/Qualifiers
source                  1..9
                        mol_type = protein
                        organism = Streptococcus pneumoniae
SEQUENCE: 61
ARDDSAFDY                                                                        9
```

-continued

| | | |
|---|---|---|
| SEQ ID NO: 62<br>FEATURE<br>source | moltype = AA   length = 9<br>Location/Qualifiers<br>1..9<br>mol_type = protein<br>organism = Streptococcus pneumoniae | |
| SEQUENCE: 62<br>MQASQSTWT | | 9 |
| SEQ ID NO: 63<br>FEATURE<br>source | moltype = AA   length = 14<br>Location/Qualifiers<br>1..14<br>mol_type = protein<br>organism = Streptococcus pneumoniae | |
| SEQUENCE: 63<br>AKGCSGENCF YMDD | | 14 |
| SEQ ID NO: 64<br>FEATURE<br>source | moltype = AA   length = 9<br>Location/Qualifiers<br>1..9<br>mol_type = protein<br>organism = Streptococcus pneumoniae | |
| SEQUENCE: 64<br>QQCYNAPLT | | 9 |
| SEQ ID NO: 65<br>FEATURE<br>source | moltype = AA   length = 22<br>Location/Qualifiers<br>1..22<br>mol_type = protein<br>organism = Streptococcus pneumoniae | |
| SEQUENCE: 65<br>TREIGAVVVD ATSLGWLGYF DY | | 22 |
| SEQ ID NO: 66<br>FEATURE<br>source | moltype = AA   length = 10<br>Location/Qualifiers<br>1..10<br>mol_type = protein<br>organism = Streptococcus pneumoniae | |
| SEQUENCE: 66<br>QQYNNWPPVT | | 10 |
| SEQ ID NO: 67<br>FEATURE<br>source | moltype = AA   length = 8<br>Location/Qualifiers<br>1..8<br>mol_type = protein<br>organism = Streptococcus pneumoniae | |
| SEQUENCE: 67<br>AGWGRTQD | | 8 |
| SEQ ID NO: 68<br>FEATURE<br>source | moltype = AA   length = 9<br>Location/Qualifiers<br>1..9<br>mol_type = protein<br>organism = Streptococcus pneumoniae | |
| SEQUENCE: 68<br>MQYTFWPHT | | 9 |
| SEQ ID NO: 69<br>FEATURE<br>source | moltype = AA   length = 14<br>Location/Qualifiers<br>1..14<br>mol_type = protein<br>organism = Streptococcus pneumoniae | |
| SEQUENCE: 69<br>TKEGAPPGKY AFDI | | 14 |
| SEQ ID NO: 70<br>FEATURE<br>source | moltype = AA   length = 11<br>Location/Qualifiers<br>1..11<br>mol_type = protein<br>organism = Streptococcus pneumoniae | |
| SEQUENCE: 70<br>QHRGEWPPGA T | | 11 |
| SEQ ID NO: 71<br>FEATURE<br>source | moltype = AA   length = 11<br>Location/Qualifiers<br>1..11<br>mol_type = protein<br>organism = Streptococcus pneumoniae | |
| SEQUENCE: 71<br>LKDSSQYSFD A | | 11 |

```
SEQ ID NO: 72          moltype = AA  length = 9
FEATURE                Location/Qualifiers
source                 1..9
                       mol_type = protein
                       organism = Streptococcus pneumoniae
SEQUENCE: 72
QQFKGYPLT                                                                  9

SEQ ID NO: 73          moltype = AA  length = 9
FEATURE                Location/Qualifiers
source                 1..9
                       mol_type = protein
                       organism = Streptococcus pneumoniae
SEQUENCE: 73
ARGDGYNFF                                                                  9

SEQ ID NO: 74          moltype = AA  length = 9
FEATURE                Location/Qualifiers
source                 1..9
                       mol_type = protein
                       organism = Streptococcus pneumoniae
SEQUENCE: 74
QQINSYPRT                                                                  9

SEQ ID NO: 75          moltype = AA  length = 18
FEATURE                Location/Qualifiers
source                 1..18
                       mol_type = protein
                       organism = Streptococcus pneumoniae
SEQUENCE: 75
AKCGAEDSTT VWLNWFDP                                                       18

SEQ ID NO: 76          moltype = AA  length = 9
FEATURE                Location/Qualifiers
source                 1..9
                       mol_type = protein
                       organism = Streptococcus pneumoniae
SEQUENCE: 76
QQRADWPLT                                                                  9

SEQ ID NO: 77          moltype = AA  length = 13
FEATURE                Location/Qualifiers
source                 1..13
                       mol_type = protein
                       organism = Streptococcus pneumoniae
SEQUENCE: 77
AKPNYFGSGS PDY                                                            13

SEQ ID NO: 78          moltype = AA  length = 10
FEATURE                Location/Qualifiers
source                 1..10
                       mol_type = protein
                       organism = Streptococcus pneumoniae
SEQUENCE: 78
LQCSNWPMYT                                                                10

SEQ ID NO: 79          moltype = AA  length = 14
FEATURE                Location/Qualifiers
source                 1..14
                       mol_type = protein
                       organism = Streptococcus pneumoniae
SEQUENCE: 79
VKEQDYGYYR TADH                                                           14

SEQ ID NO: 80          moltype = AA  length = 9
FEATURE                Location/Qualifiers
source                 1..9
                       mol_type = protein
                       organism = Streptococcus pneumoniae
SEQUENCE: 80
QQYDKYPWT                                                                  9

SEQ ID NO: 81          moltype = AA  length = 19
FEATURE                Location/Qualifiers
source                 1..19
                       mol_type = protein
                       organism = Streptococcus pneumoniae
```

```
SEQUENCE: 81
VRVAVPAATY TRGNDAFDI                                                    19

SEQ ID NO: 82        moltype = AA  length = 9
FEATURE              Location/Qualifiers
source               1..9
                     mol_type = protein
                     organism = Streptococcus pneumoniae
SEQUENCE: 82
LQHSSFPWT                                                                9

SEQ ID NO: 83        moltype = AA  length = 10
FEATURE              Location/Qualifiers
source               1..10
                     mol_type = protein
                     organism = Streptococcus pneumoniae
SEQUENCE: 83
TTAHGPVGDH                                                              10

SEQ ID NO: 84        moltype = AA  length = 10
FEATURE              Location/Qualifiers
source               1..10
                     mol_type = protein
                     organism = Streptococcus pneumoniae
SEQUENCE: 84
QQYYTTPSIT                                                              10

SEQ ID NO: 85        moltype = AA  length = 19
FEATURE              Location/Qualifiers
source               1..19
                     mol_type = protein
                     organism = Streptococcus pneumoniae
SEQUENCE: 85
ARAGGCSSTR CHTTPGFDY                                                    19

SEQ ID NO: 86        moltype = AA  length = 10
FEATURE              Location/Qualifiers
source               1..10
                     mol_type = protein
                     organism = Streptococcus pneumoniae
SEQUENCE: 86
QQYYTTPPIT                                                              10

SEQ ID NO: 87        moltype = AA  length = 11
FEATURE              Location/Qualifiers
source               1..11
                     mol_type = protein
                     organism = Streptococcus pneumoniae
SEQUENCE: 87
ASLSGTNAFD I                                                            11

SEQ ID NO: 88        moltype = AA  length = 8
FEATURE              Location/Qualifiers
source               1..8
                     mol_type = protein
                     organism = Streptococcus pneumoniae
SEQUENCE: 88
QQRSSGRT                                                                 8

SEQ ID NO: 89        moltype = AA  length = 13
FEATURE              Location/Qualifiers
source               1..13
                     mol_type = protein
                     organism = Streptococcus pneumoniae
SEQUENCE: 89
AKPRGYSYGY FDY                                                          13

SEQ ID NO: 90        moltype = AA  length = 9
FEATURE              Location/Qualifiers
source               1..9
                     mol_type = protein
                     organism = Streptococcus pneumoniae
SEQUENCE: 90
QQYGISPRT                                                                9

SEQ ID NO: 91        moltype = AA  length = 9
FEATURE              Location/Qualifiers
```

| | | |
|---|---|---|
| source | 1..9<br>mol_type = protein<br>organism = Streptococcus pneumoniae | |
| SEQUENCE: 91<br>APPARRLDY | | 9 |
| SEQ ID NO: 92<br>FEATURE<br>source | moltype = AA  length = 9<br>Location/Qualifiers<br>1..9<br>mol_type = protein<br>organism = Streptococcus pneumoniae | |
| SEQUENCE: 92<br>MQGTHHPWT | | 9 |
| SEQ ID NO: 93<br>FEATURE<br>source | moltype = AA  length = 9<br>Location/Qualifiers<br>1..9<br>mol_type = protein<br>organism = Streptococcus pneumoniae | |
| SEQUENCE: 93<br>ARSNAGHEA | | 9 |
| SEQ ID NO: 94<br>FEATURE<br>source | moltype = AA  length = 9<br>Location/Qualifiers<br>1..9<br>mol_type = protein<br>organism = Streptococcus pneumoniae | |
| SEQUENCE: 94<br>QQYYSTPLT | | 9 |
| SEQ ID NO: 95<br>FEATURE<br>source | moltype = AA  length = 11<br>Location/Qualifiers<br>1..11<br>mol_type = protein<br>organism = Streptococcus pneumoniae | |
| SEQUENCE: 95<br>ARDIPHANLD Y | | 11 |
| SEQ ID NO: 96<br>FEATURE<br>source | moltype = AA  length = 9<br>Location/Qualifiers<br>1..9<br>mol_type = protein<br>organism = Streptococcus pneumoniae | |
| SEQUENCE: 96<br>LQHTTFPWT | | 9 |
| SEQ ID NO: 97<br>FEATURE<br>source | moltype = AA  length = 14<br>Location/Qualifiers<br>1..14<br>mol_type = protein<br>organism = Streptococcus pneumoniae | |
| SEQUENCE: 97<br>VKDRVPPGDV PGDF | | 14 |
| SEQ ID NO: 98<br>FEATURE<br>source | moltype = AA  length = 10<br>Location/Qualifiers<br>1..10<br>mol_type = protein<br>organism = Streptococcus pneumoniae | |
| SEQUENCE: 98<br>QQRRTWPPLT | | 10 |
| SEQ ID NO: 99<br>FEATURE<br>source | moltype = AA  length = 12<br>Location/Qualifiers<br>1..12<br>mol_type = protein<br>organism = Streptococcus pneumoniae | |
| SEQUENCE: 99<br>ATLLLRDNQL DV | | 12 |
| SEQ ID NO: 100<br>FEATURE<br>source | moltype = AA  length = 8<br>Location/Qualifiers<br>1..8<br>mol_type = protein<br>organism = Streptococcus pneumoniae | |
| SEQUENCE: 100<br>MQGTHWRT | | 8 |
| SEQ ID NO: 101 | moltype = AA  length = 14 | |

-continued

```
FEATURE                 Location/Qualifiers
source                  1..14
                        mol_type = protein
                        organism = Streptococcus pneumoniae
SEQUENCE: 101
VKEQGFGYYR TADY                                                          14

SEQ ID NO: 102          moltype = AA  length = 9
FEATURE                 Location/Qualifiers
source                  1..9
                        mol_type = protein
                        organism = Streptococcus pneumoniae
SEQUENCE: 102
HQYDKYPWT                                                                9

SEQ ID NO: 103          moltype = AA  length = 8
FEATURE                 Location/Qualifiers
source                  1..8
                        mol_type = protein
                        organism = Streptococcus pneumoniae
SEQUENCE: 103
ARRNDFNI                                                                 8

SEQ ID NO: 104          moltype = AA  length = 9
FEATURE                 Location/Qualifiers
source                  1..9
                        mol_type = protein
                        organism = Streptococcus pneumoniae
SEQUENCE: 104
QQYGSSPFT                                                                9

SEQ ID NO: 105          moltype = AA  length = 16
FEATURE                 Location/Qualifiers
source                  1..16
                        mol_type = protein
                        organism = Streptococcus pneumoniae
SEQUENCE: 105
SIWWGTSVQY PLVLDY                                                        16

SEQ ID NO: 106          moltype = AA  length = 10
FEATURE                 Location/Qualifiers
source                  1..10
                        mol_type = protein
                        organism = Streptococcus pneumoniae
SEQUENCE: 106
QQYSKWPPIT                                                               10

SEQ ID NO: 107          moltype = AA  length = 14
FEATURE                 Location/Qualifiers
source                  1..14
                        mol_type = protein
                        organism = Streptococcus pneumoniae
SEQUENCE: 107
VKEQDYGYYR TADH                                                          14

SEQ ID NO: 108          moltype = AA  length = 9
FEATURE                 Location/Qualifiers
source                  1..9
                        mol_type = protein
                        organism = Streptococcus pneumoniae
SEQUENCE: 108
QQYDKYPWT                                                                9

SEQ ID NO: 109          moltype = AA  length = 9
FEATURE                 Location/Qualifiers
source                  1..9
                        mol_type = protein
                        organism = Streptococcus pneumoniae
SEQUENCE: 109
ARGHGFNAY                                                                9

SEQ ID NO: 110          moltype = AA  length = 9
FEATURE                 Location/Qualifiers
source                  1..9
                        mol_type = protein
                        organism = Streptococcus pneumoniae
SEQUENCE: 110
QQYGNSPRT                                                                9
```

```
SEQ ID NO: 111          moltype = AA   length = 13
FEATURE                 Location/Qualifiers
source                  1..13
                        mol_type = protein
                        organism = Streptococcus pneumoniae
SEQUENCE: 111
TTVRNMADLS LNH                                                       13

SEQ ID NO: 112          moltype = AA   length = 9
FEATURE                 Location/Qualifiers
source                  1..9
                        mol_type = protein
                        organism = Streptococcus pneumoniae
SEQUENCE: 112
QQYDDSRWT                                                             9

SEQ ID NO: 113          moltype = AA   length = 11
FEATURE                 Location/Qualifiers
source                  1..11
                        mol_type = protein
                        organism = Streptococcus pneumoniae
SEQUENCE: 113
ATGNRGSLPR R                                                         11

SEQ ID NO: 114          moltype = AA   length = 9
FEATURE                 Location/Qualifiers
source                  1..9
                        mol_type = protein
                        organism = Streptococcus pneumoniae
SEQUENCE: 114
MQALRSPYT                                                             9

SEQ ID NO: 115          moltype = AA   length = 11
FEATURE                 Location/Qualifiers
source                  1..11
                        mol_type = protein
                        organism = Streptococcus pneumoniae
SEQUENCE: 115
VRDGWDTFFD S                                                         11

SEQ ID NO: 116          moltype = AA   length = 9
FEATURE                 Location/Qualifiers
source                  1..9
                        mol_type = protein
                        organism = Streptococcus pneumoniae
SEQUENCE: 116
MQGRYWPYT                                                             9

SEQ ID NO: 117          moltype = AA   length = 6
FEATURE                 Location/Qualifiers
source                  1..6
                        mol_type = protein
                        organism = Streptococcus pneumoniae
SEQUENCE: 117
VNFQLG                                                                6

SEQ ID NO: 118          moltype = AA   length = 9
FEATURE                 Location/Qualifiers
source                  1..9
                        mol_type = protein
                        organism = Streptococcus pneumoniae
SEQUENCE: 118
QQYGNSPRT                                                             9

SEQ ID NO: 119          moltype = AA   length = 16
FEATURE                 Location/Qualifiers
source                  1..16
                        mol_type = protein
                        organism = Streptococcus pneumoniae
SEQUENCE: 119
ARAEYCSPGD CFLIDT                                                    16

SEQ ID NO: 120          moltype = AA   length = 8
FEATURE                 Location/Qualifiers
source                  1..8
                        mol_type = protein
                        organism = Streptococcus pneumoniae
SEQUENCE: 120
MQGTHWRT                                                              8
```

| SEQ ID NO: 121 | moltype = AA length = 12 |
| --- | --- |
| FEATURE | Location/Qualifiers |
| source | 1..12 |
| | mol_type = protein |
| | organism = Streptococcus pneumoniae |

SEQUENCE: 121
LRGNPPSSPT DY                                                            12

| SEQ ID NO: 122 | moltype = AA length = 9 |
| --- | --- |
| FEATURE | Location/Qualifiers |
| source | 1..9 |
| | mol_type = protein |
| | organism = Streptococcus pneumoniae |

SEQUENCE: 122
QQYNSYPLT                                                                 9

| SEQ ID NO: 123 | moltype = AA length = 12 |
| --- | --- |
| FEATURE | Location/Qualifiers |
| source | 1..12 |
| | mol_type = protein |
| | organism = Streptococcus pneumoniae |

SEQUENCE: 123
AKVVYSRPPM DV                                                            12

| SEQ ID NO: 124 | moltype = AA length = 9 |
| --- | --- |
| FEATURE | Location/Qualifiers |
| source | 1..9 |
| | mol_type = protein |
| | organism = Streptococcus pneumoniae |

SEQUENCE: 124
QQSYSTPWT                                                                 9

| SEQ ID NO: 125 | moltype = AA length = 11 |
| --- | --- |
| FEATURE | Location/Qualifiers |
| source | 1..11 |
| | mol_type = protein |
| | organism = Streptococcus pneumoniae |

SEQUENCE: 125
ARASRETGEP Y                                                             11

| SEQ ID NO: 126 | moltype = AA length = 9 |
| --- | --- |
| FEATURE | Location/Qualifiers |
| source | 1..9 |
| | mol_type = protein |
| | organism = Streptococcus pneumoniae |

SEQUENCE: 126
MQATHWPWT                                                                 9

| SEQ ID NO: 127 | moltype = DNA length = 348 |
| --- | --- |
| FEATURE | Location/Qualifiers |
| source | 1..348 |
| | mol_type = genomic DNA |
| | organism = Homo sapiens |

SEQUENCE: 127
gaggtgcagc tgttggagtc gggggggaggc ttggtacagc ctggggggtc cctgagagtc        60
tcctgtgcag cctctggatt cacctttagc aactctggca tgagttgggt ccgccaggct       120
ccagggaagg ggctggagtg ggtctcaggt attggtggtg gtggtggtag tgcatactac       180
gcagactccg tgaagggccg gttcaccatc tccagagaca attccaagaa cacgctgtat       240
ctacaaatga acaatttgag agccgaggac acggccgtat actactgtgc gaaaggagtt       300
accagttttg actactgggg ccagggaatc ctggtcaccg tctcctca                    348

| SEQ ID NO: 128 | moltype = DNA length = 354 |
| --- | --- |
| FEATURE | Location/Qualifiers |
| source | 1..354 |
| | mol_type = genomic DNA |
| | organism = Homo sapiens |

SEQUENCE: 128
gaggtgcagc tggtggagtc tgggggaggc ttggtccagc ctggggggtc cctgagactc        60
tcctgtgcag cctctggatt caccgtcagt agcgactata tgagttgggt ccgccaggct       120
ccagggaagg ggctggagtg ggtctcagtt atgtatagcg gggtagcac atactacgca       180
gacgccgtga aggacagatt caccatctcc agagacaatt ccaagaatat actgtatctt       240
caaatgaaca gcctgagagc cgaggacacg gcggtttatt actgtgcgag agatccgggg       300
ataaggaacg gtatgggcgt ctggggccaa gggaccacgg tcaccgtctc ctca             354

| SEQ ID NO: 129 | moltype = DNA length = 363 |
| --- | --- |
| FEATURE | Location/Qualifiers |

```
source                  1..363
                        mol_type = genomic DNA
                        organism = Homo sapiens
SEQUENCE: 129
gaggtgcagc tgttggagtc tgggggagcc ttggtacagc cggggggtc cctgagactt    60
tcctgtgcag cctctggatt cacctttacc agctttgcca tgggctgggt ccgccaggct   120
ccagggaagg ggctggagtg ggtctcagct gtgactggca gtggttatta caaaaactat   180
gcagactccg tgaagggccg gttcaccatc tccagagaca attccgacaa tactctctat   240
ctgcaaatga acagcctgag aggcgacgac acggccctat attactgtgc gaaagcacat   300
agaggtgact ggaataactt cttgactat tggggccagg gaaccctggt caccgtctcc    360
tca                                                                 363

SEQ ID NO: 130          moltype = DNA   length = 345
FEATURE                 Location/Qualifiers
source                  1..345
                        mol_type = genomic DNA
                        organism = Homo sapiens
SEQUENCE: 130
caggtgcagc tgcaggagtc gggcccagga ctagtgaagc cttcggagac cctgtccctc    60
acctgctctg tgtctgctga ctccttcagt ccttacaagt ggagctggat ccggcagccc   120
ccagggaagg gactggaatg gattggatat atctattcca gtgggaacac caactacaac   180
cccccctca agagtcgagt caccatatca ctggacacgt ccaagaatca ggtctccctg    240
aggctgagct ctgtgaccgc tgcggacacg gccatgtatt actgtgcgag agagtggagt   300
ggttttgatt tctggggcca aggaacaatg gtcaccgtct cttca                   345

SEQ ID NO: 131          moltype = DNA   length = 345
FEATURE                 Location/Qualifiers
source                  1..345
                        mol_type = genomic DNA
                        organism = Homo sapiens
SEQUENCE: 131
gaggtgcagc tggtggagtc tgggggaggc ttggtccagc ctggggggtc cctgagactc    60
tcctgtgcag cctctggatt cacctttact aactattgga tgagctgggt ccgccaggct   120
ccagggaagg ggctggagtg ggtggccaac ataaagcaag atggacgtga gacatactat   180
gtggactctg tgaagggccg attcaccatc tccagacaa ctcagtgtct                240
ctacagatga gtagcctgag agccgaggac acgccgtgt attactgtgc gcgagggcag    300
tggctggcct ccggggcca gggaaccctg gtcaccgtct cctca                    345

SEQ ID NO: 132          moltype = DNA   length = 348
FEATURE                 Location/Qualifiers
source                  1..348
                        mol_type = genomic DNA
                        organism = Homo sapiens
SEQUENCE: 132
gaggtgcagc tggtggagtc tgggggaggc ttggtccaga ttgggggtc cctgagactc     60
tcctgtgcag cctctggatt cacctttagt acctattgga tgagctgggt ccgccaggct   120
ccagggaagg ggctggagtg cgtggccagc ataaagtga atggaagtga gagatactat    180
gtggactctg tgaagggccg attcaccatc tccagacaga acgccaagaa ctcactgcat   240
ctgcagatgg acagcctgag agccgcggac acgctgtgt atttctgtgc gagaggccgg    300
aacaacttcc gacactgggg ccagggaacc ctggtcaccg tctcctca                348

SEQ ID NO: 133          moltype = DNA   length = 378
FEATURE                 Location/Qualifiers
source                  1..378
                        mol_type = genomic DNA
                        organism = Homo sapiens
SEQUENCE: 133
gaggtgcagc tggtggagtc tgggggaggc ttggtccagc ctggggggtc cctgagactc    60
tcctgtgcag cctctggatt cgccatcagt ggtaactaca gtagttgggt ccgccaggct   120
ccagggaagg gcctggagtg ggtctcactt atttattgga ctgatgacaa agtctacgca   180
gactccgtga agggcagatt caccatctcc agggacgtct ccaagaacat ggtgcatctt   240
caaatgagca gcctgagagt cgaggacacg gctgtttatt actgtgcgag agaattaggt   300
gtttttcatt cagggggga ccagtggctg ggcccttag actgctgggg ccagggaacc    360
ctggtcaccg tctcctca                                                 378

SEQ ID NO: 134          moltype = DNA   length = 360
FEATURE                 Location/Qualifiers
source                  1..360
                        mol_type = genomic DNA
                        organism = Homo sapiens
SEQUENCE: 134
gaggtgcagc tggtggagtc tggggaggc ttggtgcagc cagggcagtc cctgagactt     60
tcctgtacag tttctggatt cagcgtagaa gaccatggtc tgaactgggt ccgccaggct   120
ccagggaagg ggctggagtg ggtagggttc attagaagga aaagttgctc tggdgacagaa  180
tacgccgcgt ctgtgaaagg ccgattcacc atctcaagag atgattccaa gagcgccgtc   240
tatctgcaaa tgaacagcct gaagatggag gacacaggcg tatattattg tcttcgctgg  300
acgggtggag tgagttttgg tgcctactgg ggccagggaa ccctggtcac cgtctcctca   360

SEQ ID NO: 135          moltype = DNA   length = 348
```

| FEATURE | Location/Qualifiers |
|---|---|
| source | 1..348 |
| | mol_type = genomic DNA |
| | organism = Homo sapiens |

SEQUENCE: 135

```
gaggtgcagc tggtggagtc cgggggaggc ttagttcagc ctgggggtc cctgagactc    60
tcctgtgcag cctctggatt caccttcact agctggatgc actgggtccg ccaagctcca  120
gggaagggc tggtgtgggt ctcacatatt aatactgatg ggagtagcac aagctacgcg   180
gactccgtga agggccgatt caccatctcc agagacaacg ccaagaacac gctgtatctg  240
caaatgaaca gtctgagagc cgaggacacg gctgtgtatt actgtgcaag agattattac  300
cactccgttg actactgggg ccagggaacc ctggtcaccg tctcctca             348
```

| SEQ ID NO: 136 | moltype = DNA  length = 351 |
|---|---|
| FEATURE | Location/Qualifiers |
| source | 1..351 |
| | mol_type = genomic DNA |
| | organism = Homo sapiens |

SEQUENCE: 136

```
caggtgcagc tgcaggagtc gggcccagga atggtgaagc cttcggagac cctgtccctc    60
atctgcagtg tctctggtgc ctccgtcagt cgtgaccact ggagctggat ccgccagtcc  120
ccagggaagg gactggagtg gattgtctat atatataaca gtgagagcat cgaatacaat  180
ccctcctca agagtcgagt caccatatcc gtagacacg ccaagaacca ggtctcctg     240
acagtgactt ctgtgaccgc tgcagacacg gccttctatt actgtgcgcg aggggccagat 300
gcccacaaaa ctggctactg gggcccggga accctggtca ccgtctcctc a             351
```

| SEQ ID NO: 137 | moltype = DNA  length = 351 |
|---|---|
| FEATURE | Location/Qualifiers |
| source | 1..351 |
| | mol_type = genomic DNA |
| | organism = Homo sapiens |

SEQUENCE: 137

```
gaggtgcagc tggtggagtc cgggggaggc ttagttcagc ctgggggtc gctgagactc     60
tcctgcgcag cctctggatt caccttcagt aacttctgga tgtactgggt ccgccaagtt  120
ccagggaagg ggctggtgtg cgtctcacgt attaatagag atgggagtat cacattgtac   180
gcggactccg tgagggccg attcaccatc tccagagaca acgccaagaa cacgctgtgt    240
ctgcaaatga acagtctgag agtcgaggac acggctgtgt attactgtgc aagagattcc  300
tataccagcc ctgactactg gggccagggg accctggtca ccgtctcctc a              351
```

| SEQ ID NO: 138 | moltype = DNA  length = 360 |
|---|---|
| FEATURE | Location/Qualifiers |
| source | 1..360 |
| | mol_type = genomic DNA |
| | organism = Homo sapiens |

SEQUENCE: 138

```
gaggtgcagc tggtggagtc tggggggaggc ttggtaaagc cggggggagtc ccttagactc    60
tcctgtgcga cctcaggatt aactttcagt aacgtatgga tgagctgggt ccgccaggct  120
ccagggaagg ggctggagtg ggttgggcgt cttaaaaaca agcctgatgg tggaacaaca   180
gactacgcag cacccgtgaa gggcagattc accatctcaa gagatgattc aaaaaccacg   240
ctgtatctgg aaatgaacag cctgaaagtc gaggacacag ccgtgtatta ctgtaccaca  300
gataacggag tcaaggcttt tgatatctgg ggccaaggga caatggtcac cgtctcttca   360
```

| SEQ ID NO: 139 | moltype = DNA  length = 354 |
|---|---|
| FEATURE | Location/Qualifiers |
| source | 1..354 |
| | mol_type = genomic DNA |
| | organism = Homo sapiens |

SEQUENCE: 139

```
gaggtgcagc tggtggagtc cgggggaggc ttagttcagc ctgggggtc cctgagactc     60
tcctgtgcag cctctggatt caccttcagt acctactgga tgcactgggt ccgccaaact  120
ccggagaagg ggctggtatg ggtctcacgt attcatcctg atgggagtaa cacagcctac   180
gcggactccg tgaagggccg attcaccatc tccagagaca acgccaagaa cacgctgtat   240
ctgcaaatga atagtctgag agtcgaggac acggcttttt attattgtac aagagggggt  300
tccggggcta cgatcaatta ctggggccag ggaatcctgg tcaccgtctc ctca           354
```

| SEQ ID NO: 140 | moltype = DNA  length = 372 |
|---|---|
| FEATURE | Location/Qualifiers |
| source | 1..372 |
| | mol_type = genomic DNA |
| | organism = Homo sapiens |

SEQUENCE: 140

```
caggtgcagc tgcaggagtc gggcccaggg ctggtgaagc cttcacagac cctgtccctc     60
acctgcactg tctctggtgg ctccatcagc ggtggtactt actcctggac ctggatccgg  120
cagcccgccg gaagggact ggagtggatt gggcgtattt ttgctagtgg gagcaccaac     180
tacaattcct ccctcaagag tcgagtcacc attttagtag acacgtccaa gaaccgtttc   240
tccctgagcc tgagctctgt gaccgccgca gacacggcca tgtattactg tgcgagagat  300
cgagccggta tagatggcta caattactac tttgactact ggggccaggg aaccctggtc    360
accgtctcct ca                                                          372
```

| SEQ ID NO: 141 | moltype = DNA  length = 359 |
|---|---|

```
FEATURE          Location/Qualifiers
source           1..359
                 mol_type = genomic DNA
                 organism = Homo sapiens
SEQUENCE: 141
aggtgcagct ggtgcagtct ggggctgagg tgaagaagcc tggggcctca gtgaaggttt   60
cctgcaagac atctggatac accctcacca gttactatat gcactgggtg cgacaggccc  120
ctggacaagg gcttgagtgg ctgggagtga tcaggcctac ggacgctagc acaaggtccg  180
cacagaagtt ccagggcaga atcaccatga ccagggacac gtccacgagc acactctaca  240
tggagctgag tagcctgaga tctgaagaca cggccgtgta ctattgtgcg agagaagtgg  300
cagcagaagg taaagctttc gactactggg gccaggaaac cctggtcacc gtctcctca   359

SEQ ID NO: 142   moltype = DNA   length = 348
FEATURE          Location/Qualifiers
source           1..348
                 mol_type = genomic DNA
                 organism = Homo sapiens
SEQUENCE: 142
gaggtgcagc tggtggagtc tgggggaggc ttggtccagc ctgggggtc cctgagactc    60
tcctgtgcag cctctggatt cacctttagt agctattgga tgagctgggt ccgccaggct  120
ccagggaagg gactggagtg ggtgggcaaa ataaaggaag acggaagtga gaaatactat  180
gtggactctg tgaagggccg attcgccatc tccagagaca acgccaagaa ctccctgtct  240
ctgcaaatga acagcctgag agccgaggac acggccgtgt attactgtgc gagaggtcaa  300
tcatatccgg gaatttgggg ccaagggaca atggtcaccg tctcttca                348

SEQ ID NO: 143   moltype = DNA   length = 363
FEATURE          Location/Qualifiers
source           1..363
                 mol_type = genomic DNA
                 organism = Homo sapiens
SEQUENCE: 143
caggtgcagc tgcaggagtc gggcccagga ctggtgaagc cttcggagac cctgtccctc    60
acctgcactg tctctggtgg ctccatcact aattactact ggggctggat ccggcagccc  120
ccaggggagg gactggagtg gattggctat atctattaca gtggaagcac caactacaac  180
ccctccctca agagtcgagt caccatatca gtagacacgt ccaagaacca gttctcccta  240
aagctgacct ctgtaaccgc cgcagacacg gccgtgtatt actgtgcggg tcgggcttac  300
agtagtggtt actactacct aattgactac tggggccagg gaaccctggt caccgtctcc  360
tca                                                                  363

SEQ ID NO: 144   moltype = DNA   length = 321
FEATURE          Location/Qualifiers
source           1..321
                 mol_type = genomic DNA
                 organism = Homo sapiens
SEQUENCE: 144
gaaattgtgt tgacgcagtc tccaggcacc ctgtctttgt ctccagggga aagagccacc    60
ctctcctgca gggccagtca gagtgttacc tacttagctg gtaccagca gaaacctggc   120
caggctccca ggctcctctt ctatggtaca tccagcaggg ccactggcat cccagacagg  180
ttcagtggca gtgggtctgg gacagacttc actctcacca tcagcagagt ggagcctgaa  240
gattttgcag tgtattactg tcagcagttt ggcagctcac ctccggacac tttcggcgga  300
gggaccaagg tggaaatcaa a                                              321

SEQ ID NO: 145   moltype = DNA   length = 332
FEATURE          Location/Qualifiers
source           1..332
                 mol_type = genomic DNA
                 organism = Homo sapiens
SEQUENCE: 145
ttgtgatgac tcagtctcca ctctccctgc ccgtcaccct tggacagccg gcctccatct    60
cctgcagggc tagtcaaggc ctcgaacaca gtgatggaaa cacctacttg agttggtttc   120
agcagaggcc aggccgatct ccccggcgcc taatttataa ggtttctaac cgggactctg  180
gggtcccaga cagattcagt ggcagtgggt caggcactga tttcacactg aaatcacca   240
gggtggaggc tgaggatgtt ggagtttatt actgcatgca agttacacac tggccgagga  300
cgttcggcca agggaccaag gtggaaatca aa                                  332

SEQ ID NO: 146   moltype = DNA   length = 321
FEATURE          Location/Qualifiers
source           1..321
                 mol_type = genomic DNA
                 organism = Homo sapiens
SEQUENCE: 146
gaaattgtgt tgacacagtc tccaggcacc ctgtcgttgt ctccagggga aagagccacc    60
ctctcctgca gggccagtca gagtattagt ccccacttgg cctggtacca acagaaacct   120
ggccagtctc ccaggctcct catatatgat gcatccaaca gggccactgg catcccagcc  180
aggttcagtg gcagtgagtc tgggacagac ttcactctca gcatcagcag cctagagcct  240
gaagattttg cagtttatta ctgtcagcag agtggcgact ggcctctcac tttcggcgga  300
gggaccaagg tggagatcaa a                                              321

SEQ ID NO: 147   moltype = DNA   length = 324
```

```
FEATURE              Location/Qualifiers
source               1..324
                     mol_type = genomic DNA
                     organism = Homo sapiens
SEQUENCE: 147
gaaattgtgt tgacgcagtc tccaggcacc ctgtctttgt ctccagggga aagagccacc    60
ctctcctgca gggccagtca gagtgtttac agcatctact tcgcctggta ccagcagaaa   120
cccggccagg ctcccaggcc cctcatttat ggtgtctcca cagggccac tggcatccca    180
gacaggttca gtggcagtgg gtctgggaca gacttcactc tcaccatcag cagactggag   240
ccagaagatt ttgcagtgta ttactgtcag cagtatggta gtttacctcg gacgttcggc   300
caagggacca aggtggaaat caaa                                           324

SEQ ID NO: 148       moltype = DNA   length = 332
FEATURE              Location/Qualifiers
source               1..332
                     mol_type = genomic DNA
                     organism = Homo sapiens
SEQUENCE: 148
ttgtgatgac tcagtctcca ctctccctgc ccgtcaccct tggacagccg gcctccatct    60
cctgcaggtc tagtcgaagc ctcgtataca gtgatggagg cacctacttg aattggtttc   120
agcagaggcc aggccaatct ccaaggcgcc taatttggca cgtttctaac cgggactctg   180
gggtcccaga cagattcagc ggcagtgggt caggcactga tttcacactg aaaatcagca   240
gggtggaggc tgaggatgtt ggggtttatt actgcatgca aggtacacac tggccttaca   300
cttttggcca ggggaccaag gtggaaatca aa                                  332

SEQ ID NO: 149       moltype = DNA   length = 321
FEATURE              Location/Qualifiers
source               1..321
                     mol_type = genomic DNA
                     organism = Homo sapiens
SEQUENCE: 149
gacatccaga tgacccagtc tccatcttcc ctgtctgcat ctgtaggaga cagagtcacc    60
atcacttgcc aggcgagtca ggacattagg aagcttttaa attggtatca gcagagacca   120
gggaaagccc ctaacctcct gatctacgat gcatccaatt tggaaacagg ggtcccatca   180
aggttcagtg gaagtggatc tgggacacat tttagtttca ccatcaccag cctgcagcct   240
gaagatattg caacatatta ctgtcaacag tttgaaagtt cccctcgcac cttcggccct   300
gggaccaaag tggatatcaa a                                              321

SEQ ID NO: 150       moltype = DNA   length = 327
FEATURE              Location/Qualifiers
source               1..327
                     mol_type = genomic DNA
                     organism = Homo sapiens
SEQUENCE: 150
gaaatagtga tgacgcagtc tccagccacc ctgtctgtgt ctccagggga aacagccacc    60
ctctcctgca gggccagtca gagtgttaac agcttcttag cctggtacca gcagaaacct   120
ggccaggctc ccaggctcct catctatgct gcatccacca gggccactgg tgtcccagcc   180
aggttcagtg gcagtgggtc tgggacagag ttcactctca ccatcagcag cctgcagtct   240
gaagattttg cagtttacta ctgtcaccag tataaaaact ggcctccgat gggcactttc   300
ggccctggga ccaaagtgga tatcaaa                                        327

SEQ ID NO: 151       moltype = DNA   length = 318
FEATURE              Location/Qualifiers
source               1..318
                     mol_type = genomic DNA
                     organism = Homo sapiens
SEQUENCE: 151
gacatccaga tgacccagtc tccttccacc ctgtcttctt ctgtcggaga cagagtcact    60
atcacttgcc gggccagtca gaatattggt gtctccttgg cctggtatca gcagaaacca   120
gggaaagccc ctaacctcct gatctataag gcgtcttatt tagaaacggg ggtcccatca   180
aggttcagcg gcagtggatc tgggacagaa ttcactctca ccatcagcag cctacagcct   240
gatgattttg caacttatta ttgccaacag tatgatattt atttgacatt cggccaaggg   300
accaaggtgg aaatcaaa                                                  318

SEQ ID NO: 152       moltype = DNA   length = 332
FEATURE              Location/Qualifiers
source               1..332
                     mol_type = genomic DNA
                     organism = Homo sapiens
SEQUENCE: 152
ttgtgatgac tcagtctcca ctctccctgc ccgtcaccct tggacagccg gcctccatct    60
cctgcaggtc tagtcaaagt ctcgcacaca gtgatggaaa tacctacttg aattggtttc   120
agcagaggcc aggccaatct ccaaggcgcc taatttataa ggtttctaac cgggactctg   180
gggtcccaga cagattcagc ggcagtgggt caggcactga tttcacactg aaaatcagca   240
gggtggaggc tgaggatgtt ggggtttatt actgcatgca aggtacacac tggccgtaca   300
cttttggcca ggggaccaag gtggaaatca aa                                  332

SEQ ID NO: 153       moltype = DNA   length = 339
FEATURE              Location/Qualifiers
```

```
source                     1..339
                           mol_type = genomic DNA
                           organism = Homo sapiens
SEQUENCE: 153
gacatcgtga tgacccagtc tccagactcc ctggctgtgt ctctgggcga gagggccacc    60
atcaactgca agtccagcca gagtgtttta tacagcccca acaataagaa ttacttagct   120
tggttccagc agaagccagg acagcctcct aaattactca tttactgggc atctatccgg   180
gactccgggg tccctgaccg attcagtggc agcgggtctg ggacagattt cactctcacc   240
gtcagcagtc tgcaggctga cgatgtggca gtttattact gtcagcaata tgctgctact   300
ccgtggacgt tcggccaagg gaccaaggtg gaaatcaaa                          339

SEQ ID NO: 154             moltype = DNA   length = 332
FEATURE                    Location/Qualifiers
source                     1..332
                           mol_type = genomic DNA
                           organism = Homo sapiens
SEQUENCE: 154
ttgtgatgac tcagtctcca ctctccctgc ccgtcaccct tggacagccg gcctccatct    60
cctgcagttc tagtcaaagc ctcgtataca gtgatggaaa cacctacttg agttggtttc   120
agcagaggcc aggccaatct ccccggcgcc taatttataa ggtttctaac cgggactctg   180
gggtcccaga cagattcagc ggcagtgggt caggcactga tttcacactg agaatcagca   240
gggtggaggc tgaggatgtt gggtttatt actgcatgca aggttcacac tggccgctca    300
ctttcggcgg agggaccaag gtggagatca aa                                 332

SEQ ID NO: 155             moltype = DNA   length = 339
FEATURE                    Location/Qualifiers
source                     1..339
                           mol_type = genomic DNA
                           organism = Homo sapiens
SEQUENCE: 155
gacatcgtga tgacccagtc tccagactcc ctggctgtgt ctctgggcga gagggccacc    60
atcaactgca agtccagcct gagtgtttta tccagctcca ataatgagaa ctacttagct   120
tggtaccagc agaaaccagg acagcctcct aagctgctca tttactgggc atctacccgg   180
ggatccgggg tccctggccg attcagtggc agcgggtctg ggacagattt cactctcacc   240
atcagcagcc tgcaggctga agatgtggca gtttattact gtcaccaata ttatactact   300
ccccttcgctt tcggccctgg gaccaaagtg gatatcaaa                         339

SEQ ID NO: 156             moltype = DNA   length = 321
FEATURE                    Location/Qualifiers
source                     1..321
                           mol_type = genomic DNA
                           organism = Homo sapiens
SEQUENCE: 156
gacatccaga tgacccagtc tccgtcctcc ctgtctgcat ctgtgggaga cagtgtcacc    60
atcacttgcc gggcaagtca gagcattagc agctatttaa attggtatca ccaaaaacca   120
gggaaagccc ctaaactcct gatctatggt gcatccactt gcaaagtgg ggtcccatca    180
aggttcagtg gcagtggatc tgggacagat ttcactctca ccatcagcag tctgcaaacct   240
gacgattttg caacttacta ctgtcaacag agtcacagtt cccctctcac tttcggcgga   300
gggaccaagg tggagatcaa a                                             321

SEQ ID NO: 157             moltype = DNA   length = 318
FEATURE                    Location/Qualifiers
source                     1..318
                           mol_type = genomic DNA
                           organism = Homo sapiens
SEQUENCE: 157
gacatccaga tgacccagtc tccttccacc ctgtctgcct ctgtaggaga cagagtcacc    60
atcacttgtc gggccagtcg gagtcttggt agctggttgg cctggtatca gcagagccca   120
gggaaagccc ctaagctcct gatctataag gcgtctactt tagaaagtgg ggtcccatca   180
cggttcagcg gcagtggatc tgggacagaa ttcactctca ccatcagcag cctgcagcct   240
gatgattttg caacttatta ctgccaacag tattatagct tctacacttt tggccagggg   300
accaaggtgg aaatcaaa                                                 318

SEQ ID NO: 158             moltype = DNA   length = 339
FEATURE                    Location/Qualifiers
source                     1..339
                           mol_type = genomic DNA
                           organism = Homo sapiens
SEQUENCE: 158
gacatcgtga tgacccagtc tgcagactcc ctggctgtgt ctctgggcga gagggccacc    60
atcaactgca agtccagcca gagtcttttc tacagttcca acaagaagaa ctacttagct   120
tggtaccagc agaagccagg acagcctcct aaactgatca tttactgggc atctacccgg   180
gaatccgggg tccctgaccg attcagtggc agcgggtctg ggacagattt cactctcacc   240
atcaccagcc tgcgggctga agatgtggca gtttattact gtcagcaata ttatactcct   300
cctctcacat tcggcggagg gaccaaggtg gaaatcaaa                          339

SEQ ID NO: 159             moltype = DNA   length = 321
FEATURE                    Location/Qualifiers
```

```
source                    1..321
                          mol_type = genomic DNA
                          organism = Homo sapiens
SEQUENCE: 159
gaaatagtga tgacgcagtc tccagccacc ctgtctgtgt ctccagggga aagagccacc    60
ctctcctgca gggccagtca gagtgttagc ggcgacttag tctggtacca gcagaaacct   120
ggccaggctc ccaggctcct catctatggt gccaccacca gggcctctgg tgtcccagcc   180
aggttcagtg gcagtgggtc tgggacagag ttcactctca ccatcagcag cctgcagtct   240
gaagattttg caatttatta ctgtcagcag tataataact ggccccggac gttcggccaa   300
gggaccaagg tggaaatcaa a                                             321

SEQ ID NO: 160            moltype = DNA  length = 321
FEATURE                   Location/Qualifiers
source                    1..321
                          mol_type = genomic DNA
                          organism = Homo sapiens
SEQUENCE: 160
gaaatagtga tgacgcagtc tccagccacc ctgtctgtgt ctccagggga aagagccacc    60
ctctcctgca gggccagtca gagtgttggc aacaacttag cctggtttca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatca ctgtcaacac tatcataact ggcctccac ttttggccag   300
gggaccaagg tggaaatcaa a                                             321

SEQ ID NO: 161            moltype = DNA  length = 366
FEATURE                   Location/Qualifiers
source                    1..366
                          mol_type = genomic DNA
                          organism = Homo sapiens
SEQUENCE: 161
caggtgcagc tggtggagtc tgggggaggc gtggtccagc ctgggaggtc cctgagactc    60
tcctgtgcag cctctggatt caccttcagc aaccatggca tgcactggct ccgccagact   120
ccaggcaagg ggctggagtg ggtggcagtc atttcatatg atggaagtac caaatactat   180
gcagactccg tgaagggccg atgcaccctc tccagagaca attccaagga aacggtgttt   240
ctgcaaatga acagcctgag acctgaggac acggctgtgt attattgtgc gaaagggtgt   300
tctaatggtg gtaactgctt tttgattgac tactggggcc cgggaaccct ggtcaccgtc   360
tcctca                                                              366

SEQ ID NO: 162            moltype = DNA  length = 369
FEATURE                   Location/Qualifiers
source                    1..369
                          mol_type = genomic DNA
                          organism = Homo sapiens
SEQUENCE: 162
gaggtgcagc tgttggagtc gggggagac ttggtgcagc ctgggggtc cctgagactc    60
tcctgtgcag cctctggatt cgacttcagt atttatggca tgaactgggt ccgccaggct   120
ccagggaagg ggcttgaatg ggtctcagtt attagtgtg atggcactat catatactac   180
gcagactccg tgaagggccg gttcactatc tccagagaca attccaagaa cacactgttt   240
ttgcaagtga acagcgtgag agccgaggac acggccgtat attactgtgc gaagggggc   300
tactatgaat cggggactat gcgggctttt gatatctggg gccaagggac aatggtcacc   360
gtctcttca                                                           369

SEQ ID NO: 163            moltype = DNA  length = 351
FEATURE                   Location/Qualifiers
source                    1..351
                          mol_type = genomic DNA
                          organism = Homo sapiens
SEQUENCE: 163
gaggtgcagc tggtggagga gtctggggga ggcttggtcc agcctggggg gtccctgaga    60
ctctcctgtg cagcctctgg atacaccttt agtagttatt caatgagttg ggtccgccag   120
gctccaggga aggggctgga gtgggtggc agcattaagc cagaaggaag tgagaaattc   180
tatgtggact ctgtgaaggg ccgattcact atctccagag acaacgccaa gaactcactg   240
tatctgcaaa tgaacagcct gagaggcgag gacacgctg tctactactg tgcgagaggg   300
gaatctaatt tccgatactg gcaccaggga accctgtca ccgtctcctc a             351

SEQ ID NO: 164            moltype = DNA  length = 357
FEATURE                   Location/Qualifiers
source                    1..357
                          mol_type = genomic DNA
                          organism = Homo sapiens
SEQUENCE: 164
gaggtgcagc tggtggagtc tgggggagcc ttggtccagc ctgggggtc cctgagactc    60
tcctgtgcag cctctggatt catcttcagt aactcttgga tgggctggtt ccgccaggct   120
ccagggaagc ggccggagtt cgtggccaac ataaaaccag atggaagtga gaattccat   180
gtggactctg tgaagggccg attcaccatc tccagagaca cgccgagaa ctcactgtat   240
ctgctgatga cagcctgag agccgaggac acggctgtct attactgcgc gagagatagc   300
acttccccgg cccgttttgg gtactggggc caggaaccc tggtcaccgt ctcctca      357

SEQ ID NO: 165            moltype = DNA  length = 354
```

```
FEATURE                 Location/Qualifiers
source                  1..354
                        mol_type = genomic DNA
                        organism = Homo sapiens
SEQUENCE: 165
gaggtgcagc tggtggagac tggaggaggc ttgatccagc ctgggggtc cctgaggctc      60
tcctgtgcag cctctgggtt aaacgtcaat agttactaca tgaactgggt ccgccaggct    120
ccagggaagg ggctggagtg ggtctcagtt atttatagcg gtggtggcac aaactacgca    180
gactccgtga ggggccgatt catcatctcc agagacaatt ccaggaacgc gctttatctt    240
caaatgaaca gcctgagagc cgaggacacg gccgtgtatt actgtgcgac gggcgggatg    300
accagtagtt ggtacggcta ctggggccag ggaaccctgg tcaccgtctc ctca          354

SEQ ID NO: 166          moltype = DNA    length = 374
FEATURE                 Location/Qualifiers
source                  1..374
                        mol_type = genomic DNA
                        organism = Homo sapiens
SEQUENCE: 166
aggtgcagct ggtgcagtct ggggccgagg tgaagaagcc tggggcctca gtgaaggttt     60
cctgcaaggc atctgaatac actttcatca actaccttgt gttctgggtg cgacaggccc    120
ctggacaagg gcttgagtgg atgggagaaa tgaaccccac tcgtgggagc acaagctacg    180
cacagaagtt ccaggggaga gtcaccatga ccagggacgt ccacgagc acagtctaca      240
tggagttgag cagcctgaga tctgacgaca cggccgttta ttactgctcc atgggtccgc    300
cctattgtac tggtggaagc tgttactccg cctgtgattt ctggggcccg ggaaccctgg    360
tcaccgtctc ctca                                                      374

SEQ ID NO: 167          moltype = DNA    length = 372
FEATURE                 Location/Qualifiers
source                  1..372
                        mol_type = genomic DNA
                        organism = Homo sapiens
SEQUENCE: 167
gaggtgcagc tggtggagtc tggggaggc ttgatgaaac ctgggggtc ccttagactc       60
tcctgtgcag tctctgggtt cactttcact aacgcctggc tgagctgggt ccgccagcct    120
ccagggaagg ggctggagtg ggttggccgt gcttacagca gttctggcgg ttggacaatg    180
gactactctt cacccgtgag gggcagattc accatcacaa gagacgattc aaaaaacaca    240
ctgtatctgc aaatgaacaa cctgaaaacc gaggacacag ccgtgtatta ctgtaccaca    300
gatattggca aaggctggta cacgcactat cctgacctct ggggccaggg aaccctggtc    360
accgtctcct ca                                                        372

SEQ ID NO: 168          moltype = DNA    length = 363
FEATURE                 Location/Qualifiers
source                  1..363
                        mol_type = genomic DNA
                        organism = Homo sapiens
SEQUENCE: 168
caggtgcagc tggtggagtc tggggaggc gtggtccagc ctgggaagtc cctcagactc      60
tcctgtgtag cctctggatt caccttaagt acctgtggca tgcactgggt ccgccaggct    120
ccaggcaagg ggctggagtg ggtggcagtt acaacatatg atggagatcg taaatataat    180
gtagactccg tgaagggccg attcaccatc tccagagaca attccaagaa cacggtgtat    240
ctgcaaatgg acgcctcaa agccgaggac acggctgtgt atcactgtgt gaagaatat     300
agttggggtt actacagaac tgcggactac tggggccagg gaaccctggt caccgtctcc    360
tca                                                                  363

SEQ ID NO: 169          moltype = DNA    length = 351
FEATURE                 Location/Qualifiers
source                  1..351
                        mol_type = genomic DNA
                        organism = Homo sapiens
SEQUENCE: 169
gaggtgcagc tggtggagtc cggggagggc ttagttcagc cgggggggtc cctgagactc     60
tcctgtgtag cctctggatt caccttcagt acttactgga tgcactgggt ccgccaacct    120
ccggggaagg ggctggtgtg ggtctcacgt attaatcctg atggcagtag cacaaactac    180
gcggactccg tgaacggccg attcaccatc tccagagaca acgccaagaa cacgctgtat    240
cttgaaatga acagtttgag agtcgaggac acagctctct attactgtgc aagaagtcct    300
gggggttact ttgactactg gggccacagc accctggtca ccgtctcctc a             351

SEQ ID NO: 170          moltype = DNA    length = 348
FEATURE                 Location/Qualifiers
source                  1..348
                        mol_type = genomic DNA
                        organism = Homo sapiens
SEQUENCE: 170
gaggtgcagc tggtggagtc tggggaggc ttggtgaagc ctgggggtc ccttacactc       60
tcctgtgcag tctctggatt cactttcagt accggctgga tgagctgggt ccgccaggct    120
ccagggaagg ggctggactg ggttggccgt attaaaagca aaactgctgg tgggacaaca    180
gactatgctg cacccgtgaa agacagattc accatctcaa gagatgattc aaaaaacacg    240
ctgtatctgc aactgagcag ccttaaaacc gaggacacag ccgtgtatta ctgtaccaca    300
gatgacctga aaaactgggg ccaggaacc ctggtcaccg tctcctca                  348
```

```
SEQ ID NO: 171           moltype = DNA  length = 387
FEATURE                  Location/Qualifiers
source                   1..387
                         mol_type = genomic DNA
                         organism = Homo sapiens
SEQUENCE: 171
gaggtgcagc tggtggagtc tgggggaggc ttggtgcagc cggggggtc cctgagactc    60
tcctgtgcag cctctggatt caccttcagt agttatatgca tgaactgggt ccgccaggtc  120
ccgggaaagg ggctggagtg ggtctcatac acaagtacta aaagtgatat caaatactac   180
gcggactctg tggaaggccg attcaccatt tccagagaca atgccaagaa ctcattgtat   240
ctgcaaatga acagcctgag agacgaagac acggctgtct attattgtgc gagaggacga   300
gattgttatg ggggtaactg cgtcatctac ttccactact acggtttgga cgtctgggc   360
caagggacca cggtcaccgt ctcctca                                        387

SEQ ID NO: 172           moltype = DNA  length = 369
FEATURE                  Location/Qualifiers
source                   1..369
                         mol_type = genomic DNA
                         organism = Homo sapiens
SEQUENCE: 172
caggtgcagc tggtggagtc tgggggaggc gtggtccagc ctgggggtc cctgagactc    60
tcctgtgtag tctctggatt caccctcagt tcctgtggca tgcattgggt ccgccagtct   120
ccaggcaagg ggctggagtg gctgtcagtt agcacctatg atggagatgg caatcagaaa   180
tactatgcgc cctccgtgaa gggccgattc ctcatctcca gagacacttc gaagaacacg   240
gtgtatctcc aatgaacag cctgacagct gaggacacgg ctctatatta ttgtgtgaaa   300
gagagtgcca ctggctggta tcgcaccgct gattactggg gccaggaac cctggtcacc    360
gtctcctca                                                            369

SEQ ID NO: 173           moltype = DNA  length = 366
FEATURE                  Location/Qualifiers
source                   1..366
                         mol_type = genomic DNA
                         organism = Homo sapiens
SEQUENCE: 173
gaggtgcagc tggtggagtc tgggggaggc ttggtccagc ctgggggtc cttgagactc    60
tcctgtgcag cctctggatt caccgtcagt agcatattca tgagctgggt ccgccaggct   120
ccagggcagg ggctggagtg ggtctcagtc atctataccg atggaaaaac atattatgca   180
cactccgtgg agggccgatt caccatctcc agagacgatt ccaagaatat ggtgtatctt   240
caattgagca gcctgagaac tgaggacacg gctgtttatt actgtgcgag agatattcca   300
acgacatttg gaataggtga agcttttgat atctggggcc aggggacaat ggtcaccgtc   360
tcttca                                                               366

SEQ ID NO: 174           moltype = DNA  length = 347
FEATURE                  Location/Qualifiers
source                   1..347
                         mol_type = genomic DNA
                         organism = Homo sapiens
SEQUENCE: 174
aggtgcagct ggtgcagtct ggggctgagg tgaagaagcc tggggcctca gtgaagcttt    60
cctgcaagac atctggatac tccttcacca gcaactattt cactgggtg cgacaggccc   120
ctggacaagg acttgagtgg atgggaatgg tctacccaaa tgatggtact acaacctacg   180
ctcagaagtt tcaggcaga gtcaccatga ccagtgagac gtccacaacc acaatctaca   240
tggacctgag cggcctgaca tctgaggaca cggccatata ttactgtgct agagacgatt   300
cggcctttga ctactgggc cagggaaccc tggtcaccgt ctcctca                   347

SEQ ID NO: 175           moltype = DNA  length = 363
FEATURE                  Location/Qualifiers
source                   1..363
                         mol_type = genomic DNA
                         organism = Homo sapiens
SEQUENCE: 175
caggtgcagc tggtggagtc tgggggaggc gtggtccagc ctggggaggtc cctgagactc    60
tcctgtgaag cctctggatt catcttcagt agcaatgtg ccgcctgggt ccgccaggct    120
ccaggcaagg ggctggagtg ggtggcagtt atatcatctg atggaagtag agatactat   180
gcagactcaa tgaagggccg attcaccatc tccagagaca actccaagaa cacgctgtat   240
ctgcaattga acagcctgag agctgacgac acggctgtct attactgtgc gaaaggtgt   300
agtggtgaaa attgcttcta tatggacgac tgggggcaaag ggaccacggt caccgtctcc   360
tca                                                                  363

SEQ ID NO: 176           moltype = DNA  length = 386
FEATURE                  Location/Qualifiers
source                   1..386
                         mol_type = genomic DNA
                         organism = Homo sapiens
SEQUENCE: 176
aggtgcagct ggtgcagtct ggggctgagg tgaagaagcc tggggcctca gtgaaggtct    60
cctgcaaggc atctggatac accttcagac agaactattt ccactgggtg cgacaggccc   120
ctggacaagg gcttgagtgg atgggagtaa tcaacccgag tgatggtagt acaaagttcg   180
```

```
cacagaagtt ccagggcaga gtcagcatga ccagggacac gtccacgagc acagtttaca    240
tggacctgag cagtctgaca tctgaggaca cggccgtcta ttattgtacg agagagatcg    300
gcgcagtggt agtagatgct acgtcgttgg ggtggttggg ctactttgac tactggggcc    360
agggaaccct ggtcaccgtc tcctca                                          386

SEQ ID NO: 177           moltype = DNA   length = 345
FEATURE                  Location/Qualifiers
source                   1..345
                         mol_type = genomic DNA
                         organism = Homo sapiens
SEQUENCE: 177
gaggtgcagc tggtggagtc tgggggaggc ttggtccagc cggggggtc cctgagtctc      60
tcctgtgaag cctctggatt aaccttcagt ggctactgga tgaactgggt ccgccaggct    120
ccagggaagg ggctggagtg ggtggccaac ataaatccaa aaggaagtga gaggagatac    180
gtggagtctg tgcagggccg attcaccgtc tccagagaca acccgaagaa caccctgtat    240
ttgcaaatga acagcctgag agtcgaggac acggctctgt attactgtgc gggctggggg    300
agaacccagg actggggcca gggagccctg gtcaccgtct cctca                    345

SEQ ID NO: 178           moltype = DNA   length = 363
FEATURE                  Location/Qualifiers
source                   1..363
                         mol_type = genomic DNA
                         organism = Homo sapiens
SEQUENCE: 178
caggtgcagc tggtggagtc tgggggaggc gtggtccagc ctgggaggtc cctgagactc      60
tcctgtgcag cctctggatt cacccttcag aattatggca tgcactgggt ccgccaggct    120
ccagggaagg ggctggagtg ggttgcagtt gtgtcggcaa ggggaggaac tacatattat    180
gcagactccg tgaagggccg attcaccatc tccagagaca attccaagaa cacgatgtct    240
ctgcaaatga acgcctgag acctgacgac acggctgtgt atttttgtac gaaagaagga    300
gcaccacctg gaaaatatgc ttttgatatc tggggccaag gacaatggt caccgtctct    360
tca                                                                   363

SEQ ID NO: 179           moltype = DNA   length = 360
FEATURE                  Location/Qualifiers
source                   1..360
                         mol_type = genomic DNA
                         organism = Homo sapiens
SEQUENCE: 179
gaggtgcagc tggtggagtc tgggggaggc ttggtccagc ctggaggatc cctgagactc      60
tcctgcgcag cctccggatt cacccttcagt gactaccgca tggactgggt ccgccaggct    120
ccagggaggg ggctggagtg gattgcccgt attagacaca gagatgcagg ctatagcaca    180
gaatacgccg cgtctgtgag gggcagattc accgtctcaa gagatgactc acagagtaca    240
ctgtacctgc agatgaacag cttgaaagcc gacgacacgg ccgtgtatat ttgtcttaaa    300
gattcttcgc aatactcttt tgatgcgtgg ggccaaggga caatggtcac cgtctcttca    360

SEQ ID NO: 180           moltype = DNA   length = 339
FEATURE                  Location/Qualifiers
source                   1..339
                         mol_type = genomic DNA
                         organism = Homo sapiens
SEQUENCE: 180
gacatcgtga tgacccagtc tccagactcc ctggctgtgt ctctgggcga gagggccacc      60
atcaactgca agtccagtca gagtatttta tccagatcca caataagaa ctacttagcc     120
tggtaccagc agaaaccagg acagcctcct aaattgctcc tttattgggc atctacccgg    180
gaatccgggg tccctgaccg attcagtgtc agcgggtctg ggtcagattt cactctcacc    240
atcagtagcc tgcaggctga ggatgtggca gtttattact gtcagcagta ttataatgct    300
cccctcactt tcggcggagg gaccaaggtg gagatcaaa                            339

SEQ ID NO: 181           moltype = DNA   length = 321
FEATURE                  Location/Qualifiers
source                   1..321
                         mol_type = genomic DNA
                         organism = Homo sapiens
SEQUENCE: 181
gaaattgtgt tgacacagtc tccagccacc ctgtctttgt ctccagggga aagggccacc      60
ctctcctgca gggccagtca gactgttagc aggtacttag cctggtacca acaaaagcct    120
ggccaggctc ccaggctcct catctatgct gcatccaaca gggccactgg catcccaacc    180
aggttcagtg gcagtgggtc tgggacagac ttcactctca ccatcagcag cctagagcct    240
gaagattttg catttttatta ctgtcagcag cgtagcaact ggcctgccac tttcggcgga    300
gggaccaagg tggagatcaa a                                               321

SEQ ID NO: 182           moltype = DNA   length = 321
FEATURE                  Location/Qualifiers
source                   1..321
                         mol_type = genomic DNA
                         organism = Homo sapiens
SEQUENCE: 182
gacatccaga tgacccagtc tccttcctcc ctgtctgcat ctgtaggaga cagtgtcacc      60
atcacttgcc aggcgagtca ggacattaga gaccgtttaa attggtatca gcagaagcca    120
```

```
gggaaagccc ctaacctcct gatctacgat gcatcaagtt tggaaacagg ggtcccatca    180
aggttcagag gaagtggatc tgggacagat tttactttca ccatcagcag cctgcagcct    240
gaagatattg caacatatta ctgtcaacag tttgttagtt ccctcgaac tttcggcccg     300
gggaccaaag tggatatcaa a                                              321

SEQ ID NO: 183         moltype = DNA   length = 330
FEATURE                Location/Qualifiers
source                 1..330
                       mol_type = genomic DNA
                       organism = Homo sapiens
SEQUENCE: 183
gaaattgtgt tgacgcagtc tccaggcatc ctgtctttgt ctccagggga aagagccacc    60
ctctcctgca gggccagtca gagtgttagc agcaggtcct tgtcctgta ccagcagaga     120
cctggcctgg ctcccaggct cctcatctat gctgcatcca gcagggccgc tgtcacccca    180
gacaggttca ctgccagcgg gtctgggaca gacttcactc tcaccatcag cagtctggag    240
cctgaagatt ttgcagtgta ttactgtcag cactatggta cctcacctcc gaggtacact    300
tttgggcagg ggaccaaggt ggagatcaaa                                     330

SEQ ID NO: 184         moltype = DNA   length = 339
FEATURE                Location/Qualifiers
source                 1..339
                       mol_type = genomic DNA
                       organism = Homo sapiens
SEQUENCE: 184
gacatcgtga tgacccagtc cccagactcc ctggctgtgt ctctgggcga gagggccacc    60
atcaactgca agtccagcca gagtgtttta cacagctgca acataagaa ctactttgct     120
tggtaccagc agaaaccagg acagcctcct aagctgctca ttcactgggc atctacccgg    180
gcatccgggg tccctgaccg attcagtggc agcgggtctg ggacagattt cactctcacc    240
atcagcagcc tgcaggctga agatgtgaca atttattact gtcagcaata ttatagtact    300
ccgtacactt ttggccaggg gaccaaggtg gaaatcaaa                           339

SEQ ID NO: 185         moltype = DNA   length = 327
FEATURE                Location/Qualifiers
source                 1..327
                       mol_type = genomic DNA
                       organism = Homo sapiens
SEQUENCE: 185
gaaattgtgt tgacgcagtc tccaggcacc ctgtctttgt ctccagggga aagagccacc    60
ctctcctgca gggccagtcc gagtcttgac agcgcctact agccggta ccagcagaag      120
cctggccagg ctcccaggct cctcatctat ggtgcatcct ccagggtcac tggcatccca    180
gataggttca gtggcagtgc gtcagggaca gacttcactc tcaccatcag cagactggag    240
cctgaagatt ttgcagtgta ctactgtcag cggtatggta actcacctcc gtacactttt    300
ggccagggga ccaaggtgga gatcaaa                                         327

SEQ ID NO: 186         moltype = DNA   length = 339
FEATURE                Location/Qualifiers
source                 1..339
                       mol_type = genomic DNA
                       organism = Homo sapiens
SEQUENCE: 186
gacatcgtga tgacccagtc tccagactcc ctggctgtgt ctctgggcga gagggccacc    60
atcagctgca agtccagcca gagtctttta tacagttcca gcaataagaa ctacctagct    120
tggttccagc agaaaccagg acaggctcct aagttgctca tttactgggc atctacccgg    180
gaatccgggg tccctgaccg attcagtggc agcgggtctg ggacagattt cactctcacc    240
atcagcagcc tgcagactga agatgtggca gtttattatt gtctgcaata tcgtagtgct    300
ccgttcactt tcggcggagg gaccaaggtg gagatcaaa                           339

SEQ ID NO: 187         moltype = DNA   length = 321
FEATURE                Location/Qualifiers
source                 1..321
                       mol_type = genomic DNA
                       organism = Homo sapiens
SEQUENCE: 187
gacatccaga tgacccagtc tccttccacc cagtctgcat ctgtaggaga cagagtcacc    60
atcacttgcc gggccagtca gagtattagt agttggttgg cctggtatca gcagaaacca    120
gggaaagccc ctaaggtcct gatctatgcg gtgtctagtt tagaaagtgg ggtcccatca    180
aggttcagcg gcagtggatc tgggacagaa ttcactctca ccatcagcag cctgcagcct    240
gaggattttg caacttatta ctgccaacaa tatagtactt atccctggac gttcggccca    300
gggaccaagg tggaaatcaa a                                              321

SEQ ID NO: 188         moltype = DNA   length = 321
FEATURE                Location/Qualifiers
source                 1..321
                       mol_type = genomic DNA
                       organism = Homo sapiens
SEQUENCE: 188
gaaatagtga tgacgcagtc tccagcctcc ctgtctgtgt ctccagggga aacagccacc    60
ctctcctgca gggccagtca gagtgttggc agcacctag cctggtacca gcagaagccc      120
gccaggctc ccaggctcct catctataat gtattcacca gggccgctgg tgtcccagcc      180
```

```
aggttcagtg gcagtgggtc taggacggag ttcactctca ccatcagcag cctgcagtct    240
gaagattttg cagtttatta ctgtcagcag tatagtacct ggctgtggac gttcggccaa    300
gggaccaagg tggaaatcaa a                                              321

SEQ ID NO: 189          moltype = DNA  length = 321
FEATURE                 Location/Qualifiers
source                  1..321
                        mol_type = genomic DNA
                        organism = Homo sapiens
SEQUENCE: 189
gacatccaga tgacccagtc tccatcctcc ctgtctgcat ctgtaggaga cagagtcacc    60
atcacttgcc gggcaagtca gcgcattagc agctacttga attggtatca gcagaaacca   120
gggaaagccc ctaacctcct gatctacgct gcagccagtt tgcatgatgg ggtcccatca   180
aggttcagtg gcagtggatc tgggacagat ttcactctca ccatcagcag tctgcaacct   240
gaagattttg caacttatta ttgtcaacag cgttacagaa tcccgtacag ttttggcccg   300
gggaccaagg tggagatcaa a                                              321

SEQ ID NO: 190          moltype = DNA  length = 336
FEATURE                 Location/Qualifiers
source                  1..336
                        mol_type = genomic DNA
                        organism = Homo sapiens
SEQUENCE: 190
gatattgtga tgactcagtc tccactctcc ctgtccgtca cccctggaga gccggcctcc    60
atctcctgca ggtctagtca gagcctcctt cagggtaatg gacacaacta tttgattgg   120
tacctgcaga agccaggaca gtctccacaa ctccttgatt atttgggttc tattcgggcc   180
tccggggtcc ctgacaggtt cagtggcagt ggatcaggca cagattttat actgaaaatc   240
agcagagtgg aggctgagga tgttggggtt tattactgca tgcgagctct acaaactccg   300
tacactttg gccaggggac caaggtggaa atcaaa                               336

SEQ ID NO: 191          moltype = DNA  length = 321
FEATURE                 Location/Qualifiers
source                  1..321
                        mol_type = genomic DNA
                        organism = Homo sapiens
SEQUENCE: 191
gacatccaga tgacccagtc gccttccacc ctgtctgcat ctgttggaga cagagtcacc    60
ctcacttgtc gggccagtga gactcttaat aactggttgg cctggtttca gcaaaagcca   120
gggaaagccc ctaccctcct gatctatgag gcgtctagtt tagaaagtgg ggtcccatca   180
aggttcagcg gcagtggatc tgggacagac ttcgctctca ccatcagcag cctgcagccc   240
gatgattttg caacttatta ttgccaccag tataataaat accgtggac gttcggccaa   300
gggaccaagg tggagatcaa a                                              321

SEQ ID NO: 192          moltype = DNA  length = 318
FEATURE                 Location/Qualifiers
source                  1..318
                        mol_type = genomic DNA
                        organism = Homo sapiens
SEQUENCE: 192
gacatccaga tgacccagtc tccttccacc ttgtctgcat ctgtaggaga cagagtcacc    60
atcacttgtc gggccagtca gagtattagt ggctggttgg cctggtatca gcagaaacca   120
gggaaagccc ctaagctcct gatctataag gcgtctagtt tagaaagtgg ggtcccatca   180
aggttcagcg gcagtggatc tgggacagag ttcactctca ccatcagcag cctgcagcct   240
gatgattttg caacttatta ctgccagcag tattatagtt ggggaacgtt cggccaaggg   300
accaaggtgg agatcaaa                                                  318

SEQ ID NO: 193          moltype = DNA  length = 336
FEATURE                 Location/Qualifiers
source                  1..336
                        mol_type = genomic DNA
                        organism = Homo sapiens
SEQUENCE: 193
gatattgtga tgacccagac tccactctcc ttacctgtca cccttggaca gccggcctcc    60
atctcctgca tatctagtca aggcctcgta cacagtgatg gaaacaccta cttgagttgg   120
cttcagcaga ggccaggcca gcctccaaga ctcctgattt ataagatttc taaccggttc   180
tctggggtcc cagacagatt cagtggcagt ggggcaggga cagatttcac actgaaaatc   240
agcagggtgg aagctgagga tgtcggggtt tattactgca tgcaagcttc acaatctacg   300
tggacgctcg gccaagggac caaggtggag atcaaa                              336

SEQ ID NO: 194          moltype = DNA  length = 339
FEATURE                 Location/Qualifiers
source                  1..339
                        mol_type = genomic DNA
                        organism = Homo sapiens
SEQUENCE: 194
gacatcgtga tgacccagtc tccagactcc ctggctgtgc ctctgggcga gagggccacc    60
atcaactgca gtccagcca gactgtttta tccagttcca acaataagaa ctacttagtt   120
tggtaccagc agaaaccagg acagcctcct aagttgctcc tttactgggc gtctacccgg   180
gcatccgggg tccctgaccg attcagtggg agcgggtctg ggacagattt cactctcacc   240
```

```
attagcagtc tgcaggctga agatgtggca gtttattact gtcagcaatg ttataatgct   300
ccgctcactt tcggccgagg gaccaaggtg gagatcaaa                          339

SEQ ID NO: 195          moltype = DNA   length = 324
FEATURE                 Location/Qualifiers
source                  1..324
                        mol_type = genomic DNA
                        organism = Homo sapiens
SEQUENCE: 195
gaaatagtga tgacgcagtc tccagccacc ctgtctgtgt ttccagggga aggagtcacc   60
ctctcctgca gggccagtca gagtattagc aacaacttgg cctggtacca gcagaaacct   120
ggccaggctc ccaggctcct catgtatgat gcatccacca gggccactgg tatcccagcc   180
aggttcagtg gcagtgggtc tgggacagag ttcactctca ccatcagcag cctgcagtct   240
gaagatttcg cagtttatta ctgtcagcag tataataact ggcctccggt cacgttcggc   300
caagggacca aggtggaaat caaa                                          324

SEQ ID NO: 196          moltype = DNA   length = 332
FEATURE                 Location/Qualifiers
source                  1..332
                        mol_type = genomic DNA
                        organism = Homo sapiens
SEQUENCE: 196
ttgtgatgac tcagtctcca ctctccctgc ccgtcaccct tggacagtcg gcctccgtct   60
cctgcaggtc aagtcaaagc ctcggcccca gtgacggaag cacccgcttg gattggtttc   120
aacagaggcc aggccaatct ccaaggcgcc taatttatgc ggtttctaac cgggactctg   180
gggtcccaga cagattcagc ggcagcgggt caggcagtga tttcacactg agaatcagca   240
gagtggaggc tgaggatgtt gggtttatt actgcatgca atatacatac tggcctcaca   300
cttttggcca ggggaccaag gtggaaatca aa                                 332

SEQ ID NO: 197          moltype = DNA   length = 327
FEATURE                 Location/Qualifiers
source                  1..327
                        mol_type = genomic DNA
                        organism = Homo sapiens
SEQUENCE: 197
gaaattgtgt tgacacagtc tccagccacc ctgtctttgt ctccagggga aagagccacc   60
ctctcctgca gggccagtca gagtgttagc agttccttag cctggtacca acaaaaacct   120
ggccaggctc ccaggctcct catctatgat gcatccaaga gggccactga catcccagcc   180
aggttcagtg gcagtgggtc tgggacagac ttcactctca ccatcagcag cctagagcct   240
gaagattttg cggtttatta ctgtcagcac cggggggagt ggcctccggg ggccactttc   300
ggccctggga ccaaagtgga tatcaaa                                       327

SEQ ID NO: 198          moltype = DNA   length = 321
FEATURE                 Location/Qualifiers
source                  1..321
                        mol_type = genomic DNA
                        organism = Homo sapiens
SEQUENCE: 198
gacatccagt tgacccagtc tccatccttc ctgtctgcat ctgtaggaga cagagtcacc   60
atcacttgcc gggccagtca gggcattgat actcgtttga tctggtatca acagaagcca   120
ggggaagccc ctaagctcct gatctatgaa gcatccactt tgcaaagtgg ggcccccatca   180
aggttcagcg gcagtggatt cgggacagaa ttcactctca caatcagcag tctgcagcct   240
gaagactttg caacttatta ctgtcaacag tttaaaggtt acccgctcac tttcggcggg   300
gggaccaagg tggagatcaa a                                             321

SEQ ID NO: 199          moltype = DNA   length = 345
FEATURE                 Location/Qualifiers
source                  1..345
                        mol_type = genomic DNA
                        organism = Homo sapiens
SEQUENCE: 199
caggtgcagc tgcaggagtc gggcccagga ctggtgaagc cttcggagac cctgtccctc   60
acctgcactg tctctggtgg ctccatcagt agtcactact ggagctggat ccggcagccc   120
ccagcgaagg gactggagtg gattgggtat atctatcaca gtgggatgac caactacaac   180
ccctccctca agagtcgagt caccatatca atagacacgt ccaagaacca gttctccctg   240
aagttgagct ctgtgaccgc tgcggacacg gccgtgtatt actgtgcgag aggtgatggc   300
tacaatttct tctggggcca gggaacgctg gtcaccgtct cctca                   345

SEQ ID NO: 200          moltype = DNA   length = 375
FEATURE                 Location/Qualifiers
source                  1..375
                        mol_type = genomic DNA
                        organism = Homo sapiens
SEQUENCE: 200
caggtgcagc tggtggagtc tgggggaggc gtggtccagc ctgggggtc cctgagactc   60
tcctgtgcag cgtctggact cacgttcagt aaccaagatt tccactgggt ccgccaggct   120
ccaggcaagg ggctggaatg ggtggcattt atacgttatg atggaggttt taaaaactat   180
gcagactccg tgaaggccg attcaccatc tccagagaca attcccagaa atgctgtat    240
ctgcaaatgg acagcctgag agttgaagac acggctgtgt attactgtgc gaagtgcggc   300
```

```
gcagaggact ctactactgt ctggctgaat tggttcgacc cctggggcca gggaaccctg    360
gtcaccgtct cctca                                                    375

SEQ ID NO: 201          moltype = DNA  length = 360
FEATURE                 Location/Qualifiers
source                  1..360
                        mol_type = genomic DNA
                        organism = Homo sapiens
SEQUENCE: 201
gaggtgcagc tgttggagtc tgggggaggc ttggtagagc ctggggggtc cctgagactc     60
tcctgtgcag cctctggatt cacctttagc agctatgcca tgagctgggt ccgccaggct    120
ccagggaagg ggctggagtg ggtctcagct attagtgaca gtggtggtag cacatactac    180
gcagactccg tgaagggccg gttcaccatc tccagagaca agtccaagaa cacgctgtat    240
ctgcaaatga acagcctgag agccgaggac acggccgtat attactgtgc gaaaccgaat    300
tactttggtt cggggagtcc cgactactgg ggccaggaa cgctggtcac cgtctcctca    360

SEQ ID NO: 202          moltype = DNA  length = 345
FEATURE                 Location/Qualifiers
source                  1..345
                        mol_type = genomic DNA
                        organism = Homo sapiens
SEQUENCE: 202
caggtgcagc tgcaggagtc gggcccagga ctggtgaagc cttcggagac cctgtccctc     60
acctgcactg tctctggtgc ctccatcagt agtcactact ggagctggat ccggcagccc    120
ccagggaagg gactggagtg gattgggtat atctatcaca gtgggattac caactacaac    180
ccctccctca agagtcgagt caccatatca atagacacgt ccaagaacca gtactccctg    240
aagctgagct ctgtgaccgc tgcggacacg gccgtgtatt actgtgcgag aggtgatggc    300
tacaatttct actggggcca gggaacgctg gtcaccgtct cctca                   345

SEQ ID NO: 203          moltype = DNA  length = 378
FEATURE                 Location/Qualifiers
source                  1..378
                        mol_type = genomic DNA
                        organism = Homo sapiens
SEQUENCE: 203
gaggtgcagc tggtggagtc tgggggaggt gtggtacggc ctgggggtc cctgagactc     60
tcctgtgcag cctctggatt cacctttgat gattatggca tgacctgggt ccgccaagct    120
ccagggaagg ggctggagtg gatctctggt atttgttgca acggtggttg ctcaggttat    180
gcagactctg tgaagggccg attcaccatc tccagacaa cgccaagaa cacgctgttt    240
ctggtcatga acagtctgag agccgaggac acggccttgt attactgtgt gagagtggca    300
gtaccagctg ctacatacac ccgagggaat gatgcttttg atatttgggg ccaagggaca    360
atggtcaccg tctcttca                                                 378

SEQ ID NO: 204          moltype = DNA  length = 357
FEATURE                 Location/Qualifiers
source                  1..357
                        mol_type = genomic DNA
                        organism = Homo sapiens
SEQUENCE: 204
gaggtgcagc tggtggagtc tgggggaggc ttggtagagc ctggggggtc cctcagactc     60
tcctgtgcag tctctggttt cactttcact gacgcctgga tgacctgggt ccgccaggct    120
ccagggaagg ggctagattg ggttggccat gtaaaaagta aatatgatgg tgcgacaaca    180
gagtacgctg cacccgtgca aggcagattc accatctcaa gagatgattc aaagaagaca    240
atatatctgc aaatgaacag cctgaacacc gaggacacag cgtctatttt tgtaccaca    300
gctcatggcc cggtgggtga ccattgggc cagggaacac tggtcaccgt ctcctca      357

SEQ ID NO: 205          moltype = DNA  length = 378
FEATURE                 Location/Qualifiers
source                  1..378
                        mol_type = genomic DNA
                        organism = Homo sapiens
SEQUENCE: 205
gaggtgcagc tggtggagtc tgggggaggc ttggtccagc cgggggggtc cctgagactc     60
tcctgtgcag cctcttggatt cagctttgat acctcttgga tgacctgggt ccgccaggct    120
ccagggaagg ggctggagtg ggtggccacc ataaaccagg tggaagtga caaatactat    180
gtggactctg tgaagggccg attcaccatc tccagagaca cgccaagaa ctcactgtat    240
ctgcaaatga acagcctgcg agccgaggac acggctgtat attactgtgc gagagcgggc    300
gggtgtagct ctaccagatg ccatacaacc ccgggattg actactgggg ccagggagcg    360
ctggtcaccg tctcctca                                                 378

SEQ ID NO: 206          moltype = DNA  length = 353
FEATURE                 Location/Qualifiers
source                  1..353
                        mol_type = genomic DNA
                        organism = Homo sapiens
SEQUENCE: 206
tgcagctgca ggagtcgggc ccaggactgg tgaagccttc ggagaccctg tccctcacct     60
gcactgtctc tggtagctcc atcagcagta gtagttacta ctgggctgg gtccgccagt    120
cccccaggga aggactggag tggattggga gtatctatca cagtgggacc atctactaca    180
```

```
acccgtccct caggagtcga gtcaccatat ccgtagacac gtccaagaac cagttctccc    240
tgaagctgaa ctctgtgacc gccgcagaca cggctgttta ttactgtgcg agtcttagtg    300
gcacaaatgc ttttgatatc tggggccaag ggacaatggt caccgtctct tca           353
```

```
SEQ ID NO: 207              moltype = DNA  length = 360
FEATURE                     Location/Qualifiers
source                      1..360
                            mol_type = genomic DNA
                            organism = Homo sapiens
SEQUENCE: 207
gaggtgcagc tgttggagtc tggggggggc ttggtacagc ctgggggtc cctgagactc     60
tcctgtgcag cctctggatt caccttagc agccatgaca tgagttgggt ccgcctggct    120
ccagggaagg ggccggagtg ggtctcagct cttggtgctg gagatgcttg gacacactac    180
gcaaactccg tgaggggccg gttcaccatc tccagacga attccaagaa cacgctgtat    240
ctgcaaatga acagcctgag agccgaagac acggccgtgt atttctgtgc gaaacccgt    300
ggatactcct atggctactt tgactactgg ggccaaggaa cgctggtcac cgtctcctca    360
```

```
SEQ ID NO: 208              moltype = DNA  length = 351
FEATURE                     Location/Qualifiers
source                      1..351
                            mol_type = genomic DNA
                            organism = Homo sapiens
SEQUENCE: 208
gaggtgcagc tggtggagtc tgggggaggc ttggtccagc ctgggggtc cctgagactc     60
tcctgtggag cctctggatt cacctttagt acctattgga tgacctgggt ccgccaggct    120
ccagggaagg gcctggagtg ggtggccaat ataaaccaag atggaagtga gaaacaatat    180
gtggactctg tgaagggccg attcaccatc tccagagaca acgccaagaa ctcactgtat    240
ctgcagatga acagcctgag agtcgaggat acggctattt attactgtgc gagaccccca    300
gctcgccgac ttgactactg gggccaggga tcgctggtca ccgtctcctc a             351
```

```
SEQ ID NO: 209              moltype = DNA  length = 348
FEATURE                     Location/Qualifiers
source                      1..348
                            mol_type = genomic DNA
                            organism = Homo sapiens
SEQUENCE: 209
gaggtgcagc tggtggagtc cggggaggc ttagttcagc ctgggggtc cctgagactc      60
tcctgtgcag cctctgaatt caccttcagt gactactgga tgcactgggt ccgccaagct    120
ccagggaagg ggctggtctg ggtctcacgt attaatactg acgggagtac cacaacctac    180
gcggactccg tgaagggccg attcaccatc tccagagaca acgccaagaa cacgctgtat    240
ctacaaatga acagtctgag ggccgaggac acggctgtgt attactgtgc aagatctaat    300
gcggggcacg aagcgtgggg ccagggaacg ctggtcaccg tctcctca                 348
```

```
SEQ ID NO: 210              moltype = DNA  length = 353
FEATURE                     Location/Qualifiers
source                      1..353
                            mol_type = genomic DNA
                            organism = Homo sapiens
SEQUENCE: 210
aggtgcagct ggtgcagtct ggggctgagg tgaagaagcc tggggcctca gtgagggttt     60
cctgcaaggc atctggatac accttcacca actactggat acactgggtg cgacaggccc    120
ctggacaagg gcttgagtgg atgggaatga tcgcccctaa ggaaggttac acattctacg    180
cacagcaatt acagggcaga gtcaccgtga ccagggacac gtcgacgagc gcggtttaca    240
tggagctgaa cagcctgaga tctgaggaca cggccgtata tttctgtgcg agagacattc    300
cccacgctaa tttggactat tggggccagg gacgctggt caccgtctcc tca            353
```

```
SEQ ID NO: 211              moltype = DNA  length = 363
FEATURE                     Location/Qualifiers
source                      1..363
                            mol_type = genomic DNA
                            organism = Homo sapiens
SEQUENCE: 211
gaggtgcagc tgttggagtc tgggggagga ttggtacagc ctgggggtc cctgagactc      60
tcctgtgcag cctctggatt cacctttagc gattataca tgaattgggt ccgccaggct    120
ccagggaagg ggctgagtg ggtctcagct attagagaga gtggtgacag cacatactac    180
gcagactccg tgacgggccg gttcaccatc tccaggaca attccagaaa cacactttat    240
ctgcacatga acagcctgag agccgaggac acggccatgt atttttgtgt gaaagacagg    300
gtgccgccgg gtgacgtgcc gggtgacttc tggggcccgg aacgctggt caccgtctcc    360
tca                                                                  363
```

```
SEQ ID NO: 212              moltype = DNA  length = 321
FEATURE                     Location/Qualifiers
source                      1..321
                            mol_type = genomic DNA
                            organism = Homo sapiens
SEQUENCE: 212
gacatccagt tgacccagtc tccatccttc ctgtctgcat ctgtaggaga cagagtcacc     60
atcacttgcc gggccagtca ggacatgacc cattctttag cctggtatca gcaaaaacca    120
gggaaagccc ctaacctcct gatctataat gcatacactt tgcaaagtgg ggtcccatca    180
```

```
aggttcagcg gcagtggatc tgggacagaa ttcactctca caatcagcag cctgcagcct   240
gaagattttg caacttatta ctgtcaacag attaatagtt accctcgaac ttttggccag   300
gggaccaagg tggagatcaa a                                             321

SEQ ID NO: 213           moltype = DNA  length = 321
FEATURE                  Location/Qualifiers
source                   1..321
                         mol_type = genomic DNA
                         organism = Homo sapiens
SEQUENCE: 213
gaaattgtgt tgacacagtc tccaggcacc ctgtctttgt ctccagggga aagagccact   60
ctctcctgca gggccagtca gaatattggc accgccttag cctggtacca acagaaacct   120
ggccaggctc ccagactcat catctatgaa acatccaaca gggccactga cgtcccagcc   180
aggttcagtg gcagtgggtc tgggacagac ttcactctca ccatcagcag cctggagcgt   240
gaagattttg ccctttatta ctgtcaacag cgtgccgact ggccgctcac tttcggcgga   300
gggaccaagg tggagatcaa a                                             321

SEQ ID NO: 214           moltype = DNA  length = 324
FEATURE                  Location/Qualifiers
source                   1..324
                         mol_type = genomic DNA
                         organism = Homo sapiens
SEQUENCE: 214
gaaattgtgt tgacacagtc tccagccacc ctgtctttgt ctccagggga aagagccacc   60
ctctcctgca gggccagtca gagtgttagc agctacttag cctggtacca acagagacct   120
ggccaggctc ccaggctcgt catctatgct gcatccaaca gggccactgg catcccagcc   180
aggttcagtg gcagtgggtc tgggacagac ttcactctca ccatcagcag cctagagcct   240
gaagattttg cagtttatta ctgtctgcag tgtagcaact ggcccatgta cacttttggc   300
caggggacca aggtggagat caaa                                          324

SEQ ID NO: 215           moltype = DNA  length = 321
FEATURE                  Location/Qualifiers
source                   1..321
                         mol_type = genomic DNA
                         organism = Homo sapiens
SEQUENCE: 215
gacatccagt tgacccagtc tccatccttc ctgtctgcat ctgtagggga cagagtcacc   60
atcacttgcc gggccagtca ggacattacc gattctttag cctggtatca gcaaaaacca   120
gggaaagccc ctaacctcct gatctatact gcatccactt tgcaaagtgg ggtcccatca   180
aggttcagcg gcagtggatc tgggacagaa ttcactctca caatcagcag cctgcagcct   240
gaagatttta caacttatta ctgtcaacag attaatagtt accctcgaac ttttggccag   300
gggaccaagg tggagatcaa a                                             321

SEQ ID NO: 216           moltype = DNA  length = 321
FEATURE                  Location/Qualifiers
source                   1..321
                         mol_type = genomic DNA
                         organism = Homo sapiens
SEQUENCE: 216
gacatccaga tgacccagtc tccatcctcc ctgtctgcat ctgtaggaga cagagtcacc   60
atcacttgcc gggcaagtca gggcattaga aatgatttag gctggtatca gcagaaaacca  120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caagttatta ctgtctacag catagtagtt cccgtggac gttcggccag    300
gggaccaagg tggaaatcaa a                                             321

SEQ ID NO: 217           moltype = DNA  length = 342
FEATURE                  Location/Qualifiers
source                   1..342
                         mol_type = genomic DNA
                         organism = Homo sapiens
SEQUENCE: 217
gacatcgtga tgacccagtc tccagactcc ctggctgtgt ctctgggcga gagggccgcc   60
atcaactgca agtccagcca gagtgtctta gacagctcaa acatgaagag gtacttagcc   120
tggtatcagc tgaaagcagg acagcctcct aaggttgctca tttacttggc ttccacccgg   180
gaatccgggg tccccggaccg attcagtggc agcgggtccg ggacagattt caatctcact   240
atcagcagcc tgcaggctga agatgtggca gtttattact gtcagcaata ttatacaacc   300
ccttcgatcc ccttcggcca agggacacga ctggagatta aa                      342

SEQ ID NO: 218           moltype = DNA  length = 342
FEATURE                  Location/Qualifiers
source                   1..342
                         mol_type = genomic DNA
                         organism = Homo sapiens
SEQUENCE: 218
gacatcgtga tgacccagtc tccagactcc ctggctgtgt ctctgggcga gagggccacc   60
atcaactgca agtccagcca gagtgtttta tacagctcca acaataagaa ctacttagct   120
tggtaccagc agaaaccagg tcagcctcct aagatgctca tttactgggc atctacccgg   180
gagtccgggg tccctgaccg attcagtggc agcgggtctg gacagatttc cactctcacc   240
```

```
atcagcagcc tgcaggctga agatgtggca gtttattact gtcagcaata ttatactact   300
cctcccatca ccttcggcca agggacacga ctggagatta aa                      342

SEQ ID NO: 219          moltype = DNA   length = 318
FEATURE                 Location/Qualifiers
source                  1..318
                        mol_type = genomic DNA
                        organism = Homo sapiens
SEQUENCE: 219
gaaattgtgt tgacacagtc tccagccacc ctgtctttgt ctccagggga aagagccacc   60
ctctcctgca gggccagtca gagtgttagt atctacttag cctggtacca acagaaacct   120
ggccaggctc ccaggctcct catctatgat tcatccaaca gggccactgg catcccagcc   180
aggttcagtg gcagtgggtc tgggacagac ttcactctca ccatcagcag cctagagccc   240
gaagattttg cggtttatta ctgtcagcag cgtagcagcg ggcgaacgtt cggccaaggg   300
accaaggtgg agatcaaa                                                 318

SEQ ID NO: 220          moltype = DNA   length = 324
FEATURE                 Location/Qualifiers
source                  1..324
                        mol_type = genomic DNA
                        organism = Homo sapiens
SEQUENCE: 220
gaaattgtgt tgacgcagtc tccaggcacc ctgtctttgt ctccagggga aagagccacc   60
ctctcctgca gggccagtca gactgttacc aacaactact agcctggtta ccaacacaaa   120
cctggcctgg cgcccaggct cctcatcttt gatgcatcca tcagggccac tggcatccca   180
gacaggttca gtggcagtgg gtctggggca gacttcactc tcaccatcag cagactggag   240
cctgaagatt ttacattcta ttactgtcag caatatggta tttcacctcg aacttttggc   300
caggggacca aggtggagat caaa                                          324

SEQ ID NO: 221          moltype = DNA   length = 336
FEATURE                 Location/Qualifiers
source                  1..336
                        mol_type = genomic DNA
                        organism = Homo sapiens
SEQUENCE: 221
gatattgtga tgacccagac tccactctct ctgtccgtca cccctggaca gccggcctcc   60
atctcctgca gtctagtca gagtctcctg gatagtgatg gaaggaccta tttcttttgg   120
tatttgcaga agccaggcca gtctccacaa ctcctgatct atgaagtttc caaccggttc   180
tctggagtgc cagataggtt cagtggcagc gggtcaggga cagatttcac actgaaaatc   240
agccgggtgg agtctgaaga tgttggggtt tattactgca tgcaaggtac acaccatccg   300
tggacgttcg gccaagggac caaggtggaa atcaaa                             336

SEQ ID NO: 222          moltype = DNA   length = 340
FEATURE                 Location/Qualifiers
source                  1..340
                        mol_type = genomic DNA
                        organism = Homo sapiens
SEQUENCE: 222
gacatcgtga tgacccagtc tccagactcc ctggctgtgt ctctgggcga gagggccacc   60
gtcaactgca gtccagcca gagtgtttta tacagctcca acagtaagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtgtattact gtcagcaata ttatagtact   300
cctctcactt tcggcggagg gaccaaggtg gagatcaaac                         340

SEQ ID NO: 223          moltype = DNA   length = 322
FEATURE                 Location/Qualifiers
source                  1..322
                        mol_type = genomic DNA
                        organism = Homo sapiens
SEQUENCE: 223
gacatccaga tgacccagtc tccatcctcc ctgtctgcat ctgtgggaga cagagtcacc   60
atcacttgcc gggcaagtca gggcattggg aatgatttag gctggtatca gcatgaacca   120
gggaaagccc ctaagcgcct gatctatgca gcatccagtt tgcaaagtgg ggtcccatcg   180
aggttcagcg gcagtgcatc tgggacagaa ttcactctca caatcaccag cctgcagcct   240
gaagattttg caacttatta ctgtctacaa catactactt cccgtggac gttcggccaa   300
gggaccaagg tggaaatcaa ac                                            322

SEQ ID NO: 224          moltype = DNA   length = 325
FEATURE                 Location/Qualifiers
source                  1..325
                        mol_type = genomic DNA
                        organism = Homo sapiens
SEQUENCE: 224
gaaattgtgt tgacacagtc tccagccacc ctgtctttgt ctccagggga aagagccacc   60
ctctcctgca gggccagtca gagtgttggc agtcacttcg cctggtacca acagaaacct   120
ggccaggctc ccaggctcct catctatggt gcatccaaca gggcccctgg catcccacct   180
aggttcagtg ccagtggatc tgggacagac ttcactctca ccatcagcag cctagagcct   240
```

```
gaagattttg caatttatta ctgtcaacag cgtaggacct ggcctccgct aaccttcggc   300
caagggacac gactggagat taaac                                         325

SEQ ID NO: 225          moltype = DNA   length = 357
FEATURE                 Location/Qualifiers
source                  1..357
                        mol_type = genomic DNA
                        organism = Homo sapiens
SEQUENCE: 225
gaggtgcagc tggtggagtc tgggggaggc ttggtacagc ctggagggtc cctgagactc    60
tcctgtgtag cctctggatt cagtttcagt ggtcatgaaa tgaactgggt ccgccagcct   120
ccagggaagg ggctggagtg ggtttcacac attggcagtg gtggtgatta tataggttac   180
gcagactctg tgaagggccg attcaccgtc tctagagaca cgccaagaa tttactctat    240
ctgcaaatga acagcctgag agccgacgac acggctgttt attactgtgc gaccttgctt   300
ttgcgagaca accaactgga cgtctggggc caagggacca cggtcaccgt ctcctca      357

SEQ ID NO: 226          moltype = DNA   length = 363
FEATURE                 Location/Qualifiers
source                  1..363
                        mol_type = genomic DNA
                        organism = Homo sapiens
SEQUENCE: 226
caggtgcagc tggtggagtc tgggggaggc gtggtccagc cagggaggtc cctaagactc    60
tcctgtgcag cctctggatt caccctcagt agttgtggca tgcactggat ccgccaggct   120
ccaggcaagg ggctggagtg ggtggcagtt ataacatatg atggacgaag tcacttcaac   180
gcagacgccg tgaagggccg attcaccatc tccagagaca gatccatgaa cacggtgtct   240
ctgcaaatgg acagcctgag acccgaggac acggctgttt attactgtgt caaagaacaa   300
ggctttggtt actaccggac cgccgactac tggggccagg gaacccctggt caccgtctcc   360
tca                                                                363

SEQ ID NO: 227          moltype = DNA   length = 342
FEATURE                 Location/Qualifiers
source                  1..342
                        mol_type = genomic DNA
                        organism = Homo sapiens
SEQUENCE: 227
caggtgcagc tgcaggagtc gggcccagga ctggtgaggc cttcggagac cctgtccctc    60
acctgcactg tctctggtgg ctccatcagt agtgaccact ggagttggat ccggcagccc   120
ccagggaagg gactggagtg gattgggaat gtctattaca gtgggcgcac ctactacaac   180
ccctccttca gagtcgagt caccatatca gtagccacgt ccaagaacca gttctccctg    240
aaggtgacct ctgtgaccgc cgcagacacg gccatttatt actgtgcgag gcgaaatgat   300
tttaatatct ggggccaggg gacaatggtc accgtctctt ca                     342

SEQ ID NO: 228          moltype = DNA   length = 369
FEATURE                 Location/Qualifiers
source                  1..369
                        mol_type = genomic DNA
                        organism = Homo sapiens
SEQUENCE: 228
gaggtgcagc tgttggagtc tgggggaggc ttggtacagc ctgggggtc cctgagactc     60
tcctgtgcag cctctggatt caccttagt aaatatgccg tgagctgggt ccgccaggct    120
ccagggaagg ggctggagtg ggtctcagct gtcagtggta atggtgactc cacatactac   180
gcagaccccg tgaggggccg gttcaccatc tccagagaca attccaagaa caccctgtat   240
ctgcaaatga acagcctgag agccgaggac acggccctat attactgttc gatctggtgg   300
gggacttcag tacagtaccc attggtgctc gactactggg gctgggaac cctggtcacc    360
gtctcctca                                                          369

SEQ ID NO: 229          moltype = DNA   length = 363
FEATURE                 Location/Qualifiers
source                  1..363
                        mol_type = genomic DNA
                        organism = Homo sapiens
SEQUENCE: 229
caggtgcagc tggtggagtc gggggaggc gtggtccagc ctggggaggtc cctaagactc    60
ctgtgtgcag cctctggatt caccctcagt acttgtggca tgcactggat ccgccagact   120
cctggcaagg ggctggagtg ggtggcagtt aaaacatatg acggaagaga ggagttctac   180
gcagactccg tgaagggccg attcaccatt tccagagacg agtccatgaa cacgctgtct   240
ttgcagatga acagcctgag acctgaagac acggctgtat attactgtgt caaagaacaa   300
gactacggtt actaccggac cgccgaccac tggggccagg gaacccctggt caccgtctcc   360
tca                                                                363

SEQ ID NO: 230          moltype = DNA   length = 351
FEATURE                 Location/Qualifiers
source                  1..351
                        mol_type = genomic DNA
                        organism = Homo sapiens
SEQUENCE: 230
caggtgcagc tgcaggaggc gggcccagga ctggtgaagc cttcacagac cctgtccctc    60
acctgcactg tctctggtgg ctccatcagc agtggtggtt actactggag ctggatccgc   120
```

```
cagcacccag ggaagggcct ggagtggatt gggtacatct attacagtgg gagcacctac    180
tacaacccgt ccctcaagag tcgagtcacc atatcagtag acacgtccaa gaaccagtat    240
tccctgaagc tgagttctgt gaccgccgca gacacggccg tatattactg tgcgagaggg    300
catggcttca acgcctactg gggccaggga accctggtca ccgtctcctc a             351

SEQ ID NO: 231          moltype = DNA   length = 366
FEATURE                 Location/Qualifiers
source                  1..366
                        mol_type = genomic DNA
                        organism = Homo sapiens
SEQUENCE: 231
gaggtgcagc tggtggagtc cggggggaggc ttggtaaagc cggggagtc ccttagactc     60
tcgtgtgcaa cctctggagt caacttcaac atcgcctgga tgacctgggt ccgccaggct    120
ccagggaagg gactggagtg ggttggccgt attaaaagca aaattggtgg tgggacaaca    180
gactatgctg cacccgtgaa aggcagattc accatgtcaa tagatgattc aaaaaatacc    240
ctatatctgc aaatgaacag cctgaaaacc gaggacacag ccgtgtatta ttgtaccaca    300
gtccgcaata tggccgactt gtcccttaat cactggggcc agggaaccct ggtcaccgtc    360
tcctca                                                               366

SEQ ID NO: 232          moltype = DNA   length = 354
FEATURE                 Location/Qualifiers
source                  1..354
                        mol_type = genomic DNA
                        organism = Homo sapiens
SEQUENCE: 232
gaggtgcagc tggtggagtc tgggggaggc ttggtacagc ctggagcgtc cctgacactg     60
tcatgtgtag tctctggatt caccttcatt ggcactgaaa tgacctggat tcgccaggct    120
ccagggaagg ggctggaggg actttcgtac atcagtggga gtggcgggac aacatactac    180
gcagagtctg tgaggggccg attcaccatc tccagagaca cgccaagaa gtcactgttt     240
ctgcaaatga ccagcctgac agccgaggac acggctgttt actactgtgc gacaggcaac    300
cggggatcac ttcctcgccg ctggggccag ggaaccctgg tcaccgtctc ctca           354

SEQ ID NO: 233          moltype = DNA   length = 354
FEATURE                 Location/Qualifiers
source                  1..354
                        mol_type = genomic DNA
                        organism = Homo sapiens
SEQUENCE: 233
gaggtgcagc tggtggagtt tgggggaggc ttggtccagc ctggggggtc cctgagactc     60
tcctgtgtag cctctggatt cacctttagt tcctcttgga tgagttgggt ccgccaggct    120
ccagggaagg ggctggagtg cgtgggcaac ataaagccgg atgcaagttt ggtgtcctat    180
gtggactctg tgaagggccg agtcaccatc tccagagaca cgccaagaa ttcactgttt     240
ctggatatga gcagcctgag agtcgaggac acggccgtct actactgtgt gagagacggg    300
tgggacacct tctttgactc ctggggccag ggaaccctgg tcaccgtctc ctca           354

SEQ ID NO: 234          moltype = DNA   length = 339
FEATURE                 Location/Qualifiers
source                  1..339
                        mol_type = genomic DNA
                        organism = Homo sapiens
SEQUENCE: 234
gaggtgcagc tggtggagtc cggggggaggc ttagttcagc cggggggggtc cctgagactc    60
tcctgtgcag cctctggatt cacctttagt aactactgga tgaggtgggt ccgccaatct    120
ccagggaagg ggctggtgtg ggtctcacat attaaccctg atgggagttt tacaaactac    180
gcggactccg tgaagggccg attcaccatc tccagagaca caccaagaa cacactgtat     240
ctgcaaatga acagtctgag agccgaggac acggctgtgt attactgtgt gaattttcaa    300
ctggggtggg gccaggggaac cctggtcacc gtctcctca                          339

SEQ ID NO: 235          moltype = DNA   length = 369
FEATURE                 Location/Qualifiers
source                  1..369
                        mol_type = genomic DNA
                        organism = Homo sapiens
SEQUENCE: 235
caggtgcagc tggtggagtc tgggggaggc gtagtccagc ctggggaggtc cctgaaactc     60
tcctgtgcag tcgctggatt caccttcagg acctatgcta tgcactgggt ccgccaggct    120
ccaggcaggg ggctggagtg ggttggcactt atatcaaatg atggaaccaa aaaatactca    180
gcagactccg tgaggggcca cttcaccatc tccagagaca attccaagga cacgctgtat    240
ctgcaaatga acagcctgcg acctgacgac acggctgtct attactgtgc gagagcggag    300
tattgtagtc ctggtgactg cttccttatt gacacctggg gccagggaac cctggtcacc    360
gtctcctca                                                            369

SEQ ID NO: 236          moltype = DNA   length = 357
FEATURE                 Location/Qualifiers
source                  1..357
                        mol_type = genomic DNA
                        organism = Homo sapiens
```

```
SEQUENCE: 236
caggtgcagc tggtggagtc tgggggaggc gtggtccagc ctgggaggtc cctgagactc   60
tcctgtgcag tgtctggatt cacctgagt agatacggca tgcactgggt ccgccaggct  120
ccaggcaagg ggctggagtg ggtggtagtt atatggcatg atggaagtaa tacatactat  180
gcagactccg tgaagggccg attcaccatc tccagagaca actccaagaa cacggtgtat  240
ctgcaaatga acagcctcag agtcgaggac acggctatgt attactgtct gagaggcaac  300
ccacctagca gccccaccga ctactggggc cagggaaccc tggtcaccgt ctcctca     357

SEQ ID NO: 237          moltype = DNA  length = 357
FEATURE                 Location/Qualifiers
source                  1..357
                        mol_type = genomic DNA
                        organism = Homo sapiens
SEQUENCE: 237
gaggtgcagc tgttggagtc tgggggaggc ttggtacagc ctgggggtc cctgagactc    60
tcctgtgaag tctctggatt catctttagc aactatgcca tgacctgggt ccgccaggct  120
ccagggaagg ggctgcagtg ggtctcagct attggcacta gtggtggtga cacacactac  180
gcagactccg tgaagggccg gttcaccatc tccagacaca attcccagaa caccctgttt  240
ctgcagatga acagcctgag agccgaggac acggccatat attactgtgc gaaagtcgtt  300
tatagcaggc ctcctatgga cgtctggggc caagggacca cggtcaccgt ctcctca     357

SEQ ID NO: 238          moltype = DNA  length = 354
FEATURE                 Location/Qualifiers
source                  1..354
                        mol_type = genomic DNA
                        organism = Homo sapiens
SEQUENCE: 238
gaggtgcagc tggtggagtc tgggggaggc ttggtccagc ctgggggtc cctgagactc    60
tcctgtgcag cctctggatt cacctttagt aatcgttgga tgagttgggt ccgccaggct  120
ccagggaagg ggctggaatg ggtggccaac ataaacggag atggaagtca gaaacactat  180
gtggactctg tgaggggccg attcaccatc tccagagaca acgccaagaa ctcactgtct  240
ctgcaaatgg acagcctgag agtcgaggat acggccgtgt attattgcgc gagagcatcg  300
agggagaccg tgaaccttta ctggggccag ggaaccctgg tcaccgtctc ctca        354

SEQ ID NO: 239          moltype = DNA  length = 329
FEATURE                 Location/Qualifiers
source                  1..329
                        mol_type = genomic DNA
                        organism = Homo sapiens
SEQUENCE: 239
ttgtgatgac tcagtctcca ctctccctgc ccgtcaccct tggacagtcg gcctccatct   60
cctgcaggtc tagtcgaagc ctcgtattca gtgatggaaa cacctacttg aattggtttc  120
agcaggagg aggccgatct ccaaggcgcc taatttataa ggttctaag cgggactctg    180
gggtcccaga cagattcagc ggcagtgggt cagacactga tttcacactg aaaatcagca  240
gggtggagc tgaggatgtt gggggtttatt actgcatgca aggtacacac tggcggacgt  300
tcggccaagg gaccaaggtg gagatcaaa                                    329

SEQ ID NO: 240          moltype = DNA  length = 321
FEATURE                 Location/Qualifiers
source                  1..321
                        mol_type = genomic DNA
                        organism = Homo sapiens
SEQUENCE: 240
gacatccaga tgacccagtc tccttccaca ctgtctgcat ctgtgggaga cagagtcacc   60
atcacttgcc gggccagtca gagtattaat tcctggttgg cctggtatca gcggaaacca  120
gggaaaaccc ctaaactcct catctatgag gcgtccagtt tagaaagtgg ggtcccatca  180
aggttcagcg gcagtagatc tgggacagag ttcaccctca ccatcagcag cctgcaggct  240
gatgattttg caacttatta ctgccaccag tatgataaat atccgtggac gttcggccaa  300
gggaccaagg tggagatcaa a                                            321

SEQ ID NO: 241          moltype = DNA  length = 324
FEATURE                 Location/Qualifiers
source                  1..324
                        mol_type = genomic DNA
                        organism = Homo sapiens
SEQUENCE: 241
gaaattgtgt tgacgcagtc tccaggcacc ctgtctttgt ctccagggga aagagccacc   60
ctctcctgca gggccagtca gagtgtgacc aacaactatt tggtctggca ccagcagaaa  120
cctggccagg ctcccaggct cctcatttct gatgcatcca acagggccac tggcatccca  180
gacaggttca gtggcagtgg gtctgggaca gacttcactc tcaccatcaa cagactggag  240
cctgaagatt tcgcagtgta ttactgtcag caatacggta gctcaccttt cactttcggc  300
cctgggacca aagtggatat caaa                                         324

SEQ ID NO: 242          moltype = DNA  length = 324
FEATURE                 Location/Qualifiers
source                  1..324
                        mol_type = genomic DNA
                        organism = Homo sapiens
```

```
SEQUENCE: 242
gaaatagtga tgacgcagtc tccagccacc ctgtctgtgt ctccagggga aagagtcacc    60
ctctcctgca gggccagtca gagtattggc agcagcttag cctggtacct gcagaaacct   120
ggccaggctc ccagagtcct catctatggt gcatccacca ggaccctgg cacccccagc   180
aggttcagtg gcagtgggtc tgggacagag ttcactctca ccatcagcag cctgcagtct   240
gaagatcttg cgatttatta ttgtcaacag tatagtaagt ggcctccgat caccttcggc   300
caagggacac gactggagat taaa                                          324

SEQ ID NO: 243              moltype = DNA   length = 321
FEATURE                     Location/Qualifiers
source                      1..321
                            mol_type = genomic DNA
                            organism = Homo sapiens
SEQUENCE: 243
gacatccaga tgacccagtc tcctccatc ctgtctgcat ctgtaggaga cagagtcacc    60
atcaattgcc gggccagtca gagtattaat gcctggttgg cctggtatca gcagaaacca   120
gggaaagccc ctaaattcct aatttataag gcgtctagtt tagaaagtgg ggtctcgtca   180
aggttcagtg gcagtggatc tgggacagaa ttcaccctca tcatcagcag cctgcagcct   240
gatgattttg caacttatta ctgccaacag tatgataaat atccgtggac gttcggccgg   300
gggaccaagg tggagatcaa a                                             321

SEQ ID NO: 244              moltype = DNA   length = 324
FEATURE                     Location/Qualifiers
source                      1..324
                            mol_type = genomic DNA
                            organism = Homo sapiens
SEQUENCE: 244
gaaattgtgt tgacgcagtc tccaggcacc ctgtctttct ctccagggga tagagccacc    60
ctctcctgca gggccagtca gagtgttagc agcagctcct tagcctggta ccagcagaga   120
cctggccagg ctcccagcct cctcatctat ggtgcatccg gcagggccac tggcatccca   180
gacaggttca gtggcagtgg gtctgggaca gacttcactc tcaccatcag cagactggaa   240
cctgaagatt ttgcagtgta ttactgtcag cagtatggta actcacctcg gacgttcggc   300
caagggacca aggtggagat caaa                                          324

SEQ ID NO: 245              moltype = DNA   length = 324
FEATURE                     Location/Qualifiers
source                      1..324
                            mol_type = genomic DNA
                            organism = Homo sapiens
SEQUENCE: 245
gaaattgtgt tgacgcagtc tccaggcacc ctgtctttgt ctccagggga aagagccacc    60
ctctcctgca gggccagtca gagtgtcagc agcacctact taaactggta ccagcagaag   120
cctggccagg ctcccaggct cctcatctat ggtgcgtcca gcagggccac tggcatccca   180
gacaggttca gtggcagtgg gtctgggaca gacttcactc taaccatcag cagactggaa   240
cctgaagact ttgcagtgta ctactgtcag caatatgatg actcacggtg gacgttcggc   300
caagggacca aggtggaaat caaa                                          324

SEQ ID NO: 246              moltype = DNA   length = 336
FEATURE                     Location/Qualifiers
source                      1..336
                            mol_type = genomic DNA
                            organism = Homo sapiens
SEQUENCE: 246
gatattgtga tgactcagtc tccactctcc ctgcccgtca cccctggaga gccggcctcc    60
atctcctgca ggtctggtca gagcctcctg tatagtgatg gaaacaacta tttggattgg   120
tatctgcaga agccagggca gtctccacag ctcctgatct atttgggttc taatcgggcc   180
tccggggtcc ctgacaggtt cagtggcagt gaatcaggca cagattttac actgaaaatc   240
agcagagtgg aggctgggga tgttgggatt tattactgca tgcaagctct acgaagtccg   300
tacactttg gccaggggac caaggtgag atcaaa                              336

SEQ ID NO: 247              moltype = DNA   length = 332
FEATURE                     Location/Qualifiers
source                      1..332
                            mol_type = genomic DNA
                            organism = Homo sapiens
SEQUENCE: 247
ttgtgatgac tcagtctcca ctctccctgc ccgtcaccct tggacagccg gcctccatct    60
cctgcaggtc tagtcaaagc cccgtataca gtgatggaaa cacctacctg aattggtttc   120
agcagaggcc aggccaatct ccaaggcgcc taatttataa ggtttctaac cgggactccg   180
gggtcccaga cagattcagc ggcagtgggt caggcactga tttcacactg aatatcagca   240
gggtggaggc tgaggacgtt gggggtttatt actgcatgca aggtagatac tggccgtaca   300
cttttggcca ggggaccaag gtggagatca aa                                 332

SEQ ID NO: 248              moltype = DNA   length = 324
FEATURE                     Location/Qualifiers
source                      1..324
                            mol_type = genomic DNA
                            organism = Homo sapiens
```

```
SEQUENCE: 248
gaaattgtgt tgacgcagtc tccaggcacc ctgtctttct ctccagggga tagagccacc    60
ctctcctgca gggccagtca gagtgtaagc agcagcgcct tagcctggta ccagcagaaa   120
cctggccagg ctcccagcct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta actcacctcg gacgttcggc   300
caagggacca aggtggaaat caaa                                          324

SEQ ID NO: 249            moltype = DNA   length = 330
FEATURE                   Location/Qualifiers
source                    1..330
                          mol_type = genomic DNA
                          organism = Homo sapiens
SEQUENCE: 249
ttgtgatgac tcagtctcca ctctccctgc ccgtcaccct tggacagtcg gcctccatct    60
cctgcaggtc tagtcgaagc ctcgtattca gtgatggaaa cacctacttg aattggtttc   120
agcagaggcc aggccgatct ccaaggcgcc taatttataa ggtttctaag cgggactctg   180
gggtcccaga cagattcagc ggcagtgggt cagacactga tttcacactg aaaatcagca   240
gggtggaggc tgaggatgtt ggggtttatt actgcatgca aggtacacac tggcggacgt   300
tcggccaagg gaccaaggtg gaaatcaaac                                    330

SEQ ID NO: 250            moltype = DNA   length = 321
FEATURE                   Location/Qualifiers
source                    1..321
                          mol_type = genomic DNA
                          organism = Homo sapiens
SEQUENCE: 250
gacatccaga tgacccagtc tccttcctca ctgtctgcat ctgtagggga cagaatcacc    60
atcacttgtc gggcgagtca gggcattaac aattatttag cctggtttca gcagaagcca   120
gggaaagccc ctaagaccct gatctactct acatccactt tgcaaagtgg ggtcccatca   180
aagttcagcg gcagtggatc tgggacagtt ttcactctca ccatcagcag cctgcagcct   240
gaagattttg caacttatta ctgtcaacaa tataatagtt accgctcac tttcggcgga   300
gggaccaagg tggagatcaa a                                             321

SEQ ID NO: 251            moltype = DNA   length = 321
FEATURE                   Location/Qualifiers
source                    1..321
                          mol_type = genomic DNA
                          organism = Homo sapiens
SEQUENCE: 251
gacatccaga tgacccagtc tccatcctcc ctgtctgcat ctgtaggaga cagagtcacc    60
atcacttgcc gggcaagtca gaccattagc aactatttaa attggtttca gcagaaacca   120
gggaaagccc ctaggctcct gatctatgct gcatccagtt tgcaaagtgg tgtcccatca   180
aggttcagtg gcagtggatc tgtgacagat ttcactctca ccatcagcag tctgcaacct   240
gaagattttg caacttactt ctgtcaacag agttacagca cccgtggac gttcggccaa   300
gggaccaagg tggaaatcaa a                                             321

SEQ ID NO: 252            moltype = DNA   length = 332
FEATURE                   Location/Qualifiers
source                    1..332
                          mol_type = genomic DNA
                          organism = Homo sapiens
SEQUENCE: 252
ttgtgatgac tcagtctcca ttctccctgc ccgtcaccct tggacagccg gcctccatct    60
cctgcaggtc tagtcaaagc ctcgtataca gtgatggaaa cacctacttg aattggtttc   120
agcagaggcc aggccaatct ccaaggcgcc tgatttataa gctttctaac cgggactctg   180
gggtcccaga cagattcagc ggcagtgggt caggcactga tttcacactg aaaatcagca   240
gggtggaggc tgaggatgtt ggggtttatt actgcatgca agctacacac tggccttgga   300
cgttcggcca agggaccaag gtggaaatca aa                                 332

SEQ ID NO: 253            moltype = AA    length = 116
FEATURE                   Location/Qualifiers
source                    1..116
                          mol_type = protein
                          organism = Homo sapiens
SEQUENCE: 253
EVQLLESGGG LVQPGGSLRV SCAASGFTFS NSGMSWVRQA PGKGLEWVSG IGGGGGSAYY    60
ADSVKGRFTI SRDNSKNTLY LQMNNLRAED TAVYYCAKGV TSFDYWGQGI LVTVSS       116

SEQ ID NO: 254            moltype = AA    length = 118
FEATURE                   Location/Qualifiers
source                    1..118
                          mol_type = protein
                          organism = Homo sapiens
SEQUENCE: 254
EVQLVESGGG LVQPGGSLRL SCAASGFTVS SDYMSWVRQA PGKGLEWVSV MYSGGSTYYA    60
DAVKDRFTIS RDNSKNILYL QMNSLRAEDT AVYYCARDPG IRNGMGVWGQ GTTVTVSS    118

SEQ ID NO: 255            moltype = AA    length = 121
```

```
FEATURE              Location/Qualifiers
source               1..121
                     mol_type = protein
                     organism = Homo sapiens
SEQUENCE: 255
EVQLLESGGA LVQPGGSLRL SCAASGFTFT SFAMGWVRQA PGKGLEWVSA VTGSGYYKNY    60
ADSVKGRFTI SRDNSDNTLY LQMNSLRGDD TALYYCAKAH RGDWNNFFDY WGQGTLVTVS   120
S                                                                  121

SEQ ID NO: 256       moltype = AA  length = 115
FEATURE              Location/Qualifiers
source               1..115
                     mol_type = protein
                     organism = Homo sapiens
SEQUENCE: 256
QVQLQESGPG LVKPSETLSL TCSVSADSFS PYKWSWIRQP PGKGLEWIGY IYSSGNTNYN    60
PPLKSRVTIS LDTSKNQVSL RLSSVAAADT AMYYCAREWS GFDFWGQGTM VTVSS        115

SEQ ID NO: 257       moltype = AA  length = 115
FEATURE              Location/Qualifiers
source               1..115
                     mol_type = protein
                     organism = Homo sapiens
SEQUENCE: 257
EVQLVESGGG LVQPGGSLRL SCAASGFTFT NYWMSWVRQA PGKGLEWVAN IKQDGRETYY    60
VDSVKGRFTI SRDNAKNSVS LQMSSLRAED TAVYYCARGQ WLAFRGQGTL VTVSS        115

SEQ ID NO: 258       moltype = AA  length = 116
FEATURE              Location/Qualifiers
source               1..116
                     mol_type = protein
                     organism = Homo sapiens
SEQUENCE: 258
EVQLVESGGG LVQIGGSLRL SCAASGFTFS TYWMSWVRQA PGKGLECVAS IKEDGSERYY    60
VDSVKGRFTI SRDNAKNSLH LQMDSLRAAD TAVYFCARGR NNFRHWGQGT LVTVSS       116

SEQ ID NO: 259       moltype = AA  length = 126
FEATURE              Location/Qualifiers
source               1..126
                     mol_type = protein
                     organism = Homo sapiens
SEQUENCE: 259
EVQLVESGGG LVQPGGSLRL SCAASGFAIS GNYMSWVRQA PGKGLEWVSL IYWTDDTVYA    60
DSVKGRFTIS RDVSKNMVHL QMSSLRVEDT AVYYCARELG VFHSGGDQWL GPLDCWGQGT   120
LVTVSS                                                             126

SEQ ID NO: 260       moltype = AA  length = 120
FEATURE              Location/Qualifiers
source               1..120
                     mol_type = protein
                     organism = Homo sapiens
SEQUENCE: 260
EVQLVESGGG LVQPGQSLRL SCTVSGFSVE DHGLNWVRQA PGKGLEWVGF IRRKSSGGTE    60
YAASVKGRFT ISRDDSKSAV YLQMNSLKME DTGVYYCLRW TGGVSFGAYW GQGTLVTVSS   120

SEQ ID NO: 261       moltype = AA  length = 116
FEATURE              Location/Qualifiers
source               1..116
                     mol_type = protein
                     organism = Homo sapiens
SEQUENCE: 261
EVQLVESGGG LVQPGGSLRL SCAASGFTFT SWMHWVRQAP GKGLVWVSHI NTDGSSTSYA    60
DSVKGRFTIS RDNAKNTLYL QMNSLRAEDT AVYYCARDYY HSVDYWGQGT LVTVSS       116

SEQ ID NO: 262       moltype = AA  length = 117
FEATURE              Location/Qualifiers
source               1..117
                     mol_type = protein
                     organism = Homo sapiens
SEQUENCE: 262
QVQLQESGPG MVKPSETLSL ICSVSGASVS RDHWSWIRQS PGKGLEWIVY IYNSESIEYN    60
PSLKSRVTIS VDTSKNQVSL TVTSVTAADT AFYYCARGPD AHKTGYWGPG TLVTVSS      117

SEQ ID NO: 263       moltype = AA  length = 117
FEATURE              Location/Qualifiers
source               1..117
                     mol_type = protein
                     organism = Homo sapiens
```

```
SEQUENCE: 263
EVQLVESGGG LVQPGGSLRL SCAASGFTFS NFWMYWVRQV PGKGLVCVSR INRDGSITLY      60
ADSVRGRFTI SRDNAKNTLY LQMNSLRVED TAVYYCARDS YTSPDYWGQG TLVTVSS       117

SEQ ID NO: 264              moltype = AA  length = 120
FEATURE                     Location/Qualifiers
source                      1..120
                            mol_type = protein
                            organism = Homo sapiens
SEQUENCE: 264
EVQLVESGGG LVKPGESLRL SCATSGLTFS NVWMSWVRQA PGKGLEWVGR LKNKPDGGTT      60
DYAAPVKGRF TISRDDSKTT LYLEMNSLKV EDTAVYYCTT DNGVKAFDIW GQGTMVTVSS    120

SEQ ID NO: 265              moltype = AA  length = 118
FEATURE                     Location/Qualifiers
source                      1..118
                            mol_type = protein
                            organism = Homo sapiens
SEQUENCE: 265
EVQLVESGGG LVQPGGSLRL SCAASGFTFS TYWMHWVRQT PEKGLVWVSR IHPDGSNTAY      60
ADSVKGRFTI SRDNAKNTLY LQMNSLRVED TAFYYCTRGG SGATINYWGQ GILVTVSS      118

SEQ ID NO: 266              moltype = AA  length = 124
FEATURE                     Location/Qualifiers
source                      1..124
                            mol_type = protein
                            organism = Homo sapiens
SEQUENCE: 266
QVQLQESGPG LVKPSQTLSL TCTVSGGSIS GGTYSWTWIR QPAGKGLEWI GRIFASGSTN      60
YNSSLKSRVT ILVDTSKNLF SLSLSSVTAA DTAMYYCARD RAGIDGYNYY FDWGQGTLV     120
TVSS                                                                 124

SEQ ID NO: 267              moltype = AA  length = 119
FEATURE                     Location/Qualifiers
source                      1..119
                            mol_type = protein
                            organism = Homo sapiens
SEQUENCE: 267
VQLVQSGAEV KKPGASVKVS CKTSGYTLTS YYMHWVRQAP GQGLEWLGVI RPTDASTRSA      60
QKFQGRITMT RDTSTSTLYM ELSSLRSEDT AVYYCAREVA AEGKAFDYWG QGTLVTVSS     119

SEQ ID NO: 268              moltype = AA  length = 116
FEATURE                     Location/Qualifiers
source                      1..116
                            mol_type = protein
                            organism = Homo sapiens
SEQUENCE: 268
EVQLVESGGG LVQPGGSLRL SCAASGFTFS SYWMSWVRQA PGKGLEWVGK IKEDGSEKYY      60
VDSVKGRFAI SRDNAKNSLS LQMNSLRAED TAVYYCARGQ SYPGIWGQGT MVTVSS        116

SEQ ID NO: 269              moltype = AA  length = 121
FEATURE                     Location/Qualifiers
source                      1..121
                            mol_type = protein
                            organism = Homo sapiens
SEQUENCE: 269
QVQLQESGPG LVKPSETLSL TCTVSGGSIT NYYWGWIRQP PGEGLEWIGY IYYSGSTNYN      60
PSLKSRVTIS VDTSKNQFSL KLTSVTAADT AVYYCAGRAY SSGYYYLIDY WGQGTLVTVS    120
S                                                                    121

SEQ ID NO: 270              moltype = AA  length = 107
FEATURE                     Location/Qualifiers
source                      1..107
                            mol_type = protein
                            organism = Homo sapiens
SEQUENCE: 270
EIVLTQSPGT LSLSPGERAT LSCRASQSVT YLAWYQQKPG QAPRLLFYGT SSRATGIPDR      60
FSGSGSGTDF TLTISRVEPE DFAVYYCQQF GSSPPDTFGG GTKVEIK                  107

SEQ ID NO: 271              moltype = AA  length = 110
FEATURE                     Location/Qualifiers
source                      1..110
                            mol_type = protein
                            organism = Homo sapiens
SEQUENCE: 271
VMTQSPLSLP VTLGQPASIS CRASQGLEHS DGNTYLSWFQ QRPGRSPRRL IYKVSNRDSG      60
VPDRFSGSGS GTDFTLEITR VEAEDVGVYY CMQVTHWPRT FGQGTKVEIK               110

SEQ ID NO: 272              moltype = AA  length = 107
```

```
FEATURE                 Location/Qualifiers
source                  1..107
                        mol_type = protein
                        organism = Homo sapiens
SEQUENCE: 272
EIVLTQSPGT LSLSPGERAT LSCRASQSIS PHLAWYQQKP GQSPRLLIYD ASNRATGIPA    60
RFSGSESGTD FTLSISSLEP EDFAVYYCQQ SGDWPLTFGG GTKVEIK                 107

SEQ ID NO: 273          moltype = AA   length = 108
FEATURE                 Location/Qualifiers
source                  1..108
                        mol_type = protein
                        organism = Homo sapiens
SEQUENCE: 273
EIVLTQSPGT LSLSPGERAT LSCRASQSVY SIYFAWYQQK PGQAPRPLIY GVSNRATGIP    60
DRFSGSGSGT DFTLTISRLE PEDFAVYYCQ QYGSLPRTFG QGTKVEIK                108

SEQ ID NO: 274          moltype = AA   length = 110
FEATURE                 Location/Qualifiers
source                  1..110
                        mol_type = protein
                        organism = Homo sapiens
SEQUENCE: 274
VMTQSPLSLP VTLGQPASIS CRSSRSLVYS DGGTYLNWFQ QRPGQSPRRL IWHVSNRDSG    60
VPDRFSGSGS GTDFTLKISR VEAEDVGVYY CMQGTHWPYT FGQGTKVEIK              110

SEQ ID NO: 275          moltype = AA   length = 107
FEATURE                 Location/Qualifiers
source                  1..107
                        mol_type = protein
                        organism = Homo sapiens
SEQUENCE: 275
DIQMTQSPSS LSASVGDRVT ITCQASQDIR KLLNWYQQRP GKAPNLLIYD ASNLETGVPS    60
RFSGSGSGTH FSFTITSLQP EDIATYYCQQ FESFPRTFGP GTKVDIK                 107

SEQ ID NO: 276          moltype = AA   length = 109
FEATURE                 Location/Qualifiers
source                  1..109
                        mol_type = protein
                        organism = Homo sapiens
SEQUENCE: 276
EIVMTQSPAT LSVSPGETAT LSCRASQSVN SFLAWYQQKP GQAPRLLIYA ASTRATGVPA    60
RFSGSGSGTE FTLTISSLQS EDFAVYYCHQ YKNWPPMGTF GPGTKVDIK               109

SEQ ID NO: 277          moltype = AA   length = 106
FEATURE                 Location/Qualifiers
source                  1..106
                        mol_type = protein
                        organism = Homo sapiens
SEQUENCE: 277
DIQMTQSPST LSSSVGDRVT ITCRASQNIG VSLAWYQQKP GKAPNLLIYK ASYLETGVPS    60
RFSGSGSGTE FTLTISSLQP DDFATYYCQQ YDIYLTFGQG TKVEIK                  106

SEQ ID NO: 278          moltype = AA   length = 110
FEATURE                 Location/Qualifiers
source                  1..110
                        mol_type = protein
                        organism = Homo sapiens
SEQUENCE: 278
VMTQSPLSLP VTLGQPASIS CRSSQSLAHS DGNTYLNWFQ QRPGQSPRRL IYKVSNRDSG    60
VPDRFSGSGS GTDFTLKISR VEAEDVGVYY CMQGTHWPYT FGQGTKVEIK              110

SEQ ID NO: 279          moltype = AA   length = 113
FEATURE                 Location/Qualifiers
source                  1..113
                        mol_type = protein
                        organism = Homo sapiens
SEQUENCE: 279
DIVMTQSPDS LAVSLGERAT INCKSSQSVL YSPNNKNYLA WFQQKPGQPP KLLIYWASIR    60
DSGVPDRFSG SGSGTDFTLT VSSLQADDVA VYYCQQYAAT PWTFGQGTKV EIK          113

SEQ ID NO: 280          moltype = AA   length = 110
FEATURE                 Location/Qualifiers
source                  1..110
                        mol_type = protein
                        organism = Homo sapiens
SEQUENCE: 280
VMTQSPLSLP VTLGQPASIS CSSSQSLVYS DGNTYLSWFQ QRPGQSPRRL IYKVSNRDSG    60
VPDRFSGSGS GTDFTLRISR VEAEDVGVYY CMQGSHWPLT FGGGTKVEIK              110
```

```
SEQ ID NO: 281          moltype = AA   length = 113
FEATURE                 Location/Qualifiers
source                  1..113
                        mol_type = protein
                        organism = Homo sapiens
SEQUENCE: 281
DIVMTQSPDS LAVSLGERAT INCKSSLSVL SSSNNENYLA WYQQKPGQPP KLLIYWASTR    60
GSGVPGRFSG SGSGTDFTLT ISSLQAEDVA VYYCHQYYTT PFAFGPGTKV DIK          113

SEQ ID NO: 282          moltype = AA   length = 107
FEATURE                 Location/Qualifiers
source                  1..107
                        mol_type = protein
                        organism = Homo sapiens
SEQUENCE: 282
DIQMTQSPSS LSASVGDSVT ITCRASQSIS SYLNWYHQKP GKAPKLLIYG ASTLQSGVPS    60
RFGGSGSGTD FTLTISSLQP DDFATYYCQQ SHSSPLTFGG GTKVEIK                 107

SEQ ID NO: 283          moltype = AA   length = 106
FEATURE                 Location/Qualifiers
source                  1..106
                        mol_type = protein
                        organism = Homo sapiens
SEQUENCE: 283
DIQMTQSPST LSASVGDRVT ITCRASRSLG SWLAWYQQSP GKAPKLLIYK ASTLESGVPS    60
RFSGSGSGTE FTLTISSLQP DDFATYYCQQ YYSFYTFGQG TKVEIK                  106

SEQ ID NO: 284          moltype = AA   length = 113
FEATURE                 Location/Qualifiers
source                  1..113
                        mol_type = protein
                        organism = Homo sapiens
SEQUENCE: 284
DIVMTQSADS LAVSLGERAT INCKSSQSLF YSSNKKNYLA WYQQKPGQPP KLIIYWASTR    60
ESGVPDRFSG SGSGTDFTLT ITSLRAEDVA VYYCQQYYTP PLTFGGGTKV EIK          113

SEQ ID NO: 285          moltype = AA   length = 107
FEATURE                 Location/Qualifiers
source                  1..107
                        mol_type = protein
                        organism = Homo sapiens
SEQUENCE: 285
EIVMTQSPAT LSVSPGERAT LSCRASQSVS GDLVWYQQKP GQAPRLLIYG ATTRASGVPA    60
RFSGSGSGTE FTLTISSLQS EDFAIYYCQQ YNNWPRTFGQ GTKVEIK                 107

SEQ ID NO: 286          moltype = AA   length = 107
FEATURE                 Location/Qualifiers
source                  1..107
                        mol_type = protein
                        organism = Homo sapiens
SEQUENCE: 286
EIVMTQSPAT LSVSPGERAT LSCRASQSVG NNLAWFQQKP GQAPRLLIYG ASTRATGIPA    60
RFSGSGSGTE FTLTISSLQS EDFAVYHCQH YHNWPPTFGQ GTKVEIK                 107

SEQ ID NO: 287          moltype = AA   length = 122
FEATURE                 Location/Qualifiers
source                  1..122
                        mol_type = protein
                        organism = Homo sapiens
SEQUENCE: 287
QVQLVESGGG VVQPGRSLRL SCAASGFTFS NHGMHWLRQT PGKGLEWVAV ISYDGSTKYY    60
ADSVKGRCTL SRDNSKETVF LQMNSLRPED TAVYYCAKGC SNGGNCFLID YWGPGTLVTV   120
SS                                                                 122

SEQ ID NO: 288          moltype = AA   length = 123
FEATURE                 Location/Qualifiers
source                  1..123
                        mol_type = protein
                        organism = Homo sapiens
SEQUENCE: 288
EVQLLESGGD LVQPGGSLRL SCAASGFDFS IYGMNWVRQA PGKGLEWVSV ISGDGTIIYY    60
ADSVKGRFTI SRDNSKNTLF LQVNSVRAED TAVYYCAKGG YYESGTMRAF DIWGQGTMVT   120
VSS                                                                123

SEQ ID NO: 289          moltype = AA   length = 116
FEATURE                 Location/Qualifiers
```

```
source                  1..116
                        mol_type = protein
                        organism = Homo sapiens
SEQUENCE: 289
EVQLVESGGG LVQPGGSLRL SCAASGYTFS SYSMSWVRQA PGKGLEWVAS IKPEGSEKFY    60
VDSVKGRFTI SRDNAKNSLY LQMNSLRGED TAVYYCARGE SNFRYWHQGT LVTVSS       116

SEQ ID NO: 290          moltype = AA   length = 119
FEATURE                 Location/Qualifiers
source                  1..119
                        mol_type = protein
                        organism = Homo sapiens
SEQUENCE: 290
EVQLVESGGA LVQPGGSLRL SCAASGFIFS NSWMGWFRQA PGKRPEFVAN IKPDGSEKFH    60
VDSVKGRFTI SRDNAENSLY LLMNSLRAED TAVYYCARDS TSPARFGYWG QGTLVTVSS    119

SEQ ID NO: 291          moltype = AA   length = 118
FEATURE                 Location/Qualifiers
source                  1..118
                        mol_type = protein
                        organism = Homo sapiens
SEQUENCE: 291
EVQLVETGGG LIQPGGSLRL SCAASGLNVN SYYMNWVRQA PGKGLEWVSV IYSGGGTNYA    60
DSVRGRFIIS RDNSRNALYL QMNSLRAEDT AVYYCATGGM TSSWYGYWGQ GTLVTVSS    118

SEQ ID NO: 292          moltype = AA   length = 124
FEATURE                 Location/Qualifiers
source                  1..124
                        mol_type = protein
                        organism = Homo sapiens
SEQUENCE: 292
VQLVQSGAEV KKPGASVKVS CKASEYTFIN YLVFWVRQAP GQGLEWMGEM NPTRGSTSYA    60
QKFQGRVTMT RDTSTSTVYM ELSSLRSDDT AVYYCSMGPP YCTGGSCYSA CDFWGPGTLV   120
TVSS                                                               124

SEQ ID NO: 293          moltype = AA   length = 124
FEATURE                 Location/Qualifiers
source                  1..124
                        mol_type = protein
                        organism = Homo sapiens
SEQUENCE: 293
EVQLVESGGG LMKPGGSLRL SCAVSGFTFT NAWLSWVRQP PGKGLEWVGR AYSSSGGWTM    60
DYSSPVRGRF TITRDDSKNT LYLQMNNLKT EDTAVYYCTT DIGKGWYTHY PDLWGQGTLV   120
TVSS                                                               124

SEQ ID NO: 294          moltype = AA   length = 121
FEATURE                 Location/Qualifiers
source                  1..121
                        mol_type = protein
                        organism = Homo sapiens
SEQUENCE: 294
QVQLVESGGG VVQPGKSLRL SCVASGFTLS TCGMHWVRQA PGKGLEWVAV TTYDGDRKYN    60
VDSVKGRFTI SRDNSKNTVY LQMDGLKAED TAVYHCVKEY SWGYYRTADY WGQGTLVTVS   120
S                                                                  121

SEQ ID NO: 295          moltype = AA   length = 117
FEATURE                 Location/Qualifiers
source                  1..117
                        mol_type = protein
                        organism = Homo sapiens
SEQUENCE: 295
EVQLVESGGG LVQPGGSLRL SCVASGFTFS TYWMHWVRQP PGKGLVWVSR INPDGSSTNY    60
ADSVNGRFTI SRDNAKNTLY LEMNSLRVED TALYYCARSP GGYFDYWGHS TLVTVSS     117

SEQ ID NO: 296          moltype = AA   length = 116
FEATURE                 Location/Qualifiers
source                  1..116
                        mol_type = protein
                        organism = Homo sapiens
SEQUENCE: 296
EVQLVESGGG LVKPGGSLTL SCAVSGFTFS TGWMSWVRQA PGKGLDWVGR IKSKTAGGTT    60
DYAAPVKDRF TISRDDSKNT LYLQLSSLKT EDTAVYYCTT DDLKNWGQGT LVTVSS      116

SEQ ID NO: 297          moltype = AA   length = 129
FEATURE                 Location/Qualifiers
source                  1..129
                        mol_type = protein
                        organism = Homo sapiens
```

```
                                     -continued

SEQUENCE: 297
EVQLVESGGG LVQPGGSLRL SCAASGFTFS SYSMNWVRQV PGKGLEWVSY TSTKSDIKYY    60
ADSVEGRFTI SRDNAKNSLY LQMNSLRDED TAVYYCARGR DCYGGNCVIY FHYYGLDVWG   120
QGTTVTVSS                                                          129

SEQ ID NO: 298          moltype = AA  length = 121
FEATURE                 Location/Qualifiers
source                  1..121
                        mol_type = protein
                        organism = Homo sapiens
SEQUENCE: 298
QVQLVESGGG VVQPGGSLRL SCVVSGFTLS SCGMHWVRQS PGKGLEWLSV STYDGNQKYY    60
AASVKGRFLI SRDTSKNTVY LHMNSLTAED TALYYCVKES ATGWYRTADY WGQGTLVTVS   120
S                                                                  121

SEQ ID NO: 299          moltype = AA  length = 122
FEATURE                 Location/Qualifiers
source                  1..122
                        mol_type = protein
                        organism = Homo sapiens
SEQUENCE: 299
EVQLVESGGG LVQPGGSLRL SCAASGFTVS SIFMSWVRQA PGQGLEWVSV IYTDGKTYYA    60
HSVEGRFTIS RDDSKNMVYL QLSSLRTEDT AVYYCARDIP TTFGIGEAFD IWGQGTMVTV   120
SS                                                                 122

SEQ ID NO: 300          moltype = AA  length = 115
FEATURE                 Location/Qualifiers
source                  1..115
                        mol_type = protein
                        organism = Homo sapiens
SEQUENCE: 300
VQLVQSGAEV KKPGASVKLS CKTSGYSFTS NYLHWVRQAP GQGLEWMGMV YPNDGTTTYA    60
QKFQGRVTMT SETSTTTIYM DLSGLTSEDT AIYYCARDDS AFDYWGQGTL VTVSS        115

SEQ ID NO: 301          moltype = AA  length = 121
FEATURE                 Location/Qualifiers
source                  1..121
                        mol_type = protein
                        organism = Homo sapiens
SEQUENCE: 301
QVQLVESGGG VVQPGRSLRL SCEASGFIFS SNGMHWVRQA PGKGLEWVAV ISSDGSRRYY    60
ADSMKGRFTI SRDNSKNTLY LQLNSLRADD TAVYYCAKGC SGENCFYMDD WGKGTTVTVS   120
S                                                                  121

SEQ ID NO: 302          moltype = AA  length = 128
FEATURE                 Location/Qualifiers
source                  1..128
                        mol_type = protein
                        organism = Homo sapiens
SEQUENCE: 302
VQLVQSGAEV KKPGASLKVS CKASGYTFRQ NYFHWVRQAP GQGLEWMGVI NPSDGSTKFA    60
QKFQGRVSMT RDTSTSTVYM DLSSLTSEDT AVYYCTREIG AVVVDATSLG WLGYFDYWGQ   120
GTLVTVSS                                                           128

SEQ ID NO: 303          moltype = AA  length = 115
FEATURE                 Location/Qualifiers
source                  1..115
                        mol_type = protein
                        organism = Homo sapiens
SEQUENCE: 303
EVQLVESGGG LVQPGGSLSL SCEASGLTFS GYWMNWVRQA PGKGLEWVAN INPEGSERRY    60
VESVQGRFTV SRDNPKNTLY LQMNSLRVED TALYYCAGWG RTQDWGQGAL VTVSS        115

SEQ ID NO: 304          moltype = AA  length = 121
FEATURE                 Location/Qualifiers
source                  1..121
                        mol_type = protein
                        organism = Homo sapiens
SEQUENCE: 304
QVQLVESGGG VVQPGRSLRL SCAASGLTFS NYGMHWVRQA PGKGLEWVAV VSARGGTTYY    60
ADSVKGRFTI SRDNSKNTMS LQMNGLRPDD TAVYFCTKEG APPGKYAFDI WGQGTMVTVS   120
S                                                                  121

SEQ ID NO: 305          moltype = AA  length = 120
FEATURE                 Location/Qualifiers
source                  1..120
                        mol_type = protein
                        organism = Homo sapiens
```

```
SEQUENCE: 305
EVQLVESGGG LVQPGGSLRL SCAASGFTFS DYRMDWVRQA PGRGLEWIAR IRHRDAGYST    60
EYAASVRGRF TVSRDDSQST LYLQMNSLKA DDTAVYICLK DSSQYSFDAW GQGTMVTVSS   120

SEQ ID NO: 306           moltype = AA  length = 113
FEATURE                  Location/Qualifiers
source                   1..113
                         mol_type = protein
                         organism = Homo sapiens
SEQUENCE: 306
DIVMTQSPDS LAVSLGERAT INCKSSQSIL SRSNNKNYLA WYQQKPGQPP KLLLYWASTR    60
ESGVPDRFSV SGSGSDFTLT ISSLQAEDVA VYYCQQYYNA PLTFGGGTKV EIK          113

SEQ ID NO: 307           moltype = AA  length = 107
FEATURE                  Location/Qualifiers
source                   1..107
                         mol_type = protein
                         organism = Homo sapiens
SEQUENCE: 307
EIVLTQSPAT LSLSPGERAT LSCRASQTVS RYLAWYQQKP GQAPRLLIYA ASNRATGIPT    60
RFSGSGSGTD FTLTISSLEP EDFAFYYCQQ RSNWPATFGG GTKVEIK                 107

SEQ ID NO: 308           moltype = AA  length = 107
FEATURE                  Location/Qualifiers
source                   1..107
                         mol_type = protein
                         organism = Homo sapiens
SEQUENCE: 308
DIQMTQSPSS LSASVGDSVT ITCQASQDIR DRLNWYQQKP GKAPNLLIYD ASSLETGVPS    60
RFRGSGSGTD FTFTISSLQP EDIATYYCQQ FVSFPRTFGP GTKVDIK                 107

SEQ ID NO: 309           moltype = AA  length = 110
FEATURE                  Location/Qualifiers
source                   1..110
                         mol_type = protein
                         organism = Homo sapiens
SEQUENCE: 309
EIVLTQSPGI LSLSPGERAT LSCRASQSVS SRSLSWYQQR PGLAPRLLIY AASSRAAVTP    60
DRFTASGSGT DFTLTISSLE PEDFAVYYCQ HYGTSPPRYT FGQGTKVEIK              110

SEQ ID NO: 310           moltype = AA  length = 113
FEATURE                  Location/Qualifiers
source                   1..113
                         mol_type = protein
                         organism = Homo sapiens
SEQUENCE: 310
DIVMTQSPDS LAVSLGERAT INCKSSQSVL HSSNNKNYFA WYQQKPGQPP KLLIHWASTR    60
ASGVPDRFSG SGSGTDFTLT ISSLQAEDVT IYYCQQYYST PYTFGQGTKV EIK          113

SEQ ID NO: 311           moltype = AA  length = 109
FEATURE                  Location/Qualifiers
source                   1..109
                         mol_type = protein
                         organism = Homo sapiens
SEQUENCE: 311
EIVLTQSPGT LSLSPGERAT LSCRASPSLD SAYLAWYQQK PGQAPRLLIY GASSRVTGIP    60
DRFSGSASGT DFTLTISRLE PEDFAVYYCQ RYGNSPPYTF GQGTKVEIK               109

SEQ ID NO: 312           moltype = AA  length = 113
FEATURE                  Location/Qualifiers
source                   1..113
                         mol_type = protein
                         organism = Homo sapiens
SEQUENCE: 312
DIVMTQSPDS LAVSLGERAT ISCKSSQSLL YSSSNKNYLA WFQQKPGQAP KLLIYWASTR    60
ESGVPDRFSG SGSGTDFTLT ISSLQTEDVA VYYCLQYRSA PFTFGGGTKV EIK          113

SEQ ID NO: 313           moltype = AA  length = 107
FEATURE                  Location/Qualifiers
source                   1..107
                         mol_type = protein
                         organism = Homo sapiens
SEQUENCE: 313
DIQMTQSPST QSASVGDRVT ITCRASQSIS SWLAWYQQKP GKAPKVLIYA VSSLESGVPS    60
RFSGSGSGTE FTLTISSLQP EDFATYYCQQ YSTYPWTFGP GTKVEIK                 107

SEQ ID NO: 314           moltype = AA  length = 107
FEATURE                  Location/Qualifiers
```

```
source                  1..107
                        mol_type = protein
                        organism = Homo sapiens
SEQUENCE: 314
EIVMTQSPAS LSVSPGETAT LSCRASQSVG STLAWYQQKP GQAPRLLIYN VFTRAAGVPA    60
RFSGSGSRTE FTLTISSLQS EDFAVYYCQQ YSTWLWTFGQ GTKVEIK                  107

SEQ ID NO: 315          moltype = AA   length = 107
FEATURE                 Location/Qualifiers
source                  1..107
                        mol_type = protein
                        organism = Homo sapiens
SEQUENCE: 315
DIQMTQSPSS LSASVGDRVT ITCRASQRIS SYLNWYQQKP GKAPNLLIYA AASLHDGVPS    60
RFSGSGSGTD FTLTISSLQP EDFATYYCQQ RYRIPYSFGP GTKVEIK                  107

SEQ ID NO: 316          moltype = AA   length = 112
FEATURE                 Location/Qualifiers
source                  1..112
                        mol_type = protein
                        organism = Homo sapiens
SEQUENCE: 316
DIVMTQSPLS LSVTPGEPAS ISCRSSQSLL QGNGHNYLDW YLQKPGQSPQ LLIYLGSIRA    60
SGVPDRFSGS GSGTDFILKI SRVEAEDVGV YYCMRALQTP YTFGQGTKVE IK            112

SEQ ID NO: 317          moltype = AA   length = 107
FEATURE                 Location/Qualifiers
source                  1..107
                        mol_type = protein
                        organism = Homo sapiens
SEQUENCE: 317
DIQMTQSPST LSASVGDRVT LTCRASETLN NWLAWFQQKP GKAPTLLIYE ASSLESGVPS    60
RFSGSGSGTD FALTISSLQP DDFATYYCHQ YNKYPWTFGQ GTKVEIK                  107

SEQ ID NO: 318          moltype = AA   length = 106
FEATURE                 Location/Qualifiers
source                  1..106
                        mol_type = protein
                        organism = Homo sapiens
SEQUENCE: 318
DIQMTQSPST LSASVGDRVT ITCRASQSIS GWLAWYQQKA GKAPKLLIYK ASSLESGVPS    60
RFSGSGSGTE FTLTISSLQP DDFATYYCQQ YYSWGTFGQG TKVEIK                   106

SEQ ID NO: 319          moltype = AA   length = 112
FEATURE                 Location/Qualifiers
source                  1..112
                        mol_type = protein
                        organism = Homo sapiens
SEQUENCE: 319
DIVMTQTPLS LPVTLGQPAS ISCISSQSLV HSDGNTYLSW LQQRPGQPPR LLIYKISNRF    60
SGVPDRFSGS GAGTDFTLKI SRVEAEDVGV YYCMQASQST WTLGQGTKVE IK            112

SEQ ID NO: 320          moltype = AA   length = 113
FEATURE                 Location/Qualifiers
source                  1..113
                        mol_type = protein
                        organism = Homo sapiens
SEQUENCE: 320
DIVMTQSPDS LAVPLGERAT INCTSSQTVL SSSNNKNYLV WYQQKPGQPP KLLLYWASTR    60
ASGVPDRFSG SGSGTDFTLT ISSLQAEDVA VYYCQQCYNA PLTFGRGTKV EIK           113

SEQ ID NO: 321          moltype = AA   length = 108
FEATURE                 Location/Qualifiers
source                  1..108
                        mol_type = protein
                        organism = Homo sapiens
SEQUENCE: 321
EIVMTQSPAT LSVFPGEGVT LSCRASQSIS NNLAWYQQKP GQAPRLLMYD ASTRATGIPA    60
RFSGSGSGTE FTLTISSLQS EDFAVYYCQQ YNNWPPVTFG QGTKVEIK                 108

SEQ ID NO: 322          moltype = AA   length = 110
FEATURE                 Location/Qualifiers
source                  1..110
                        mol_type = protein
                        organism = Homo sapiens
SEQUENCE: 322
VMTQSPLSLP VTLGQSASVS CRSSQSLGPS DGSTRLDWFQ QRPGQSPRRL IYAVSNRDSG    60
VPDRFSGSGS GSDFTLRISR VEAEDVGVYY CMQYTYWPHT FGQGTKVEIK               110
```

```
SEQ ID NO: 323           moltype = AA   length = 109
FEATURE                  Location/Qualifiers
source                   1..109
                         mol_type = protein
                         organism = Homo sapiens
SEQUENCE: 323
EIVLTQSPAT LSLSPGERAT LSCRASQSVS SSLAWYQQKP GQAPRLLIYD ASKRATDIPA    60
RFSGSGSGTD FTLTISSLEP EDFAVYYCQH RGEWPPGATF GPGTKVDIK               109

SEQ ID NO: 324           moltype = AA   length = 107
FEATURE                  Location/Qualifiers
source                   1..107
                         mol_type = protein
                         organism = Homo sapiens
SEQUENCE: 324
DIQLTQSPSF LSASVGDRVT ITCRASQGID TRLIWYQQKP GEAPKLLIYE ASTLQSGAPS    60
RFSGSGFGTE FTLTISSLQP EDFATYYCQQ FKGYPLTFGG GTKVEIK                 107

SEQ ID NO: 325           moltype = AA   length = 115
FEATURE                  Location/Qualifiers
source                   1..115
                         mol_type = protein
                         organism = Homo sapiens
SEQUENCE: 325
QVQLQESGPG LVKPSETLSL TCTVSGGSIS SHYWSWIRQP PAKGLEWIGY IYHSGMTNYN    60
PSLKSRVTIS IDTSKNQFSL KLSSVTAADT AVYYCARGDG YNFFWGQGTL VTVSS        115

SEQ ID NO: 326           moltype = AA   length = 125
FEATURE                  Location/Qualifiers
source                   1..125
                         mol_type = protein
                         organism = Homo sapiens
SEQUENCE: 326
QVQLVESGGG VVQPGGSLRL SCAASGLTFS NQDFHWVRQA PGKGLEWVAF IRYDGGFKNY    60
ADSVKGRFTI SRDNSQKMLY LQMDSLRVED TAVYYCAKCG AEDSTTVWLN WFDPWGQGTL   120
VTVSS                                                              125

SEQ ID NO: 327           moltype = AA   length = 120
FEATURE                  Location/Qualifiers
source                   1..120
                         mol_type = protein
                         organism = Homo sapiens
SEQUENCE: 327
EVQLLESGGG LVEPGGSLRL SCAASGFTFS SYAMSWVRQA PGKGLEWVSA ISDSGGSTYY    60
ADSVKGRFTI SRDKSKNTLY LQMNSLRAED TAVYYCAKPN YFGSGSPDYW GQGTLVTVSS   120

SEQ ID NO: 328           moltype = AA   length = 115
FEATURE                  Location/Qualifiers
source                   1..115
                         mol_type = protein
                         organism = Homo sapiens
SEQUENCE: 328
QVQLQESGPG LVKPSETLSL TCTVSGASIS SHYWSWIRQP PGKGLEWIGY IYHSGITNYN    60
PSLKSRVTIS IDTSKNQYSL KLSSVTAADT AVYYCARGDG YNFYWGQGTL VTVSS        115

SEQ ID NO: 329           moltype = AA   length = 126
FEATURE                  Location/Qualifiers
source                   1..126
                         mol_type = protein
                         organism = Homo sapiens
SEQUENCE: 329
EVQLVESGGG VVRPGGSLRL SCAASGFTFD DYGMTWVRQA PGKGLEWISG ICCNGGCSGY    60
ADSVKGRFTI SRDNAKKSLF LVMNSLRAED TALYYCVRVA VPAATYTRGN DAFDIWGQGT   120
MVTVSS                                                             126

SEQ ID NO: 330           moltype = AA   length = 119
FEATURE                  Location/Qualifiers
source                   1..119
                         mol_type = protein
                         organism = Homo sapiens
SEQUENCE: 330
EVQLVESGGG LVEPGGSLRL SCAVSGFTFT DAWMTWVRQA PGKGLDWVGH VKSKYDGATT    60
EYAAPVQGRF TISRDDSKKT IYLQMNSLNT EDTGVYFCTT AHGPVGDHWG QGTLVTVSS   119

SEQ ID NO: 331           moltype = AA   length = 126
FEATURE                  Location/Qualifiers
source                   1..126
                         mol_type = protein
                         organism = Homo sapiens
```

```
                              -continued

SEQUENCE: 331
EVQLVESGGG LVQPGGSLRL SCAASGFSFD TSWMTWVRQA PGKGLEWVAT INQGGSDKYY    60
VDSVKGRFTI SRDNAKNSLY LQMNSLRAED TAVYYCARAG GCSSTRCHTT PGFDYWGQGA   120
LVTVSS                                                              126

SEQ ID NO: 332          moltype = AA   length = 117
FEATURE                 Location/Qualifiers
source                  1..117
                        mol_type = protein
                        organism = Homo sapiens
SEQUENCE: 332
QLQESGPGLV KPSETLSLTC TVSGSSISSS SYYWGWVRQS PGKGLEWIGS IYHSGTIYYN    60
PSLRSRVTIS VDTSKNQFSL KLNSVTAADT AVYYCASLSG TNAFDIWGQG TMVTVSS      117

SEQ ID NO: 333          moltype = AA   length = 120
FEATURE                 Location/Qualifiers
source                  1..120
                        mol_type = protein
                        organism = Homo sapiens
SEQUENCE: 333
EVQLLESGGG LVQPGGSLRL SCAASGFTFS SHDMSWVRLA PGKGPEWVSA LGAGDAWTHY    60
ANSVRGRFTI SRDDSKNTLY LQMNSLRAED TAVYFCAKPR GYSYGYFDYW GQGTLVTVSS   120

SEQ ID NO: 334          moltype = AA   length = 117
FEATURE                 Location/Qualifiers
source                  1..117
                        mol_type = protein
                        organism = Homo sapiens
SEQUENCE: 334
EVQLVESGGG LVQPGGSLRL SCGASGFTFS TYWMTWVRQA PGKGLEWVAN INQDGSEKQY    60
VDSVKGRFTI SRDNAKNSLY LQMNSLRVED TAIYYCARPP ARRLDYWGQG SLVTVSS      117

SEQ ID NO: 335          moltype = AA   length = 116
FEATURE                 Location/Qualifiers
source                  1..116
                        mol_type = protein
                        organism = Homo sapiens
SEQUENCE: 335
EVQLVESGGG LVQPGGSLRL SCAASEFTFS DYWMHWVRQA PGKGLVWVSR INTDGSTTTY    60
ADSVKGRFTI SRDNAKNTLY LQMNSLRAED TAVYYCARSN AGHEAWGQGT LVTVSS       116

SEQ ID NO: 336          moltype = AA   length = 117
FEATURE                 Location/Qualifiers
source                  1..117
                        mol_type = protein
                        organism = Homo sapiens
SEQUENCE: 336
VQLVQSGAEV KKPGASVRVS CKASGYTFTN YWIHWVRQAP GQGLEWMGMI APKEGYTFYA    60
QQLQGRVTVT RDTSTSAVYM ELNSLRSEDT AVYFCARDIP HANLDYWGQG TLVTVSS      117

SEQ ID NO: 337          moltype = AA   length = 121
FEATURE                 Location/Qualifiers
source                  1..121
                        mol_type = protein
                        organism = Homo sapiens
SEQUENCE: 337
EVQLLESGGG LVQPGGSLRL SCAASGFTFS DYTMNWARQA PGKGLEWVSA IRESGDSTYY    60
ADSVTGRFTI SRDNSRNTLY LHMNSLRAED TAMYFCVKDR VPPGDVPGDF WGPGTLVTVS   120
S                                                                   121

SEQ ID NO: 338          moltype = AA   length = 107
FEATURE                 Location/Qualifiers
source                  1..107
                        mol_type = protein
                        organism = Homo sapiens
SEQUENCE: 338
DIQLTQSPSF LSASVGDRVT ITCRASQDMT HSLAWYQQKP GKAPNLLIYN AYTLQSGVPS    60
RFSGSGSGTE FTLTISSLQP EDFATYYCQQ INSYPRTFGQ GTKVEIK                 107

SEQ ID NO: 339          moltype = AA   length = 107
FEATURE                 Location/Qualifiers
source                  1..107
                        mol_type = protein
                        organism = Homo sapiens
SEQUENCE: 339
EIVLTQSPGT LSLSPGERAT LSCRASQNIG TALAWYQQKP GQAPRLIIYE TSNRATDVPA    60
RFSGSGSGTD FTLTISSLER EDFALYYCQQ RADWPLTFGG GTKVEIK                 107

SEQ ID NO: 340          moltype = AA   length = 108
```

```
FEATURE                 Location/Qualifiers
source                  1..108
                        mol_type = protein
                        organism = Homo sapiens
SEQUENCE: 340
EIVLTQSPAT LSLSPGERAT LSCRASQSVS SYLAWYQQRP GQAPRLVIYA ASNRATGIPA    60
RFSGSGSGTD FTLTISSLEP EDFAVYYCLQ CSNWPMYTFG QGTKVEIK                108

SEQ ID NO: 341          moltype = AA  length = 107
FEATURE                 Location/Qualifiers
source                  1..107
                        mol_type = protein
                        organism = Homo sapiens
SEQUENCE: 341
DIQLTQSPSF LSASVGDRVT ITCRASQDIT DSLAWYQQKP GKAPNLLIYT ASTLQSGVPS    60
RFSGSGSGTE FTLTISSLQP EDFTTYYCQQ INSYPRTFGQ GTKVEIK                 107

SEQ ID NO: 342          moltype = AA  length = 107
FEATURE                 Location/Qualifiers
source                  1..107
                        mol_type = protein
                        organism = Homo sapiens
SEQUENCE: 342
DIQMTQSPSS LSASVGDRVT ITCRASQGIR NDLGWYQQKP GKAPKRLIYA ASSLQSGVPS    60
RFSGSGSGTE FTLTISSLQP EDFASYYCLQ HSSFPWTFGQ GTKVEIK                 107

SEQ ID NO: 343          moltype = AA  length = 114
FEATURE                 Location/Qualifiers
source                  1..114
                        mol_type = protein
                        organism = Homo sapiens
SEQUENCE: 343
DIVMTQSPDS LAVSLGERAA INCKSSQSVL DSSNMKRYLA WYQLKAGQPP RLLIYLASTR    60
ESGVPDRFSG SGSGTDFNLT ISSLQAEDVA VYYCQQYYTT PSITFGQGTR LEIK         114

SEQ ID NO: 344          moltype = AA  length = 114
FEATURE                 Location/Qualifiers
source                  1..114
                        mol_type = protein
                        organism = Homo sapiens
SEQUENCE: 344
DIVMTQSPDS LAVSLGERAT INCKSSQSVL YSSNNKNYLA WYQQKPGQPP KMLIYWASTR    60
ESGVPDRFSG SGSGTDFTLT ISSLQAEDVA VYYCQQYYTT PPITFGQGTR LEIK         114

SEQ ID NO: 345          moltype = AA  length = 106
FEATURE                 Location/Qualifiers
source                  1..106
                        mol_type = protein
                        organism = Homo sapiens
SEQUENCE: 345
EIVLTQSPAT LSLSPGERAT LSCRASQSVS IYLAWYQQKP GQAPRLLIYD SSNRATGIPA    60
RFSGSGSGTD FTLTISSLEP EDFAVYYCQQ RSSGRTFGQG TKVEIK                  106

SEQ ID NO: 346          moltype = AA  length = 108
FEATURE                 Location/Qualifiers
source                  1..108
                        mol_type = protein
                        organism = Homo sapiens
SEQUENCE: 346
EIVLTQSPGT LSLSPGERAT LSCRASQTVT NNYLAWYQHK PGLAPRLLIF DASIRATGIP    60
DRFSGSGSGA DFTLTISRLE PEDFTFYYCQ QYGISPRTFG QGTKVEIK                108

SEQ ID NO: 347          moltype = AA  length = 112
FEATURE                 Location/Qualifiers
source                  1..112
                        mol_type = protein
                        organism = Homo sapiens
SEQUENCE: 347
DIVMTQTPLS LSVTPGQPAS ISCKSSQSLL DSDGRTYFFW YLQKPGQSPQ LLIYEVSNRF    60
SGVPDRFSGS GSGTDFTLKI SRVESEDVGV YYCMQGTHHP WTFGQGTKVE IK           112

SEQ ID NO: 348          moltype = AA  length = 113
FEATURE                 Location/Qualifiers
source                  1..113
                        mol_type = protein
                        organism = Homo sapiens
SEQUENCE: 348
DIVMTQSPDS LAVSLGERAT VNCKSSQSVL YSSNSKNYLA WYQQKPGQPP KLLIYWASTR    60
ESGVPDRFSG SGSGTDFTLT ISSLQAEDVA VYYCQQYYST PLTFGGGTKV EIK          113
```

```
SEQ ID NO: 349          moltype = AA  length = 107
FEATURE                 Location/Qualifiers
source                  1..107
                        mol_type = protein
                        organism = Homo sapiens
SEQUENCE: 349
DIQMTQSPSS LSASVGDRVT ITCRASQGIG NDLGWYQHEP GKAPKRLIYA ASSLQSGVPS    60
RFSGSASGTE FTLTITSLQP EDFATYYCLQ HTTFPWTFGQ GTKVEIK                 107

SEQ ID NO: 350          moltype = AA  length = 108
FEATURE                 Location/Qualifiers
source                  1..108
                        mol_type = protein
                        organism = Homo sapiens
SEQUENCE: 350
EIVLTQSPAT LSLSPGERAT LSCRASQSVG SHFAWYQQKP GQAPRLLIYG ASNRAPGIPP    60
RFSASGSGTD FTLTISSLEP EDFAIYYCQQ RRTWPPLTFG QGTRLEIK                108

SEQ ID NO: 351          moltype = AA  length = 119
FEATURE                 Location/Qualifiers
source                  1..119
                        mol_type = protein
                        organism = Homo sapiens
SEQUENCE: 351
EVQLVESGGG LVQPGGSLRL SCVASGFSFS GHEMNWVRQP PGKGLEWVSH IGSGGDYIGY    60
ADSVKGRFTV SRDNAKNLLY LQMNSLRADD TAVYYCATLL LRDNQLDVWG QGTTVTVSS   119

SEQ ID NO: 352          moltype = AA  length = 121
FEATURE                 Location/Qualifiers
source                  1..121
                        mol_type = protein
                        organism = Homo sapiens
SEQUENCE: 352
QVQLVESGGG VVQPGRSLRL SCAASGFTLS SCGMHWIRQA PGKGLEWVAV ITYDGRSHFN    60
ADAVKGRFTI SRDRSMNTVS LQMDSLRPED TAVYYCVKEQ GFGYYRTADY WGQGTLVTVS  120
S                                                                  121

SEQ ID NO: 353          moltype = AA  length = 114
FEATURE                 Location/Qualifiers
source                  1..114
                        mol_type = protein
                        organism = Homo sapiens
SEQUENCE: 353
QVQLQESGPG LVRPSETLSL TCTVSGGSIS SDHWSWIRQP PGKGLEWIGN VYYSGRTYYN    60
PSFKSRVTIS VATSKNQFSL KVTSVTAADT AIYYCARRND FNIWGQGTMV TVSS         114

SEQ ID NO: 354          moltype = AA  length = 123
FEATURE                 Location/Qualifiers
source                  1..123
                        mol_type = protein
                        organism = Homo sapiens
SEQUENCE: 354
EVQLLESGGG LVQPGGSLRL SCAASGFTFS KYAVSWVRQA PGKGLEWVSA VSGNGDSTYY    60
ADPVRGRFTI SRDNSKNTLY LQMNSLRAED TALYYCSIWW GTSVQYPLVL DYWGLGTLVT  120
VSS                                                                123

SEQ ID NO: 355          moltype = AA  length = 121
FEATURE                 Location/Qualifiers
source                  1..121
                        mol_type = protein
                        organism = Homo sapiens
SEQUENCE: 355
QVQLVESGGG VVQPGRSLRL LCAASGFTLS TCGMHWIRQT PGKGLEWVAV KTYDGREEFY    60
ADSVKGRFTI SRDESMNTLS LQMNSLRPED TAVYYCVKEQ DYGYYRTADH WGQGTLVTVS  120
S                                                                  121

SEQ ID NO: 356          moltype = AA  length = 117
FEATURE                 Location/Qualifiers
source                  1..117
                        mol_type = protein
                        organism = Homo sapiens
SEQUENCE: 356
QVQLQEAGPG LVKPSQTLSL TCTVSGGSIS SGGYYWSWIR QHPGKGLEWI GYIYYSGSTY    60
YNPSLKSRVT ISVDTSKNQY SLKLSSVTAA DTAVYYCARG HGFNAYWGQG TLVTVSS     117

SEQ ID NO: 357          moltype = AA  length = 122
FEATURE                 Location/Qualifiers
```

```
source                   1..122
                         mol_type = protein
                         organism = Homo sapiens
SEQUENCE: 357
EVQLVESGGG LVKPGESLRL SCATSGVNFN IAWMTWVRQA PGKGLEWVGR IKSKIGGGTT    60
DYAAPVKGRF TMSIDDSKNT LYLQMNSLKT EDTAVYYCTT VRNMADLSLN HWGQGTLVTV   120
SS                                                                 122

SEQ ID NO: 358           moltype = AA   length = 118
FEATURE                  Location/Qualifiers
source                   1..118
                         mol_type = protein
                         organism = Homo sapiens
SEQUENCE: 358
EVQLVESGGG LVQPGASLTL SCVVSGFTFI GTEMTWIRQA PGKGLEGLSY ISGSGGTTYY    60
AESVRGRFTI SRDNAKKSLF LQMTSLTAED TAVYYCATGN RGSLPRRWGQ GTLVTVSS    118

SEQ ID NO: 359           moltype = AA   length = 118
FEATURE                  Location/Qualifiers
source                   1..118
                         mol_type = protein
                         organism = Homo sapiens
SEQUENCE: 359
EVQLVEFGGG LVQPGGSLRL SCVASGFTFS SSWMSWVRQA PGKGLECVGN IKPDASLVSY    60
VDSVKGRVTI SRDNAKNSLF LDMSSLRVED TAVYYCVRDG WDTFFDSWGQ GTLVTVSS    118

SEQ ID NO: 360           moltype = AA   length = 113
FEATURE                  Location/Qualifiers
source                   1..113
                         mol_type = protein
                         organism = Homo sapiens
SEQUENCE: 360
EVQLVESGGG LVQPGGSLRL SCAASGFTFS NYWMRWVRQS PGKGLVWVSH INPDGSFTNY    60
ADSVKGRFTI SRDNTKNTLY LQMNSLRAED TAVYYCVNFQ LGWGQGTLVT VSS         113

SEQ ID NO: 361           moltype = AA   length = 123
FEATURE                  Location/Qualifiers
source                   1..123
                         mol_type = protein
                         organism = Homo sapiens
SEQUENCE: 361
QVQLVESGGG VVQPGRSLKL SCAVAGFTFR TYAMHWVRQA PGRGLEWVAL ISNDGTKKYS    60
ADSVRGHFTI SRDNSKDTLY LQMNSLRPDD TAVYYCARAE YCSPGDCFLI DTWGQGTLVT   120
VSS                                                                123

SEQ ID NO: 362           moltype = AA   length = 119
FEATURE                  Location/Qualifiers
source                   1..119
                         mol_type = protein
                         organism = Homo sapiens
SEQUENCE: 362
QVQLVESGGG VVQPGRSLRL SCAVSGFTFS RYGMHWVRQA PGKGLEWVVV IWHDGSNTYY    60
ADSVKGRFTI SRDDSKNTVY LQMNSLRVED TAMYYCLRGN PPSSPTDYWG QGTLVTVSS   119

SEQ ID NO: 363           moltype = AA   length = 119
FEATURE                  Location/Qualifiers
source                   1..119
                         mol_type = protein
                         organism = Homo sapiens
SEQUENCE: 363
EVQLLESGGG LVQPGGSLRL SCEVSGFIFS NYAMTWVRQA PGKGLQWVSA IGTSGGDTHY    60
ADSVKGRFTI SRHNSQNTLY LQMNSLRAED TAIYYCAKVV YSRPPMDVWG QGTTVTVSS   119

SEQ ID NO: 364           moltype = AA   length = 118
FEATURE                  Location/Qualifiers
source                   1..118
                         mol_type = protein
                         organism = Homo sapiens
SEQUENCE: 364
EVQLVESGGG LVQPGGSLRL SCAASGFTFS NRWMSWVRQA PGKGLEWVAN INEDGSQKHY    60
VDSVRGRFTI SRDNAKNSLS LQMDSLRVED TAVYYCARAS RETGEPYWGQ GTLVTVSS    118

SEQ ID NO: 365           moltype = AA   length = 109
FEATURE                  Location/Qualifiers
source                   1..109
                         mol_type = protein
                         organism = Homo sapiens
```

-continued

```
SEQUENCE: 365
VMTQSPLSLP VTLGQSASIS CRSSRSLVFS DGNTYLNWFQ QRPGRSPRRL IYKVSKRDSG    60
VPDRFSGSGS DTDFTLKISR VEAEDVGVYY CMQGTHWRTF GQGTKVEIK              109

SEQ ID NO: 366          moltype = AA   length = 107
FEATURE                 Location/Qualifiers
source                  1..107
                        mol_type = protein
                        organism = Homo sapiens
SEQUENCE: 366
DIQMTQSPST LSASVGDRVT ITCRASQSIN SWLAWYQRKP GKTPKLLIYE ASSLESGVPS    60
RFSGSRSGTE FTLTISSLQA DDFATYYCHQ YDKYPWTFGQ GTKVEIK                107

SEQ ID NO: 367          moltype = AA   length = 108
FEATURE                 Location/Qualifiers
source                  1..108
                        mol_type = protein
                        organism = Homo sapiens
SEQUENCE: 367
EIVLTQSPGT LSLSPGERAT LSCRASQSVT NNYLVWHQQK PGQAPRLLIS DASNRATGIP    60
DRFSGSGSGT DFTLTINRLE PEDFAVYYCQ QYGSSPFTFG PGTKVDIK               108

SEQ ID NO: 368          moltype = AA   length = 108
FEATURE                 Location/Qualifiers
source                  1..108
                        mol_type = protein
                        organism = Homo sapiens
SEQUENCE: 368
EIVMTQSPAT LSVSPGERVT LSCRASQSIG SSLAWYLQKP GQAPRVLIYG ASTRTPGTPA    60
RFSGSGSGTE FTLTISSLQS EDLAIYYCQQ YSKWPPITFG QGTRLEIK               108

SEQ ID NO: 369          moltype = AA   length = 107
FEATURE                 Location/Qualifiers
source                  1..107
                        mol_type = protein
                        organism = Homo sapiens
SEQUENCE: 369
DIQMTQSPSI LSASVGDRVT INCRASQSIN AWLAWYQQKP GKAPKFLIYK ASSLESGVSS    60
RFSGSGSGTE FTLIISSLQP DDFATYYCQQ YDKYPWTFGR GTKVEIK                107

SEQ ID NO: 370          moltype = AA   length = 108
FEATURE                 Location/Qualifiers
source                  1..108
                        mol_type = protein
                        organism = Homo sapiens
SEQUENCE: 370
EIVLTQSPGT LSFSPGDRAT LSCRASQSVS SSSLAWYQQR PGQAPSLLIY GASSRATGIP    60
DRFSGSGSGT DFTLTISRLE PEDFAVYYCQ QYGNSPRTFG QGTKVEIK               108

SEQ ID NO: 371          moltype = AA   length = 108
FEATURE                 Location/Qualifiers
source                  1..108
                        mol_type = protein
                        organism = Homo sapiens
SEQUENCE: 371
EIVLTQSPGT LSLSPGERAT LSCRASQSVS STYLNWYQQK PGQAPRLLIY GASTRATGIP    60
DRFSGSGSGA DFTLTISRLE PEDFAVYYCQ QYDDSRWTFG QGTKVEIK               108

SEQ ID NO: 372          moltype = AA   length = 112
FEATURE                 Location/Qualifiers
source                  1..112
                        mol_type = protein
                        organism = Homo sapiens
SEQUENCE: 372
DIVMTQSPLS LPVTPGEPAS ISCRSGQSLL YSDGNNYLDW YLQKPGQSPQ LLIYLGSNRA    60
SGVPDRFSGS ESGTDFTLKI SRVEAGDVGI YYCMQALRSP YTFGQGTKVE IK          112

SEQ ID NO: 373          moltype = AA   length = 110
FEATURE                 Location/Qualifiers
source                  1..110
                        mol_type = protein
                        organism = Homo sapiens
SEQUENCE: 373
VMTQSPLSLP VTLGQPASIS CRSSQSPVYS DGNTYLNWFQ QRPGQSPRRL IYKVSNRDSG    60
VPDRFSGSGS GTDFTLNISG VEAEDVGVYY CMQGRYWPYT FGQGTKVEIK             110

SEQ ID NO: 374          moltype = AA   length = 108
FEATURE                 Location/Qualifiers
```

```
source                  1..108
                        mol_type = protein
                        organism = Homo sapiens
SEQUENCE: 374
EIVLTQSPGT LSFSPGDRAT LSCRASQSVS SSALAWYQQK PGQAPSLLIY GASSRATGIP    60
DRFSGSGSGT DFTLTISRLE PEDFAVYYCQ QYGNSPRTFG QGTKVEIK                108

SEQ ID NO: 375          moltype = AA  length = 109
FEATURE                 Location/Qualifiers
source                  1..109
                        mol_type = protein
                        organism = Homo sapiens
SEQUENCE: 375
VMTQSPLSLP VTLGQSASIS CRSSRSLVFS DGNTYLNWFQ QRPGRSPRRL IYKVSKRDSG    60
VPDRFSGSGS DTDFTLKISR VEAEDVGVYY CMQGTHWRTF GQGTKVEIK               109

SEQ ID NO: 376          moltype = AA  length = 107
FEATURE                 Location/Qualifiers
source                  1..107
                        mol_type = protein
                        organism = Homo sapiens
SEQUENCE: 376
DIQMTQSPSS LSASVGDRIT ITCRASQGIN NYLAWFQQKP GKAPKTLIYS TSTLQSGVPS    60
KFSGSGSGTV FTLTISNLQP EDFATYYCQQ YNSYPLTFGG GTKVEIK                 107

SEQ ID NO: 377          moltype = AA  length = 107
FEATURE                 Location/Qualifiers
source                  1..107
                        mol_type = protein
                        organism = Homo sapiens
SEQUENCE: 377
DIQMTQSPSS LSASVGDRVT ITCRASQTIS NYLNWFQQKP GKAPRLLIYA ASSLQSGVPS    60
RFSGSGSVTD FTLTISSLQP EDFATYFCQQ SYSTPWTFGQ GTKVEIK                 107

SEQ ID NO: 378          moltype = AA  length = 110
FEATURE                 Location/Qualifiers
source                  1..110
                        mol_type = protein
                        organism = Homo sapiens
SEQUENCE: 378
VMTQSPFSLP VTLGQPASIS CRSSQSLVYS DGNTYLNWFQ QRPGQSPRRL IYKLSNRDSG    60
VPDRFSGSGS GTDFTLKISR VEAEDVGVYY CMQATHWPWT FGQGTKVEIK              110
```

HUMAN *STREPTOCOCCUS PNEUMONIAE* ANTIBODIES AND USES THEREFOR

CROSS-REFERENCE TO RELATED APPLICATIONS

This application claims priority to and is a continuation application of U.S. application Ser. No. 15/058,814 filed on Mar. 2, 2016, which claims priority to and is a divisional application of U.S. application Ser. No. 13/740,934 filed on Jan. 14, 2013, now U.S. Pat. No. 9,279,815, issued on Mar. 8, 2016, which claims priority to U.S. Provisional Application No. 61/593,654, filed Feb. 1, 2012. The contents of each of which are incorporated herein by reference in its entirety.

STATEMENT OF FEDERALLY FUNDED RESEARCH

This invention was made with government support under grant numbers P20RR015577, P20RR015577-10S1, P30RR031152, P30AR053483, and U19A1062629, and contract number HHSN266200500026C (N01-AI500026), awarded by the National Institutes of Health. The government has certain rights in the invention.

TECHNICAL FIELD OF THE INVENTION

The present invention relates generally to the fields of microbiology, immunology and pathology. More particularly, it concerns the development of human monoclonal antibodies for use in the diagnosis, prevention and therapy of *Streptococcus pneumoniae* infections.

INCORPORATION-BY-REFERENCE OF MATERIALS FILED ON COMPACT DISC

This application includes an electronically submitted sequence listing in .txt format. The .XML file contains a sequence listing entitled "OMRF1023CONXML" created on Dec. 15, 2022 and is 383,790 bytes in size. The sequence listing contained in this .XML file is part of the specification and is hereby incorporated by reference herein in its entirety.

BACKGROUND OF THE INVENTION

*Streptococcus pneumoniae* is a ubiquitous human pathogen causing a range of clinical infections, such as otitis media, pneumonia, meningitis, and bacteremia. The more serious manifestations are especially virulent in immunocompromised and elderly individuals. Over 90 different *S. pneumoniae* serotypes have been characterized, each having a different capsular polysaccharide structure. These polysaccharides are immunogenic in adults, and the Pneumovax®23 vaccine consists of a cocktail of 23 of the most common and/or virulent *S. pneumoniae* strains. The vaccine is recommended for everyone over the age of sixty, as well as all immunocompromised individuals, to ensure seroprotection against these strains.

The serology of the response to Pneumovax®23, as well as the conjugate vaccine Prevnar® (used to immunize children), has been studied in depth with regard to the humoral polyclonal IgG and IgA responses in both sera and saliva (Anttila et al., 1999; Nieminen et al., 1998a; Nieminen et al., 1998b). The memory and antibody secreting cell (ASC) response to these vaccines has also been previously explored on a cellular level with B cell ELISpot assays and flow cytometry Nieminen et al., 1998b; Clutterbuck et al., 2006), and the presence of both responses after vaccination is now well established. However, utilizing ASCs to produce human monoclonal antibodies would provide a novel way to fully elucidate the recall response to pathogen serotypes after vaccination, and even provides a window to explore the evolution of past responses.

Antibodies that cross-react to two or more pneumococcal polysaccharides are present in sera both pre- and post-immunization (Lee et al., 1984; Soininen et al., 2000); however, whether this is due to single antibody specificities that are capable of cross-reacting or rather due to broad polyclonal antibody specificities is not known. Although it has been reported that immunization with Pneumovax®23 in patients with SLE does not induce new auto-specificities (Elkayam et al., 2005), one report has shown that kidney-binding antibodies in a patient with SLE also cross-reacted with pneumococcal polysaccharide (Chowdhry et al., 2005). Thus, it is possible that antibodies produced from B cells in SLE donors may show increased poly-reactivity or auto-reactivity. It is only possible to determine such per-antibody phenomenon by the characterization of human monoclonal antibodies from SLE donors.

SUMMARY OF THE INVENTION

Thus, in accordance with the present invention, there is provided a human monoclonal antibody panel comprising a plurality of antibodies, wherein antibodies in said panel bind to at least 15 serotypes of *Streptococcus pneumoniae*. The antibodies in said panel may bind to at least 18 *S. pneumoniae* serotypes or 21 *S. pneumoniae* serotypes. At least 15 antibodies may be serotype specific, at least 17 antibodies may be serotype specific, or 19 antibodies may be serotype specific. The antibody panel may be attached to a support, such as a bead, a dipstick, a filter, a membrane, a plate, or a chip. The serotypes may be selected from 1, 2, 3, 4, 5, 6B, 8, 9N, 9V, 11B, 14, 15B, 17F, 18C, 19A, 19F, 20, 22F, 23F, 33F and CWPS. The antibody panel may comprise an antibody that reacts with two serotypes.

In another embodiment, there is provided a method of assessing a *Streptococcus pneumoniae* in a subject comprising obtaining a first antibody-containing sample from said subject and assessing binding of antibodies in said sample to a human monoclonal antibody panel comprising a plurality of antibodies, wherein antibodies in said panel bind to at least 15 serotypes of *Streptococcus pneumoniae*. The antibodies in said panel may bind to at least 18 *S. pneumoniae* serotypes or 21 *S. pneumoniae* serotypes. At least 15 antibodies may be serotype specific, at least 17 antibodies may be serotype specific, or 19 antibodies may be serotype specific. The antibody panel may be attached to a support, such as a bead, a dipstick, a filter, a membrane, a plate, or a chip. The serotypes may be selected from 1, 2, 3, 4, 5, 6B, 8, 9N, 9V, 11B, 14, 15B, 17F, 18C, 19A, 19F, 20, 22F, 23F, 33F and CWPS. The antibody panel may comprise an antibody that reacts with two serotypes.

The subject may be immunocompromised and/or 60 years old or older. The subject may be suspected of having a *Streptococcus pneumoniae*. The method may further comprise treating said subject with an anti-*Streptococcus pneumoniae* therapy if said first antibody-containing sample is found to be positive for one or more serotypes. The method may further comprise treating said subject with vancomycin or levoflaxin if first said antibody-containing sample is found to be positive for serotype 19A and/or 19F. The first antibody-containing sample may be blood, serum, plasma, sputum, or saliva.

The method may further comprise obtaining a second antibody-containing sample from said subject and assessing binding of antibodies in said second sample to a human monoclonal antibody panel comprising a plurality of antibodies, wherein antibodies in said panel bind to at least 15 serotypes of Streptococcus pneumoniae. The second antibody-containing sample may be blood, serum, plasma, sputum, or saliva. The subject may have been treated with an anti-Streptococcus pneumoniae therapy after determining that said first antibody-containing sample was positive for one or more serotypes, and a reduction in antibody titer to serotypes from said first sample indicates that said anti-Streptococcus pneumoniae therapy is effective at treating Streptococcus pneumoniae. The subject may have been treated with an antibiotic after determining that said first antibody-containing sample was positive for one or more serotypes, and the absence of a reduction in antibody titer to serotypes from said first sample indicates that said anti-Streptococcus pneumoniae therapy is ineffective at treating Streptococcus pneumonia, and optionally the method may further comprise treating said subject with a different anti-Streptococcus pneumoniae therapy.

In yet another embodiment, there is provided an antibody that binds selectively to Streptococcus pneumonia, wherein said antibody has heavy and light chain CDRs selected from those set forth in Table 2. The antibody may be a single chain antibody, a single domain antibody, a chimeric antibody, a Fab fragment, or an IgG. The antibody may further comprise an antibiotic linked thereto, such as one linked to said antibody through a photolabile linker or through an enzymatically-cleaved linker. The antibody may be conjugated to a nanoparticle or a liposome.

In still yet another embodiment, there is provided a method of treating a Streptococcus pneumoniae infection in a subject comprising administering to said subject an antibody as described above. The method may further comprise administering to said subject a second anti-Streptococcus pneumoniae treatment, which can be given at the same time as said antibody or given before and/or after said antibody. The antibody may be a single chain antibody, a single domain antibody, a chimeric antibody, a Fab fragment or an IgG.

The antibody may further comprises an antibiotic linked thereto, such one linked to said antibody through a photolabile linker or through an enzymatically-cleaved linker. The antibody may be conjugated to a liposome or nanoparticle. Multiple anti-Streptococcus pneumonia antibodies are administered, such as multiple anti-Streptococcus pneumonia antibodies that bind to 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 Streptococcus pneumonia serotypes.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A to 1B show Pneumovax®23 causes a massive ASC burst which can be used as a source of high affinity anti-polysaccharide antibodies. (FIG. 1A) PBMCs were harvested from four donors 7 days after vaccination with Pneumovax®23. They were stained and sorted for cells which are CD3 and CD20 negative and CD19 intermediate. The dot plots presented indicate a large ASC burst in all four donors (CD27 high, CD38 high; circular gate). Averaging the percentage of ASCs from these four donors, designated as Con1, Con2, SLE1, and SLE2, 16.3% of total B cells in the peripheral blood are ASCs. (FIG. 1B) The ASCs indicated in A. are sorted into 96-well plates. RT-PCR and several rounds of nested PCR are performed to prepare the V regions for cloning. The DNA is then cloned into expression vectors, amplified, and transfected into the HEK293 human cell line.

FIGS. 2A to 2C show on average, 77% of antibodies produced after vaccination with Pneumovax®23 bind to a vaccine component. (FIG. 2A) An average of 77% (Con1, 62%; Con2, 90%; SLE1, 75%; SLE2, 75%) of the antibodies expressed bind to S. pneumoniae capsule or cell wall polysaccharide by ELISA. (FIG. 2B) While a significant percentage of antibodies are cross-reactive (12%), most of the antibodies produced are specific to a single serotype. (FIG. 2C) 52% of the antibodies from SLE2 are poly-reactive, binding to at least two of the following five antigens: Ro, La, Sm, nRNP, or cardiolipin.

FIGS. 3A to 3D show an individual can produce multiple antibodies to the same serotype, some of which are specific and others of which cross-react. (FIG. 3A.) Serotypes 9N and 9V have very similar structures, yet Con1p2D02 binds only 9N and SLE1p1E01 binds only 9V. (FIG. 3B) Conversely, Con1p4B03 binds to both 9N and 9V. As shown by both affinity and avidity measurements, the binding to 9N is stronger than to 9V. (FIG. 3C) SLE1p1A03 binds to 9N, but cross-reacts with 14 rather than 9V. Its affinity and avidity for both 9N and 14 are similar. (FIG. 3D) SLE2p2D03 binds to both 19A and 19F, which also share similar structures. The affinity to 19A and 19F is similar, however, the avidity to 19A is 4 times stronger than to 19F. Affinity ELISAs are performed by coating plates with a single purified polysaccharide using serial dilutions of the antibody. Affinities (Kd's) are expressed in molarity. Avidity chaotropic ELISAs are performed in the same manner, but a 15 minute elution step using various dilutions of ammonium thiocyanate is added. Avidity graphs are presented as percent binding retained ($OD_{405}$ with $SCN/OD_{405}$ without SCN*100) versus the log of the thiocyanate concentration. The avidity is equal to the concentration of ammonium thiocyanate causing a 50% reduction (or retention) of binding.

FIGS. 4A to 4C show B cells generate cross-reactive antibodies to serotypes 15B and 14, as well as 17F and 33F. (FIG. 4A) Two antibodies, SLE2p2G06 and SLE2p2C04 bind solely to 17F or 33F respectively. (FIG. 4B) SLE2p1C03, however, binds to both serotypes. The affinity for 33F is an order of magnitude better than the affinity for 17F, however, their avidities are similar. (FIG. 4C) SLE2p1B01 binds to both 15B and 14. Although the affinity is almost an order of magnitude higher for 15B, it actually shows two-fold higher avidity for 14.

FIGS. 6A to 6B show the specificity of ASCs induced by Pneumovax®23 is determined by a donor's memory response invoked by the vaccine. (FIG. 6A) The 'anamnestic fingerprint' from the four donors. None had previously received Pneumovax®23, thus the ASC 'recall' antibodies cloned resulted from memory due to previous exposure to *S. pneumoniae*. Each donor has a unique "fingerprint" of serotypes against which they have produced antibodies. (FIG. 6B) After eliminating members of clonal pools and combining all four graphs, the donors have very different 'pneumococcal fingerprints' with only three serotypes (9V, 15B and 17F) being represented from three donors, and only two from all four (8 and 33F).

FIGS. 7A to 7B show Cross-reactive and poly-reactive antibodies are shown from each donor. The ELISA curves from FIG. 2A are reproduced here also showing antibodies which are (FIG. 7A) cross-reactive in red and (FIG. 7B) poly-reactive in orange. Three of the four cross-reactive antibodies from SLE2 are also poly-reactive (but none from the other donors).

DETAILED DESCRIPTION OF THE INVENTION

Figure 5:
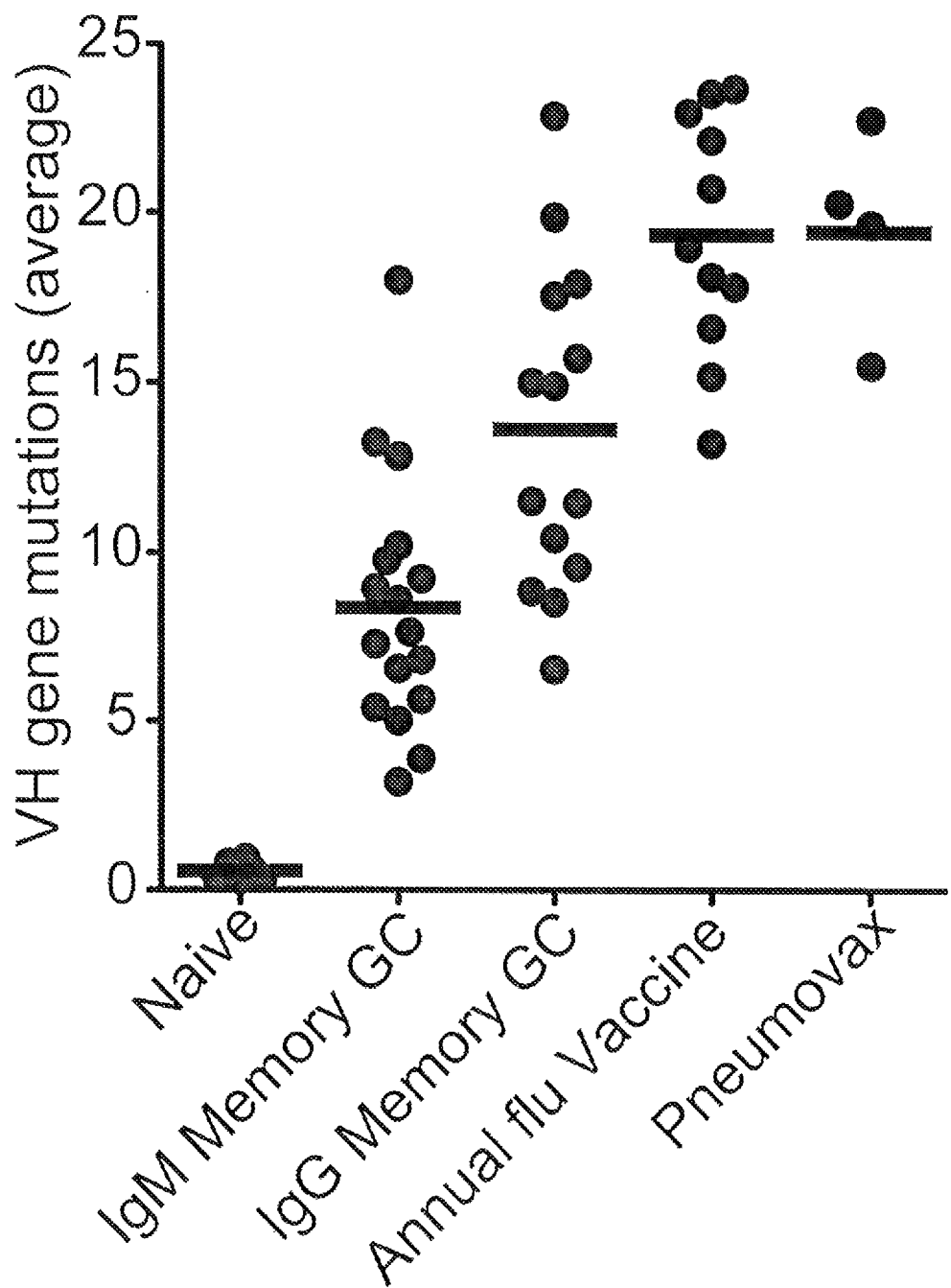
FIG. 5 shows ASCs resulting from vaccination with Pneumovax®23 produce antibodies which are highly mutated. Each data point is the average frequency of somatic mutations (nucleotide) per sequence from each donor (n values in Methods). On average, the anti-polysaccharide ASCs had accumulated a similar number of mutations as anti-influenza ASCs after seasonal influenza vaccination[14]. GC=germinal center populations.

To explore the antibody response generated by the Pneumovax®23 vaccine, the inventor generated and characterized large numbers of high affinity human monoclonal antibodies to the *S. pneumoniae* serotypes present in the vaccine from SLE patients and healthy controls. Although human monoclonal antibodies to *S. pneumoniae* have been made in the past (Baxendale and Goldblatt, 2006; Baxendale et al., 2000; Zhou et al., 2002; Zhou et al., 2004), these studies have been limited by two factors: one, they employed Fab expression library screens and two, they employed random production of hybridomas. In addition, previous studies have either focused on one serotype (6B and 23F) or have utilized vaccination with the conjugate vaccine Prevnar that consists of only seven capsular serotypes. In contrast, the inventor's technique provides cross-sectional characterization of the anti-polysaccharide response at one particular point in time, seven days post vaccination; thus, every cell used to clone an antibody has arisen from a memory response to this particular vaccination. This system will inform on a number of still unanswered questions in the field of polysaccharide immune responses and autoimmunity. In particular, the data here specifically address the percentage of human monoclonal polysaccharide antibodies that cross-react between different serotypes, how an individual's ASC response to Pneumovax®23 is a result of previous exposure to *S. pneumoniae*, and how this response differs in donors with SLE. As a result, there are now available a wide range of fully human monoclonal antibodies to *S. pneumoniae* that can be applied to diagnostic, theranostic and therapeutic applications. These and other aspects of the invention are described in detail below.

II. *STREPTOCOCCUS PNEUMONIAE*

A. General

*Streptococcus pneumoniae*, or pneumococcus, is Gram-positive, alpha-hemolytic, bile-soluble aerotolerant, anaerobic member of the genus *Streptococcus*. A significant human pathogenic bacterium, *S. pneumoniae* was recognized as a major cause of pneumonia in the late 19th century, and is the subject of many humoral immunity studies.

*S. pneumoniae* can be differentiated from *Streptococcus viridans*, some of which are also alpha-hemolytic, using an optochin test, as *S. pneumoniae* is optochin-sensitive. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance.

The genome of *S. pneumoniae* is a closed, circular DNA structure that contains between 2.0 and 2.1 million basepairs, depending on the strain. It has a core set of 1553 genes, plus 154 genes in its virulome, which contribute to virulence, and 176 genes that maintain a noninvasive phenotype. Genetic information can vary up to 10% between strains.

*S. pneumoniae* is part of the normal upper respiratory tract flora, but, as with many natural flora, it can become pathogenic under the right conditions (e.g., if the immune system of the host is suppressed). Invasins, such as pneumolysin, an antiphagocytic capsule, various adhesins and immunogenic cell wall components are all major virulence factors.

Community-acquired pneumonia (CAP) is becoming more and more common, and represents an important cause of mortality and morbidity worldwide. While a number of different pathogens can give rise to CAP, *Streptococcus pneumoniae* is one of the most common.

CAP is often acquired via inhalation or aspiration of pulmonary pathogenic organisms into a lung segment or lobe. Less commonly, CAP results from secondary bacteremia from a distant source.

Severe CAP normally develops in patients with cardiopulmonary disease, diminished splenic function, and/or pathogenic virulence, but even young and/or healthy hosts can develop severe CAP if the causative pathogen is sufficiently virulent. Complications in CAP depend on the infecting pathogen and patient health. Myocardial infarction can be precipitated by fever due to community-acquired pneumonia (CAP). Also, patients with CAP who have impaired splenic function may develop overwhelming pneumococcal sepsis, potentially leading to death within 12-24 hours, regardless of the antimicrobial regimen used.

CAP morbidity and mortality are highest in elderly patients and in immunocompromised hosts. Other factors that predict an increased risk of mortality in patients with CAP include the presence of significant comorbidities, an increased respiratory rate, hypotension, fever, multilobar involvement, anemia, and hypoxia.

B. Related Disease States

Despite the name, *S. pneumoniae* causes many types of pneumococcal infections other than pneumonia, including acute sinusitis, otitis media, meningitis, bacteremia, sepsis, osteomyelitis, septic arthritis, endocarditis, peritonitis, pericarditis, cellulitis, and brain abscess.

C. Multi-Drug Resistance

A growing concern in *S. pneumoniae* therapy is the resistance of strains many to penicillin and other beta-lactams (like amoxicillin), which is increasing worldwide. The major mechanism of resistance involves the introduction of mutations in genes encoding penicillin-binding proteins. This development complicates treatment immensely, and also adds unnecessary cost when therapies fail.

In 2000, Whitney et al. examined data on invasive pneumococcal disease in patients identified from 1995 to 1998 in the Active Bacterial Core Surveillance program of the Centers for Disease Control and Prevention. During 1998, 4013 cases of invasive *Streptococcus pneumoniae* disease were reported, and isolates were available for 3475 (87%). Overall, 24% of isolates from 1998 were resistant to penicillin. Penicillin-resistant isolates were more likely than susceptible isolates to have a high level of resistance to other antimicrobial agents. Serotypes included in the 7-valent conjugate and 23-valent pneumococcal polysaccharide vaccines accounted for 78% and 88% of penicillin-resistant strains, respectively. Between 1995 and 1998, the proportion of isolates that were resistant to three or more classes of drugs increased from 9% to 14%; there also were increases in the proportions of isolates that were resistant to penicillin (from 21% to 25%), cefotaxime (from 10% to 14%), meropenem (from 10% to 16%), erythromycin (from 11% to 15%), and trimethoprim-sulfamethoxazole (from 25% to 29%). These trends are like to continue, putting greater pressure on clinicians to resort to drugs such as vancomycin and levoflaxin.

D. Diagnosis

*S. pneumoniae* can be differentiated from other *Streptococcus* infections based on the alpha-hemolytic test. *Streptococcus viridans*, some of which are also alpha-hemolytic, can be distinguished using an optochin test, as *S. pneumoniae* is optochin-sensitive but *S. viridans* is not. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance.

In terms of distinguishing serotypes, antibodies are currently available to serotypes 1, 3, 4, 5, 6B, 7F, 8, 9N, 9V, 12F, 14, 18C, 19F and 23F (ARUP Laboratories, Salt Lake City, UT).

E. Treatments

Antibiotics are the treatment of choice for *S. pneumoniae* infects, with ventilation (oxygen supplement) as supportive therapy of bacterial pneumonia. The antibiotic choice depends on the the microorganisms most commonly causing pneumonia in the geographical region, as well as nature of the specific organism, the immune status and underlying health of the individual, the severity of infection, and prior treatment history. In the United Kingdom, amoxicillin is used as first-line therapy in the vast majority of patients who acquire pneumonia in the community, sometimes with added clarithromycin. In North America, where the "atypical" forms of community-acquired pneumonia are becoming more common, clarithromycin, azithromycin, or fluoroquinolones as single therapy, have displaced the amoxicillin as first-line therapy. Local patterns of antibiotic-resistance should always be considered when initiating pharmacotherapy. In hospitalized individuals or those with immune deficiencies, local guidelines determine the selection of antibiotics. These antibiotics are typically given through an intravenous line. Specifically, *S. pneumoniae* is treated with amoxicillin (or erythromycin in patients allergic to penicillin), and with cefuroxime and erythromycin in severe cases.

III. PRODUCING MONOCLONAL ANTIBODIES

A. General Methods

It will be understood that monoclonal antibodies binding to *S. pneumoniae* will have utilities in several applications. These include the production of diagnostic kits for use in detecting and diagnosing disease. In these contexts, one may link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

In the case of human monoclonal antibodies, one may instead simply look for an individual already known to have generated an immune response, in this case, to have been exposed to *S. pneumoniae* or immunized with Pneumovax®23. In order to identify subjects with immunity to various *S. pneumoniae* strains, one could generally obtain blood from subjects and test them for *S. pneumoniae* antibodies. Many antibodies described in this invention were generated in this way using peripheral blood from otherwise healthy individuals previously infected with *S. pneumoniae*.

Following immunization or obtaining of cells from previously infected subjects as described above, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this invention were generated using the HMMA2.5 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). The hybridomas secreting the influenza antibodies in this invention were obtained by electrofusion.

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Invention

Antibodies according to the present invention may be defined, in the first instance, by their binding specificity. Those of skill in the art, by assessing the binding affinity of a given antibody using techniques well known to those of skill in the art, can determine whether such antibodies fall within the scope of the instant claims.

In the context of the present invention, the antibody specificity relates to the *S. pneumoniae* serotype. There are 24 different serotypes represented by Pneumovax®23, represented by the following designations: 1, 2, 3, 4, 5, 6B, 7F, 8, 9N, 9V, 10A, 11A, 12F, 14, 15B, 17F, 18C, 19F, 19A, 20, 22F, 23F, 33F and CWPS. The CDR region sequences for representative antibodies are included in the appended sequence listing.

Another way of categorizing the antibodies of the present invention is by their activity. This could include the ability to neutralize or kill *Streptococcus pneumoniae* in the presence or absence of complement. Finally, the antibody may be defined in particular by reference to heavy/light chain variable region sequences. The present inventor provides the following antibodies that have demonstrated activity against *Streptococcus pneumoniae* in an opsonophagocytosis assay (OPA) that measures antibody mediated uptake of bacteria by a phagocytic cell line. The also can be presented by variable regions as set out in Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy® vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies can generated by subcloning heavy and light chain Fv DNAs from the cloning vector into a second vector, such as a Lonza pConIgG1 or pConK2 plasmid vector, transfected into 293 Freestyle cells or Lonza CHO cells, and antibodies can then be collected and purified from the cell supernatants.

pCon Vectors' are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric or CDR-grafted antibody). In yet a further embodiment, the antibody is a fully human recombinant antibody. Alternatively, one may wish to make more subtle modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4); sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include:

arginine and lysine; glutamate and aspartate; serine and threonine; glutamine and asparagine; and valine, leucine and isoleucine.

The present invention also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

E. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. PASSIVE IMMUNIZATION AND TREATMENT OF *S. PNEUMONIAE* INFECTIONS

A. Formulation and Administration

Passive transfer of antibodies, known as artificially acquired passive immunity, generally will involve the use of intravenous or intramuscular injections. Such immunity generally lasts for only a short period of time, but provides immediate protection. The antibodies will be formulated in a carrier suitable for injection, i.e., sterile and syringeable. Thus, the present invention provides pharmaceutical compositions comprising anti-*S. pneumoniae* antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapy

In order to increase the effectiveness of the antibody therapy of the present invention, it may be desirable to combine this treatment with other agents effective at treating or preventing *S. pneumonia* infections, e.g., antibiotics. This process may involve administering to the patient the antibody of the present invention and the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the antibody treatment of the present invention is "A" and the secondary treatment is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the secondary agent will follow general protocols for that drug, taking into account the toxicity, if any. It is expected that the treatment cycles would be repeated as necessary.

1. Amoxicillin and Erythromycin

Amoxicillin. Amoxicillin (INN), formerly amoxycillin (BAN), and abbreviated amox, is a moderate-spectrum, bacteriolytic, β-lactam antibiotic used to treat bacterial infections caused by susceptible microorganisms. It is usually the drug of choice within the class because it is better absorbed, following oral administration, than other β-lactam antibiotics. Amoxicillin is one of the most common antibiotics prescribed for children. This drug acts by inhibiting the synthesis of bacterial cell walls. It inhibits cross-linkage between the linear peptidoglycan polymer chains that make up a major component of the cell walls of both Gram-positive and Gram-negative bacteria.

It has two ionizable groups in the physiological range (the amino group in alpha-position to the amide carbonyl group and the carboxyl group). Amoxicillin is susceptible to degradation by 3-lactamase-producing bacteria, which are resistant to a broad spectrum of β-lactam antibiotics, such as penicillin. For this reason, it is often combined with clavulanic acid, a β-lactamase inhibitor, and marketed under one name. This increases effectiveness by reducing its susceptibility to β-lactamase resistance.

Amoxicillin is used in the treatment of a number of infections including: acute otitis media, streptococcal pharyngitis, pneumonia, skin infections, urinary tract infections, *salmonella*, lyme disease, and *chlamydia* infections. It is used to prevent bacterial endocarditis in high risk people who are having dental work done, to prevent strep pneumococus infections in those without a spleen, and for both the prevention and treatment of anthrax. It is also a treatment for cystic acne. The UK however does not recommend its use for infectious endocarditis prophylaxis. These recommendations have not appeared to have changed the rates of infection.

Side-effects are as those for other beta-lactam antibiotics. Side-effects include nausea, vomiting, rashes, and antibiotic-associated colitis. Loose bowel movements (diarrhea) also may occur. Rarer, but patient-reported, side-effects include mental changes, lightheadedness, insomnia, confusion, anxiety, sensitivity to lights and sounds, and unclear thinking. Immediate medical care is required upon the first signs of these side-effects.

The onset of an allergic reaction to amoxicillin can be very sudden and intense—emergency medical attention must be sought as quickly as possible. The initial onset of such a reaction often starts with a change in mental state, skin rash with intense itching (often beginning in fingertips and around groin area and rapidly spreading), and sensations of fever, nausea, and vomiting. Any other symptoms that seem even remotely suspicious must be taken very seriously. However, more mild allergy symptoms, such as a rash, can occur at any time during treatment, even up to a week after treatment has ceased. For some people who are allergic to amoxicillin the side effects can be deadly. Use of the amoxicillin/clavulanic acid combination for more than one week has caused mild hepatitis in some patients. Young children having ingested acute overdoses of amoxicillin manifested lethargy, vomiting and renal dysfunction.

Amoxicillin in trihydrate form is available as capsules, chewable and dispersible tablets plus syrup and pediatric suspension for oral use, and as the sodium salt for intravenous administration (although the IV formulation is not available in the United States). Amoxicillin is most commonly taken orally. The liquid forms are helpful where the patient might find it difficult to take tablets or capsules.

Erythromycin. Erythromycin is a macrolide antibiotic that has an antimicrobial spectrum similar to or slightly wider than that of penicillin, and is often used for people who have an allergy to penicillins. For respiratory tract infections, it has better coverage of atypical organisms, including *mycoplasma* and Legionellosis. It was first marketed by Eli Lilly and Company, and it is today commonly known as EES (erythromycin ethylsuccinate, an ester prodrug that is commonly administered).

In structure, this macrocyclic compound contains a 14-membered lactone ring with ten asymmetric centers and two sugars (L-cladinose and D-desosamine), making it a compound very difficult to produce via synthetic methods. Erythromycin is produced from a strain of the actinomycete Saccharopolyspora erythraea.

U.S. Pat. No. 2,653,899, which covers the drug, was granted in 1953. The product was launched commercially in 1952 under the brand name Ilosone (after the Philippine region of Iloilo where it was originally collected from). Erythromycin was formerly also called Ilotycin.

Over the years since the discovery of erythromycin A and its activity as an antimicrobial, many attempts have been made to synthesize it in the laboratory. However, the presence of ten stereospecific carbons and several points of distinct substitution has made the total synthesis of erythromycin A a formidable task. Complete syntheses of erythromycins' related structures and precursors such as 6-deoxyerythronolide B have been accomplished, giving way to possible syntheses of different erythromycins and other macrolide antimicrobials. However, Woodward and colleagues did successfully complete the synthesis of erythromycin A in 1981.

Erythromycin is available in enteric-coated tablets, slow-release capsules, oral suspensions, ophthalmic solutions, ointments, gels, and injections. Brand names include Robimycin, E-Mycin, E.E.S. Granules, E.E.S.-200, E.E.S.-400, E.E.S.-400 Filmtab, Erymax, Ery-Tab, Eryc, Ranbaxy, Erypar, EryPed, Eryped 200, Eryped 400, Erythrocin Stearate Filmtab, Erythrocot, E-Base, Erythroped, Ilosone, MY-E, Pediamycin, Zineryt, Abboticin, Abboticin-ES, Erycin, PCE Dispertab, Stiemycine, Acnasol and Tiloryth.

Gastrointestinal disturbances, such as diarrhea, nausea, abdominal pain, and vomiting, are very common because erythromycin is a motilin agonist. Because of this, erythromycin tends not to be prescribed as a first-line drug. However, erythromycin may be useful in treating gastroparesis due to this pro-motility effect. Intravenous erythromycin may also be used in endoscopy as an adjunct to clear gastric contents. More serious side-effects include arrhythmia with prolonged QTc intervals including Torsades-de-Pointe and reversible deafness. Allergic reactions range from urticaria to anaphylaxis. Cholestasis, Stevens-Johnson syndrome, and toxic epidermal necrolysis are some other rare side-effects that may occur.

Exposure to erythromycin (especially long courses at antimicrobial doses, and also through breastfeeding) has been linked to an increased probability of pyloric stenosis in young infants. Erythromycin used for feeding intolerance in young infants has not been associated with hypertrophic pyloric stenosis.

Erythromycin estolate has been associated with reversible hepatotoxicity in pregnant women in the form of elevated serum glutamic-oxaloacetic transaminase and is not recommended during pregnancy. Some evidence suggests similar hepatotoxicity in other populations.

It can also affect the central nervous system, causing psychotic reactions, nightmares and night sweats. It may also alter the effectiveness of combined oral contraceptive pills because of its effect on the gut flora. Erythromycin is an inhibitor of the cytochrome P450 system, which means that it can have a rapid effect on levels of other drugs metabolised by this system, e.g., warfarin.

Erythromycin displays bacteriocidal activity, especially at higher concentrations, but the mechanism is not fully understood. By binding to the 50S subunit of the bacterial 70s rRNA complex, protein synthesis and subsequent structure and function processes critical for life or replication are inhibited. Erythromycin interferes with aminoacyl translocation, preventing the transfer of the tRNA bound at the A site of the rRNA complex to the P site of the rRNA complex. Without this translocation, the A site remains occupied and, thus, the addition of an incoming tRNA and its attached amino acid to the nascent polypeptide chain is inhibited. This interferes with the production of functionally useful proteins, which is the basis of this antimicrobial action.

2. Clarithromycin, Azithromycin, Fluoroquinolones and Cefuroxime

Clarithromycin. Clarithromycin is a macrolide antibiotic used to treat pharyngitis, tonsillitis, acute maxillary sinusitis, acute bacterial exacerbation of chronic bronchitis, pneumonia (especially atypical pneumonias associated with *Chlamydia pneumoniae* or TWAR), skin and skin structure infections. In addition, it is sometimes used to treat Legionellosis, *Helicobacter pylori*, and lyme disease. Clarithromycin is available under several brand names, for example Crixan, Clarac, Biaxin, Klaricid, Klacid, Klaram, Klabax, Klacid, Claripen, Clarem, Claridar, Fromilid, Clacid, Clacee, Vikrol, Infex and Clariwin, Resclar.

Clarithromycin was invented by researchers at the Japanese drug company Taisho Pharmaceutical in the 1970s. The product emerged through efforts to develop a version of the antibiotic erythromycin that did not experience acid instability in the digestive tract, causing side effects, such as nausea and stomach ache. Taisho filed for patent protection for the drug around 1980 and subsequently introduced a branded version of its drug, called Clarith, to the Japanese market in 1991. In 1985 Taisho partnered with the American company Abbott Laboratories for the international rights, and Abbott also gained FDA approval for Biaxin in October 1991. The drug went generic in Europe in 2004 and in the US in mid-2005.

Antibacterial spectrum is the same as erythromycin but it is active against *Mycobacterium avium* complex (MAV), *M. leprae* and atypical mycobacteria.

Clarithromycin prevents bacteria from growing by interfering with their protein synthesis. Clarithromycin binds to the subunit 50S of the bacterial ribosome and thus inhibits the translation of peptides. Clarithromycin has similar antimicrobial spectrum as erythromycin but is more effective against certain gram-negative bacteria, particularly *Legionella pneumophila*. Besides this bacteriostatic effect, clarithromycin also has bactericidal effect on certain strains such as *Haemophilus influenzae, Streptococcus pneumoniae* and *Neisseria gonorrhoeae*.

Unlike erythromycin, clarithromycin is acid-stable and can therefore be taken orally without being protected from gastric acids. It is readily absorbed, and diffused into most tissues and phagocytes. Due to the high concentration in phagocytes, clarithromycin is actively transported to the site of infection. During active phagocytosis, large concentrations of clarithromycin are released. The concentration of clarithromycin in the tissues can be over 10 times higher than in plasma. Highest concentrations were found in liver and lung tissue.

Clarithromycin has a fairly rapid first-pass hepatic metabolism. However, 14-hydroxy clarithromycin, clarithromycin's metabolite, is almost twice as active and has a half life of 7 hours compared to clarithromycin's 5. Clarithromycin and its metabolites main routes of elimination are urinary and biliary excretion. Of all the drugs in its class, clarithromycin has the best bioavailability at 50%, which makes it amenable to oral administration.

Most common side-effects are gastrointestinal, including diarrhea, nausea, extreme irritability, abdominal pain and vomiting, facial swelling. Less common side-effects include headaches, hallucinations (auditory and visual), dizziness/motion sickness, rashes, alteration in senses of smell and taste, including a metallic taste that lasts the entire time one takes it. Dry mouth, panic and/or anxiety attacks and nightmares have also been reported albeit less frequently. In more serious cases it has been known to cause jaundice, cirrhosis, and kidney problems including renal failure. Uneven heartbeats, chest pain, and shortness of breath have also been reported while taking this drug.

Adverse effects of clarithromycin in the central nervous system include dizziness, ototoxicity and headaches, but delirium and mania are also uncommon side effects. When taken along with some statins, drugs used to reduce blood serum cholesterol levels, muscle pain may occur. There is also the risk of oral candidiasis, due to the increased yeast production in the body from the antibiotics.

Azithromycin. Azithromycin is an azalide, a subclass of macrolide antibiotics. Azithromycin is one of the world's best-selling antibiotics, marketed in the United States under the name Zithromax, and under a variety of brand names and generic labels worldwide. It is derived from erythromycin; however, it differs in chemical structure from erythromycin in that a methyl-substituted nitrogen atom is incorporated into the lactone ring, thus making the lactone ring 15-membered.

Azithromycin is used to treat or prevent certain bacterial infections, most often those causing middle ear infections, strep throat, pneumonia, typhoid, and sinusitis. In recent years, it has been used primarily to prevent bacterial infections in infants and those with weaker immune systems. It is also effective against certain sexually transmitted infections, such as non-gonococcal urethritis, *chlamydia*, and cervicitis. Recent studies have indicated it also to be effective against late-onset asthma, but these findings are controversial and not widely accepted.

Azithromycin is used to treat many different infections including acute otitis media, streptococcal pharyngitis, gastrointestinal infections such as traveler's diarrhea, respiratory tract infections such as pneumonia, cellulitis, babesiosis, *bartonella*, chancroid, *chlamydia*, cholera, donovanosis, leptospirosis, lyme disease, malaria, *Mycobacterium avium* complex, *neisseria* meningitis, pelvic inflammatory disease, pertussis, scrub typhus, syphilis, toxoplasmosis, and *salmonella*. It is used to prevent bacterial endocarditis and some sexually transmitted illnesses post sexual assault.

It has a similar antimicrobial spectrum as erythromycin, but is more effective against certain Gram-negative bacteria, in particular, *Haemophilus influenzae*. Azithromycin resistance has been described and is endemic in many areas. It is notably ineffective against MRSA. Azithromycin has been shown to be effective against malaria when used in combination with artesunate or quinine; the optimal dose for this is not yet known.

Most common side-effects are gastrointestinal: diarrhea (5%), nausea (3%), abdominal pain (3%), and vomiting. Fewer than 1% of patients stop taking the drug due to side-effects. Nervousness, dermatologic reactions, and anaphylaxis have been reported. As with all antimicrobial agents, pseudomembranous colitis can occur during and up to several weeks after azithromycin therapy. This drug may interfere with the effectiveness of birth control pills; other forms of contraception may be required during the treatment period. Azithromycin suspension has an objectionable taste, so can be difficult to administer to young children, i.e., 2-5 years, who may spit it out.

Occasional patients have developed cholestatic hepatitis or delirium. Accidental intravenous overdosage in an infant caused severe heart block, resulting in residual encephalopathy.

Azithromycin prevents bacteria from growing by interfering with their protein synthesis. Azithromycin binds to the 50S subunit of the bacterial ribosome, and thus inhibits translation of mRNA. Nucleic acid synthesis is not affected.

Unlike erythromycin, azithromycin is acid-stable and can therefore be taken orally with no need of protection from gastric acids. It is readily absorbed, but its absorption is greater on an empty stomach. Time to peak concentration in adults is 2.1 to 3.2 hours for oral dosage forms and one to two hours after a dose. Due to the high concentration in phagocytes, azithromycin is actively transported to the site of infection. During active phagocytosis, large concentrations of azithromycin are released. The concentration of azithromycin in the tissues can be over 50 times higher than in plasma. This is due to ion trapping and the high lipid solubility (Volume of distribution is too low).

Azithromycin's half-life allows a large single dose to be administered and yet maintain bacteriostatic levels in the infected tissue for several days. The new extended-release formulation of azithromycin "Zmax," A-Max is a liquid oral suspension that releases the drug in a single 2-g dose. With the macrolide technology of Zmax, this allows the drug to bypass the stomach, reducing gastrointestinal side-effects of high-dose azithromycin.

Azithromycin is commonly administered in tablet or oral suspension (a one-dose version was made available in 2005). It is also available for intravenous injection and in a 1% ophthalmic solution. Tablets come in doses of 250 mg and 500 mg. Oral suspension comes in strengths of 100 mg/5 mL and 200 mg/5 mL. The 250 mg tablets are often dispensed in packages of six and commonly referred to as a "Z-Pak," whereas the 500 mg tablets are commonly available commercially in a pack of three tablets, or "Tri-Pak," intended as a three-day treatment. A common dose of oral azithromycin therapy consists of a "double dose" of medication on the first day of treatment and subsequent treatment for four or five additional days. With the "Z-Pak," this means two 250 mg tablets (a total of 500 mg) on the first day and one 250 mg tablet once daily for the next four days.

Pfizer brand-name, i.e., Zithromax, azithromycin tablets are mottled pink, unscored, film-coated, modified-oval-shaped tablets containing azithromycin monohydrate and the following inactive ingredients: butylated hydroxytoluene, calcium phosphate, carmine, colloidal silicon dioxide, FD&C red #40 lake, FD&C yellow #6 lake, hypromellose (2910, 15 cP), lactose monohydrate, magnesium stearate, pregelatinized starch, sodium lauryl sulfate, talc, titanium dioxide, and triacetin.

Fluoroquinolones. The quinolones are a family of synthetic broad-spectrum antibiotics. The term quinolone(s) refers to potent synthetic chemotherapeutic antibacterials. The first generation of the quinolones begins with the introduction of nalidixic acid in 1962 for treatment of urinary tract infections in humans. Nalidixic acid was discovered by George Lesher and coworkers in a distillate during an attempt at chloroquine synthesis. They prevent bacterial DNA from unwinding and duplicating.

Quinolones, in comparison to other antibiotic classes, have the highest risk of causing colonization with MRSA and *Clostridium difficile*. For this reason, a general avoidance of fluoroquinolones is recommended based on the available evidence and clinical guidelines. The majority of quinolones in clinical use belong to the subset fluoroquinolones, which have a fluorine atom attached to the central ring system, typically at the 6-position or C-7 position. Debates are still taking place as to whether or not the effectiveness of fluoroquinolones for the treatment of respiratory disorders is similar to that of other antibiotic classes.

Fluoroquinolone use for pneumonia is increasing, and with it so is bacterial resistance to fluoroquinolones. The majority of the prescribing of fluoroquinolones is inappropriate, with less than four percent of people prescribed quinolones being appropriate according to clinical guidelines. Clinical guidelines in Canada recommend fluoroquinolones only for outpatient treatment of pneumonia in a small number of patients, such as those with certain comorbid conditions, e.g., patients with a history of COPD, or those with recent use of antibiotics. For severe forms of community-acquired pneumonia, the fluoroquinolones are associated with improved treatment rates, but with no differences found in mortality between other antibiotic classes.

Fluoroquinolones are not recommended as first-line antibiotics for acute sinusitis, as this condition is usually self-limiting, and the risks outweigh the benefits in comparison to other antibiotic classes.

Antibiotics including fluoroquinolones can be effective in some cases of bronchitis. However, only about 5-10% of bronchitis cases are caused by a bacterial infection; most cases of bronchitis are caused by a viral infection and are self-limiting and resolve themselves in a few weeks. It has been recommended that antibiotics are limited in most cases to those whose symptoms fail to resolve on their own.

Fluoroquinolones are often used for genitourinary infections; in general they are recommended only after other antibiotic regimens have failed. However, for serious acute cases of pyelonephritis or bacterial prostatitis where the patient may need to be hospitalised, fluoroquinolones are recommended as first-line therapy. Prostatitis has been termed "the waste basket of clinical ignorance" by prominent Stanford University urologist Dr. Thomas Stamey. Campbell's Urology, the urologist's most authoritative reference text, identifies only about 5% of all patients with prostatitis as having bacterial prostatitis, which can be "cured" at least in the short term by antibiotics. In other words, 95% of men with prostatitis have little hope for a cure with antibiotics alone, since they do not actually have any identifiable bacterial infection.

In general, fluoroquinolones are well tolerated, with most side effects being mild to moderate. On occasion, serious adverse effects occur. Some of the serious adverse effects that occur more commonly with fluoroquinolones than with other antibiotic drug classes include CNS and tendon toxicity. The currently marketed quinolones have safety profiles similar to those of other antimicrobial classes. Fluoroquinolones are sometimes associated with an QTc interval prolongation and cardiac arrhythmias, convulsions, tendon rupture, torsade de pointes and hypoglycemia.

These adverse reactions are a class effect of all quinolones; however, certain quinolones are more strongly associated with increased toxicity to certain organs. For example, moxifloxacin carries a higher risk of QTc prolongation, and gatifloxacin has been most frequently linked to disturbed blood sugar levels, although all quinolones carry these risks. Some quinolones were withdrawn from the market because of these adverse events (for example, sparfloxacin was associated with phototoxicity and QTc prolongation, thrombocytopenia and nephritis were seen with tosufloxacin, and hepatotoxicity with trovafloxacin). Simultaneous use of corticosteroids is present in almost one-third of quinolone-associated tendon rupture. The risk of adverse events is further increased if the dosage is not properly adjusted, for example if there is renal insufficiency.

The serious events may occur during therapeutic use at therapeutic dose levels or with acute overdose. At therapeutic doses, they include: CNS toxicity, cardiovascular toxicity, tendon/articular toxicity, and, rarely, hepatic toxicity. Caution is required in patients with liver disease. Events that may occur in acute overdose are rare, and include renal failure and seizure. Susceptible groups of patients, such as children and the elderly, are at greater risk of adverse reactions during therapeutic use. Adverse reactions may manifest during, as well as after fluoroquinolone therapy has been completed.

The CNS is an important target for fluoroquinolone-mediated neurotoxicity. Adverse event reporting in Italy by doctors showed fluoroquinolones among the top three prescribed drugs for causing adverse neurological and psychiatric effects. These neuropsychiatric effects included tremor, confusion, anxiety, insomnia, agitation, and, in severe cases, psychosis. Moxifloxacin came out worst among the quinolones for causing CNS toxicity.

The basic pharmacophore, or active structure, of the fluoroquinolone class is based upon the quinoline ring system. The addition of the fluorine atom at C6 is what distinguishes the successive-generation fluoroquinolones from the first-generation quinolones. The addition of the C6 fluorine atom has since been demonstrated to not be required for the antibacterial activity of this class (circa 1997).

Various substitutions made to the quinoline ring resulted in the development of numerous fluoroquinolone drugs available today. Each substitution is associated with a number of specific adverse reactions, as well as increased activity against bacterial infections, whereas the quinoline ring, in and of itself, has been associated with severe and even fatal adverse reactions.

Cefuroxime. Cefuroxime is a second-generation cephalosporin antibiotic that has been widely available in the USA as Ceftin since 1977. GlaxoSmithKline sells the antibiotic in the United Kingdom (and other countries, such as Australia, Turkey, Israel, Bangladesh, Thailand, Hungary and Poland) under the name Zinnat.

As for the other cephalosporins, although as a second-generation it is less susceptible to beta-lactamase and so may have greater activity against *Haemophilus influenzae, Neisseria gonorrhoeae* and Lyme disease. Unlike other second generation cephalosporins, cefuroxime can cross the blood-brain-barrier.

Cefuroxime is generally well tolerated and side effects are usually transient. Cefuroxime, if ingested with food, is both better absorbed and less likely to cause its most common side effects of diarrhea, nausea, vomiting, headaches/migraines, dizziness and abdominal pain.

Although there is a widely quoted cross-allergy risk of 10% between cephalosporins and penicillin, recent assessments have shown no increased risk for cross-allergy for cefuroxime and several other $2^{nd}$ generation or later cephalosporins.

3. Vancomycin and Levoflaxin

Vancomycin. Vancomycin (INN) is a glycopeptide antibiotic used in the prophylaxis and treatment of infections caused by Gram-positive bacteria. It has traditionally been reserved as a drug of "last resort," used only after treatment with other antibiotics had failed, although the emergence of vancomycin-resistant organisms means that it is increasingly being displaced from this role by linezolid (Zyvox) available PO and IV and daptomycin (Cubicin) IV and quinupristin/dalfopristin (Synercid) IV.

Vancomycin was first isolated in 1953 by Edmund Kornfeld (working at Eli Lilly) from a soil sample collected from the interior jungles of Borneo by a missionary. The organism that produced it was eventually named *Amycolatopsis orientalis*. The original indication for vancomycin was for the treatment of penicillin-resistant *Staphylococcus aureus*. One advantage that was quickly apparent is that staphylococci did not develop significant resistance despite serial passage in culture media containing vancomycin. The rapid development of penicillin resistance by staphylococci led to the compound's being fast-tracked for approval by the FDA in 1958. Eli Lilly first marketed vancomycin hydrochloride under the trade name Vancocin and as COVANC from Nucleus, India.

Vancomycin never became the first-line treatment for *Staphylococcus aureus* for several reasons. First, it possesses poor oral bioavailability. Also, it must be given intravenously for most infections. In addition, β-Lactamase-resistant semi-synthetic penicillins such as methicillin (and its successors, nafcillin and cloxacillin) were subsequently developed, which have better activity against non-MRSA staphylococci.

An oral form of vancomycin was originally approved by the FDA in 1986 for the treatment of *Clostridium difficile*-induced pseudomembranous colitis. It is not orally absorbed into the blood and remains in the gastrointestinal tract to eradicate *C. difficle*. This product is currently marketed by ViroPharma in the USA.

Vancomycin biosynthesis occurs via different nonribosomal protein synthases (NRPSs). The enzymes determine the amino acid sequence during its assembly through its 7 modules. Before Vancomycin is assembled through NRPS, the amino acids are first modified. L-tyrosine is modified to become the β-hydroxychlorotyrosine (β-hTyr) and 4-hydroxyphenylglycine (HPG) residues. On the other hand, acetate is used to derive the 3,5 dihydroxyphenylglycine ring (3,5-DPG).

Nonribosomal peptide synthesis occurs through distinct modules that can load and extend the protein by one amino acid through the amide bond formation at the contact sites of the activating domains. Each module typically consists of an adenylation (A) domain, a peptidyl carrier protein (PCP) domain, and a condensation (C) or elongation domain. In the A domain, the specific amino acid is activated by converting into an aminoacyl adenylate enzyme complex attached to a 4' phosphopantetheine cofactor by thioesterification. The complex is then transferred to the PCP domain with the expulsion of AMP. The PCP domain uses the attached 4'-phosphopantethein prosthetic group to load the growing peptide chain and their precursors. In the biosynthesis of Vancomycin, additional modification domains are present, such as the epimerization (E) domain, which is used isomerizes the amino acid from one stereochemistry to another, and a thioesterase domain (TE) is used as a catalyst for cyclization and releases of the molecule via a thioesterase scission.

After the linear heptapeptide molecule is synthesized, Vancomycin has to undergo further modifications, such as oxidative cross-linking and glycosylation, in trans, by distinct enzymes, referred to as tailoring enzymes, in order to become biologically active. To convert the linear heptapeptide, eight enzymes are used. With the help of these enzymes, β-hydroxyl groups are introduced onto tyrosine residues 2 and 6, and coupling occurs for rings 5 and 7, rings 4 and 6, and rings 4 and 2. In addition, a haloperoxidase is used to attach the chlorine atoms onto rings 2 and 6 via an oxidative process.

Vancomycin acts by inhibiting proper cell wall synthesis in Gram-positive bacteria. Due to the different mechanism by which Gram-negative bacteria produce their cell walls and the various factors related to entering the outer membrane of Gram-negative organisms, vancomycin is not active against Gram-negative bacteria (except some non-gonococcal species of *Neisseria*).

The large hydrophilic molecule is able to form hydrogen bond interactions with the terminal D-alanyl-D-alanine moieties of the NAM/NAG-peptides. Under normal circumstances, this is a five-point interaction. This binding of vancomycin to the D-Ala-D-Ala prevents cell wall synthesis in two ways. It prevents the synthesis of the log polymers of N-acetylmuramic acid (NAM) and N-acetylglucosamine (NAG) that form the backbone strands of the bacterial cell wall, and it prevents the backbone polymers that do manage to form from cross-linking with each other.

Although vancomycin levels are usually monitored, in an effort to reduce adverse events, the value of this is not beyond debate. Peak and trough levels are usually monitored, and, for research purposes, the area under the curve is also sometimes used. Toxicity is best monitored by looking at trough values. Common adverse drug reactions (≥1% of patients) associated with IV vancomycin include: local pain, which may be severe and/or thrombophlebitis.

Damage to the kidneys and to the hearing were a side-effect of the early impure versions of vancomycin, and these were prominent in the clinical trials conducted in the mid-1950s. Later trials using purer forms of vancomycin found that nephrotoxicity is an infrequent adverse effect (0.1-1% of patients), but that this is accentuated in the presence of aminoglycosides.

Rare adverse effects (<0.1% of patients) include: anaphylaxis, toxic epidermal necrolysis, erythema multiforme, red man syndrome (see below), superinfection, thrombocytopenia, neutropenia, leucopenia, tinnitus, dizziness and/or ototoxicity (see below).

It has recently been emphasized that vancomycin can induce platelet-reactive antibodies in the patient, leading to severe thrombocytopenia and bleeding with florid petechial hemorrhages, ecchymoses, and wet purpura.

Vancomycin must be given intravenously (IV) for systemic therapy, since it does not cross through the intestinal lining. It is a large hydrophilic molecule that partitions poorly across the gastrointestinal mucosa. The only indication for oral vancomycin therapy is in the treatment of pseudomembranous colitis, where it must be given orally to reach the site of infection in the colon. Following oral administration, the fecal concentration of vancomycin is around 500 µg/mL (sensitive strains of C. difficile have a mean inhibitory concentration of ≤2 µg/mL)

Inhaled vancomycin has also been used (off-label), via nebulizer, for treatment of various infections of the upper and lower respiratory tract.

The caustic nature of vancomycin makes IV therapy using peripheral lines a risk for thrombophlebitis. Ideally, central lines, PICCs, or infusion ports should be used.

Vancomycin has traditionally been considered a nephrotoxic and ototoxic drug, based on observations by early investigators of elevated serum levels in renally impaired patients that had experienced ototoxicity, and subsequently through case reports in the medical literature. However, as the use of vancomycin increased with the spread of MRSA beginning in the 1970s, it was recognised that the previously reported rates of toxicity were not being observed. This was attributed to the removal of the impurities present in the earlier formulation of the drug, although those impurities were not specifically tested for toxicity.

Subsequent reviews of accumulated case reports of vancomycin-related nephrotoxicity found that many of the patients had also received other known nephrotoxins, in particular, aminoglycosides. Most of the rest had other confounding factors, or insufficient data regarding the possibility of such, that prohibited the clear association of vancomycin with the observed renal dysfunction. The most methodologically-sound investigations indicate that the actual incidence of vancomycin-induced nephrotoxicity is around 5-7%. To put this into context, similar rates of renal dysfunction have been reported for cefamandole and benzylpenicillin, two reputedly non-nephrotoxic antibiotics.

In addition, evidence to relate nephrotoxicity to vancomycin serum levels is inconsistent. Some studies have indicated an increased rate of nephrotoxicity when trough levels exceed 10 µg/mL, but others have not reproduced these results. Nephrotoxicity has also been observed with concentrations within the "therapeutic" range as well. In essence, the reputation of vancomycin as a nephrotoxin is over-stated, and it has not been demonstrated that maintaining vancomycin serum levels within certain ranges will prevent its nephrotoxic effects, when they do occur.

Attempts to establish rates of vancomycin-induced ototoxicity are even more difficult due to the scarcity of quality evidence. The current consensus is that clearly related cases of vancomycin ototoxicity are rare. The association between vancomycin serum levels and ototoxicity is also uncertain. While cases of ototoxicity have been reported in patients whose vancomycin serum level exceeded 80 µg/mL, cases have been reported in patients with therapeutic levels as well. Thus, it also remains unproven that therapeutic drug monitoring of vancomycin for the purpose of maintaining "therapeutic" levels will prevent ototoxicity.

Another area of controversy and uncertainty concerns the question of whether, and, if so, to what extent, vancomycin increases the toxicity of other nephrotoxins. Clinical studies have yielded variable results, but animal models indicate that there probably is some increased nephrotoxic effect when vancomycin is added to nephrotoxins such as aminoglycosides. However, a dose- or serum level-effect relationship has not been established.

Levofloxacin. Levofloxacin is a synthetic chemotherapeutic antibiotic of the fluoroquinolone drug class and is used to treat severe or life-threatening bacterial infections or bacterial infections that have failed to respond to other antibiotic classes. It is sold under various brand names, such as Levaquin and Tavanic, the most common. In form of ophthalmic solutions it is known as Oftaquix, Quixin and Iquix.

Levofloxacin is a chiral fluorinated carboxyquinolone. Investigation of ofloxacin, an older drug that is the racemic mixture, found that the 1 form [the (−)-(S) enantiomer] is more active. This specific component is levofloxacin. Levofloxacin is available in tablet form, injection, oral solution, as well as used in prescription eye and ear drops.

Levofloxacin interacts with a number of other drugs, as well as a number of herbal and natural supplements. Such interactions increase the risk of cardiotoxicity and arrhythmias, anticoagulation, the formation of non-absorbable complexes, as well as increasing the risk of toxicity.

Levofloxacin is associated with a number of serious and life-threatening adverse reactions as well as spontaneous tendon ruptures and irreversible peripheral neuropathy. Such reactions may manifest long after therapy had been completed and in severe cases may result in life-long disabilities. Hepatoxicity has also been reported with the use of levofloxacin.

As of 2011 the FDA has added two Black box warnings for this drug in reference to spontaneous tendon ruptures and the fact that levofloxacin may cause worsening of myasthenia gravis symptoms, including muscle weakness and breathing problems. Such an adverse reaction is a potentially life-threatening event and may require ventilatory support.

Levofloxacin is used to treat a number of infections including: respiratory tract infections, cellulitis, urinary tract infections, prostatitis, anthrax, endocarditis, meningitis, pelvic inflammatory disease, and traveler's diarrhea.

In the adult population Oral and I.V. levofloxacin is limited to the treatment of proven serious and life-threatening bacterial infections such as Urinary Tract Infections, Community-acquired pneumonia, Skin and Skin Structure Infections, Nosocomial Pneumonia, Chronic bacterial prostatitis, Inhalational Anthrax, Acute Bacterial Sinusitis, Acute Bacterial Exacerbation of Chronic Bronchitis, and Acute Pyelonephritis.

Oral and I.V. Levaquin are not licensed by the FDA for use in children other than the exception (inhalational anthrax), due to the risk of reversible or irreversible injury to the musculoskeletal system. Although claimed to be effective, levofloxacin is not to be considered a first line agent for inhalational anthrax in the pediatric population due to severe adverse reactions involving the musculoskeletal system and other serious adverse reactions, including fatalities.

The CDC revoked its recommendation regarding the use of fluoroquinolones (ciprofloxacin) as a first-line agent in treating anthrax (in part) due to the risk of adverse reactions documented within the Antimicrobial Postexposure Prophylaxis for Anthrax study (aka Cipro 60-day study). However, the fluoroquinolones are licensed to treat lower respiratory infections in children with cystic fibrosis in the UK.

Serious adverse events occur more commonly with fluoroquinolones than with any other antibiotic drug classes. In most adverse reactions are mild to moderate; however, on occasion, serious adverse effects occur. There have been a number of regulatory actions taken as a result of such adverse reactions, which included published warnings, additional warnings and safety information added to the package inserts, which includes Black Box Warnings together with the issuance of "Dear Doctor Letters" concerning the recent addition of the Black Box Warnings.

In 2004, the FDA requested new warning labels to be added to all of the Fluoroquinolones, including levofloxacin, regarding peripheral neuropathy (irreversible nerve damage), tendon damage, heart problems (prolonged QT Interval/torsades de pointes), pseudomembranous colitis, rhabdomyolysis (muscle wasting), Stevens-Johnson Syndrome, as well as concurrent usage of NSAIDs contributing to the severity of these reactions. Subsequent to this, on Jun. 25, 2007, the FDA required the manufacturer to add an additional warning to the package inserts that stated that "Other serious and sometimes fatal events, some due to hypersensitivity, and some due to uncertain etiology, have been reported in patients receiving therapy with quinolones, including levofloxacin."

Serious visual complications have also been reported to occur with ophthalmic fluoroquinolone therapy, which may also occur with levofloxacin eye drops, especially corneal perforation, but also evisceration and enucleation. This increased incidents of corneal perforation may be due to fluoroquinolones causing alterations in stromal collagen, leading to a reduction in tectonic strength. As noted previously permanent double vision (diplopia) has also been reported.

Levofloxacin is the L-isomer of the racemate ofloxacin, a quinolone antimicrobial agent. In chemical terms, levofloxacin, a chiral fluorinated carboxyquinolone, is the pure (−)-(S)-enantiomer of the racemic drug substance ofloxacin. The chemical name is (−)-(S)-9fluoro-2,3-dihydro-3-methyl-10-(4-methyl-1-piperazinyl)-7-oxo-7H-pyrido[1,2,3-de]-1,4benzoxazine-6-carboxylic acid hemihydrate. The empirical formula is $C_{18}H_{20}FN_3O_4 \cdot \frac{1}{2}H_2O$, and the molecular weight is 370.38. Levofloxacin is a light-yellowish-white to yellow-white crystal or crystalline powder.

Levofloxacin pharmacokinetics are linear and predictable after single and multiple oral or IV dosing regimens. Levofloxacin is rapidly and, in essence, completely absorbed after oral administration. Peak plasma concentrations are usually attained one to two hours after oral dosing. The plasma concentration profile of levofloxacin after IV administration is similar and comparable in extent of exposure (AUC) to that observed for LEVAQUIN Tablets when equal doses (mg/mg) are administered. Levofloxacin is excreted largely as unchanged drug in the urine. The mean terminal plasma elimination half-life of levofloxacin ranges from approximately 6 to 8 hours following single or multiple doses of levofloxacin given orally or intravenously. Glucuronidation and hydroxylation have been cited as one of the major metabolic pathways for levofloxacin hydrochloride. However the drug card for levofloxacin (DB01137) states that the biotransformation information is not available. Specific information regarding biotransformation does not appear to be readily available within the package inserts.

Levofloxacin is a broad-spectrum antibiotic that is active against both Gram-positive and Gram-negative bacteria. It functions by inhibiting DNA gyrase, a type II topoisomerase, and topoisomerase iv, which is an enzyme necessary to separate replicated DNA, thereby inhibiting cell division.

The fluoroquinolones interfere with DNA replication by inhibiting an enzyme complex called DNA gyrase. This can also affect mammalian cell replication. In particular, some congeners of this drug family display high activity not only against bacterial topoisomerases but also against eukaryotic topoisomerases, and are toxic to cultured mammalian cells and in vivo tumor models. Although the quinolone is highly toxic to mammalian cells in culture, its mechanism of cytotoxic action is not known. Quinolone-induced DNA damage was first reported in 1986.

V. ANTIBODY CONJUGATES

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, antibiotics, therapeutic enzymes, radionuclides, anti-cancer agents, antiviral agents, chelating agents, cytokines, growth factors, and oligo- or polynucleotides.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine[211], [14]carbon, [51]chromium, [36]chlorine, [57]cobalt, [58]cobalt, copper[67], $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (0' Shannessy et al., 1987). This approach has been reported to produce diagnostically and therapeutically promising antibodies which are currently in clinical evaluation.

VI. IMMUNODETECTION METHODS

In still further embodiments, the present invention concerns immunodetection methods for binding, purifying, removing, quantifying and otherwise generally detecting S. pneumonia. While such methods can be applied in a traditional detection sense, a more specific use will involve the generation of a antibody panel that is capable of distinguishing a single S. pneumoniae serotype from most of the serotypes listed above. By identifying the specific serotype responsible for an infection, one can better assess the need and type of therapy. Also, protective immunity is primarily attributed to serotype-specific IgG. Measurement of specific pneumococcal antibodies are clinically useful in two settings: (1) to determine protective status of a patient, and (2) to assess B-cell functionality in a patient with recurrent infection. Use of antibodies in accordance with the present invention in a competitive format will facilitate this type of assay as well.

Some immunodetection methods include enzyme linked immunosorbent assay (ELISA), radioimmunoassay (MA), immunoradiometric assay, fluoroimmunoassay, chemiluminescent assay, bioluminescent assay, and Western blot to mention a few. In particular, a competitive assay for the detection and quantitation of antibodies in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing S. pneumoniae, and contacting the sample with a first antibody in accordance with the present invention, as the case may be, under conditions effective to allow the formation of immunocomplexes.

These methods include methods for purifying S. pneumoniae or related antigens from a sample. The antibody will preferably be linked to a solid support, such as in the form of a column matrix, and the sample suspected of containing the *S. pneumoniae* or antigenic component will be applied to the immobilized antibody. The unwanted components will be washed from the column, leaving the *S. pneumoniae* antigen immunocomplexed to the immobilized antibody, which is then collected by removing the organism or antigen from the column.

The immunobinding methods also include methods for detecting and quantifying the amount of *S. pneumoniae* or related components in a sample and the detection and quantification of any immune complexes formed during the binding process. Here, one would obtain a sample suspected of containing *S. pneumoniae* or its antigens, and contact the sample with an antibody that binds *S. pneumoniae* or components thereof, followed by detecting and quantifying the amount of immune complexes formed under the specific conditions. In terms of antigen detection, the biological sample analyzed may be any sample that is suspected of containing *S. pneumoniae* or *S. pneumoniae* antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *S. pneumoniae* or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (MA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the *S. pneumoniae* or *S. pneumoniae* antigen is added to the wells. After binding and washing to remove non-specifically bound immune complexes, the bound antigen may be detected. Detection may be achieved by the addition of another anti-*S. pneumoniae* antibody that is linked to a detectable label. This type of ELISA is a simple "sandwich ELISA." Detection may also be achieved by the addition of a second anti-*S.*

*pneumoniae* antibody, followed by the addition of a third antibody that has binding affinity for the second antibody, with the third antibody being linked to a detectable label.

In another exemplary ELISA, the samples suspected of containing the *S. pneumoniae* or *S. pneumoniae* antigen are immobilized onto the well surface and then contacted with the anti-*S. pneumoniae* antibodies of the invention. After binding and washing to remove non-specifically bound immune complexes, the bound anti-*S. pneumoniae* antibodies are detected. Where the initial anti-*S. pneumoniae* antibodies are linked to a detectable label, the immune complexes may be detected directly. Again, the immune complexes may be detected using a second antibody that has binding affinity for the first anti-*S. pneumoniae* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of *S. pneumoniae* antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled *S. pneumoniae* monoclonal antibodies to determine the amount of *S. pneumoniae* antibodies in a sample. The basic format would include contacting a known amount of *S. pneumoniae* monoclonal antibody (linked to a detectable label) with *S. pneumoniae* antigen or particle. The *S. pneumoniae* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunodetection Kits

In still further embodiments, the present invention concerns immunodetection kits for use with the immunodetection methods described above. As the S. pneumoniae antibodies are generally used to detect S. pneumoniae or S. pneumoniae antigens, the antibodies will be included in the kit. The immunodetection kits will thus comprise, in suitable container means, a first antibody that binds to S. pneumoniae or S. pneumoniae antigen, and optionally an immunodetection reagent.

In certain embodiments, the antibody may be pre-bound to a solid support, such as a column matrix, dipstick, membrane, particle (e.g., bead or nanoparticle) or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the S. pneumoniae or S. pneumoniae antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Immunization and donors. Donors received Pneumovax®23 (Merck, Whitehouse Station, NJ) as standard of care vaccination based upon their age or SLE status. Healthy donors Con1 and Con2 were both Caucasian, age 62 and 61 respectively. Lupus donor SLE1 was an African American, age 47, SLE2 was a Caucasian, age 45. All protocols were approved by the IRB and patients consented to participate in this study. Blood was drawn (~40-60 ml) into ACD tubes (BD, Franklin Lakes, NJ) by venipuncture seven days post vaccination and were stored no longer than 18 hours before processing.

Cell isolation and flow cytometry. Peripheral blood mononuclear cells (PBMC) were isolated from fresh blood using lymphocyte separation medium (Cellgro, Manassas, VA) and suspended in 2% inactivated fetal calf serum in PBS. Cells were then counted and stained within two hours of the isolation. Antibodies used for the staining were anti-CD3 and anti-CD20 conjugated to FITC, anti-CD38 conjugated to APC-Cy5.5, anti-CD27 conjugated to PE, anti-CD19 conjugated to PE-Alexa610 (all from Invitrogen/Caltag, Carlsbad, CA), anti-IgG conjugated to APC (BD Biosciences, San Jose CA), and anti-IgM conjugated to biotin (Southern Biotech, Birmingham, AL) followed by streptavidin-PE-Cy7 (Invitrogen/Caltag). The B cells were bulk sorted ($CD3/CD20^{neg}$, $CD19^{low}$, $CD38^{high}$, $CD27^{very\ high}$, $IgG^{positive}$) using a Becton-Dickinson FACS Aria cytometer (BD Biosciences, San Jose, CA) and then single cell sorted into 96-well PCR plates with a Cytomation MoFlo cytometer (Dako, Carpinteria, CA).

Single cell RT-PCR and PCR of antibody variable region genes. As detailed in prior studies (Smith et al., 2009; Wrammert et al., 2008), the plates receiving the single cells sorted above contain 10 microliters of a hypotonic buffer consisting of 10 mM Tris-HCl with 40 U/µl of RNase inhibitor (Promega, Madison, WI) in each well. After the sort, plates were immediately frozen on dry ice and stored at −80° C. A One-Step RT-PCR kit (Qiagen, Valencia, CA) was used to amplify $V_H$ and $V_K$ message using a cocktail of sense primers to the leader regions of each of the gene families and antisense primers to the constant regions of the heavy and kappa chains. One microliter of the RT-PCR mixture was then amplified in separate heavy and kappa chain PCR reactions to first obtain sequences, and another microliter was used for the final PCR reactions to incorporate restriction sites for further cloning. The variable regions were then cloned into expression vectors (containing full length $IgG_1$ heavy or kappa constant regions), maxi-prepped (Roche, Indianapolis IN), and co-transfected into the HEK293A cell line using polyethyleneimine (PEI) (Polysciences, Warrington, PA). The transfected cells were allowed to secrete antibodies into serum-free DMEM supplemented with 1% Nutridoma (Roche, Indianapolis, IN) for five days. The antibodies were then purified using protein A-agarose beads (Pierce, Rockford, IL). Antibody purity and integrity were verified by SDS-PAGE and concentrations were obtained with a Nanodrop spectrophotometer (Fisher, Pittsburgh, PA).

Polysaccharide affinity and avidity ELISAs. To screen for binding, ELISAs were first performed by coating plates with cocktails of five or six *S. pneumoniae* polysaccharides, screening all 23 (ATCC, Manassas, VA) in this manner. Positive binders in this cocktail assay were then re-screened against each of the individual polysaccharides. As cell wall polysaccharide (CWPS) is an impurity in nearly all of the coat polysaccharides (Xu et al., 2005), antibodies that bound to all four groups were further tested on purified cell wall polysaccharide (CWPS) (Miravista Labs, Indianapolis, IN) to confirm CWPS binding. Wells were coated with 10 µg of each polysaccharide (or total mixed polysaccharide), blocked with 20% FCS and developed with anti-human IgG-HRP (Jackson ImmunoResearch, West Grove, PA) and Super Aqua Blue substrate (EBiosciences, San Diego CA). The absorbance was measured at 405 nm on a microplate reader (Molecular Devices, Sunnyvale, CA). Antibody affinities (Kd) were calculated by curve fitting analysis of individual ELISA curves plotted from a dilution series of 16 two-fold dilutions of antibody beginning at 10 µg/ml. For avidity ELISAs, one concentration of antibody was used (1 µg/ml) and an elution step was added before the addition of the conjugate. This elution step used varying concentrations of ammonium thiocyanate (3M to 0.06M, 8 total dilutions) in PBS, as well as PBS alone. The percent of binding retained was calculated for each dilution of ammonium thiocyanate. These values were graphed versus thiocyanate concentration and the concentration of thiocyanate which caused 50% retention (or loss) of binding was calculated by fitting the data with a dose-response/sigmoidal curve with hillslope correction.

Autoantigen ELISAs. All antibodies were also tested for binding to five autoantigens, Ro, La, Sm, nRNP, and cardiolipin. For each, except cardiolipin, 1 unit of antigen (ImmunoVision, Springdale, AR) was coated per well on high bind plates. Plates were blocked with 0.1% BSA in PBS, antibodies were added at 1 µg/ml and developed as per polysaccharide ELISAs above. For anti-cardiolipin ELISAs, cardiolipin solution at ~5 mg/ml (Sigma, St. Louis, MO) was diluted 1 to 1000 in ethanol and 50 µl/well was allowed to evaporate in medium bind plates. Plates were blocked with 0.5% adult bovine serum in PBS and antibodies were screened at 10 µg/ml and developed as above.

Analysis of sequences and curve fitting. All curve fitting was performed using the GraphPad Prism software, with background subtraction or percent retention values calculated and averaged using Excel. Variable region sequences were analyzed using the International Immunogenetics Information System (IMGT, Montpellier, France), as well as with in-house software and/or Vector NTI (Invitrogen, Carlsbad, CA). Clonally related antibodies were defined as those having the same VDJ/VJ usage in the heavy and light chains respectively, as well as highly related $V_H D_H$, $D_H J_H$, and $V_K J_K$ junctions. Average nucleotide somatic hypermutation values were obtain by analyzing sequences (using IMGT) for the number of nucleotide changes from germline in each antibody sequence. Resulting per-antibody values were then averaged to obtain average mutation rates per donor. The n value for these analyses included: naïve cells from six donors (n=18, 42, 21, 34, 15, 36); IgM germinal center/memory cells from 17 donors (n=56, 158, 18, 91, 17, 10, 16, 30, 19, 28, 11, 36, 29, 13, 22, 20, 64); IgG germinal center/memory cells from 13 donors (n=110, 37, 19, 28, 174, 40, 25, 15, 21, 18, 22, 24, 19, 71); anti-influenza ASCs from 11 donors (n=63, 18, 33, 46, 49, 11, 36, 11, 30, 35, 25). These donors were previously described in (Wrammert et al., 2008). The anti-polysaccharide ASC sequences are from the four donors in this study (Con1, 39; Con2, 49; SLE1, 24; SLE2, 25).

Example 2—Results

Pneumovax®23 induces a strong ASC response which is more robust in healthy controls as compared to SLE patients. Four individuals were immunized with Pneumovax®23. Blood was drawn seven days post vaccination and PBMCs were isolated by Ficoll gradient. The cells were then stained and $CD38^{high}/CD27^{very\ high}$ cells were enumerated. The inventor's previous results using these techniques after influenza vaccination (Wrammert et al., 2008) showed an ASC burst ranging from 1% to 16% of total peripheral blood B cells at day seven (average 6.4%). Pneumovax®23 induces an even more robust ASC response (FIG. 1A), with the two healthy donors having ASCs representing 22.8% to 24.7% of their total peripheral blood B cells, especially as this is a primary vaccination for each donor. Although both SLE donors had half as many ASCs as the healthy donors, the overall percentages (10.6% and 7.1%) are still quite high. This strong anamnestic response is likely due to the fact that *S. pneumoniae* is a ubiquitous organism that causes both clinical and subclinical disease among the general population. FIG. 1B shows a schematic representation of the process for making human monoclonal antibodies from antibody secreting cells. This technique has been previously described in detail (Smith et al., 2009; Wrammert et al., 2008). In total, including non-binding antibodies, 137 antibodies were produced and characterized (Con1, n=39; Con2, n=49; SLE1, n=24; SLE2, n=25).

A large majority of polysaccharide antibodies produced from the ASCs bind to a single serotype. Polysaccharide ELISA curves are shown in FIG. 2A, where each curve represents one antibody. A cutoff of an $OD_{405}$ of 1.5 was used as an arbitrary separation between high to moderate affinity antibodies and low to non-binding antibodies. Percentages were calculated using this cutoff as a means to determine which antibodies had significant binding. Averaged across the four donors, 76% of the antibodies (Con1, 62%; Con2, 90%; SLE1 75%; SLE2, 75%) bound to *S. pneumoniae* serotype polysaccharide or cell wall polysaccharide from the vaccine. Of the hmAbs generated, SLE donors showed no significant difference in the number of high-affinity antibodies isolated. A list of all antibodies with positive binding is shown in Table 1, which details serotype bound, number of total clonal siblings characterized, as well as $V_H$ and $V_K$ usage. Of the antibodies which bound to polysaccharide (76% of the total), an average of 88% of the antibodies characterized from the four donors are serotype specific (FIG. 2B) (Con1, 88%; Con2, 90%; SLE1 94%; SLE2, 80%). The observation that 88% of the antibodies currently in the serum bind to carbohydrate epitopes in a manner specific even among very closely related structures reinforces the well known specificity of the antibody repertoire.

TABLE 1

Summary of anti-*S. pneumoniae* antibodies (SEQ ID NOS: 1 through 126)

| Ab | # of Clones | Serotype(s) | Kd (M)* | OPA** | VH gene | JH gene | Heavy CDR3 | VK gene | JK gene | Kappa CDR3 |
|---|---|---|---|---|---|---|---|---|---|---|
| Con1p2 C01 | 3 | 20 | 1.1E-08 | 512 | VH3-66 | JH6 | AKGVTSFDY | VK3-20 | JK4 | QQFGSSPPDT |
| Con1p2 C04 | 1 | 1 | 2.2E-10 | none | VH3-23 | JH4 | ARDPGIRNGMGV | VK2-30 | JK1 | MQVTHWPRT |
| Con1p2 D02 | 1 | 9N | 3.9E-10 | 256 | VH3-23 | JH4 | AKAHRGDWNNFFDY | VK3-11 | JH4 | QQSGDWPLT |
| Con1p2 D03 | 1 | 19F/19A | 1.2E-08 | 1024/none | VH4-59 | JH3 | AREWSGFDF | VK3-20 | JK1 | QQYGSLPRT |
| Con1p2 E01 | 3 | 8 | 7.7E-11 | 512 | VH3-7 | JH4 | ARGQWLAF | VK2-30 | JK2 | MQGTHWPYT |
| Con1p3 C02 | 1 | 2 | 1.4E-10 | 4096 | VH3-7 | JH4 | ARGRNNFRH | VK1-33 | JK3 | QQFESFPRT |
| Con1p3 C03 | 1 | 22F | 1.8E-10 | 32 | VH3-66 | JH4 | ARELGVFHSGGDQWLGPLDC | VK3-15 | JK3 | HQYKNWPPMGT |
| Con1p3 G01 | 2 | 2 | 1.4E-10 | 2048 | VH3-49 | JH4 | RWTGGVSFGAY | VK1-5 | JK1 | QQYDIYLT |
| Con1p3 G06 | 1 | 8 | 2.1E-08 | 16 | VH3-74 | JH4 | ARDYYHSVDY | VK2-30 | JK2 | MQGTHWPYT |
| Con1p4 B01 | 2 | 33F | 4.0E-08 | 256 | VH4-59 | JH4 | ARGPDAHKTGY | VK4-1 | JK1 | QQYAATPWT |
| Con1p4 B03 | 1 | 9N/9V | 5.6E-10 | 128/128 | VH3-74 | JH4 | ARDSYTSPDY | VK2-30 | JK4 | MQGSHWPLT |
| Con1p4 C01 | 1 | 8 | 9.5E-10 | 128 | VH3-15 | JH3 | TTDNGVKAFDI | VK4-1 | JK3 | HQYYTTPFA |
| Con1p4 G01 | 1 | 6B | 3.1E-10 | 256 | VH3-74 | JH4 | TRGGSGATINY | VK1-39 | JK4 | QQSHSSPLT |
| Con1p6 C01 | 1 | 9V | 3.0E-08 | 256 | VH4-61 | JH4 | ARDRAGIDGYNYYFDY | VK1-5 | JK2 | QQYYSFYT |
| Con1p6 D04 | 1 | CWPS | 4.2E-08 | none | VH1-46 | JH4 | AREVAAEGKAFDY | VK4-1 | JK4 | QQYYTPPLT |
| Con1p6 E03 | 1 | 3 | 8.9E-10 | 128 | VH3-7 | JH3 | ARGQSYPGI | VK3-15 | JK1 | QQYNNWPRT |
| Con1p6 E06 | 1 | 17F/33F | 9.4E-09 | 8/none | VH4-59 | JH4 | AGRAYSSGYYYLIDY | VK3-15 | JK2 | QHYHNWPPT |
| Con2p3 C04 | 3 | CWPS | 7.9E-11 | none | VH3-30 | JH4 | AKGCSNGGNCFLIDY | VK4-1 | JK4 | QQYYNAPLT |
| Con2p3 C05 | 1 | 4 | 1.8E-10 | 256 | VH3-23 | JH3 | AKGGYYESGTMRAFDI | VK3-11 | JK4 | QQRSNWPAT |
| Con2p3 F03 | 2 | 2 | 1.5E-10 | 4096 | VH3-7 | JH4 | ARGESNFRY | VK1-33 | JK3 | QQFVSFPRT |
| Con2p3 G05 | 9 | 18C | 2.8E-10 | 64 | VH3-7 | JH4 | ARDSTSPARFGY | VK3-20 | JK2 | QHYGTSPPRYT |
| Con2p4 B03 | 1 | 1 | 3.4E-08 | none | VH3-53 | JH4 | ATGGMTSSWYGY | VK4-1 | JK2 | QQYYSTPYT |
| Con2p4 C02 | 5 | 9N/9V | 2.7E-10 | 512/8 | VH1-46 | JH4 | SMGPPYCTGGSCYSACDF | VK3-20 | JK2 | QRYGNSPPYT |
| Con2p4 D06 | 5 | 9V | 2.6E-10 | 2048 | VH3-15 | JH5 | TTDIGKGWYTHYPDL | VK4-1 | JK4 | LQYRSAPFT |
| Con2p5 A06 | 2 | CWPS | 5.1E-10 | none | VH3-30 | JH4 | VKEYSWGYYRTADY | VK1-5 | JK1 | QQYSTYPWT |
| Con2p5 B06 | 3 | 1 | 1.4E-10 | none | VH3-74 | JH4 | ARSPGGYFDY | VK3-15 | JK1 | QQYSTWLWT |
| Con2p5 C04 | 1 | 8 | 2.3E-08 | 32 | VH3-15 | JH4 | TTDDLKN | VK1-39 | JK2 | QQRYRIPYS |
| Con2p5 E05 | 1 | 2 | 2.8E-10 | 2048 | VH3-48 | JH6 | ARGRDCYGGNCVIYFHYYGLDV | VK2-28 | JK2 | MRALQTPYT |
| Con2p6 B03 | 3 | CWPS | 6.4E-11 | none | VH3-30 | JH4 | VKESATGWYRTADY | VK1-5 | JK1 | HQYNKYPWT |

TABLE 1-continued

Summary of anti-*S. pneumoniae* antibodies (SEQ ID NOS: 1 through 126)

| Ab | # of Clones | Sero-type(s) | Kd (M)* | OPA** | VH gene | JH gene | Heavy CDR3 | VK gene | JK gene | Kappa CDR3 |
|---|---|---|---|---|---|---|---|---|---|---|
| Con2p6 C05 | 1 | 33F | 3.3E-09 | none | VH3-66 | JH3 | ARDIPTTFGIGEAFDI | VK1-5 | JK1 | QQYYSWGT |
| Con2p6 G04 | 1 | 22F | 4.4E-10 | 128 | VH1-46 | JH4 | ARDDSAFDY | VK2-24 | JK1 | MQASQSTWT |
| Con2p7 D03 | 1 | CWPS | 1.8E-09 | none | VH3-30 | JH6 | AKGCSGENCFYMDD | VK4-1 | JK4 | QQCYNAPLT |
| Con2p8 B01 | 1 | 22F | 2.3E-08 | none | VH1-46 | JH4 | TREIGAVVVDATSLGWLGYFDY | VK3-15 | JK1 | QQYNNWPPVT |
| Con2p8 B05 | 2 | 15B | 1.7E-10 | none | VH3-7 | JH4 | AGWGRTQD | VK2-30 | JK2 | MQYTFWPHT |
| Con2p8 E03 | 1 | 23F | 3.3E-08 | none | VH3-30 | JH3 | TKEGAPPGKYAFDI | VK3-11 | JK3 | QHRGEWPPGAT |
| Con2p8 F05 | 1 | 11A | 1.8E-10 | none | VK3-72 | JH3 | LKDSSQYSFDA | VK1-9 | JK4 | QQFKGYPLT |
| SLE1p1 A02 | 3 | 5 5. | 1E-10 | 1024 | VH4-59 | JH4 | ARGDYNFF | VK1-9 | JK2 | QQINSYPRT |
| SLE1p1 A03 | 1 | 14/9N | 1.7E-10 | 512/32 | VH3-30 | JH5 | AKCGAEDSTTVWLNWFDP | VK3-11 | JK4 | QQRADWPLT |
| SLE1p1 B05 | 3 | 5 | 9.5E-10 | none | VH3-23 | JH4 | AKPNYFGSGSPDY | VK3-11 | JK2 | LQCSNWPMYT |
| SLE1p1 C04 | 1 | 5 | 2.8E-10 | 2048 | VH4-59 | JH4 | VKEQDYGYYRTADH | VK1-6 | JK2 | QQYDKYPWT |
| SLE1p1 E01 | 2 | 9V/9N | 6.2E-11 | 512/256 | VH3-20 | JH3 | VRVAVPAATYTRGNDAFDI | VK1-17 | JK1 | LQHSSFPWT |
| SLE1p1 F02 | 1 | 14 | 1.0E-09 | none | VH3-15 | JH4 | TTAHGPVGDH | VK4-1 | JK5 | QQYTTPSIT |
| SLE1p1 G05 | 1 | 15B | 1.6E-10 | none | VH3-7 | JH4 | ARAGGCSSTRCHTTPGFDY | VK4-1 | JK5 | QQYTTPPIT |
| SLE1p2 A02 | 1 | 5 | 1.4E-10 | 512 | VH4-39 | JH3 | ASLSGTNAFDI | VK3-11 | JK1 | QQRSSGRT |
| SLE1p2 D04 | 1 | 8 | 7.4E-09 | 256 | VH3-23 | JH4 | AKPRGYSYGYFDY | VK3D-20 | JK2 | QQYGISPRT |
| SLE1p3 A02 | 1 | 17F | 2.7E-09 | none | VH3-7 | JH4 | APPARRLDY | VK2-29 | JK1 | MQGTHHPWT |
| SLE1p3 A04 | 1 | 4 3. | 8E-08 | none | VH3-74 | JH4 | ARSNAGHEA | VK4-1 | JK4 | QQYYSTPLT |
| SLE1p3 B03 | 1 | 20 | 1.5E-09 | none | VH1-46 | JH4 | ARDIPHANLDY | VK1-17 | JK1 | LQHTTFPWT |
| SLE1p3 C03 | 1 | 33F | 1.1E-09 | 128 | VH3-23 | JH4 | VKDRVPPGDVPGDF | VK3-11 | JK5 | QQRRTWPPLT |
| SLE2p1 A01 | 2 | 23F | 2.5E-09 | none | VH3-48 | JH6 | ATLLLRDNQLDV | VK2-30 | JK1 | MQGTHWRT |
| SLE2p1 A06 | 1 | CWPS | 7.9E-10 | none | VH3-33 | JH4 | VKEQGFGYYRTADY | VK1-5 | JK1 | HQYDKYPWT |
| SLE2p1 B01 | 2 | 15B/14 | 2.0E-10 | 256/256 | VH4-59 | JH3 | ARRNDFNI | VK3-20 | JK3 | QQYGSSPFT |
| SLE2p1 C03 | 1 | 17F/33F | 2.9E-10 | none | VH3-23 | JH4 | SIWWGTSVQYPLVLDY | VK3D-15 | JK5 | QQYSKWPPIT |
| SLE2p1 C04 | 1 | CWPS | 2.0E-09 | none | VH3-30 | JH5 | VKEQDYGYYRTADH | VK1-5 | JK1 | QQYDKYPWT |
| SLE2p1 D02 | 5 | 5 | 2.0E-10 | none | VH4-61 | JH4 | ARGHGFNAY | VK3-20 | JK1 | QQYGNSPRT |
| SLE2p1 D04 | 1 | 6B | 8.8E-11 | 512 | VH3-15 | JH4 | TTVRNMADLSLNH | VK3-20 | JK1 | QQYDDSRWT |
| SLE2p2 A01 | 1 | 18C | 4.2E-09 | none | VH3-48 | JK4 | ATGNRGSLPRR | VK2D-28 | JK2 | MQALRSPYT |
| SLE2p2 C04 | 1 | 33F | 4.9E-09 | none | VH3-7 | JH4 | VRDGWDTFFDS | VK2-30 | JK2 | MQGRYWPYT |
| SLE2p2 D03 | 1 | 19A/19F | 1.1E-09 | none/8192 | VH3-74 | JH4 | VNFQLG | VK3-20 | JK1 | QQYGNSPRT |
| SLE2p2 E04 | 1 | 8 | 5.1E-10 | 1024 | VH3-30-3 | JH5 | ARAEYCSPGDCFLIDT | VK2-30 | JK1 | MQGTHWRT |
| SLE2p2 F01 | 1 | CWPS | 9.6E-10 | none | VH3-33 | JH4 | LRGNPPSSPTDY | VK1-16 | JK4 | QQYNSYPLT |

TABLE 1-continued

Summary of anti-*S. pneumoniae* antibodies (SEQ ID NOS: 1 through 126)

| Ab | # of Clones | Sero-type(s) | Kd (M)* | OPA** | VH gene | JH gene | Heavy CDR3 | VK gene | JK gene | Kappa CDR3 |
|---|---|---|---|---|---|---|---|---|---|---|
| SLE2p2 G01 | 1 | 5 | 1.4E-09 | none | VH3-23 | JH6 | AKVVYSRPPMDV | VK1D-39 | JK1 | QQSYSTPWT |
| SLE2p2 G06 | 1 | 17F | 4.8E-11 | 128 | VH3-7 | JH4 | ARASRETGEPY | VK2-30 | JK1 | MQATHWPWT |

*Calculated ELISA affinities, averaged for the clonal family. The affinity listed from cross-reactive antibodies is for the serotype which is most strongly bound (the serotype listed first in the serotype column).
**Opsonophagocytosis assay (OPA) measures antibody mediated uptake of bacteria: values 4 or less are considered negative ("none").
The number of clones indicates the total number of members of the clonal family

TABLE 2

Selected Heavy and Light Chain Sequences from Antibodies of Table 1 (SEQ ID NOS. 127-252)

| Con1 Heavy | Seq ID No: | |
|---|---|---|
| Con1p2-c01h | 127 | GAGGTGCAGCTGTTGGAGTCGGGGGAGGCTTGGTACAGCCTGGGGGGTCCCTGAGAGTCTCCTGTGCAGC<br>CTCTGGATTCACCTTTAGCAACTCTGGCATGAGTTGGGTCCGCCAGGCTCCAGGGAAGGGGCTGGAGTGGGT<br>CTCAGGTATTGTGGTGGTGGTGGTAGTGCATACTACGCAGACTCCGTGAAGGGCCGGTTCACCATCTCCAG<br>AGACAATTCCAAGAACACGCTGTATCTACAAATGAACAATTTGAGAGCCGAGGACACGGCCGTATACTACT<br>GTGCGAAAGGAGTTACCAGTTTTGACTACTGGGGCCAGGGAATCCTGGTCACCGTCTCCTCA |
| Con1p2-c04h | 128 | GAGGTGCAGCTGGTGGAGTCTGGGGGAGGCTTGGTCCAGCCTGGGGGGTCCCTGAGACTCTCCTGTGCAGCC<br>TCTGGATTCACCGTCAGTAGCGACTATATGAGTTGGGTCCGCCAGGCTCCAGGGAAGGGGCTGGAGTGGGTC<br>TCAGTTATGTATAGCGGGGGTAGCACATACTACGCAGACGCCGTGAAGGACAGATTCACCATCTCCAGAGA<br>CAATTCCAAGAATATACTGTATCTTCAAATGAACAGCCTGAGAGCCGAGGACACGGCCGTTTATTACTGTGC<br>GAGAGATCCCGGGATAAGGAACGGTATGGCGTCTGGGGCCAAGGGACCACGGTCACCGTCTCCTCA |
| Con1p2-d02h | 129 | GAGGTGCAGCTGTTGGAGTCTGGGGGAGCCTTGGTACAGCCGGGGGGTCCCTGAGACTTTCCTGTGCAGCC<br>TCTGGATTCACCTTTACCAGCTTTGCCATGGGCTGGGTCCGCCAGGCTCCAGGGAAGGGGCTGGAGTGGGTC<br>TCAGCTGTGACTGGCAGTGGTTATTACAAAAACTATGCAGACTCCGTGAAGGGCCGGTTCACCATCTCCAGA<br>GACAATTCCGACAATACTCTCTATCTGCAAATGAACAGCCTGAGAGGCGACGACACGGCCCTATATTACTGT<br>GCGAAAGCACATAGAGGTGACTGGAATAACTTCTTTGACTATTGGGGCCAGGGAACCCTGGTCACCGTCTCC<br>TCA |
| Con1p2-d03h | 130 | CAGGTGCAGCTGCAGGAGTCGGGCCCAGGACTAGTGAAGCCTTCGGAGACCCTGTCCCTCACCTGCTCTGTG<br>TCTGCTGACTCCTTCAGTCCTTACAAGTGGAGCTGGATCCGGCAGCCCCCAGGGAAGGGACTGGAATGGATT<br>GGATATATCTATTCCAGTGGGAACACCAACTACAACCCCCCCCTCAAGAGTCGAGTCACCATATCACTGGAC<br>ACGTCCAAGAATCAGGTCTCCCTGAGGCTGAGCTCTGTGACCGCTGCGGACACGGCCATGTATTACTGTGCG<br>AGAGTGGAGTGGTTTTGATTTCTGGGGCCAAGGAACAATGGTCACCGTCTCTTCA |
| Con1p2-e01h | 131 | GAGGTGCAGCTGGTGGAGTCTGGGGGAGGCTTGGTCCAGCCTGGGGGGTCCCTGAGACTCTCCTGTGCAGCC<br>TCTGGATTCACCTTTACTAACTATTGGATGAGCTGGGTCCGCCAGGCTCCAGGGAAGGGGCTGGAGTGGGTG<br>GCCAACATAAAGCAAGATGGACGTGAGACATACTATGTGGACTCTGTGAAGGGCCGATTCACCATCTCCAG<br>AGACAACGCCAAGAACTCAGTGTCTCTACAGATGAGTAGCCTGAGAGCCGAGGACACGGCCGTGTATTACT<br>GTGCGCGAGGGCAGTGGCTGGCCTTCCGGGGCCAGGGAACCCTGGTCACCGTCTCCTCA |
| Con1p3-c02h | 132 | GAGGTGCAGCTGGTGGAGTCTGGGGGAGGCTTGGTCCAGATTGGGGGGTCCCTGAGACTCTCCTGTGCAGCC<br>TCTGGATTCACCTTTAGTACCTATTGGATGAGCTGGGTCCGCCAGGCTCCAGGGAAGGGGCTGGAGTGCGTG<br>GCCAGCATAAAGGAGGATGGAAGTGAGAGATACTATGTGGACTCTGTGAAGGGCCGATTCACCATCTCCAG<br>AGACAACGCCAAGAACTCACTGCATCTGCAGATGAACAGCCTGAGAGCCGCGGACACGGCCGTGTATTTCT<br>GTGCGAGAGGCCGGAACAACTTCCGACACTGGGGCCAGGGAACCCTGGTCACCGTCTCCTCA |
| Con1p3-c03h | 133 | GAGGTGCAGCTGGTGGAGTCTGGGGGAGGCTTGGTCCAGCCTGGGGGGTCCCTGAGACTCTCCTGTGCAGCC<br>TCTGGATTCGCCATCAGTGGTAACTACATGAGTTGGGTCCGCCAGGCTCCAGGGAAGGGGCTGGAGTGGGTC<br>TCACTTATTTATTGGACTGATGACACAGTCTACGCAGACTCCGTGAAGGGCAGATTCACCATCTCCAGGGAC<br>GTCTCCAAGAACATGGTGCATCTTCAAATGAGCAGCCTGAGAGTCGAGGACACGGCTGTTTATTACTGTGCG<br>AGAGAATTAGGTGTTTTTCATTCAGGGGGGACCAGTGGCTGGGCCCTTTAGACTGCTGGGGCAGGGAACC<br>CTGGTCACCGTCTCCTCA |
| Con1p3-g01h | 134 | GAGGTGCAGCTGGTGGAGTCTGGGGGAGGCTTGGTGCAGCCAGGGCAGTCCCTGAGACTTTCCTGTACAGTT<br>TCTGGATTCAGCGTAGAAGACCATGGTCTGAACTGGGTCCGCCAGGCTCCAGGGAAGGGGCTGGAGTGGGT<br>AGGGTTCATTAGAAGGAAAAGTTCTGGTGGGACAGAATACGCCGCTGTCTGTGAAAGGCCGATTCACCATCTC<br>AAGAGATGATTCCAAGAGCGCCGTCTATCTGCAAATGAACAGCCTGAAGATGGAGGACACAGGCGTATATT<br>ATTGTCTTCGCTGGACGGGTGGAGTGAGTTTTGGTGCCTACTGGGGCCAGGGAACCCTGGTCACCGTCTCCT<br>CA |
| Con1p3-g06h | 135 | GAGGTGCAGCTGGTGGAGTCCGGGGGAGGCTTAGTTCAGCCTGGGGGGTCCCTGAGACTCTCCTGTGCAGCC<br>TCTGGATTCACCTTCACTAGCTGGATGCACTGGGTCCGCCAAGCTCCAGGGAAGGGGCTGGTGTGGGTCTCA<br>CATATTAATACTGATGGGAGTAGCACAAGCTACGCGGACTCCGTGAAGGGCCGATTCACCATCTCCAGAGAC<br>AACGCCAAGAACACGCTGTATCTGCAAATGAACAGTCTGAGAGCCGAGGACACGGCTGTGTATTACTGTGCG<br>AAGAGATTATTACCACTCCGTTGACTACTGGGGCCAGGGAACCCTGGTCACCGTCTCCTCA |

TABLE 2-continued

Selected Heavy and Light Chain Sequences from Antibodies of Table 1 (SEQ ID NOS. 127-252)

| Con1p4-b01h | 136 | CAGGTGCAGCTGCAGGAGTCGGGCCCAGGAATGGTGAAGCCTTCGGAGACCCTGTCCCTCATCTGCAGTGTC<br>TCTGGTGCCTCCGTCAGTCGTGACCACTGGAGCTGGATCCGCCAGTCCCCAGGGAAGGGACTGGAGTGGATT<br>GTCTATATATATAACAGTGAGAGCATCGAATACAATCCCTCCCTCAAGAGTCGAGTCACCATATCCGTAGAC<br>ACGTCCAAGAACCAGGTCTCCCTGACAGTGACTTCTGTGACCGCTGCAGACACGGCCTTCTATTACTGTGCG<br>CGAGGGCCAGATGCCCACAAAACTGGCTACTGGGGCCCGGGAACCCTGGTCACCGTCTCCTCA |
| --- | --- | --- |
| Con1p4-b03h | 137 | GAGGTGCAGCTGGTGGAGTCCGGGGGAGGCTTAGTTCAGCCTGGGGGGTCGCTGAGACTCTCCTGCGCAGC<br>CTCTGGATTCACCTTCAGTAACTTCTGGATGTACTGGGTCCGCCAAGTTCCAGGGAAGGGGCTGGTGTGCGT<br>CTCACGTATTAATAGAGATGGGAGTATCACATTGTACGCGGACTCCGTGAGGGGCCGATTCACCATCTCCAG<br>AGACAACGCCAAGAACACGCTGTATCTGCAAATGAACAGTCTGAGAGTCGAGGACACGGCTGTGTATTACT<br>GTGCAAGAGATTCCTATACCAGCCCTGACTACTGGGGCCAGGGGACCCTGGTCACCGTCTCCTCA |
| Con1p4-c01h | 138 | GAGGTGCAGCTGGTGGAGTCTGGGGGAGGCTTGGTAAAGCCGGGGGAGTCCCTTAGACTCTCCTGTGCGAC<br>CTCAGGATTAACTTTCAGTAACGTATGGATGAGCTGGGTCCGCCAGGCTCCAGGGAAGGGGCTGGAGTGGG<br>TTGGGCGTCTTAAAAACAAGCCTGATGGTGGAACAACAGACTACGCAGCACCCGTGAAGGGCAGATTCACC<br>ATCTCAAGAGATGATTCAAAAACCACGCTGTATCTGGAAATGAACAGCCTGAAAGTCGAGGACACAGCCGT<br>GTATTACTGTACCACAGATAACGGAGTCAAGGCTTTTGATATCTGGGGCCAAGGGACAATGGTCACCGTCTC<br>TTCA |
| Con1p4-g01h | 139 | GAGGTGCAGCTGGTGGAGTCCGGGGGAGGCTTAGTTCAGCCTGGGGGGTCCCTGAGACTCTCCTGTGCAGCC<br>TCTGGATTCACCTTCAGTACCTACTGGATGCACTGGGTCCGCCAAACTCCGGAGAAGGGGCTGGTATGGGTC<br>TCACGTATTCATCCTGATGGGAGTAACAGCCTACGCGGACTCCGTGAAGGGCCGATTCACCATCTCCAGA<br>GACAACGCCAAGAACACGCTGTATCTGCAAATGAATAGTCTGAGAGTCGAGGACACGGCTTTTTATTATTGT<br>ACAAGAGGGGGTTCCGGGGCTACGATCAATTACTGGGGCCAGGGAATCCTGGTCACCGTCTCCTCA |
| Con1p6-c01h | 140 | CAGGTGCAGCTGCAGGAGTCGGGCCCAGGGCTGGTGAAGCCTTCACAGACCCTGTCCCTCACCTGCACTGTC<br>TCTGGTGGCTCCATCAGCGGTGGTACTTACTCCTGGACCTGGATCCGGCAGCCCGCCGGGAAGGGACTGGAG<br>TGGATTGGGCGTATTTTTGCTAGTGGGAGCACCAACTACAATTCCTCCCTCAAGAGTCGAGTCACCATTTTAG<br>TAGACACGTCCAAGAACCTGTTCTCCCTGAGCCTGAGCTCTGTGACCGCCGCAGACACGGCCATGTATTACT<br>GTGCGAGAGATCGAGCGGTATAGATGGCTACAATTACTACTTTGACTACTGGGGCCAGGGAACCCTGGTCA<br>CCGTCTCCTCA |
| Con1p6-d04h | 141 | AGGTGCAGCTGGTGCAGTCTGGGGCTGAGGTGAAGAAGCCTGGGGCCTCAGTGAAGGTTTCCTGCAAGACA<br>TCTGGATACACCCTCACCAGTTACTATATGCACTGGGTGCGACAGGCCCCTGGACAAGGGCTTGAGTGGCTG<br>GGAGTGATCAGGCCTACGACGCTAGCACAAGGTCCGCACAGAAGTTCCAGGGCAGAATCACCATGACCAG<br>GGACACGTCCACGAGCACACTCTACATGGAGCTGAGTAGCCTGAGATCTGAAGACACGGCCGTGTACTATTG<br>TGCGAGAGAAGTGGCAGCAGAAGGTAAAGCTTTCGACTACTGGGGCCAGGGAACCCTGGTCACCGTCTCCT<br>CA |
| Con1p6-e03h | 142 | GAGGTGCAGCTGGTGGAGTCTGGGGGAGGCTTGGTCCAGCCTGGGGGGTCCCTGAGACTCTCCTGTGCAGCC<br>TCTGGATTCACCTTTAGTAGCTATTGGATGAGCTGGGTCCGCCAGGCTCCAGGGAAGGGACTGGAGTGGGTG<br>GGCAAAATAAAGGAAGACGGAAGTGAGAAATACTATGTGGACTCTGTGAAGGGCCGATTCGCCATCTCCAG<br>AGACAACGCCAAGAACTCCCTGTCTCTGCAAATGAACAGCCTGAGAGCCGAGGACACGCCGTGTATTACT<br>GTGCGAGAGGTCAATCATATCCGGAATTTGGGGCCAAGGGACAATGGTCACCGTCTCTTCA |
| Con1p6-e06h | 143 | CAGGTGCAGCTGCAGGAGTCGGGCCCAGGACTGGTGAAGCCTTCGGAGACCCTGTCCCTCACCTGCACTGTC<br>TCTGGTGGCTCCATCACTAATTACTACTGGGGCTGGATCCGGCAGCCCCCAGGGAAGGACTGGAGTGGATT<br>GGCTATATCTATTACAGTGGAAGCACCAACTACAACCCCTCCCTCAAGAGTCGAGTCACCATATCAGTAGAC<br>ACGTCCAAGAACCAGTTCTCCCTAAAGCTGACCTCTGTAACCGCCGCAGACACGGCCGTGTATTACTGTGCG<br>GGTCGGGCTTACAGTAGTGGTTACTACTACCTAATTGACTACTGGGGCCAGGGAACCCTGGTCACCGTCTCC<br>TCA |

| Con1 Kappa | Seq ID No. | |
| --- | --- | --- |
| Con1p2-c01k | 144 | GAAATTGTGTTGACGCAGTCTCCAGGCACCCTGTCTTTGTCTCCAGGGGAAAGAGCCACCCTCTCCTGCAGG<br>GCCAGTCAGAGTGTTACCTACTTAGCCTGGTACCAGCAGAAACCTGGCCAGGCTCCCAGGCTCCTCTTCTAT<br>GGTACATCCAGCAGGGCCACTGGCATCCCAGACAGGTTCAGTGGCAGTGGGTCTGGGACAGACTTCACTCTC<br>ACCATCAGCAGAGTGGAGCCTGAAGATTTTGCAGTGTATTACTGTCAGCAGTTTGGCAGCTCACCTCCGGAC<br>ACTTTCGGCGGAGGGACCAAGGTGGAAATCAAA |
| Con1p2-c04k2 | 145 | TTGTGATGACTCAGTCTCCACTCTCCCTGCCCGTCACCCTTGGACAGCCGGCCTCCATCCTCTGCAGGGCTAG<br>TCAAGGCCTCGAACACAGTGATGAAACACCTACTTGAGTTGGTTTCAGCAGAGGCCAGGCCGATCTCCCCG<br>GCGCCTAATTTATAAGGTTTCTAACCGGGACTCTGGGGTCCCAGACAGATTCAGTGGCAGTGGGTCAGGCAC<br>TGATTTCACACTGGAAATCACCAGGGTGGAGGCTGAGGATGTTGGAGTTTATTACTGCATGCAAGTTACACA<br>CTGGCCGAGGACGTTCGGCCAAGGGACCAAGGTGGAAATCAAA |
| Con1p2-d02k | 146 | GAAATTGTGTTGACACAGTCTCCAGGCACCCTGTCGTTGTCTCCAGGGGAAAGAGCCACCCTCTCCTGCAGG<br>GCCAGTCAGAGTATTAGTCCCACTTGGCCTGGTACCAACAGAAACCTGGCCAGTCTCCCAGGCTCCTCATA<br>TATGATGCATCCAACAGGGCCACTGGCATCCCAGCCAGGTTCAGTGGCAGTGAGTCTGGGACAGACTTCACT<br>CTCAGCATCAGCAGCCTAGAGCCTGAAGATTTTGCAGTTTATTACTGTCAGCAGAGTGGCGACTGGCCTCTC<br>ACTTTCGGCGGAGGGACCAAGGTGGAGATCAAA |
| Con1p2-d03k3 | 147 | GAAATTGTGTTGACGCAGTCTCCAGGCACCCTGTCTTTGTCTCCAGGGGAAAGAGCCACCCTCTCCTGCAGG<br>GCCAGTCAGAGTGTTTACAGCATCTACTTCGCCTGGTACCAGCAGAAACCCGGCCAGGCTCCCAGGCCCCTC<br>ATTTATGGTGTCTCCAACAGGGCCACTGGCATCCCAGACAGGTTCAGTGGCAGTGGGTCTGGGACAGACTTC |

TABLE 2-continued

Selected Heavy and Light Chain Sequences from Antibodies of Table 1 (SEQ ID NOS. 127-252)

|  |  |  |
|---|---|---|
|  |  | ACTCTCACCATCAGCAGACTGGAGCCAGAAGATTTTGCAGTGTATTACTGTCAGCAGTATGGTAGTTTACCT<br>CGGACGTTCGGCCAAGGGACCAAGGTGGAAATCAAA |
| Con1p2-e01k | 148 | TTGTGATGACTCAGTCTCCACTCTCCCTGCCCGTCACCCTTGGACAGCCGGCCTCCATCTCCTGCAGGTCTAG<br>TCGAAGCCTCGTATACAGTGATGGAGGCACCTACTTGAATTGGTTTCAGCAGAGGCCAGGCCAATCTCCAAG<br>GCGCCTAATTTGGCACGTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGGTACACA<br>CTGGCCTTACACTTTTGGCCAGGGGACCAAGGTGGAAATCAAA |
| Con1p3-c02k | 149 | GACATCCAGATGACCCAGTCTCCATCTTCCCTGTCTGCATCTGTAGGAGACAGAGTCACCATCACTTGCCAG<br>GCGAGTCAGGACATTAGGAAGTTTTTAAATTGGTATCAGCAGAGACCAGGGAAAGCCCCTAACCTCCTGATC<br>TACGATGCATCCAATTTGGAAACAGGGGTCCCATCAAGGTTCAGTGGAAGTGGATCTGGGACACATTTTAGT<br>TTCACCATCACCAGCCTGCAGCCTGAAGATATTGCAACATATTACTGTCAACAGTTTGAAAGTTTCCCTCGCA<br>CCTTCGGCCCTGGGACCAAAGTGGATATCAAA |
| Con1p3-c03k | 150 | GAAATAGTGATGACGCAGTCTCCAGCCACCCTGTCTGTGTCTCCAGGGGAAACAGCCACCCTCTCCTGCAGG<br>GCCAGTCAGAGTGTTAACAGCTTCTTAGCCTGGTACCAGCAGAAACCTGGCCAGGCTCCCAGGCTCCTCATC<br>TATGCTGCATCCACCAGGGCCACTGGTGTCCCAGCCAGGTTCAGTGGCAGTGGGTCTGGGACAGAGTTCACT<br>CTCACCATCAGCAGCCTGCAGTCTGAAGATTTTGCAGTTTACTACTGTCACCAGTATAAAAACTGGCCTCCG<br>ATGGGCACTTTCGGCCCTGGGACCAAAGTGGATATCAAA |
| Con1p3-g01k | 151 | GACATCCAGATGACCCAGTCTCCTTCCACCCTGTCTTCTTCTGTCGGAGACAGAGTCACTATCACTTGCCGGG<br>CCAGTCAGAATATTGGTGTCTCCTTGGCCTGGTATCAGCAGAAACCAGGGAAAGCCCCTAACCTCCTGATCT<br>ATAAGGCGTCTTATTTAGAAACGGGGGTCCCATCAAGGTTCAGCGGCAGTGGATCTGGGACAGAATTCACTC<br>TCACCATCAGCAGCCTACAGCCTGATGATTTTGCAACTTATTATTGCCAACAGTATGATATTTATTTGACATT<br>CGGCCAAGGGACCAAGGTGGAAATCAAA |
| Con1p3-g06k | 152 | TTGTGATGACTCAGTCTCCACTCTCCCTGCCCGTCACCCTTGGACAGCCGGCCTCCATCTCCTGCAGGTCTAG<br>TCAAAGTCTCGCACACAGTGATGAAATACCTACTTGAATTGGTTTCAGCAGAGGCCAGGCCAATCTCCAAG<br>GCGCCTAATTTATAAGGTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGGTACACA<br>CTGGCCGTACACTTTTGGCCAGGGGACCAAGGTGGAAATCAAA |
| Con1p4-b01k | 153 | GACATCGTGATGACCCAGTCTCCAGACTCCCTGGCTGTGTCTCTGGGCGAGAGGGCCACCATCAACTGCAAG<br>TCCAGCCAGAGTGTTTTATACAGCCCCAACAATAAGAATTACTTAGCTTGGTTCCAGCAGAAGCCAGGACAG<br>CCTCCTAAATTACTCATTTACTGGGCATCTATCCGGGACTCCGGGGTCCCTGACCGATTCAGTGGCAGCGGGT<br>CTGGGACAGATTTCACTCTCACCGTCAGCAGTCTGCAGGCTGACGATGTGGCAGTTTATTACTGTCAGCAAT<br>ATGCTGCTACTCCGTGGACGTTCGGCCAAGGGACCAAGGTGGAAATCAAA |
| Con1p4-b03k2 | 154 | TTGTGATGACTCAGTCTCCACTCTCCCTGCCCGTCACCCTTGGACAGCCGGCCTCCATCTCCTGCAGTTCTAG<br>TCAAAGCCTCGTATACAGTGATGAAACACCTACTTGAGTTGGTTTCAGCAGAGGCCAGGCCAATCTCCCCG<br>GCGCCTAATTTATAAGGTTTCTAACCGGGACTCTGGGGTCCCAGACAGATTCAGCGGCAGTGGGTCAGGCAC<br>TGATTTCACACTGAGAATCAGCAGGGTGGAGGCTGAGGATGTTGGGGTTTATTACTGCATGCAAGGTTCACA<br>CTGGCCGCTCACTTTCGGCGGAGGGACCAAGGTGGAGATCAAA |
| Con1p4-c01k | 155 | GACATCGTGATGACCCAGTCTCCAGACTCCCTGGCTGTGTCTCTGGGCGAGAGGGCCACCATCAACTGCAAG<br>TCCAGCCTGAGTGTTTTATCCAGCTCCAATAATGAGAACTACTTAGCTTGGTACCAGCAGAAACCAGGACAG<br>CCTCCTAAGCTGCTCATTTACTGGGCATCTACCCGGGAATCCGGGGTCCCTGGCCGATTCAGTGGCAGCGGG<br>TCTGGGACAGATTTCACTCTCACCATCAGCAGCCTGCAGGCTGAAGATGTGGCAGTTTATTACTGTCACCAA<br>TATTATACTACTCCCTTCGCTTTCGGCCCTGGGACCAAAGTGGATATCAAA |
| Con1p4-g01k | 156 | GACATCCAGATGACCCAGTCTCCGTCCTCCCTGTCTGCATCTGTGGGAGACAGTGTCACCATCACTTGCCGG<br>GCAAGTCAGAGCATTAGCAGCTATTTAAATTGGTATCACCAAAAACCAGGGAAAGCCCCTAAACTCCTGATC<br>TATGGTGCATCCACTTTGCAAAGTGGGGTCCCATCAAGGTTCGGTGGCAGTGGATCTGGGACAGATTTCACT<br>CTCACCATCAGCAGTCTGCAACCTGACGATTTTGCAACTTACTACTGTCAACAGAGTCACAGTTCCCCTCTCA<br>CTTTCGGCGGAGGGACCAAGGTGGAGATCAAA |
| Con1p6-c01k | 157 | GACATCCAGATGACCCAGTCTCCTTCCACCCTGTCTGCCTCTGTAGGAGACAGAGTCACCATCACTTGTCGG<br>GCCAGTCGGAGTCTTGGTAGCTGGTTGGCCTGGTATCAGCAGAGCCAGGGAAAGCCCCTAAGCTCCTGATC<br>TATAAGGCGTCTACTTTAGAAAGTGGGGTCCCATCACGGTTCAGCGGCAGTGGATCTGGGACAGAATTCACT<br>CTCACCATCAGCAGCCTGCAGCCTGATGATTTTGCAACTTATTACTGCCAACAGTATTATAGCTTCTACACTT<br>TTGGCCAGGGGACCAAGGTGGAAATCAAA |
| Con1p6-d04k | 158 | GACATCGTGATGACCCAGTCTGCAGACTCCCTGGCTGTGTCTCTGGGCGAGAGGGCCACCATCAACTGCAAG<br>TCCAGCCAGAGTCTTTTCTACAGTTCCAACAAGAAGAACTACTTAGCTTGGTACCAGCAGAAAGCCAGGACAG<br>CCTCCTAAACTGATCATTTACTGGGCATCTACCCGGGAATCCGGGGTCCCTGACCGATTCAGTGGCAGCGGG<br>TCTGGGACAGATTTCACTCTCACCATCACCAGCCTGCGGGCTGAAGATGTGGCAGTTTATTACTGTCAGCAA<br>TATTATACTCCTCCTCTCACATTCGGCGGAGGGACCAAGGTGGAAATCAAA |
| Con1p6-e03k | 159 | GAAATAGTGATGACGCAGTCTCCAGCCACCCTGTCTGTGTCTCCAGGGGAAAGAGCCACCCTCTCCTGCAGG<br>GCCAGTCAGAGTGTTAGCGGCGACTTAGTCTGGTACCAGCAGAAACCTGGCCAGGCTCCCAGGCTCCTCATC<br>TATGGTGCCACCACCAGGGCCTCTGGTGTCCCAGCCAGGTTCAGTGGCAGTGGGTCTGGGACAGAGTTCACT<br>CTCACCATCAGCAGCCTGCAGTCTGAAGATTTTGCAATTTATTACTGTCAGCAGTATAATAACTGGCCCCGG<br>ACGTTCGGCCAAGGGACCAAGGTGGAAATCAAA |
| Con1p6-e06k | 160 | GAAATAGTGATGACGCAGTCTCCAGCCACCCTGTCTGTGTCTCCAGGGGAAAGAGCCACCCTCTCCTGCAGG<br>GCCAGTCAGAGTGTTGGCAACAACTTAGCCTGGTTTCAGCAGAAACCTGGCCAGGCTCCCAGGCTCCTCATC<br>TATGGTGCATCCACCAGGGCCACTGGTATCCCAGCCAGGTTCAGTGGCAGTGGGTCTGGGACAGAGTTCACT |

TABLE 2-continued

Selected Heavy and Light Chain Sequences from Antibodies of Table 1 (SEQ ID NOS. 127-252)

CTCACCATCAGCAGCCTGCAGTCTGAAGATTTTGCAGTTTATCACTGTCAACACTATCATAACTGGCCTCCCA
CTTTTGGCCAGGGGACCAAGGTGGAAATCAAA

| Con2 Heavy | Seq ID No. | |
|---|---|---|
| Con2p3-c04h | 161 | CAGGTGCAGCTGGTGGAGTCTGGGGGAGGCGTGGTCCAGCCTGGGAGGTCCCTGAGACTCTCCTGTGCAGCC
TCTGGATTCACCTTCAGCAACCATGGCATGCACTGGCTCCGCCAGACTCCAGGCAAGGGGCTGGAGTGGGTG
GCAGTCATTTCATATGATGGAAGTACCAAATACTATGCAGACTCCGTGAAGGGCCGATGCACCCTCTCCAGA
GACAATTCCAAGGAAACGGTGTTTCTGCAAATGAACAGCCTGAGACCTGAGGACACGGCTGTGTATTATTGT
GCGAAAGGGTGTTCTAATGGTGGTAACTGCTTTTTGATTGACTACTGGGGCCCGGGAACCCTGGTCACCGTC
TCCTCA |
| Con2p3-c05h | 162 | GAGGTGCAGCTGTTGGAGTCGGGGGGAGACTTGGTGCAGCCTGGGGGGTCCCTGAGACTCTCCTGTGCAGCC
TCTGGATTCGACTTCAGTATTTATGGCATGAACTGGGTCCGCCAGGCTCCAGGGAAGGGGCTTGAATGGGTC
TCAGTTATTAGTGGTGATGGCACTATCATATACTACGCAGACTCCGTGAAGGGCCGGTTCACTATCTCCAGA
GACAATTCCAAGAACACACTGTTTTTGCAAGTGAACAGCGTGAGAGCCGAGGACACGGCCGTATATTACTGT
GCGAAGGGGGGCTACTATGAATCGGGGACTATGCGGGCTTTTGATATCTGGGGCCAAGGGACAATGGTCAC
CGTCTCTTCA |
| Con2p3-f03h | 163 | GAGGTGCAGCTGGTGGAGGAGTCTGGGGGAGGCTTGGTCCAGCCTGGGGGGTCCCTGAGACTCTCCTGTGC
AGCCTCTGGATACACCTTTAGTAGTTATTCAATGAGTTGGGTCCGCCAGGCTCCAGGGAAGGGGCTGGAGTG
GGTGGCCAGCATTAAGCCAGAAGGAAGTGAGAAATTCTATGTGGACTCTGTGAAGGGCCGATTCACTATCTC
CAGAGACAACGCCAAGAACTCACTGTATCTGCAAATGAACAGCCTGAGAGGCGAGGACACGGCTGTCTACT
ACTGTGCGAGAGGGAATCTAATTTCCGATACTGGCACCAGGGAACCCTGGTCACCGTCTCCTCA |
| Con2p3-g05h | 164 | GAGGTGCAGCTGGTGGAGTCTGGGGGAGCCTTGGTCCAGCCTGGGGGGTCCCTGAGACTCTCCTGTGCAGCC
TCTGGATTCATCTTCAGTAACTCTTGGATGGGCTGGTTCCGCCAGGCTCCAGGGAAGCGGCCGGAGTTCGTG
GCCAACATAAAACCAGATGGAAGTGAGAAATTCCATGTGGACTCTGTGAAGGGCCGATTCACCATCTCCAG
AGACAACGCCGAGAACTCACTGTATCTGCTGATGAACAGCCTGAGAGCCGAGGACACGGCTGTCTATTACTG
CGCGAGAGATAGCACTTCCCCGGCCCGTTTTGGGTACTGGGGCCAGGGAACCCTGGTCACCGTCTCCTCA |
| Con2p4-b03h | 165 | GAGGTGCAGCTGGTGGAGACTGGAGGAGGCTTGATCCAGCCTGGGGGGTCCCTGAGGCTCTCCTGTGCAGC
CTCTGGGTTAAACGTCAATAGTTACTACATGAACTGGGTCCGCCAGGCTCCAGGGAAGGGGCTGGAGTGGGT
CTCAGTTATTTATAGCGGTGGTGGCACAAACTACGCAGACTCCGTGAGGGGCCGATTCATCATCTCCAGAGA
CAATTCCAGGAACGCGCTTTATCTTCAAATGAACAGCCTGAGAGCCGAGGACACGGCCGTGTATTACTGTGC
GACGGGCGGGATGACCAGTAGTTGGTACGGCTACTGGGGCCAGGGAACCCTGGTCACCGTCTCCTCA |
| Con2p4-c02h | 166 | AGGTGCAGCTGGTGCAGTCTGGGGCCGAGGTGAAGAAGCCTGGGGCCTCAGTGAAGGTTTCCTGCAAGGCA
TCTGAATACACTTTCATCAACTACCTTGTGTTCTGGGTGCGACAGGCCCCTGGACAAGGGCTTGAGTGGATG
GGAGAAATGAACCCCACTCGTGGGAGCACAAGCTACGCACAGAAGTTCCAGGGCAGAGTCACCATGACCAG
GGACACGTCCACGAGCACAGTCTACATGGAGTTGAGCAGCTGAGATCTGACGACACGGCCGTTTATTACTG
CTCCATGGGTCCGCCCTATTGTACTGGTGGAAGCTGTTACTCCGCCTGTGATTTCTGGGGCCCGGGAACCCTG
GTCACCGTCTCCTCA |
| Con2p4-d06h | 167 | GAGGTGCAGCTGGTGGAGTCTGGGGGAGGCTTGATGAAACCTGGGGGGTCCCTTAGACTCTCCTGTGCAGTC
TCTGGGTTCACTTTCACTAACGCCTGGCTGAGCTGGGTCCGCCAGCCTCCAGGGAAGGGGCTGGAGTGGGTT
GGCCGTGCTTACAGCAGTTCTGGCGGTTGGACAATGACTACTCTTCACCCGTGAGGGGCCAGATTCACCATC
ACAAGAGACGATTCAAAAAACACACTGTATCTGCAAATGAACAACCTGAAAACCGAGGACACAGCCGTGTA
TTACTGTACCACAGATATTGGCAAAGGCTGGTACACGCACTATCCTGACCTCTGGGGCCAGGGAACCCTGGT
CACCGTCTCCTCA |
| Con2p5-a06h | 168 | CAGGTGCAGCTGGTGGAGTCTGGGGGAGGCGTGGTCCAGCCTGGGAAGTCCCTCAGACTCTCCTGTGTAGCC
TCTGGATTCACCTTAAGTACCGTGGCATGCACTGGGTCCGCCAGGCTCCAGGCAAGGGGCTGGAGTGGGTG
GCAGTTACAACATATGATGGAGATCGTAAATATAATGTAGACTCCGTGAAGGGCCGATTCACCATCTCCAGA
GACAATTCCAAGAACACGGTGTATCTGCAAATGGACAGCCTCAAAGCCGAGGACACGGCTGTGTATCACTG
TGTGAAAGAATATAGTTGGGGTTACTACAGAACTGCGGACTACTGGGGCCAGGGAACCCTGGTCACCGTCTC
CTCA |
| Con2p5-b06h | 169 | GAGGTGCAGCTGGTGGAGTCCGGGGGAGGCTTAGTTCAGCCGGGGGGTCCCTGAGACTCTCCTGTGTAGCC
TCTGGATTCACCTTCAGTACTTACTGGATGCACTGGGTCCGCCAACCTCCGGGGAAGGGGCTGGTGTGGGTC
TCACGTATTAATCCTGATGGCAGTAGCACAAACTACGCGGACTCCGTGAACGGCCGATTCACCATCTCCAGA
GACAACGCCAAGAACACGCTGTATCTTGAAATGAACAGTTTGAGAGTCGAGGACACAGCTCTATATTACTGT
GCAAGAAGTCCTGGGGGTTACTTTGACTACTGGGGCCACAGCACCCTGGTCACCGTCTCCTCA |
| Con2p5-c04h | 170 | GAGGTGCAGCTGGTGGAGTCTGGGGGAGGCTTGGTGAAGCCTGGGGGGTCCCTTACACTCTCCTGTGCAGTC
TCTGGATTCACTTTCAGTACCGGCTGGATGAGCTGGGTCCGCCAGGCTCCAGGGAAGGGGCTGGACTGGGTT
GGCCGTATTAAAAGCAAAACTGCTGGTGGGACAACAGACTATGCTGCACCCGTGAAAGACAGATTCACCAT
CTCAAGAGATGATTCAAAAAACACGCTGTATCTGCAACTGAGCAGCCTTAAAACCGAGGACACAGCCGTGT
ATTACTGTACCACAGATGACCTGAAAAACTGGGGCCAGGGAACCCTGGTCACCGTCTCCTCA |
| Con2p5-e05h | 171 | GAGGTGCAGCTGGTGGAGTCTGGGGGAGGCTTGGTCAGCCGGGGGGTCCCTGAGACTCTCCTGTGCAGC
CTCTGGATTCACCTTCAGTAGTTATAGCATGAACTGGGTCCGCCAGGCTCCAGGGAAGGGGCTGGAGTGGGT
CTCATACACAAGTACTAAAAGTGATATCAAATACTACGCGGACTCTGTGAAGGCCGATTCACCATTTCCAG
AGACAATGCCAAGAACTCATTGTATCTGCAAATGAACAGCCTGAGAGACGAAGCACGGCTGTCTATTATTG
TGCGAGAGGACGAGATTGTTATGGGGTAACTGCGTCATCTACTTCCACTACTACGGTTTGGACGTCTGGGG
CCAAGGGACCACGGTCACCGTCTCCTCA |

TABLE 2-continued

Selected Heavy and Light Chain Sequences from Antibodies of Table 1 (SEQ ID NOS. 127-252)

| | | |
|---|---|---|
| Con2p6-b03h | 172 | CAGGTGCAGCTGGTGGAGTCTGGGGGAGGCGTGGTCCAGCCTGGGGGGTCCCTGAGACTCTCCTGTGTAGTC TCTGGATTCACCCTCAGTTCCTGTGGCATGCATTGGGTCCGCCAGTCTCCAGGCAAGGGGCTGGAGTGGCTG TCAGTTAGCACCTATGATGGAGATGGCAATCAGAAATACTATGCGGCCTCCGTGAAGGGCCGATTCCTCATC TCCAGAGACACTTCGAAGAACACGGTGTATCTCCATATGAACAGCCTGACAGCTGAGGACACGGCTCTATAT TATTGTGTGAAAGAGAGTGCCACTGGCTGGTATCGCACCGCTGATTACTGGGGCCAGGGAACCCTGGTCACC GTCTCCTCA |
| Con2p6-c05h | 173 | GAGGTGCAGCTGGTGGAGTCTGGGGGAGGCTTGGTCCAGCCTGGGGGGTCCTTGAGACTCTCCTGTGCAGCC TCTGGATTCACCGTCAGTAGCATATTCATGAGCTGGGTCCGCCAGGCTCCAGGGCAGGGGCTGGAGTGGGTC TCAGTCATCTATACCGATGGAAAAACATATTATGCACACTCCGTGGAGGGCCGATTCACCATCTCCAGAGAC GATTCCAAGAATATGGTGTATCTTCAATTGAGCAGCCTGAGAACTGAGGACACGGCTGTTTATTACTGTGCG AGAGATATTCCAACGACATTTGGAATAGGTGAAGCTTTTGATATCTGGGGCCAGGGGACAATGGTCACCGTC TCTTCA |
| Con2p6-g04h | 174 | AGGTGCAGCTGGTGCAGTCTGGGGCTGAGGTGAAGAAGCCTGGGGCCTCAGTGAAGCTTTCCTGCAAGACA TCTGGATACTCCTTCACCAGCAACTATTTGCACTGGGTGCGACAGGCCCCTGGACAAGGACTTGAGTGGATG GGAATGGTCTACCCAAATGATGGTACTACAACCTACGCTCAGAAGTTTCAGGGCAGAGTCACCATGACCAGT GAGACGTCCACAACCACAATCTACATGGACCTGAGCGGCCTGACATCTGAGGACACGGCCATATATTACTGT GCTAGAGACGATTCGGCCTTTGACTACTGGGGCCAGGGAACCCTGGTCACCGTCTCCTCA |
| Con2p7-d03h | 175 | CAGGTGCAGCTGGTGGAGTCTGGGGGAGGCGTGGTCCAGCCTGGGAGGTCCCTGAGACTCTCCTGTGAAGC CTCTGGATTCATCTTCAGTAGCAATGGCATGCACTGGGTCCGCCAGGCTCCAGGCAAGGGGCTGGAGTGGGT GGCAGTTATATCATCTGATGGAAGTAGGAGATACTATGCAGACTGAGTGAAGGGCCGATTCACCATCTCCAG AGACAACTCCAAGAACACGCTGTATCTGCAATTGAACAGCCTGAGAGCTGACGACACGGCTCTGTATTACTG TGCGAAAGGCTGTAGTGGTGAAAATTGCTTCTATATGGACGACTGGGGCAAAGGGACCACGGTCACCGTCTC CTCA |
| Con2p8-b01h | 176 | AGGTGCAGCTGGTGCAGTCTGGGGCTGAGGTGAAGAAGCCTGGGGCCTCACTGAAGGTCTCCTGCAAGGCA TCTGGATACACCTTCAGCAGAACTATTTCCACTGGGTGCGACAGGCCCCTGGACAAGGGCTTGAGTGGATG GGAGTAATCAACCCGAGTGATGGTAGTACAAAGTTCGCACAGAAGTTCCAGGGCAGAGTCAGCATGACCAG GGACACGTCCACGAGCACAGTTTACATGGACCTGAGCAGTCTGACATCTGAGGACACGGCCGTCTATTATTG TACGAGAGAGATCGGCGCAGTGGTAGTAGATGCTACGTCGTTGGGGTGGTTGGGCTACTTTGACTACTGGGG CCAGGGAACCCTGGTCACCGTCTCCTCA |
| Con2p8-b05h | 177 | GAGGTGCAGCTGGTGGAGTCTGGGGGAGGCTTGGTCCAGCCGGGGGGGTCCCTGAGTCTCTCCTGTGAAGCC TCTGGATTAACCTTCAGTGGCTACTGGATGAACTGGGTCCGCCAGGCTCCAGGGAAGGGGCTGGAGTGGGTG GCCAACATAAATCCAGAAGGAAGTGAGAGGAGATACGTGGAGTCTGTGCAGGGCCGATTCACCGTCTCCAG AGACAACCCCGAAGAACACCCTGTATTTGCAAATGAACAGCCTGAGAGTCGAGGACACGGCTCTGTATTACT GTGCGGGCTGGGGGAGAACCCAGGACTGGGGCCAGGGAGCCCTGGTCACCGTCTCCTCA |
| Con2p8-e03h | 178 | CAGGTGCAGCTGGTGGAGTCTGGGGGAGGCGTGGTCCAGCCTGGGAGGTCCCTGAGACTCTCCTGTGCAGCC TCTGGACTCACCTTCAGCAATTATGGCATGCACTGGGTCCGCCAGGCTCCAGGGAAGGGGCTGGAGTGGGTT GCAGTTGTGTCGGCAAGGGGAGGAACTACATATTATGCAGACTCCGTGAAGGGCCGATTCACCATCTCCAGA GACAATTCCAAGAACACGATGTCTCTGCAAATGAACGGCCTGAGACCTGACGACACGGCTGTGTATTTTTGT ACGAAAGAAGGAGCACCACCTGGAAAATATGCTTTTGATATCTGGGGCCAAGGGACAATGGTCACCGTCTC TTCA |
| Con2p8-f05h | 179 | GAGGTGCAGCTGGTGGAGTCTGGGGGAGGCTTGGTCCAGCCTGGAGGATCCCTGAGACTCTCCTGTGCGCAGCC TCCGGATTCACCTTCAGTGACTACCGCATGGACTGGGTCCGCCAGGCTCCAGGGAGGGGGCTGGAGTGGATT GCCCGTATTAGACACAGAGATGCAGGCTATAGCACAGAATACGCCGCGTCTGTGAGGGGCAGATTCACCGT CTCAAGAGATGACTCACAGAGTACACTGTACCTGCAGATGAACAGCTTGAAAGCCGACGACACGGCCGTGT ATATTTGTCTTAAAGATTCTTCGCAATACTTTTTGATGCGTGGGGCCAAGGGACAATGGTCACCGTCTCTTC A |

| Con2 Kappa | Seq ID No. | |
|---|---|---|
| Con2p3-c04k | 180 | GACATCGTGATGACCCAGTCTCCAGACTCCCTGGCTGTGTCTCTGGGCGAGAGGGCCACCATCAACTGCAAG TCCAGTCAGAGTATTTTATCCAGATCCAACAATAAGAACTACTTAGCCTGGTACCAGCAGAAACCAGGACAG CCTCCTAAATTGCTCCTTTATTGGGCATCTACCCGGGAATCCGGGGTCCCTGACCGATTCAGTGTCAGCGGGT CTGGGTCAGATTTCACTCTCACCATCAGTAGCCTGCAGGCTGAGGATGTGGCAGTTTATTACTGTCAGCAGT ATTATAATGCTCCCCTCACTTTCGGCGGAGGGACCAAGGTGGAGATCAAA |
| Con2p3-c05k | 181 | GAAATTGTGTTGACACAGTCTCCAGCCACCCTGTCTTTGTCTCCAGGGGAAAGGGCCACCCTCTCCTGCAGG GCCAGTCAGAGTGTTAGCAGGTACTTAGCCTGGTACCAACAAAAGCCTGGCCAGGCTCCCAGGCTCCTCATC TATGCTGCATCCAACAGGGCCACTGGCATCCCAACCAGGTTCAGTGGCAGTGGGTCTGGGACAGACTTCACT CTCACCATCAGCAGCCTAGAGCCTGAAGATTTTGCATTTTATTACTGTCAGCAGCGTAGCAACTGGCCTGCC ACTTTCGGCGGAGGGACCAAGGTGGAGATCAAA |
| Con2p3-f03k | 182 | GACATCCAGATGACCCAGTCTCCTTCCTCCCTGTCTGCATCTGTAGGAGACAGTGTCACCATCACTTGCCAGG CGAGTCAGGACATTAGAGACCGTTTAAATTGGTATCAGCAGAAGCAGGGAAAGCCCCTAACCTCCTGATCT ACGATGCATCAAGTTTGGAAACAGGGGTCCCATCAAGGTTCAGAGGAAGTGGATCTGGGACAGATTTTACTT TCACCATCAGCAGCCTGCAGCCTGAAGATATTGCAACATATTACTGTCAACAGTTTGTTAGTTTCCCTCGAAC TTTCGGCCCGGGGACCAAAGTGGATATCAAA |
| Con2p3-g05k | 183 | GAAATTGTGTTGACGCAGTCTCCAGGCATCCTGTCTTTGTCTCCAGGGGAAAGAGCCACCCTCTCCTGCAGG GCCAGTCAGAGTGTTAGCAGCAGGTCCTTGTCCTGGTACCAGCAGAGACCTGGCCTGGCTCCCAGGCTCCTC ATCTATGCTGCATCCAGCAGGGCCGCTGTCACCCCAGACAGGTTCACTGCCAGCGGGTCTGGGACAGACTTC |

TABLE 2-continued

Selected Heavy and Light Chain Sequences from Antibodies of Table 1 (SEQ ID NOS. 127-252)

|  |  |  |
|---|---|---|
|  |  | ACTCTCACCATCAGCAGTCTGGAGCCTGAAGATTTTGCAGTGTATTACTGTCAGCACTATGGTACCTCACCTC<br>CGAGGTACACTTTTGGGCAGGGGACCAAGGTGGAGATCAAA |
| Con2p4-b03k | 184 | GACATCGTGATGACCCAGTCCCCAGACTCCCTGGCTGTGTCTCTGGGCGAGAGGGCCACCATCAACTGCAAG<br>TCCAGCCAGAGTGTTTTACACAGCTCCAACAATAAGAACTACTTTGCTTGGTACCAGCAGAAACCAGGACAG<br>CCTCCTAAGCTGCTCATTCACTGGGCATCTACCCGGGCATCCGGGGTCCCTGACCGATTCAGTGGCAGCGGG<br>TCTGGGACAGATTTCACTCTCACCATCAGCAGCTGCAGGCTGAAGATGTGACAATTTATTACTGTCAGCAA<br>TATTATAGTACTCCGTACACTTTTGGCCAGGGGACCAAGGTGGAAATCAAA |
| Con2p4-c02k | 185 | GAAATTGTGTTGACGCAGTCTCCAGGCACCCTGTCTTTGTCTCCAGGGGAAAGAGCCACCCTCTCCTGCAGG<br>GCCAGTCCGAGTCTTGACAGCGCCTACTTAGCCTGGTACCAGCAGAAGCCTGGCCAGGCTCCCAGGCTCCTC<br>ATCTATGGTGCATCCTCCAGGGTCACTGGCATCCCAGATAGGTTCAGTGGCAGTGCGTCAGGGACAGACTTC<br>ACTCTCACCATCAGCAGACTGGAGCCTGAAGATTTTGCAGTGTACTACTGTCAGCGGTATGGTAACTCACCT<br>CCGTACACTTTTGGCCAGGGGACCAAGGTGGAGATCAAA |
| Con2p4-d06k | 186 | GACATCGTGATGACCCAGTCTCCAGACTCCCTGGCTGTGTCTCTGGGCGAGAGGGCCACCATCAGCTGCAAG<br>TCCAGCCAGAGTGTCTTTTATACAGTTCCAGCAATAAGAACTACCTAGCTTGGTTCCAGCAGAAACCAGGACAG<br>GCTCCTAAGTTGCTCATTTACTGGGCATCTACCCGGGAATCCGGGGTCCCTGACCGATTCAGTGGCAGCGGG<br>TCTGGGACAGATTTCACTCTCACCATCAGCAGCTGCAGACTGAAGATGTGGCAGTTTATTATTGTCTGCAAT<br>ATCGTAGTGCTCCGTTCACTTTCGGCGGAGGGACCAAGGTGGAGATCAAA |
| Con2p5-a06k | 187 | GACATCCAGATGACCCAGTCTCCTTCCACCCAGTCTGCATCTGTAGGAGACAGAGTCACCATCACTTGCCGG<br>GCCAGTCAGAGTATTAGTAGTTGGTTGGCCTGGTATCAGCAGAAACCAGGGAAAGCCCCTAAGGTCCTGATC<br>TATGCGGTGTCTAGTTTAGAAAGTGGGGTCCCATCAAGGTTCAGCGGCAGTGGATCTGGGACAGAATTCACT<br>CTCACCATCAGCAGCCTGCAGCCTGAAGATTTTGCAACTTATTACTGCCAACAATATAGTACTTATCCCTGGA<br>CGTTCGGCCCAGGGACCAAGGTGGAAATCAAA |
| Con2p5-b06k | 188 | GAAATAGTGATGACGCAGTCTCCAGCCTCCCTGTCTGTGTCTCCAGGGGAAACAGCCACCCTCTCCTGCAGG<br>GCCAGTCAGAGTGTTGGCAGCACCTTAGCCTGGTACCAGCAGAAGCCCGGCCAGGCTCCCAGGCTCCTCATC<br>TATAATGTATTCACCAGGGCCGCTGGTGTCCCAGCCAGGTTCAGTGGCAGTGGGTCTAGGACGGAGTTCACT<br>CTCACCATCAGCAGCCTGCAGTCTGAAGATTTTGCAGTTTATTACTGTCAGCAGTATAGTACCTGGCTGTGGA<br>CGTTCGGCCAAGGGACCAAGGTGGAAATCAAA |
| Con2p5-c04k | 189 | GACATCCAGATGACCCAGTCTCCATCCTCCCTGTCTGCATCTGTAGGAGACAGAGTCACCATCACTTGCCGG<br>GCAAGTCAGCGCATTAGCAGCTACTTGAATTGGTATCAGCAGAAACCAGGGAAAGCCCCTAACCTCCTGATC<br>TACGCTGCAGCCAGTTTGCATGATGGGGTCCCATCAAGGTTCAGTGGCAGTGGATCTGGGACAGATTTCACT<br>CTCACCATCAGCAGTCTGCAACCTGAAGATTTTGCAACTTATTATTGTCAACAGCGTTACAGAATCCCGTACA<br>GTTTTGGCCCCGGGGACCAAGGTGGAGATCAAA |
| Con2p5-e05k | 190 | GATATTGTGATGACTCAGTCTCCACTCTCCCGTCCGTCACCCCTGGAGAGCCGGCCTCCATCTCCTGCAGGT<br>CTAGTCAGAGCCTCCTTCAGGGTAATGGACACAACTATTTGGATTGGTACCTGCAGAAGCCAGGACAGTCTC<br>CACAACTCCTGATCTATTTGGGTTCTATTCGGGCCTCCGGGGTCCCTGACAGGTTCAGTGGCAGTGGATCAG<br>GCACAGATTTTATACTGAAAATCAGCAGAGTGGAGGCTGAGGATGTTGGGGTTTATTACTGCATGCAGCTC<br>TACAAACTCCGTACACTTTTGGCCAGGGGACCAAGGTGGAAATCAAA |
| Con2p6-b03k | 191 | GACATCCAGATGACCCAGTCGCCTTCCACCCTGTCTGCATCTGTTGGAGACAGAGTCACCCTCACTTGTCGG<br>GCCAGTGAGACTCTTAATAACTGGTTGGCCTGGTTTCAGCAAAAGCCAGGGAAAGCCCCTACCCTCCTGATC<br>TATGAGGCGTCTAGTTTAGAAAGTGGAGTCCCATCAAGGTTCAGCGGCAGTGGATCTGGGACAGACTTCGCT<br>CTCACCATCAGCAGCCTGCAGCCCGATGATTTTGCAACTTATTATTGCCACCAGTATAATAAATACCCGTGG<br>ACGTTCGGCCAAGGGACCAAGGTGGAGATCAAA |
| Con2p6-c05k | 192 | GACATCCAGATGACCCAGTCTCCTTCCACCCTTGTCTGCATCTGTAGGAGACAGAGTCACCATCACTTGTCGG<br>GCCAGTCAGAGTATTAGTGGCTGGTTGGCCTGGTATCAGCAGAAAGCAGGGAAAGCCCCTAAGCTCCTGATC<br>TATAAGGCGTCTAGTTTAGAAAGTGGGGTCCCATCAAGGTTCAGCGGCAGTGGATCTGGGACAGAGTTCACT<br>CTCACCATCAGCAGCCTGCAGCCTGATGATTTTGCAACTTATTACTGCCAGCAGTATTATAGTTGGGGAACGT<br>TCGGCCAAGGGACCAAGGTGGAGATCAAA |
| Con2p6-g04k | 193 | GATATTGTGATGACCCAGACTCCACTCTCCTTACCTGTCACCCTTGGACAGCCGGCCTCCATCTCCTGCATAT<br>CTAGTCAAAGCCTCGTACACAGTGATGGAAACACCTACTTGAGTTGGCTTCAGCAGAGGCCAGGCCAGCCTC<br>CAAGACTCCTGATTTATAAGATTTCTAACCGGTTCTCTGGGGTCCCAGACAGATTCAGTGGCAGTGGGGCAG<br>GGACAGATTTCACACTGAAAATCAGCAGGGTGGAAGCTGAGGATGTCGGGGTTTATTACTGCATGCAAGCTT<br>CACAACTTACGTGGACGCTCGGCCAAGGGACCAAGGTGGAGATCAAA |
| Con2p7-d03k | 194 | GACATCGTGATGACCCAGTCTCCAGACTCCCTGGCTGTGCCTCTGGGCGAGAGGGCCACCATCAACTGCACG<br>TCCAGCCAGACTGTTTATCCAGTTCCAACAATAAGAACTACTTAGTTGGTACCAGCAGAAACCAGGACAG<br>CCTCCTAAGTTGCTCCTTTACTGGGCGTCTACCCGGGCATCCGGGGTCCCTGACCGATTCAGTGGGAGCGGG<br>TCTGGGACAGATTTCACTCTCACCATTAGCAGTCTGCAGGCTGAAGATGTGGCAGTTTATTACTGTCAGCAAT<br>GTTATAATGCTCCGCTCACTTTCGGCCGAGGGACCAAGGTGGAGATCAAA |
| Con2p8-b01ka | 195 | GAAATAGTGATGACGCAGTCTCCAGCCACCCTGTCTGTGTTTCCAGGGGAAGGAGTCACCCTCTCCTGCAGG<br>GCCAGTCAGAGTATTAGCAACAACTTGGCCTGGTACCAGCAGAAACCTGGCCAGGCTCCCAGGCTCCTCATG<br>TATGATGCATCCACCAGGGCCACTGGTATCCCAGCCAGGTTCAGTGGCAGTGGGTCTGGGACAGAGTTCACT<br>CTCACCATCAGCAGCCTGCAGTCTGAAGATTTCGCAGTTTATTACTGTCAGCAGTATAATAACTGGCCTCCGG<br>TCACGTTCGGCCAAGGGACCAAGGTGGAAATCAAA |
| Con2p8-b05k | 196 | TTGTGATGACTCAGTCTCCACTCTCCCTGCCCGTCACCCTTGGACAGTCGGCCTCCGTCTCCTGCAGGTCAAG<br>TCAAAGCCTCGGCCCCAGTGACGGAAGCACCCGCTTGGATTGGTTTCAACAGAGGCCAGGCCAATCTCCAAG<br>GCGCCTAATTTATGCGGTTTCTAACCGGGACTCTGGGGTCCCAGACAGATTCAGCGGCAGCGGGTCAGGCAG |

TABLE 2-continued

Selected Heavy and Light Chain Sequences from Antibodies of Table 1 (SEQ ID NOS. 127-252)

|  |  |  |
|---|---|---|
|  |  | TGATTTCACACTGAGAATCAGCAGAGTGGAGGCTGAGGATGTTGGGGTTTATTACTGCATGCAATATACATA<br>CTGGCCTCACACTTTTGGCCAGGGGACCAAGGTGGAAATCAAA |
| Con2p8-e03k | 197 | GAAATTGTGTTGACACAGTCTCCAGCCACCCTGTCTTTGTCTCCAGGGGAAAGAGCCACCCTCTCCTGCAGG<br>GCCAGTCAGAGTGTTAGCAGTTCCTTAGCCTGGTACCAACAAAAACCTGGCCAGGCTCCCAGGCTCCTCATC<br>TATGATGCATCCAAGAGGGCCACTGACATCCCAGCCAGGTTCAGTGGCAGTGGGTCTGGGACAGACTTCACT<br>CTCACCATCAGCAGCCTAGAGCCTGAAGATTTTGCGGTTTATTACTGTCAGCACCGGGGGGAGTGGCCTCCG<br>GGGGCCACTTTCGGCCCTGGGACCAAAGTGGATATCAAA |
| Con2p8-f05k | 198 | GACATCCAGTTGACCCAGTCTCCATCCTTCCTGTCTGCATCTGTAGGAGACAGAGTCACCATCACTTGCCGGG<br>CCAGTCAGGGCATTGATACTCGTTTGATCTGGTATCAACAGAAGCCAGGGGAAGCCCCTAAGCTCCTGATCT<br>ATGAAGCATCCACTTTGCAAAGTGGGGCCCCATCAAGGTTCAGCGGCAGTGGATTCGGGACAGAATTCACTC<br>TCACAATCAGCAGTCTGCAGCCTGAAGACTTTGCAACTTATTACTGTCAACAGTTTAAAGGTTACCCGCTCAC<br>TTTCGGCGGGGGGACCAAGGTGGAGATCAAA |

| SLE1 Heavy | Seq ID No. |  |
|---|---|---|
| SLE1p1-a02h | 199 | CAGGTGCAGCTGCAGGAGTCGGGCCCAGGACTGGTGAAGCCTTCGGAGACCCTGTCCCTCACCTGCACTGTC<br>TCTGGTGGCTCCATCAGTAGTCACTACTGGAGCTGGATCCGGCAGCCCCCAGCGAAGGGACTGGAGTGGATT<br>GGGTATATCTATCACAGTGGGATGACCAACTACAACCCCTCCCTCAAGAGTCGAGTCACCATATCAATAGAC<br>ACGTCCAAGAACCAGTTCTCCCTGAAGTTGAGCTCTGTGACCGCTGCGGACACGGCCGTGTATTACTGTGCG<br>AGAGGTGATGGCTACAATTTCTTCTGGGGCCAGGGAACGCTGGTCACCGTCTCCTCA |
| SLE1p1-a03h | 200 | CAGGTGCAGCTGGTGGAGTCTGGGGGAGGCGTGGTCCAGCCTGGGGGGTCCCTGAGACTCTCCTGTGCAGC<br>GTCTGGACTCACGTTCAGTAACCAAGATTTCCACTGGGTCCGCCAGGCTCCAGGCAAGGGGCTGGAATGGGT<br>GGCATTTATACGTTATGATGGAGGTTTTAAAAACTATGCAGACTCCGTGAAGGGCCGATTCACCATCTCCAG<br>AGACAATTCCCAGAAAATGCTGTATCTGCAAATGGACAGCCTGAGAGTTGAAGACACGGCTGTGTATTACTG<br>TGCGAAGTGCGGCGCAGAGGACTCTACTACTGTCTGGCTGAATTGGTTCGACCCCTGGGGCCAGGGAACCCT<br>GGTCACCGTCTCCTCA |
| SLE1p1-b05h | 201 | GAGGTGCAGCTGTTGGAGTCTGGGGGAGGCTTGGTAGAGCCTGGGGGGTCCCTGAGACTCTCCTGTGCAGCC<br>TCTGGATTCACCTTTAGCAGCTATGCCATGAGCTGGGTCCGCCAGGCTCCAGGGAAGGGGCTGGAGTGGGTC<br>TCAGCTATTAGTGACAGTGGTGGTAGCACATACTACGCAGACTCCGTGAAGGGCCGGTTCACCATCTCCAGA<br>GACAAGTCCAAGAACACGCTGTATCTGCAAATGAACAGCCTGAGAGCCGAGGACACGGCCGTATATTACTG<br>TGCGAAACCGAATTACTTTGGTTCGGGGAGTCCCGACTACTGGGGCCAGGGAACGCTGGTCACCGTCTCCTC<br>A |
| SLE1p1-c04h | 202 | CAGGTGCAGCTGCAGGAGTCGGGCCCAGGACTGGTGAAGCCTTCGGAGACCCTGTCCCTCACCTGCACTGTC<br>TCTGGTGCCTCCATCAGTAGTCACTACTGGAGCTGGATCCGGCAGCCCCCAGGGAAGGGACTGGAGTGGATT<br>GGGTATATCTATCACAGTGGGATTACCAACTACAACCCCTCCCTCAAGAGTCGAGTCACCATATCAATAGAC<br>ACGTCCAAGAACCAGTACTCCCTGAAGCTGAGCTCTGTGACCGCTGCGGACACGGCCGTGTATTACTGTGCG<br>AGAGGTGATGGCTACAATTTCTACTGGGGCCAGGGAACGCTGGTCACCGTCTCCTCA |
| SLE1p1-e01h | 203 | GAGGTGCAGCTGGTGGAGTCTGGGGGAGGTGTGGTACGGCTGGGGGGTCCCTGAGACTCTCCTGTGCAGC<br>CTCTGGATTCACCTTTGATGATTATGGCATGACCTGGGTCCGCCAAGCTCCAGGGAAGGGGCTGGAGTGGAT<br>CTCTGGTATTTGTTGCAACGGTGGTTGCTCAGGTTATGCAGACTCTGTGAAGGGCCGATTCACCATCTCCAGA<br>GACAACGCCAAGAAGTCCCTGTTTCTGGTCATGAACAGTCTGAGAGCCGAGGACACGGCCTTGATTACTGT<br>GTGAGAGTGGCAGTACCAGCTGCTACATACACCCGAGGGAATGATGCTTTTGATATTTGGGGCCAAGGGAC<br>AATGGTCACCGTCTCTTCA |
| SLE1p1-f02h | 204 | GAGGTGCAGCTGGTGGAGTCTGGGGGAGGCTTGGTAGAGCCTGGGGGGTCCCTCAGACTCTCCTGTGCAGTC<br>TCTGGTTTCACTTTCACTGACGCCTGGATGACCTGGGTCCGCCAGGCTCCAGGGAAGGGGCTAGATTGGGTT<br>GGCCATGTAAAAAGTAAATATGATGGTGCGACAACAGAGTACGCTGCACCCGTGCAAGGCAGATTCACCAT<br>CTCAAGAGATGATTCAAAGAAGACAATATATCTGCAAATGAACAGCCTGAACACCGAGGACACAGGCGTCT<br>ATTTTTGTACCACAGCTCATGGCCCGGTGGGTGACCATTGGGGCAGGGAACACTGGTCACCGTCTCCTCA |
| SLE1p1-g05h | 205 | GAGGTGCAGCTGGTGGAGTCTGGGGGAGGCTTGGTCCAGCCGGGGGGGTCCCTGAGACTCTCCTGTGCAGC<br>CTCTGGATTCAGCTTTGATACCTCTTGGATGACCTGGGTCCGCCAGGCTCCAGGGAAGGGGCTGGAGTGGGT<br>GGCCACCATAAACCAGGGTGGAAGTGACAAATACTATGTGGACTCTGTGAAGGGCCGATTCACCATCTCCA<br>GAGACAACGCCAAGAACTCACTGTATCTGCAAATGAACAGCTGCGAGCCGAGGACACGGCTGTATATTAC<br>TGTGCGAGAGCGGGCGGGTGTAGCTCTACCAGATGCCATACAACCCCGGGATTTGACTACTGGGGCCAGGG<br>AGCGCTGGTCACCGTCTCCTCA |
| SLE1p2-a02h | 206 | TGCAGCTGCAGGAGTCGGGCCCAGGACTGGTGAAGCCTTCGGAGACCCTGTCCCTCACCTGCACTGTCTCTG<br>GTAGCTCCATCAGCAGTAGTAGTTACTACTGGGGCTGGGTCCGCCAGTCCCCAGGGAAGGGACTGGAGTGG<br>ATTGGGAGTATCTATCACAGTGGGACCATCTACTACAACCCGTCCCTCAGGAGTCGAGTCACCATATCCGTA<br>GACACGTCCAAGAACCAGTTCTCCCTGAAGCTGAACTCTGTGACCGCCGCAGACACGGCTGTTTATTACTGT<br>GCGAGTCTTAGTGGCACAAATGCTTTTGATATCTGGGGCCAAGGGACAATGGTCACCGTCTCTTCA |
| SLE1p2-d04h | 207 | GAGGTGCAGCTGTTGGAGTCTGGGGGGGCTTGGTACAGCCTGGGGGGTCCCTGAGACTCTCCTGTGCAGCC<br>TCTGGATTCACCTTTAGCAGCCATGACATGAGTTGGGTCCGCCTGGCTCCAGGGAAGGGGCCGGAGTGGGTC<br>TCAGCTCTTGTGCTGGAGATGCTTGGACACACTACGCAAACTCCGTGAGGGGCCGGTTCACCATCTCCAGA<br>GACGATTCCAAGAACACGCTGTATCTGCAAATGAACAGCCTGAGAGCCGAAGACACGGCCGTGTATTTCTGT<br>GCGAAACCCCGTGGATACTCCTATGGCTACTTTGACTACTGGGGCCAAGGAACGCTGGTCACCGTCTCCTCA |
| SLE1p3-a02h | 208 | GAGGTGCAGCTGGTGGAGTCTGGGGGAGGCTTGGTCCAGCCTGGGGGGTCCCTGAGACTCTCCTGTGGAGCC<br>TCTGGATTCACCTTTAGTACCTATTGGATGACCTGGGTCCGCCAGGCTCCAGGGAAGGGCCTGGAGTGGGTG |

TABLE 2-continued

Selected Heavy and Light Chain Sequences from Antibodies of Table 1 (SEQ ID NOS. 127-252)

| | | |
|---|---|---|
| | | GCCAATATAAACCAAGATGGAAGTGAGAAACAATATGTGGACTCTGTGAAGGGCCGATTCACCATCTCCAG<br>AGACAACGCCAAGAACTCACTGTATCTGCAGATGAACAGCCTGAGAGTCGAGGATACGGCTATTTATTACTG<br>TGCGAGACCCCCAGCTCGCCGACTTGACTACTGGGGCCAGGGATCGCTGGTCACCGTCTCCTCA |
| SLE1p3-a04h | 209 | GAGGTGCAGCTGGTGGAGTCCGGGGGAGGCTTAGTTCAGCCTGGGGGGTCCCTGAGACTCTCCTGTGCAGCC<br>TCTGAATTCACCTTCAGTGACTACTGGATGCACTGGGTCCGCCAAGCTCCAGGGAAGGGGCTGGTCTGGGTC<br>TCACGTATTAATACTGACGGGAGTACCACAACCTACGCGGACTCCGTGAAGGGCCGATTCACCATCTCCAGA<br>GACAACGCCAAGAACACGCTGTATCTACAAATGAACAGTCTGAGGGCCGAGGACACGGCTGTGTATTACTG<br>TGCAAGATCTAATGCGGGCACGAAGCGTGGGGCCAGGGAACGCTGGTCACCGTCTCCTCA |
| SLE1p3-b03h | 210 | AGGTGCAGCTGGTGCAGTCTGGGGCTGAGGTGAAGAAGCCTGGGGCCTCAGTGAGGGTTTCCTGCAAGGCA<br>TCTGGATACACCTTCACCAACTACTGGATACACTGGGTGCGACAGGCCCCTGGACAAGGGCTTGAGTGGATG<br>GGAATGATCGCCCCTAAGGAAGGTTACACATTCTACGCACAGCAATTACAGGGCAGAGTCACCGTGACCAG<br>GGACACGTCGACGAGCGCGGTTTACATGGAGCTGAACAGCCTGAGATCTGAGGACACGGCCGTATATTTCTG<br>TGCGAGAGACATTCCCCACGCTAATTTGGACTATTGGGGCCAGGGGACGCTGGTCACCGTCTCCTCA |
| SLE1p3-c03h | 211 | GAGGTGCAGCTGTTGGAGTCTGGGGGAGGATTGGTACAGCCTGGGGGGTCCCTGAGACTCTCCTGTGCAGCC<br>TCTGGATTCACCTTTAGCGATTATACCATGAATTGGGCCCGCCAGGCTCCAGGGAAGGGGCTGGAGTGGGTC<br>TCAGCTATTAGAGAGAGTGGTGACAGCACATACTACGCAGACTCCGTGACGGGCCGGTTCACCATCTCCAGG<br>GACAATTCCAGAAACACACTTTATCTGCACATGAACAGCCTGAGAGCCGAGGACACGGCCATGTATTTTTGT<br>GTGAAAGACAGGGTGCCGCCGGGTGACGTGCCGGGTGACTTCTGGGGCCCGGGAACGCTGGTCACCGTCTC<br>CTCA |

| SLE1 Kappa | Seq ID No. | |
|---|---|---|
| SLE1p1-a02k | 212 | GACATCCAGTTGACCCAGTCTCCATCCTTCCTGTCTGCATCTGTAGGAGACAGAGTCACCATCACTTGCCGGG<br>CCAGTCAGGACATGACCCATTCTTTAGCCTGGTATCAGCAAAAACCAGGGAAAGCCCCTAACCTCCTGATCT<br>ATAATGCATACACTTTGCAAAGTGGGGTCCCATCAAGGTTCAGCGGCAGTGGATCTGGGACAGAATTCACTC<br>TCACAATCAGCAGCCTGCAGCCTGAAGATTTTGCAACTTATTACTGTCAACAGATTAATAGTTACCCTCGAA<br>CTTTTGGCCAGGGGACCAAGGTGGAGATCAAA |
| SLE1p1-a03k | 213 | GAAATTGTGTTGACACAGTCTCCAGGCACCCTGTCTTTGTCTCCAGGGGAAAGAGCCACTCTCTCCTGCAGG<br>GCCAGTCAGAATATTGGCACCGCCTTAGCCTGGTACCAACAGAAACCTGGCCAGGCTCCCAGACTCATCATC<br>TATGAAACATCCAACAGGGCCACTGACGTCCCAGCCAGGTTCAGTGGCAGTGGGTCTGGGACAGACTTCACT<br>CTCACCATCAGCAGCCTGGAGCGTGAAGATTTTGCCCTTTATTACTGTCAACAGCGTGCCGACTGGCCGCTC<br>ACTTTCGGCGGAGGGACCAAGGTGGAGATCAAA |
| SLE1p1-b05k | 214 | GAAATTGTGTTGACACAGTCTCCAGCCACCCTGTCTTTGTCTCCAGGGGAAAGAGCCACCCTCTCCTGCAGG<br>GCCAGTCAGAGTGTTAGCAGCTACTTAGCCTGGTACCAACAGAAACCTGGCCAGGCTCCCAGGCTCGTCATC<br>TATGCTGCATCCAACAGGGCCACTGGCATCCCAGCCAGGTTCAGTGGCAGTGGGTCTGGGACAGACTTCACT<br>CTCACCATCAGCAGCCTAGAGCCTGAAGATTTTGCAGTTTATTACTGTCTGCAGTGTAGCAACTGGCCCATGT<br>ACACTTTTGGCCAGGGGACCAAGGTGGAGATCAAA |
| SLE1p1-c04k | 215 | GACATCCAGTTGACCCAGTCTCCATCCTTCCTGTCTGCATCTGTAGGGGACAGAGTCACCATCACTTGCCGGG<br>CCAGTCAGGACATTACCGATTCTTTAGCCTGGTATCAGCAAAAACCAGGGAAAGCCCCTAACCTCCTGATCT<br>ATACTGCATCCACTTTGCAAAGTGGGGTCCCATCAAGGTTCAGCGGCAGTGGATCTGGGACAGAATTCACTC<br>TCACAATCAGCAGCCTGCAGCCTGAAGATTTTACAACTTATTACTGTCAACAGATTAATAGTTACCCTCGAA<br>CTTTTGGCCAGGGGACCAAGGTGGAGATCAAA |
| SLE1p1-e01k | 216 | GACATCCAGATGACCCAGTCTCCATCCTCCCTGTCTGCATCTGTAGGAGACAGAGTCACCATCACTTGCCGG<br>GCAAGTCAGGGCATTAGAAATGATTTAGGCTGGTATCAGCAGAAACCAGGGAAAGCCCCTAAGCGCCTGAT<br>CTATGCTGCATCCAGTTTGCAAAGTGGGGTCCCATCAAGGTTCAGCGGCAGTGGATCTGGGACAGAATTCAC<br>TCTCACAATCAGCAGCCTGCAGCCTGAAGATTTTGCAAGTTATTACTGTCTACAGCATAGTAGTTTCCCGTGG<br>ACGTTCGGCCAGGGGACCAAGGTGGAAATCAAA |
| SLE1p1-f02k | 217 | GACATCGTGATGACCCAGTCTCCAGACTCCCTGGCTGTGTCTCTGGGCGAGAGGGCCGCCATCAACTGCAAG<br>TCCAGCCAGAGTGTCTTAGACAGCTCCAACATGAAGAGGTACTTAGCCTGGTATCAGCTGAAAGCAGGACA<br>GCCTCCTAGGTTGCTCATTTACTTGGCTTCCACCCGGGAATCCGGGGTCCCGGACCGATTCAGTGGCAGCGG<br>GTCCGGGACAGATTTCAATCTCACTATCAGCAGCCTGCAGGCTGAAGATGTGGCAGTTTATTACTGTCAGCA<br>AATATTATACAACCCCTTCGATCACCTTCGGCCAAGGGACACGACTGGAGATTAAA |
| SLE1p1-g05k | 218 | GACATCGTGATGACCCAGTCTCCAGACTCCCTGGCTGTGTCTCTGGGCGAGAGGGCCACCATCAACTGCAAG<br>TCCAGCCAGAGTGTTTTATACAGCTCCAACAATAAGAACTACTTAGCTTGGTACCAGCAGAAACCAGGTCAG<br>CCTCCTAAGATGCTCATTTACTGGGCATCTACCCGGGAGTCCGGGGTCCCTGACCGATTCAGTGGCAGCGGG<br>TCTGGGACAGATTTCACTCTCACCATCAGCAGCCTGCAGGCTGAAGATGTGGCAGTTTATTACTGTCAGCAA<br>TATTATACTACTCCCATCACCTTCGGCCAAGGGACACGACTGGAGATTAAA |
| SLE1p2-a02k | 219 | GAAATTGTGTTGACACAGTCTCCAGCCACCCTGTCTTTGTCTCCAGGGGAAAGAGCCACCCTCTCCTGCAGG<br>GCCAGTCAGAGTGTTAGTATCTACTTAGCCTGGTACCAACAGAAACCTGGCCAGGCTCCCAGGCTCCTCATC<br>TATGATTCATCCAACAGGGCCACTGGCATCCCAGCCAGGTTCAGTGGCAGTGGGTCTGGGACAGACTTCACT<br>CTCACCATCAGCAGCCTAGAGCCCGAAGATTTTGCGGTTTATTACTGTCAGCAGCGTAGCAGCGGGCGAACG<br>TTCGGCCAAGGGACCAAGGTGGAGATCAAA |
| SLE1p2-d04k | 220 | GAAATTGTGTTGACGCAGTCTCCAGGCACCCTGTCTTTGTCTCCAGGGGAAAGAGCCACCCTCTCCTGCAGG<br>GCCAGTCAGACTGTTACCAACAACTACTTAGCCTGGTACCAACACAAACCTGGCCTGGCGCCCAGGCTCCTC<br>ATCTTTGATGCATCCATCAGGGCACTGGCATCCCAGCAGGTTCAGTGGCAGTGGGTCTGGGGCAGACTTC |

TABLE 2-continued

Selected Heavy and Light Chain Sequences from Antibodies of Table 1 (SEQ ID NOS. 127-252)

|   |   |   |
|---|---|---|
|   |   | ACTCTCACCATCAGCAGACTGGAGCCTGAAGATTTTACATTCTATTACTGTCAGCAATATGGTATTTCACCTC GAACTTTTGGCCAGGGGACCAAGGTGGAGATCAAA |
| SLE1p3-a02k | 221 | GATATTGTGATGACCCAGACTCCACTCTCTCTGTCCGTCACCCCTGGACAGCCGGCCTCCATCTCCTGCAAGT CTAGTCAGAGTCTCCTGGATAGTGATGGAAGGACCTATTTCTTTTGGTATTTGCAGAAGCCAGGCCAGTCTCC ACAACTCCTGATCTATGAAGTTTCCAACCGGTTCTCTGGAGTGCCAGATAGGTTCAGTGGCAGCGGGTCAGG GACAGATTTCACACTGAAAATCAGCCGGGTGGAGTCTGAAGATGTTGGGGTTTATTACTGCATGCAAGGTAC ACACCATCCGTGGACGTTCGGCCAAGGGACCAAGGTGGAAATCAAA |
| SLE1p3-a04k | 222 | GACATCGTGATGACCCAGTCTCCAGACTCCCTGGCTGTGTCTCTGGGCGAGAGGGCCACCGTCAACTGCAAG TCCAGCCAGAGTGTTTTATACAGCTCCAACAGTAAGAACTACTTAGCTTGGTACCAGCAGAAACCAGGACAG CCTCCTAAGCTGCTCATTTACTGGGCATCTACCCGGGAATCCGGGGTCCCTGACCGATTCAGTGGCAGCGGG TCTGGGACAGATTTCACTCTCACCATCAGCAGCCTGCAGGCTGAAGATGTGGCAGTGTATTACTGTCAGCAA TATTATAGTACTCCTCTCACTTTCGGCGGAGGGACCAAGGTGGAGATCAAAC |
| SLE1p3-b03k | 223 | GACATCCAGATGACCCAGTCTCCATCCTCCCTGTCTGCATCTGTGGGAGACAGAGTCACCATCACTTGCCGG GCAAGTCAGGGCATTGGGAATGATTTAGGCTGGTATCAGCATGAACCAGGGAAAGCCCCTAAGCGCCTGAT CTATGCAGCATCCAGTTTGCAAAGTGGGGTCCCATCGAGGTTCAGCGGCAGTGCATCTGGGACAGAATTCAC TCTCACAATCACCAGCCTGCAGCCTGAAGATTTTGCAACTTATTACTGTCTACAACATACTACTTTCCCGTGG ACGTTCGGCCAAGGGACCAAGGTGGAAATCAAAC |
| SLE1p3-c03k | 224 | GAAATTGTGTTGACACAGTCTCCAGCCACCCTGTCTTTGTCTCAGGGGAAAGAGCCACCCTCTCCTGCAGG GCCAGTCAGAGTGTTGGCAGTCACTTCGCCTGGTACCAACAGAAACCTGGCCAGGCTCCCAGGCTCCTCATC TATGGTGCATCCAACAGGGCCCCTGGCATCCCACCTAGGTTCAGTGCCAGTGGATCTGGGACAGACTTCACT CTCACCATCAGCAGCCTAGAGCCTGAAGATTTTGCAATTTATTACTGTCAACAGCGTAGGACCTGGCCTCCG CTAACCTTCGGCCAAGGGACACGACTGGAGATTAAAC |

| SLE2 Heavy | Seq ID No. |   |
|---|---|---|
| SLE2p1-a01h | 225 | GAGGTGCAGCTGGTGGAGTCTGGGGGAGGCTTGGTACAGCCTGGAGGGTCCCTGAGACTCTCCTGTGTAGCC TCTGGATTCAGTTTCAGTGGTCATGAAATGAACTGGGTCCGCCAGCCTCCAGGGAAGGGGCTGGAGTGGGTT TCACACATTGGCAGTGGTGGTGATTATATAGGTTACGCAGACTCTGTGAAGGGCCGATTCACCGTCTCTAGA GACAACGCCAAGAATTTACTCTATCTGCAAATGAACAGCCTGAGAGCCGACGACACGGCTGTTTATTACTGT GCGACCTTGCTTTTGCGAGACAACCAACTGGACGTCTGGGGCCAAGGGACCACGGTCACCGTCTCCTCA |
| SLE2p1-a06h | 226 | CAGGTGCAGCTGGTGGAGTCTGGGGGAGGCGTGGTCCAGCCAGGGAGGTCCCTAAGACTCTCCTGTGCAGC CTCTGGATTCACCCTCAGTAGTTGTGGCATGCACTGGATCCGCCAGGCTCCAGGCAAGGGGCTGGAGTGGGT GGCAGTTATAACATATGATGGACGAAGTCACTTCAACGCAGACGCCGTGAAGGGCCGATTCACCATCTCCAG AGACAGATCCATGAACACGGTGTCTCTGCAAATGGACAGCCTGAGACCCGAGGACACGGCTGTTTATTACTG TGTCAAAGAACAAGGCTTTGGTTACTACCGGACCGCCGACTACTGGGGCCAGGGAACCCTGGTCACCGTCTC CTCA |
| SLE2p1-b01h | 227 | CAGGTGCAGCTGCAGGAGTCGGGCCCAGGACTGGTGAGGCCTTCGGAGACCCTGTCCCTCACCTGCACTGTC TCTGGTGGCTCCATCAGTAGTGACCACTGGAGTTGGATCCGGCAGCCCCCAGGGAAGGGACTGGAGTGGATT GGGAATGTCTATTACAGTGGGCGCACCTACTACAACCCCTCCTTCAAGAGTCGAGTCACCATATCAGTAGCC ACGTCCAAGAACCAGTTCTCCCTGAAGGTGACCTCTGTGACCGCCGCAGACACGGCCATTTATTACTGTGCG AGGCGAAATGATTTTAATATCTGGGGCCAGGGGACAATGGTCACCGTCTCTTCA |
| SLE2p1-c03h | 228 | GAGGTGCAGCTGTTGGAGTCTGGGGGAGGCTTGGTACAGCCTGGGGGGTCCCTGAGACTCTCCTGTGCAGCC TCTGGATTCACCTTTAGTAAATATGCCGTGAGCTGGGTCCGCCAGGCTCCAGGGAAGGGGCTGGAGTGGGTC TCAGCTGTCAGTGGTAATGGTGACTCCACATACTACGCAGACCCCGTGAGGGGCCGGTTCACCATCTCCAGA GACAATTCCAAGAACACCCTGTATCTGCAAATGAACAGCCTGAGAGCCGAGGACACGGCCCTATATTACTGT TCGATCTGGTGGGGGACTTCAGTACAGTACCCATTGGTGCTCGACTACTGGGGCCTGGGAACCCTGGTCACC GTCTCCTCA |
| SLE2p1-c04h | 229 | CAGGTGCAGCTGGTGGAGTCGGGGGGAGGCGTGGTCCAGCCTGGGAGGTCCCTAAGACTCCTGTGTGCAGC CTCTGGATTCACCCTCAGTACTTGTGGCATGCACTGGATCCGCCAGACTCCTGGCAAGGGGCTGGAGTGGGT GGCAGTTAAAACATATGACGGAAGAGAGGAGTTCTACGCAGACTCCGTGAAGGGCCGATTCACCATTTCCA GAGACGAGTCCATGAACACGCTGTCTTTGCAGATGAACAGCCTGAGACCTGAAGACACGGCTGTATATTACT GTGTCAAAGAACAAGACTACGGTTACTACCGGACCGCCGACCACTGGGGCCAGGGAACCCTGGTCACCGTC TCCTCA |
| SLE2p1-d02h | 230 | CAGGTGCAGCTGCAGGAGGCGGGCCCAGGACTGGTGAAGCCTTCACAGACCCTGTCCCTCACCTGCACTGTC TCTGGTGGCTCCATCAGCAGTGGTGGTTACTACTGGAGCTGGATCCGCCAGCACCCAGGGAAGGGCCTGGAG TGGATTGGATACATCTATTACAGTGGGAGCACCTACTACAACCGTCCCTCAAGAGTCGAGTCACCATATCA GTAGACACGTCCAAGAACCAGTATTCCCTGAAGCTGAGTTCTGTGACCGCCGCAGACACGGCCGTATATTAC TGTGCGAGAGGGCATGGCTTCAACGCCTACTGGGGCCAGGGAACCCTGGTCACCGTCTCCTCA |
| SLE2p1-d04h | 231 | GAGGTGCAGCTGGTGGAGTCCGGGGGAGGCTTGGTAAAGCCGGGGAGTCCCTTAGCTCTCGTGTGCAACC TCTGGAGTCAACTTCAACATCGCCTGGATGACCTGGGTCCGCCAGGCTCCAGGGAAGGGACTGGAGTGGGT TGGCCGTATTAAAAGCAAATTGGTGGTGGGACAACAGATATGCTGCACCCGTGAAAGGCAGATTCACCA TGTCAATAGATGATTCAAAAAATACCCTATATCTGCAAATGAACAGCCTGAAAACCGAGGACACAGCCGTG TATTATTGTACCACAGTCCGCAATATGGCCGACTTGTCCCTTAATCACTGGGGCCAGGGAACCCTGGTCACC GTCTCCTCA |
| SLE2p2-a01h | 232 | GAGGTGCAGCTGGTGGAGTCTGGGGGAGGCTTGGTACAGCCTGGAGCGTCCCTGACACTGTCATGTGTAGTC TCTGGATTCACCTTCATTGGCACTGAAATGACCTGGATTCGCCAGGCTCCAGGGAAGGGGCTGGAGGGACTT TCGTACATCAGTGGGAGTGGCGGGACAACATACTACGCAGAGTCTGTGAGGGGCCGATTCACCATCTCCAG |

TABLE 2-continued

Selected Heavy and Light Chain Sequences from Antibodies of Table 1 (SEQ ID NOS. 127-252)

| | | |
|---|---|---|
| | | AGACAACGCCAAGAAGTCACTGTTTCTGCAAATGACCAGCCTGACAGCCGAGGACACGGCTGTTTACTACTG<br>TGCGACAGGCAACCGGGGATCACTTCCTCGCCGCTGGGGCCAGGGAACCCTGGTCACCGTCTCCTCA |
| SLE2p2-c04h | 233 | GAGGTGCAGCTGGTGGAGTTTGGGGGAGGCTTGGTCCAGCCTGGGGGGTCCCTGAGACTCTCCTGTGTAGCC<br>TCTGGATTCACCTTTAGTTCCTCTTGGATGAGTTGGGTCCGCCAGGCTCCAGGGAAGGGGCTGGAGTGCGTG<br>GGCAACATAAAGCCGGATGCAAGTTTGGTGTCCTATGTGGACTCTGTGAAGGGCCGAGTCACCATCTCCAGA<br>GACAACGCCAAGAATTCACTGTTTCTGGATATGAGCAGCCTGAGAGTCGAGGACACGGCCGTCTACTACTGT<br>GTGAGAGACGGGTGGGACACCTTCTTTGACTCCTGGGGCCAGGGAACCCTGGTCACCGTCTCCTCA |
| SLE2p2-d03h | 234 | GAGGTGCAGCTGGTGGAGTCCGGGGGAGGCTTAGTTCAGCCGGGGGGGTCCCTGAGACTCTCCTGTGCAGC<br>CTCTGGATTCACCTTTAGTAACTACTGGATGAGGTGGGTCCGCCAATCTCCAGGGAAGGGGCTGGTGTGGGT<br>CTCACATATTAACCCTGATGGGAGTTTTACAAACTACGCGGACTCCGTGAAGGGCCGATTCACCATCTCCAG<br>AGACAACACCAAGAACACACTGTATCTGCAAATGAACAGTCTGAGAGCCGAGGACACGGCTGTGTATTACT<br>GTGTGAATTTTCAACTGGGGTGGGCCAGGGAACCCTGGTCACCGTCTCCTCA |
| SLE2p2-e04h | 235 | CAGGTGCAGCTGGTGGAGTCTGGGGGAGGCGTAGTCCAGCCTGGGAGGTCCCTGAAACTCTCCTGTGCAGTC<br>GCTGGATTCACCTTCAGGACCTATGCTATGCACTGGGTCCGCCAGGCTCCAGGCAGGGGGCTGGAGTGGGTG<br>GCACTTATATCAAATGATGGAACCAAAAAATACTCCGCAGACTCCGTGAGGGGCCACTTCACCATCTCCAGA<br>GACAACTCCAAGGACACGCTGTATCTGCAAATGAACAGCCTGCGACCTGACGACACGGCTGTCTATTACTGT<br>GCGAGAGCGGAGTATTGTAGTCCTGGTGACTGCTTCCTTATTGACACCTGGGGCCAGGGAACCCTGGTCACC<br>GTCTCCTCA |
| SLE2p2-f01h | 236 | CAGGTGCAGCTGGTGGAGTCTGGGGGAGGCGTGGTCCAGCCTGGGAGGTCCCTGAGACTCTCCTGTGCAGTG<br>TCTGGATTCACCTTCAGTAGATACGGCATGCACTGGGTCCGCCAGGCTCCAGGCAAGGGGCTGGAGTGGGTG<br>GTAGTTATATGGCATGATGGAAGTAATACATACTATGCAGACTCCGTGAAGGGCCGATTCACCATCTCCAGA<br>GACGACTCCAAGAACACGGTGTATCTGCAAATGAACAGCCTGAGAGTCGAGGACACGGCTATGTATTACTGT<br>CTGAGAGGCAACCCACCTAGCAGCCCCACCGACTACTGGGGCCAGGGAACCCTGGTCACCGTCTCCTCA |
| SLE2p2-g01h | 237 | GAGGTGCAGCTGTTGGAGTCTGGGGGAGGCTTGGTACAGCCTGGGGGGTCCCTGAGACTCTCCTGTGAAGTC<br>TCTGGATTCATCTTTAGCAACTATGCCATGACCTGGGTCCGCCAGGCTCCAGGGAAGGGGCTGCAGTGGGTC<br>TCAGCTATTGGCACTAGTGGTGGTGACACACACTCCGCAGACTCCGTGAAGGGCCGGTTCACCATCTCCAGA<br>CACAATTCCCAGAACACCCTGTATCTGCAGATGAACAGCCTGAGAGCCGAGGACACGGCCATATATTACTGT<br>GCGAAAGTCGTTTATAGCAGGCCTCCTATGGACGTCTGGGGCCAAGGGACCACGGTCACCGTCTCCTCA |
| SLE2p2-g06h | 238 | GAGGTGCAGCTGGTGGAGTCTGGGGGAGGCTTGGTCCAGCCTGGGGGGTCCCTGAGACTCTCCTGTGCAGCC<br>TCTGGATTCACCTTTAGTAATCGTTGGATGAGTTGGGTCCGCCAGGCTCCAGGGAAGGGGCTGGAATGGGTG<br>GCCAACATAAACGAAGATGGAAGTCAGAAACACTATGTGGACTCTGTGAGGGGCCGATTCACCATCTCCAG<br>AGACAACGCCAAGAACTCACTGTCTCTGCAAATGGACAGCCTGAGAGTCGAGGATACGGCCGTGTATTATTG<br>CGCGAGAGCATCGAGGGAGACCGGTGAACCTTACTGGGGCCAGGGAACCCTGGTCACCGTCTCCTCA |

| SLE2 Kappa | Seq ID No. | |
|---|---|---|
| SLE2p1-a01k | 239 | TTGTGATGACTCAGTCTCCACTCTCCCTGCCCGTCACCCTTGGACAGTCGGCCTCCATCTCCTGCAGGTCTAG<br>TCGAAGCCTCGTATTCAGTGATGGAAACACCTACTTGAATTGGTTTCAGCAGAGGCCAGGCCGATCTCCAAG<br>GCGCCTAATTTATAAGGTTTCTAAGCGGGACTCTGGGGTCCCAGACAGATTCAGCGGCAGTGGGTCAGACAC<br>TGATTTCACACTGAAAATCAGCAGGGTGGAGGCTGAGGATGTTGGGGTTTATTACTGCATGCAAGGTACACA<br>CTGGCGGACGTTCGGCCAAGGGACCAAGGTGGAGATCAAA |
| SLE2p1-a06k | 240 | GACATCCAGATGACCCAGTCTCCTTCCACACTGTCTGCATCTGTGGGAGACAGAGTCACCATCACTTGCCGG<br>GCCAGTCAGAGTATTAATTCCTGGTTGGCCTGGTATCAGCGGAAACCAGGGAAAACCCCTAAACTCCTCATC<br>TATGAGGCGTCCAGTTTAGAAAGTGGGGTCCCATCAAGGTTCAGCGGCAGTAGATCTGGGACAGAGTTCACC<br>CTCACCATCAGCAGCCTGCAGCCTGATGATTTTGCAACTTATTACTGCCACCAGTATGATAAATATCCGTGG<br>ACGTTCGGCCAAGGGACCAAGGTGGAGATCAAA |
| SLE2p1-b01k | 241 | GAAATTGTGTTGACGCAGTCTCCAGGCACCCTGTCTTTGTCTCCAGGGGAAAGAGCCACCCTCTCCTGCAGG<br>GCCAGTCAGAGTGTGACCAACAACTATTTGGTCTGGCACCAGCAGAAACCTGGCCAGGCTCCCAGGCTCCTC<br>ATTTCTGATGCATCCAACAGGGCCACTGGCATCCCAGACAGGTTCAGTGGCAGTGGGTCTGGGACAGACTTC<br>ACTCTCACCATCAACAGACTGGAGCCTGAAGATTTCGCAGTGTATTACTGTCAGCAATACGGTAGCTCACCT<br>TTCACTTTCGGCCCTGGGACCAAAGTGGATATCAAA |
| SLE2p1-c03k | 242 | GAAATAGTGATGACGCAGTCTCCAGCCACCCTGTCTGTGTCTCAGGGGAAAGAGTCACCCTCTCCTGCAGG<br>GCCAGTCAGAGTATTGGCAGCAGCTTAGCCTGGTACCTGCAGAAACCTGGCCAGGCTCCCAGAGTCCTCATC<br>TATGGTGCATCCACCAGGACCCCTGGCACCCCAGCCAGGTTCAGTGGCAGTGGGTCTGGGACAGAGTTCACT<br>CTCACCATCAGCAGCCTGCAGTCTGAAGATCTTGCAGATTATTATTGTCAACAGTATAGTAAGTGGCCTCCGA<br>TCACCTTCGGCCAAGGGACACGACTGGAGATTAAA |
| SLE2p1-c04k | 243 | GACATCCAGATGACCCAGTCTCCCTCCATCCTGTCTGCATCTGTAGGAGACAGAGTCACCATCAATTGCCGG<br>GCCAGTCAGAGTATTAATGCCTGGTTGGCCTGGTATCAGCAGAAACAGGGAAAGCCCCTAAATTCCTAATT<br>TATAAGGCGTCTAGTTTAGAAAGTGGGGTCTCGTCAAGGTTCAGCGGCAGTGGATCTGGGACAGAATTCACC<br>CTCATCATCAGCAGCCTGCAGCCTGATGATTTTGCAACTTATTACTGCCAACAGTATGATAAATATCCGTGGA<br>CGTTCGGCCGGGGGACCAAGGTGGAGATCAAA |
| SLE2p1-d02k | 244 | GAAATTGTGTTGACGCAGTCTCCAGGCACCCTGTCTTTCTCTCCAGGGGATAGAGCCACCCTCTCCTGCAGG<br>GCCAGTCAGAGTGTTAGCAGCAGCCTTAGCCTGGTACCAGCAGAGACCTGGCCAGGCTCCCAGCCTCCTC<br>ATCTATGGTGCATCCAGCAGGGCCACTGGCATCCCAGACAGGTTCAGTGGCAGTGGGTCTGGGACAGACTTC<br>ACTCTCACCATCAGCAGACTGGAGCCTGAAGATTTTGCAGTGTATTACTGTCAGCAGTATGGTAACTCACCT<br>CGGACGTTCGGCCAAGGGACCAAGGTGGAGATCAAA |

TABLE 2-continued

Selected Heavy and Light Chain Sequences from Antibodies of Table 1 (SEQ ID NOS. 127-252)

| | | |
|---|---|---|
| SLE2p1-d04k | 245 | GAAATTGTGTTGACGCAGTCTCCAGGCACCCTGTCTTTGTCTCCAGGGGAAAGAGCCACCCTCTCCTGCAGG<br>GCCAGTCAGAGTGTCAGCAGCACCTACTTAAACTGGTACCAGCAGAAGCCTGGCCAGGCTCCCAGGCTCCTC<br>ATCTATGGTGCGTCCACCAGGGCCACTGGCATCCCAGACAGGTTCAGTGGCAGTGGGTCTGGGCAGACTTC<br>ACTCTAACCATCAGCAGACTGGAGCCTGAAGACTTTGCAGTGTACTACTGTCAGCAATATGATGACTCACGG<br>TGGACGTTCGGCCAAGGGACCAAGGTGGAAATCAAA |
| SLE2p2-a01kb | 246 | GATATTGTGATGACTCAGTCTCCACTCTCCCTGCCCGTCACCCCTGGAGAGCCGGCCTCCATCTCCTGCAGGT<br>CTGGTCAGAGCCTCCTGTATAGTGATGGAAACAACTATTTGGATTGGTATCTGCAGAAGCCAGGGCAGTCTC<br>CACAGCTCCTGATCTATTTGGGTTCTAATCGGGCCTCCGGGGTCCCTGACAGGTTCAGTGGCAGTGAATCAG<br>GCACAGATTTTACACTGAAAATCAGCAGAGTGGAGGCTGGGGATGTTGGGATTTATTACTGCATGCAAGCTC<br>TACGAAGTCCGTACACTTTTGGCCAGGGGACCAAGGTGGAGATCAAA |
| SLE2p2-c04k | 247 | TTGTGATGACTCAGTCTCCACTCTCCCTGCCCGTCACCCTTGGACAGCCGGCCTCCATCTCCTGCAGGTCTAG<br>TCAAAGCCCCGTATACAGTGATGGAAACACCTACCTGAATTGGTTTCAGCAGAGGCCAGGCCAATCTCCAAG<br>GCGCCTAATTTATAAGGTTTCTAACCGGGACTCCGGGGTCCCAGACAGATTCAGCGGCAGTGGGTCAGGCAC<br>TGATTTCACACTGAATATCAGCGGGTGGAGGCTGAGGACGTTGGGGTTTATTACTGCATGCAAGGTAGATA<br>CTGGCCGTACACTTTTGGCCAGGGGACCAAGGTGGAGATCAAA |
| SLE2p2-d03k | 248 | GAAATTGTGTTGACGCAGTCTCCAGGCACCCTGTCTTTCTCTCCAGGGGATAGAGCCACCCTCTCCTGCAGG<br>GCCAGTCAGAGTGTAAGCAGCAGCGCCTTAGCCTGGTACCAGCAGAAACCTGGCCAGGCTCCCAGCCTCCTC<br>ATCTATGGTGCATCCAGCAGGGCCACTGGCATCCCAGACAGGTTCAGTGGCAGTGGGTCTGGGACAGACTTC<br>ACTCTCACCATCAGCAGACTGGAGCCTGAAGATTTTGCAGTGTATTACTGTCAGCAGTATGGTAACTCACCT<br>CGGACGTTCGGCCAAGGGACCAAGGTGGAAATCAAA |
| SLE2p2-e04k | 249 | TTGTGATGACTCAGTCTCCACTCTCCCTGCCCGTCACCCTTGGACAGTCGGCCTCCATCTCCTGCAGGTCTAG<br>TCGAAGCCTCGTATTCAGTGATGGAAACACCTACTTGAATTGGTTTCAGCAGAGGCCAGGCCGATCTCCAAG<br>GCGCCTAATTTATAAGGTTTCTAAGCGGGACTCTGGGGTCCCAGACAGATTCAGCGGCAGTGGGTCAGACAC<br>TGATTTCACACTGAAAATCAGCAGGGTGGAGGCTGAGGATGTTGGGGTTTATTACTGCATGCAAGGTACACA<br>CTGGCGGACGTTCGGCCAAGGGACCAAGGTGGAAATCAAAC |
| SLE2p2-f01k | 250 | GACATCCAGATGACCCAGTCTCCTTCCTCACTGTCTGCATCTGTAGGGGACAGAATCACCATCACTTGTCGG<br>GCGAGTCAGGGCATTAACAATTATTTAGCCTGGTTTCAGCAGAAGCCAGGGAAAGCCCCTAAGACCCTGATC<br>TACTCTACATCCACTTTGCAAAGTGGGGTCCCATCAAAGTTCAGCGGCAGTGGATCTGGGACAGTTTTCACT<br>CTCACCATCAGCAACCTGCAGCCTGAAGATTTTGCAACTTATTACTGTCAACAATATAATAGTTACCCGCTCA<br>CTTTCGGCGGAGGGACCAAGGTGGAGATCAAA |
| SLE2p2-g01k | 251 | GACATCCAGATGACCCAGTCTCCATCCTCCCTGTCTGCATCTGTAGGAGACAGAGTCACCATCACTTGCCGG<br>GCAAGTCAGACCATTAGCAACTATTTAAATTGGTTTCAGCAGAAACCAGGGAAAGCCCCTAGGCTCCTGATC<br>TATGCTGCATCGAGTTTGCAAAGTGGGGTCCCATCAAGGTTCAGTGGCAGTGGATCTGTGACAGATTTCACT<br>CTCACCATCAGCAGTCTGCAACCTGAAGATTTTGCAACTTACTTCTGTCAACAGAGTTACAGCACCCCGTGG<br>ACGTTCGGCCAAGGGACCAAGGTGGAAATCAAA |
| SLE2p2-g06k | 252 | TTGTGATGACTCAGTCTCCATTCTCCCTGCCCGTCACCCTTGGACAGCCGGCCTCCATCTCCTGCAGGTCTAG<br>TCAAAGCCTCGTATACAGTGATGGAAACACCTACTTGAATTGGTTTCAGCAGAGGCCAGGCCAATCTCCAAG<br>GCGCCTGATTTATAAGCTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGCTACACA<br>CTGGCCTTGGACGTTCGGCCAAGGGACCAAGGTGGAAATCAAA |

Antibodies were also tested for binding against five common lupus autoantigens: Ro, La, Sm, nRNP, and cardiolipin. Antibodies which bound to at least two of these five antigens were classified as poly-reactive (whether or not they bind polysaccharide). FIG. 2C shows the percentage of poly-reactive antibodies from each donor. SLE2 shows a remarkable 52% of antibodies showing polyreactivity. Graphs similar to those in FIG. 2A, but highlighting cross-reactive or poly-reactive antibodies from each donor are shown in FIGS. 7A-B.

A small but significant percentage of anti-polysaccharide antibodies produced from ASCs bind to the polysaccharides of two distinct serotypes. Although most of the antibodies are serotype specific, 12% of the antibodies characterized bind two serotypes. Of the antibodies that bind two serotypes, one pair of polysaccharides, 9N and 9V, were dually bound by several antibodies. These two carbohydrates have very similar non-branched structures with one of four D-Glc in a 9N chain repeat being replaced by a D-Gal in 9V. Thus, it is not unexpected that some antibodies will cross-react with both serotypes. However, the inventor observed a wide variety of 9N and 9V binding antibodies, some of which cross-react and some that do not. For example, Con1p2D02 and SLE1p1E01 antibodies are mono-specific to 9N and 9V respectively (FIG. 3A), showing little to no cross-reactivity. Con1p4B03, however, binds to both serotypes, favoring 9N by an order of magnitude in affinity and by 5-times in avidity (FIG. 3B). One antibody to 9N, SLE1p1A03, does not bind to 9V, but rather cross-reacts to serotype 14 polysaccharide (FIG. 3C), with similar affinity and avidity, an observation which is difficult to explain examining only the carbohydrate sequence. Several of these cross-reacting antibodies are from the same donor, demonstrating a variety of antibodies to a certain serotype within a single individual. Serotypes 19A and 19F also have very similar structures with 19F having a D-Glc with a 1-2 linkage and 19A having a 1-3 linkage. The antibody SLE2p2D03 binds to both 19A and 19F with nearly equivalent affinities (FIG. 3D), although four-fold different avidities (favoring 19A).

The inventor also detected cross-reactivity between serotypes 15B and 14 (FIG. 4C), as well as 17F and 33F (FIGS. 4A and 4B). The antibody SLE2p1B01 slightly favors serotype 14 over serotype 15B in avidity, although not in affinity. While SLE2p2G06 and SLE2p2C04 are mono-specific for 17F and 33F respectively (FIG. 4A), SLE2p1C03 (from the same donor; FIG. 4B) cross-reacts to both serotypes with similar avidity. Overall, it is evident that although serum may cross-react between two serotypes, 85% of the actual antibodies making up this response are specific to only one polysaccharide. The inventor encountered no antibodies that reacted with more than two serotypes with a measureable affinity/avidity.

A high frequency of somatic hypermutation in these antibodies indicates frequent anamnestic anti-polysaccharide responses. As previously reported, the ASC recall response to the influenza vaccine is highly mutated, even more so than in the typical IgG germinal center memory cell. The inventor hypothesized that this was due to the repeated nature of the annual vaccine, as well as frequent exposure to various influenza strains. The antibodies obtained in this study have a similar mutation frequency (see FIG. 5). This is particularly interesting because for each donor, this was a primary vaccination. If the donors were truly naïve to these polysaccharide antigens, the ASC response would have been smaller and the sequences of the antibodies would show less mutation. Thus, this vaccine is producing an anamnestic response which can only arise from previous infection or exposure to *S. pneumoniae* strains.

Each donor displays a unique anamnestic fingerprint of antibody serotype specificities. Each of the four donors showed a remarkably different antibody response, as demonstrated by the number of antibodies produced against each serotype or cell wall polysaccharide (FIG. 6A, non-binding antibodies not shown; antibodies that cross-react are counted in the bin of the serotype with the strongest affinity). A response to certain serotypes seems to predominate in each donor. Donor Con1 shows a strong response to serotype 8 (six total antibodies, three of which are clonal), Con2 shows a strong response to serotype 18C (nine antibodies, all clonal), SLE1 and SLE2 both exhibit a strong response to serotype 5 (six antibodies, two of which are clonal and six antibodies, four of which are clonal, respectively). The inventor hypothesizes that this is due to an infection (clinically evident or not) by that serotype at some point in that donor's lifetime.

The inventor's previous study of the immune response to influenza vaccination (Wrammert et al., 2008) highlighted the strong clonality of the ASC response to that vaccine, and this is also the case after immunization with Pneumovax®23. Thus, several of the antibodies the inventor characterized are clonally related, but show very similar binding characteristics (see Table 1 to compare affinities). When displaying all four donors on a single histogram graph and reducing clonally related antibodies to a count of 1 (FIG. 6B), it is quite evident that the hmAbs isolated from each donor create a unique fingerprint with three donors binding 9V, 15B, 17F, and only serotypes 8 and 33F being bound by all four donors. Also, no subject in the study produced an antibody that bound to serotypes 7F, 10A, or 12F. Although it is difficult to mathematically show that the histograms from each donor are unique, the inventor is confident that producing 44 antibodies from Con2 gives a representative distribution of the serotypes to which this individual is having an anamnestic response and that this differs from donor to donor.

Example 3—Discussion

This is the first comprehensive analysis of the human immune response to Pneumovax®23 immunization, on a per antibody basis, utilizing antibody secreting cells (ASCs) that emerge seven days post vaccination as a source for the production of monoclonal antibodies. An analysis of these polysaccharide specific monoclonal antibodies allowed a detailed study of the human antibody repertoire to this vaccine. It also provided insight into the specificities of each antibody and surprisingly revealed an "anamnestic fingerprint" that the inventor interprets to reflect the prior infection history of each participant.

In an earlier study (Wrammert et al., 2008), the inventor found that the magnitude of the anamnestic response after influenza vaccination was such that an average of 6% of total B cells were ASCs, yet some donors made poor to non-existent responses. Using these same techniques, some vaccines (notably Anthrax AVA) routinely result in a very poor induction of a protective response (Crowe et al., 2010). Here, the inventor reports that Pneumovax®23 invoked a two- to four-fold more robust response than the strongest responses induced in some of the influenza donors, suggesting that these polysaccharides are exceptionally efficient at triggering a memory response. Earlier studies (2-4) also detected antibody secreting cells seven days post vaccination with both the polysaccharide and conjugate vaccines, averaging over 100 serotype specific cells per million PBMCs. The inventor's own ELISpot results were similar to these previous reports (data not shown), but the overall magnitude of the IgG ASC response as determined by flow cytometry was still surprising. Interestingly, one of the SLE donors, SLE2 also participated in the previous influenza study and did not make a response to the influenza vaccine, yet produced an impressive ASC response to the polysaccharide vaccine. This provides a direct comparison, albeit with a small sample size, of the vast difference in potential immune response to vaccines, especially in immunocompromised individuals.

There are several interesting differences in this study between the SLE donors and healthy controls. As discussed above, the percentage of ASCs that arose from the vaccination was considerably smaller in SLE1 and SLE2 (8.8% on average, as compared to 23.8% for Con1 and Con2). Although the percentage of high affinity antibodies generated from these donors was not different, the antibodies generated from SLE2 do appear to be quite poly-reactive against non-carbohydrate antigens. It is also important to note that three of the four cross-reactive antibodies from SLE2 are also poly-reactive (see FIGS. 7A-B). It is remarkable that although they bind to multiple self-antigens, they are still specific for only one or two polysaccharide structures. These results likely indicate a defect in B cell tolerance in this donor which is allowing cross- and poly-reactive B cells, which would otherwise be deleted or anergized, to mature and secrete antibody. Although it is unknown if this manner of poly-reactive antibody has physiological effects, it is likely that any vaccination in this individual will result such poly-reactive antibodies.

This study has greatly increased the number of reported human monoclonal antibodies to *S. pneumoniae* that have been characterized both in terms of binding and repertoire usage. These anti-polysaccharide antibodies are as highly mutated as antibodies which arise from repeated seasonal influenza vaccination. In comparing V gene usage in these antibodies to the previous reports, the inventor observes similar trends. For example, Baxendale (Baxendale and Goldblatt, 2006; Baxendale et al., 2000) suggests that VH3-48 likely contributes to an antigen binding domain that prefers epitopes from serotypes 23F and 18C, as the two VH3-48 family antibodies they characterized bound those two serotypes and Zhou found VH3-48 in the 23F study (Zhou et al., 2002), but not the 6B study (Zhou et al., 2004). Similarly, three of four VH3-48 antibodies (Table 1) characterized in this study also bind these two serotypes. The inventor have also characterized a VH3-48 which binds serotype 2 (Con2p5E05), a case of a VH3-48 binding a different serotype. They have also observed remarkable similarity in the antibodies characterized which bind cell wall polysaccharide (CWPS). Comparing two unique donors, these antibodies use either VH3-30 or closely related VH3-33. The CDR3s even show remarkable similarity, (Con2p6B03, VKESATGWYRTADY (SEQ ID NO:57); Con2p5A06, VKEYSWGYYRTADY (SEQ ID NO:49); SLE2p1A06, VKEQGFGYYRTADY (SEQ ID NO:101); SLE2p1C04, VKEQDYGYYRTADH (SEQ ID NO:107)). Thus, the chemical simplicity of repeated polysaccharide sequences seems to induce similar V gene family usage even in distinct individuals.

Although avidity has been shown to be an important correlate with protection (Anttila et al., 1999; Harris et al., 2007; Usinger and Lucas, 1999), thiocyanate ELISA is not commonly performed on monoclonal antibodies. The inventor utilizes it here because there are several complications in determining affinity by fitting simple ELISA curves. These include the magnified effects of small antibody concentration errors on affinities, uncertainty whether or not the antigen binding interaction is univalent or bivalent, and coating plates with large units of repeating epitopes. It is also possible that poly-reactive antibodies from SLE donors (and occasionally healthy controls) may interact with antigens outside of the binding site. All of these effects are minimized in the thiocyanate avidity ELISA system. FIGS. 3D and 4C both represent an antibody for which affinity and avidity ELISA binding measurements do not correlate. Both of these antibodies are from SLE2 and both antibodies are poly-reactive. The inventor is currently exploring interesting antibodies such as these in more detail, but in these cases, thiocyanate avidity is a more reliable measure of the antibody-carbohydrate interaction.

Serum cross-reactivity is typically determined by depleting the serum with a particular serotype carbohydrate and then observing binding of the serotypes still present in the serum. Soininen et al. (2000), for example, found remarkable cross-reactivity in the serum, especially in unvaccinated individuals. However, these assays require careful calibration, as well as pre-adsorption of CWPS and other polysaccharides to remove nonspecific reactivity, especially common in unvaccinated individuals (Marchese et al., 2006). Modern updates to this method, using microarray printing and reading technology (Pickering et al., 2007), for example, have greatly improved the reliability of these assays; yet until this study, one could not be definite whether observed cross-reactivity is due to actual cross-reactive individual antibodies, or the polyclonal nature of serum antibodies.

This study, focusing on cross-reactivity in monoclonal antibodies, has addressed such ambiguities. Park et al. (2009) describes cross-serotype monoclonal antibodies, deducing the common linear carbohydrate structure to which the antibodies were binding. Other reports (Baxendale et al., 2006; Baxendale et al., 2000; Zhou et al., 2004) do not specify cross-reactive antibodies, although those produced from Fab libraries were only panned with the serotype of interest. These experiments are the first, however, that characterize a large number of anti-pneumococcal human monoclonal antibodies, and although most of the antibodies are serotype specific, 15% were not. Unlike the above report, explaining the cross-reactivity of several of the monoclonal antibodies the inventor characterized is clearly not as simple as finding similar primary polysaccharide structures. While 9N/9V and 19A/19F are quite similar, 17F and 33F, and 14 and 15B do not have similar primary structures. Pickering et al. (2007), found that 9V could inhibit 9N binding, 15B inhibited 14 binding, 19F strongly inhibited 19A binding and 33F strongly inhibited 17F binding, all matching the observed results (FIGS. 3A-D and 4A-C). Interestingly, the converse is not typically the case (14 does not inhibit 15B and 17F does not inhibit 33F), but this is likely an affinity issue. Using these results to illustrate this, it is unlikely that Con1p4B03 binding to 9N could be inhibited by adding 9V polysaccharide because its affinity for 9N is over an order of magnitude higher. Overall, the inventor can say with confidence that the serum cross-reactivity observed in these studies is indeed due to individual monoclonal antibodies that bind to at least two different serotypes.

The observation that each of the donors produced a unique panel of antibodies to each of the serotypes is quite interesting. One explanation of this phenomenon is that one is seeing an "anamnestic fingerprint," or that the memory response being observed is a product of the serotypes that each of the subjects had been exposed to in the past. It is difficult to approximate how many of the 23 strains someone has been exposed to up to the time when they receive the Pneumovax®23 vaccine. The four donors whose serum was carefully examined by Pickering et al. (2007) had appreciable IgG concentrations (higher than 1 µg/ml) for 5-12 of the 22 serotypes (the samples were depleted with CWPS and 22F) indicating active plasma cells and subsequently previous exposure to those serotypes. The donors here showed antibodies to just over an average of 11 (13, 13, 9, and 10) serotypes, matching the serology in this previous study. Thus, one is observing that antibodies from the reactivation of memory cells seven days after vaccination is similar to those observed in the sera, likely from long-lived plasma cells.

While the generation of these human monoclonal antibodies elucidates basic anamnestic response, it may also serve a therapeutic purpose. As many current treatments can become ineffective due to antibiotic resistance, it is important to consider passive immunotherapeutics that can safely target pathogens. Several previous reports (Casal et al., 2002; Yuste et al., 2002) have explored the effects of specific antibodies in a mouse sepsis model. Remarkably, administering hyperimmune serum after infection was able to reduce the amount of antibiotic required for the mouse to recover by eight-fold. In addition, this synergistic effect might be effectively used in treating difficult or invasive infections, such as empyema, as well as bacteremia in immunocompromised individuals. In addition to the myriad of treatment options of fully human monoclonal antibodies, the drastically decreased risk of anaphylactic shock and of anti-treatment immune responses suggests that they will become as important in infectious diseases as they are currently in autoimmune settings.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

U.S. Pat. No. 2,653,899
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
"Antibodies: A Laboratory Manual," Cold Spring Harbor Press, Cold Spring Harbor, NY, 1988.
Anttila et al., Clin. Exp. Immunol., 118:402-407, 1999.
Atherton et al., Biol. of Reproduction, 32:155-171, 1985.
Baxendale et al., Eur. J. Immunol., 30:1214-1223, 2000.
Baxendale et al., Infect. Immun., 74:1025-1031, 2006.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
Casal et al., Antimicrob. Agents Chemother., 46:1340-1344, 2002.
Chowdhry et al., Arthritis Rheum., 52:2403-10, 2005.
Clutterbuck et al., Immunol., 119:328-337, 2006.
Crowe et al., J. Infect. Dis., 202:251-60, 2010.
De Jager et al., Semin. Nucl. Med. 23(2):165-179, 1993.
Dholakia et al., J. Biol. Chem., 264:20638-20642, 1989.
Doolittle and Ben-Zeev, Methods Mol. Biol., 109:215-237, 1999.
Elkayam et al., Autoimmunity, 38:493-496, 2005.
Gefter et al., Somatic Cell Genet., 3:231-236, 1977.
Goding, In: Monoclonal Antibodies: Principles and Practice, 2d ed., Orlando, Fla., Academic Press, 60-61, 65-66, 71-74, 1986.
Gulbis and Galand, Hum. Pathol. 24(12):1271-1285, 1993.
Harris et al., Clin. Vacc. Immunol., 14:397-403, 2007.
Khatoon et al., Ann. of Neurology, 26:210-219, 1989.
King et al., J. Biol. Chem., 269:10210-10218, 1989.
Kobasa et al., Nature, 445:319-323, 2007.
Kohler and Milstein, Eur. J. Immunol., 6:511-519, 1976.
Kohler and Milstein, Nature, 256:495-497, 1975.
Kyte and Doolittle, J. Mol. Biol., 157(1):105-132, 1982.
Lee et al., J. Immunol., 133:2706-2711, 1984.
Marchese et al., Clin. Vacc. Immunol., 13:905-912, 2006.
Morrison, Science, 229(4719):1202-1207, 1985.
Nakamura et al., In: Enzyme Immunoassays: Heterogeneous and Homogeneous Systems, Chapter 27, 1987.
Nieminen et al., Vaccine, 16:313-319, 1998.
Nieminen et al., Vaccine, 16:630-636, 1998.
O'Shannessy et al., J. Immun. Meth., 99:153-161, 1987.
Owens and Haley, J. Biol. Chem., 259:14843-14848, 1987.
Park et al., Infect. Immun., 77:3374-3379, 2009.
Persic et al., Gene, 187(1):1-8, 1997.
Pickering et al., Am. J. Clin. Pathol., 128:23-31, 2007.
Posner et al., Hybridoma, 6:611-625, 1987.
Potter and Haley, Meth. Enzymol., 91:613-633, 1983.
Smith et al., Nat. Protoc., 4:372-384, 2009.
Soininen et al., Clin. Diagn. Lab. Immunol., 7:468-476, 2000.
Tang et al., J. Biol. Chem., 271:28324-28330, 1996.
Usinger et al., Infect. Immun., 67:2366-2370, 1999.
Wawrzynczak & Thorpe, In: Immunoconjugates, Antibody Conjugates In Radioimaging And Therapy Of Cancer, Vogel (Ed.), NY, Oxford University Press, 28, 1987.
Wrammert et al., Nature, 453:667-671, 2008.
Xu et al., Anal. Biochem., 336:262-272, 2005.
Yuste et al., Clin. Exp. Immunol., 128:411-415, 2002.
Zhou et al., Infect. Immun., 70:4083-4091, 2002.
Zhou et al., Infect. Immun., 72:3505-3514, 2004.

What is claimed is:

1. A panel comprising two or more serotype-specific antibodies or binding fragments thereof that bind to *Streptococcus pneumoniae* or bind to antigens of *S. pneumoniae* immobilized on a solid support, wherein the two or more serotype-specific antibodies or binding fragments thereof comprise:
a heavy chain variable domain polypeptide selected from the group consisting of the amino acid sequence set forth in SEQ ID NOS: 253 to 257, 269, 294 to 304, 331 to 337, 351 to 354, or 360 to 364; and
a light chain variable domain polypeptide selected from the group consisting of the amino acid sequence set forth SEQ ID NOS: 286, 313 to 323, 344 to 350, 365 to 368, or 374 to 378.

2. The panel of claim 1, wherein the solid support comprises one or more beads, a dipstick, a filter, a membrane, a plate, a chip, or a column matrix, and wherein the one or more serotype-specific antibodies immobilized on the solid support are specific for a serotype of *S. pneumoniae* or an antigen of *S. pneumoniae*.

3. The panel of claim 1, wherein the one or more serotype-specific antibodies are monoclonal antibodies.

4. The panel of claim 1, wherein the one or more serotype-specific antibodies bind to at least 18 *S. pneumoniae* serotypes.

5. The panel of claim 1, wherein the one or more serotype-specific antibodies that bind to serotypes selected from at least one of:

1, 2, 3, 4, 5, 6B, 8, 9N, 9V, 11B, 14, 15B, 17F, 18C, 19A, 19F, 20, 22F, 23F, 33F, and CWPS cross react with more than one serotype;
1, 2, 3, 4, 5, 6B, 8, 9N, 9V, 11B, 14, 15B, 17F, 18C, 19A, 19F, 20, 22F, 23F, 33F, and CWPS; or
3, 6A, 6B, 6C, 19A, 19F, 22A, and 22F.

6. The panel of claim 1, wherein the serotype-specific antibodies are linked to a detectable label.

7. The panel of claim 6, wherein the detectable label comprises a radioactive tag, a fluorescent tag, or a biological or enzymatic tag.

8. A kit for the detection of *Streptococcus pneumoniae* comprising a panel comprising one or more serotype-specific antibodies or binding fragments thereof that bind to *Streptococcus pneumoniae* or bind to antigens of *S. pneumoniae* immobilized on a solid support, a suitable container, and optionally an immunodetection reagent, wherein the antibodies or binding fragments thereof comprise:
a heavy chain variable domain polypeptide selected from the group consisting of the amino acid sequence set forth in SEQ ID NOS: 253 to 257, 269, 294 to 304, 331 to 337, 351 to 354, or 360 to 364; and
a light chain variable domain polypeptide selected from the group consisting of the amino acid sequence set forth SEQ ID NOS: 286, 313 to 323, 344 to 350, 365 to 368, or 374 to 378,
wherein the panel includes antibodies or binding fragments thereof selected to bind to *S. pneumoniae* serotypes 1, 2, 3, 4, 5, 6B, 8, 9N, 9V, 11B, 14, 15B, 17F, 18C, 19A, 19F, 20, 22F, 23F, 33F, and CWPS.

9. The kit of claim 8, wherein the support comprises one or more beads, a dipstick, a filter, a membrane, a plate, a chip, or a column matrix, and wherein the one or more serotype-specific antibodies immobilized on the support are specific for a serotype of *S. pneumoniae* or an antigen of *S. pneumoniae*.

10. The kit of claim 8, wherein immunodetection reagent comprises at least a second antibody that binds an immunocomplex formed when an antibody in the antibody panel binds *S. pneumoniae* or *S. pneumoniae* antigen.

11. The kit of claim 10, wherein the one or more serotype-specific antibodies and/or the immunodetection reagent are linked to a detectable label.

12. The kit of claim 11, wherein the detectable label comprises a radioactive tag, a fluorescent tag, or a biological or enzymatic tag.

13. The kit of claim 8, wherein the kit further comprises an aliquoted composition of *S. pneumoniae* or *S. pneumoniae* antigens that may be used to prepare a standard curve.

* * * * *